United States Patent
Melvin, Jr. et al.

(10) Patent No.: US 8,124,764 B2
(45) Date of Patent: Feb. 28, 2012

(54) FUSED HETEROCYCLYC INHIBITOR COMPOUNDS

(75) Inventors: Lawrence S. Melvin, Jr., Longmont, CO (US); Michael Graupe, Pacifica, CA (US); Chandrasekar Venkataramani, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 337 days.

(21) Appl. No.: 12/502,967

(22) Filed: Jul. 14, 2009

(65) Prior Publication Data

US 2010/0029638 A1 Feb. 4, 2010

Related U.S. Application Data

(60) Provisional application No. 61/080,449, filed on Jul. 14, 2008.

(51) Int. Cl.
*C07D 401/00* (2006.01)
(52) U.S. Cl. ........ 544/331; 544/179; 544/180; 544/185; 544/215; 546/268.4; 514/183; 514/242; 514/245; 514/252.05; 514/336
(58) Field of Classification Search .................. 544/179, 544/185, 215, 180, 331; 546/268.4
See application file for complete search history.

(56) References Cited

U.S. PATENT DOCUMENTS

| | | | |
|---|---|---|---|
| 5,760,246 A | 6/1998 | Biller et al. | 548/309.7 |
| 6,403,588 B1 | 6/2002 | Hayakawa et al. | 514/249 |
| 6,855,719 B1 * | 2/2005 | Thomas et al. | 514/269 |
| 7,253,204 B2 | 8/2007 | Delorme et al. | 514/422 |
| 2002/0168761 A1 | 11/2002 | Gour et al. | 435/325 |
| 2004/0006011 A1 | 1/2004 | Gour et al. | 514/9 |
| 2005/0054850 A1 | 3/2005 | Wu et al. | 544/238 |
| 2005/0187266 A1 | 8/2005 | Su | 514/359 |
| 2005/0234066 A1 | 10/2005 | Bailey et al. | 514/252.03 |
| 2005/0288282 A1 | 12/2005 | Delorme et al. | 514/228.2 |
| 2006/0293320 A1 | 12/2006 | Schmitz et al. | 514/233.2 |
| 2007/0093492 A1 | 4/2007 | Jiaang et al. | 514/249 |
| 2007/0213330 A1 | 9/2007 | Delorme et al. | 514/235.5 |
| 2009/0005374 A1 | 1/2009 | Melvin et al. | 514/233 |
| 2009/0076021 A1 | 3/2009 | Plato | 514/252 |
| 2010/0009990 A1 | 1/2010 | Venkataramani | 514/233.2 |
| 2010/0022543 A1 | 1/2010 | Melvin et al. | 514/236.8 |
| 2010/0029638 A1 | 2/2010 | Melvin et al. | 514/233.2 |
| 2010/0310500 A1 | 12/2010 | Graupe et al. | |
| 2010/0311794 A1 | 12/2010 | Venkataramani | |

FOREIGN PATENT DOCUMENTS

| | | | |
|---|---|---|---|
| CA | 2644933 | 9/2007 | 184/46 |
| EP | 0847992 A1 | 6/1998 | |
| EP | 1 277 754 | 1/2003 | |
| JP | 2003-313126 | 11/2003 | |
| JP | 2004-002826 | 1/2004 | |
| JP | 2007-001885 | 1/2007 | |
| WO | WO 97/26240 | 7/1997 | |
| WO | WO-00/18733 A1 | 4/2000 | |
| WO | WO 01/14375 | 3/2001 | |
| WO | WO 01/19788 | 3/2001 | |
| WO | WO-01/53331 A2 | 7/2001 | |
| WO | WO 01/56989 | 8/2001 | |
| WO | WO 01/83481 | 8/2001 | |
| WO | WO 02/00651 | 1/2002 | |
| WO | WO 02/26712 | 4/2002 | |
| WO | WO 02/34748 | 5/2002 | |
| WO | WO 02/46170 | 6/2002 | |
| WO | WO 02/065979 | 8/2002 | |
| WO | WO 02/066480 | 8/2002 | |
| WO | WO 02/066481 | 8/2002 | |
| WO | WO 03/000682 | 1/2003 | |
| WO | WO 03/000689 | 1/2003 | |
| WO | WO 03/002524 | 1/2003 | |
| WO | WO 03/031446 | 4/2003 | |
| WO | WO 03/041649 | 5/2003 | |
| WO | WO 03/084948 | 10/2003 | |
| WO | WO 03/084997 | 10/2003 | |
| WO | WO 03/099221 | 12/2003 | |
| WO | WO 03/099817 | 12/2003 | |
| WO | WO-03/103151 A1 | 12/2003 | |
| WO | WO 2004/021989 | 3/2004 | |

(Continued)

OTHER PUBLICATIONS

Arbiser, J.L. (2007) "Why Targeted Therapy Hasn't Worked in Advanced Cancer", *The Journal of Clinical Investigation*, vol. 17, No. 10 pp. 2762-2765.
Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.
International Search Report for PCT/US2010/037647, International Filing Date Jun. 7, 2010, mailed Nov. 9, 2010.
Madhusudan, S. et al. (2004) "Tyrosine Kinase Inhibitors in Cancer Therapy", *Clininical Biochemistry*, vol. 37, 00.618-635. U.S. Office Action for U.S. Appl. No. 12/747,159, mailed Dec. 10, 2010.
U.S. Appl. No. 12/943,799, filed of Nov. 10, 2010.

(Continued)

*Primary Examiner* — James O Wilson
*Assistant Examiner* — Alexander R Pagano
(74) *Attorney, Agent, or Firm* — J. Elin Hartrum; Francis O. Ginah

(57) ABSTRACT

The present invention provides a compound of general Formula (I) having histone deacetylase (HDAC) and/or Cyclin-dependent kinase (CDK) inhibitory activity, a pharmaceutical composition comprising the compound, and a method useful to treat diseases using the compound.

Formula (I)

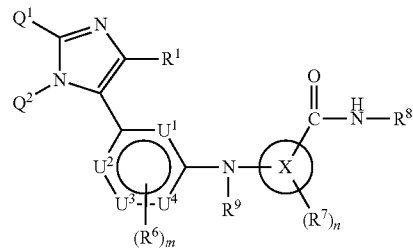

29 Claims, No Drawings

FOREIGN PATENT DOCUMENTS

| | | |
|---|---|---|
| WO | WO 2004/035525 | 4/2004 |
| WO | WO 2004/039325 | 5/2004 |
| WO | WO 2004/041191 | 5/2004 |
| WO | WO 2004/048343 | 6/2004 |
| WO | WO 2006/058007 | 6/2004 |
| WO | WO-2004/060318 A2 | 7/2004 |
| WO | WO 2004/069133 | 8/2004 |
| WO | WO 2004/069803 | 8/2004 |
| WO | WO 2004/076452 | 9/2004 |
| WO | WO 2004/080390 | 9/2004 |
| WO | WO 2004/084901 | 10/2004 |
| WO | WO 2004/092115 | 10/2004 |
| WO | WO 2004/092145 | 10/2004 |
| WO | WO 2004/110350 | 12/2004 |
| WO | WO 2005/006945 | 1/2005 |
| WO | WO 2005/030140 | 4/2005 |
| WO | WO-2005/030705 A1 | 4/2005 |
| WO | WO 2005/046594 | 5/2005 |
| WO | WO-2005/054850 A2 | 6/2005 |
| WO | WO 2005/060571 | 7/2005 |
| WO | WO-2005/070180 A2 | 8/2005 |
| WO | WO 2005/077368 | 8/2005 |
| WO | WO 2005/077373 | 8/2005 |
| WO | WO 2005/082871 | 9/2005 |
| WO | WO 2005/092899 | 10/2005 |
| WO | WO 2005/102318 | 11/2005 |
| WO | WO 2005/102325 | 11/2005 |
| WO | WO-2005/102326 A2 | 11/2005 |
| WO | WO 2005/102346 | 11/2005 |
| WO | WO 2005/102455 | 11/2005 |
| WO | WO 2005/103022 | 11/2005 |
| WO | WO 2005/112920 | 12/2005 |
| WO | WO 2005/115304 | 12/2005 |
| WO | WO 2005/115385 | 12/2005 |
| WO | WO 2006/010750 | 2/2006 |
| WO | WO 2006/038001 | 4/2006 |
| WO | WO 2006/044509 | 4/2006 |
| WO | WO 2006/058905 | 6/2006 |
| WO | WO-2006/064251 A1 | 6/2006 |
| WO | WO 2006/070943 | 7/2006 |
| WO | WO 2006/077401 | 7/2006 |
| WO | WO 2006/108059 | 10/2006 |
| WO | WO 2006/104983 | 11/2006 |
| WO | WO 2006/122011 | 11/2006 |
| WO | WO 2007/008664 | 1/2007 |
| WO | WO 2007/026251 | 3/2007 |
| WO | WO 2007/030362 | 3/2007 |
| WO | WO 2007/036732 | 4/2007 |
| WO | WO 2007/037187 | 4/2007 |
| WO | WO-2007-040440 A1 | 4/2007 |
| WO | WO 2007/055941 | 5/2007 |
| WO | WO 2007/076034 | 7/2007 |
| WO | WO 2007/076035 | 7/2007 |
| WO | WO 2007/079185 | 7/2007 |
| WO | WO 2007/087129 | 8/2007 |
| WO | WO 2007/087717 | 8/2007 |
| WO | WO-2007/093492 A1 | 8/2007 |
| WO | WO 2007/095124 | 8/2007 |
| WO | WO 2007/106192 | 8/2007 |
| WO | WO 2007/100795 | 9/2007 |
| WO | WO-2007/127137 A2 | 11/2007 |
| WO | WO 2007/135036 | 11/2007 |
| WO | WO 2008/033743 | 3/2008 |
| WO | WO 2009/002534 | 12/2008 |
| WO | WO 2009/079391 | 6/2009 |
| WO | WO 2010/009139 | 1/2010 |
| WO | WO-2010/009139 A2 | 1/2010 |
| WO | WO 2010/009155 | 1/2010 |
| WO | WO-2010/009155 A2 | 1/2010 |
| WO | WO 2010/009166 | 1/2010 |
| WO | WO-2010/009166 A1 | 1/2010 |
| WO | WO 2010/014611 | 2/2010 |
| WO | WO-2010/014611 A1 | 2/2010 |

OTHER PUBLICATIONS

Lee, M. et al. (2003) "Molecular Targets for Cell Cycle Inhibition and Cancer Therapy", *Expert Opinion on Therapeutic Patents* 17(7):745-765.

U.S. Appl. No. 61/185,126, filed Jun. 8, 2009, Gaupe et al.

U.S. Appl. No. 61/185,134, filed Jun. 8, 2009, Gaupe et al.

Acharya et al., "Rational Development of Histone Deacetylase Inhibitors as Anticancer Agents: A Review", *Molecular Pharmacology*, 2005, 68:917-932.

Alam et al., "Synthesis and SAR of aminopyridines as novel c-Jun N-terminal kinase (JNK) inhibitors", *Bioorg. Med. Chem. Lett.*, 2007, 17:3463-3467.

Buggy et al,. "CRA-024781: a novel synthetic inhibitor of histone deacetylase enzymes with antitumor activity in vitro and in vivo", *Mol. Cancer Ther.*, 2006, 5:1309-1317.

Bush & McKinsey, "Targeting Histone Deacetylases for Heart Failure," *Expert Opin. Ther. Targets*, 2009, 13(7): 767-784.

Feng et al., "Synthesis and SAR of 2-(4-fluorophenyl)-3-pyrimidin-4-ylimidazo[1,2-β]pyridine derivatives as anticoccidial agents", *Bioorg. Med. Chem. Lett.*, 2006, 5978-5981.

Gudmundsson et al., "Imidazo[1,2-β]pyridines with potent activity against herpesviruses", *Bioorg. Med. Chem. Lett.*, 2007, 17:2735-2739.

Hayakawa et al., "Synthesis and biological evaluation of imidazo[1,2-β]pyridine derivatives as novel PI3 kinase p110β inhibitors", *Bioorg. Med. Chem. Lett.*, 2007, 15:403-412.

Liang et al., "Synthesis and SAR studies of potent imidazopyridine anticoccidial agents", *Bioorg. Med. Chem. Lett.*, 2007, 17:3558-3561.

Mahboobi et al., "2-Aroylindoles and ω-Aroylbenzofurans with N-Hydroxyacrylamide Substructures as a Novel Series of Rationally Designed Histone Deacetylase Inhibitors," *J. Chem. Soc., 2007*, 50(18): 4405-4418.

Marcou et al., "Optimizing Fragment and Scaffold Docking by Use of Molecular Interaction Fingerprints", *J. Chem. Inf. Model*, 2007, 47(1):195-207.

Moradei et al., "Histone Deacetylase Inhibitors: Latest Developments, Trends, and Prospects", *Current Med. Chem.—Anti-Cancer Agents*, 2005, 529-560.

Paris et al., "Histone Deacetylase Inhibitors: From Bench to Clinic", *J. Med. Chem*, 2008, 51(6):1505-1529.

Park et al., "A Simple and Efficient Docking Method to the Cyclin-Dependent Kinase 2", *Bull. Korean Chem. Soc.*, 2007, 28(2):211-219.

Price et al., "Histone deacetylase inhibitors: an analysis of recent patenting activity", *Expert Opinion, Ther. Patents*, 2007, 745-765.

Rosato et al., *Cancer Research*, 2003, 63:3637-3645.

Vadivelan et al., "Virtual Screening Studies to Design Potent CDK2-Cyclin A Inhibitors", *J. Chem. Inf. Model*, 2007, 47(4): 1526-1535.

Vigushin et al., "Targeted Histone Deacetylase Inhibition for Cancer Therapy", *Current Cancer Drug Targets*, 2004, 4(2):205-218.

International Search Report, dated Oct. 1, 2008, issued in PCT/US2008/007963.

International Search Report, dated Mar. 23, 2009, issued in PCT/US2008/086643.

International Search Report, dated Oct. 2, 2009, issued in PCT/US2009/051964.

International Search Report, dated Oct. 12, 2009, issued in PCT/US2009/050558.

International Search Report, dated Nov. 11, 2009, issued in PCT/US2009/050577.

International Search Report and Written Opinion, dated Nov. 18, 2009, issued in PCT/US2009/050595.

Office Action for Election/Restrictions, dated Jan. 22, 2010, issued in U.S. Appl. No. 12/146,894.

\* cited by examiner

FUSED HETEROCYCLYC INHIBITOR COMPOUNDS

CROSS REFERENCE TO RELATED APPLICATION

This application claims the benefit of U.S. provisional application Ser. No. 61/080,449 filed Jul. 14, 2008. The disclosure of the application is hereby incorporated by reference.

FIELD

The present invention generally relates to a compound having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2, -3, and -8) compounds are closely related to yeast RPD3; class IIa (HDAC-4, -5, -7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor NAD$^+$ for their deacetylase function. See, for example, Marielle Paris et al., *Histone Deacetylase Inhibitors: From Bench to Clinic*, JOURNAL OF MEDICINAL CHEMISTRY 51(11): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradei et al., *Histone Deacetylase Inhibitors: Latest Developments, Trends, and Prospects,* CURR. MED. CHEM.: ANTI-CANCER AGENTS 5(5):529-560 (2005).

Cyclin-dependent kinases (CDKs) are protein kinase enzymes controlling transcription and mRNA processing for the regulation of the cell cycle. CDKs belong to a group of serine/threonine kinases phosphorylating proteins on serine and threonine amino acid residues. A CDK is activated by association with a cyclin forming a cyclin-dependent kinase complex. The CDK family has been identified to include at least 9 members, i.e., CDK1, CDK2, CDK3, CDK4, CDK5, CDK6, CDK7, CDK8 and CDK9, and CDKs pair with a specific cyclin in the various phases of the cell cycle for the progression. CDKs are considered a target for anti-cancer medication since the enzymes are major control switches for the cell cycle.

WO 2005/092899 mentions a series of compounds useful for inhibiting HDAC enzymatic activity where the compounds are amino or hydroxyl substituted aniline derivatives attached to various cyclic groups.

There is a continued need to develop new inhibitors to provide appropriate therapy for a variety of disease conditions implicated in HDAC and/or CDK activity.

SUMMARY

In various embodiments, a compound having HDAC inhibitory activity, a composition comprising the compound and a method useful to treat diseases arising from abnormal cell proliferation or differentiation are provided.

The compound is of Formula (I) or a pharmaceutically acceptable salt thereof:

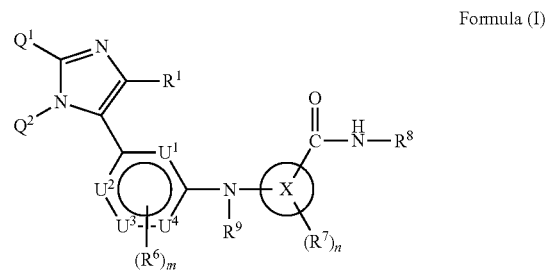

Formula (I)

wherein the substituents $Q^1$ and $Q^2$ form a cyclic moiety fused to the imidazole drawn in Formula (I) and $R^1$ represents H or a substitutable group that provides the compounds of Formula (I) with HDAC and/or CDK binding activity. The cyclic moiety itself is unsaturated, saturated, or partially saturated. The variables m and n can be zero, and when they are non-zero, the respective $R^6$ and $R^7$ groups are substituents that provide for HDAC and/or CDK inhibitory activity in the compounds. In Formula (I), the substituents $R^1$, $Q^1$, and $Q^2$ are attached to an imidazole ring; $R^6$ is attached to a 6-membered nitrogen containing heteroaryl; and $R^7$ is attached to an aryl group X. $R^9$ is a substituent providing for HDAC and/or CDK inhibitory activity in the compounds. The group

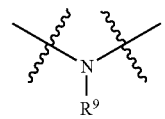

provides a "linker" between the 6-membered heteroaryl and the ring X.

In various embodiments, the $Q^1$-$Q^2$ cyclic moiety is aromatic so that a two ring fused aromatic ring system is provided attached to the 6-membered nitrogen heteroaryl.

In the 6-membered nitrogen heteroaryl, at least one of $U^1$, $U^2$, $U^3$, and $U^4$ is a ring nitrogen. In some embodiments, at least $U^4$ is a ring nitrogen. In some embodiments, both $U^1$ and $U^4$ are ring nitrogens. In some embodiments, only $U^4$ is a ring nitrogen. In some embodiments, only $U^1$ and $U^4$ are ring nitrogens.

In various embodiments, the substituents are further defined as follows:

$R^1$ is selected from the group consisting of H, halo, nitro, cyano, hydroxy, hydroxy($C_{1-10}$ alkyl), amino($C_{1-10}$ alkyl), haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, hydroxy($C_{1-10}$ alkoxy)($C_{1-10}$ alkoxy), ($C_{1-10}$ alkoxy)($C_{1-10}$ alkoxy), ($C_{1-10}$ alkoxy)($C_{1-10}$ alkyl), $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, NH$_2$—S(O)$_2$NH—, NH$_2$—CO—NH—, N—($C_{1-10}$ alkyl)sulphamoyl, N,N—($C_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein $R^1$ is optionally substituted by one or more A where such an optional substitution is chemically feasible;

$Q^1$ and $Q^2$ together form a cyclic moiety to make a fused ring together with the imidazole ring drawn in Formula (I), wherein the cyclic moiety itself is optionally substituted by one or more substituents selected from $R^1$ groups, each of which is optionally substituted by one or more A where such an optional substitution is chemically feasible;

$U^1$, $U^2$, $U^3$ and $U^4$ are independently selected from —N—, —CH—, and —CR$^6$—, with the proviso that at least one of $U^1$, $U^2$, $U^3$ and $U^4$ is —N—; in one embodiment, at least $U^4$ is —N—.

m is the number of non-hydrogen substituents $R^6$ on the N-containing 6-membered nitrogen containing heteroaryl and can be 0, 1 or 2, each $R^6$ is independently selected from the group consisting of halo, hydroxy, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, NH$_2$—S(O)$_2$NH—, N—($C_{1-10}$ alkyl)sulphamoyl and N,N—($C_{1-10}$ alkyl)$_2$sulphamoyl, wherein $R^6$ is optionally substituted by one or more B where such an optional substitution is chemically feasible;

X is phenyl, 5-membered heteroaryl, or 6-membered heteroaryl, wherein the heteroaryl contains one or more heteroatoms selected from N, S and O;

n is the number of non-hydrogen substituents $R^7$ on the ring X and can be 0, 1, 2, 3, or 4, wherein the maximum value of n depends on the nature of the ring X;

$R^7$ represents one or more optional non-hydrogen substituents on ring X, wherein when present, each $R^7$ is independently selected from the group consisting of hydroxy, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)$_2$ amino, $C_{1-10}$ alkanoylamino, N—($C_{1-10}$ alkyl)carbamoyl, N,N—($C_{1-10}$ alkyl)$_2$ carbamoyl, $C_{1-10}$ alkyl-S(O)$_a$ wherein a is 0, 1 or 2, NH$_2$—S(O)$_2$NH—, N—($C_{1-10}$ alkyl)sulphamoyl, N,N—($C_{1-10}$ alkyl)$_2$sulphamoyl, cycloalkyl, heterocyclyl and aryl;

$R^8$ is hydroxy, aryl or heteroaryl, wherein aryl or heteroaryl is substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^9$ is H or a substitutable group that provides for HDAC and/or CDK binding activity of the compounds. Examples include alkyl (e.g., $C_{1-10}$ alkyl, $C_{1-6}$ alkyl, and $C_{1-3}$ alkyl), haloalkyl (e.g., $C_{1-10}$ haloalkyl, $C_{1-6}$ haloalkyl, and $C_{1-3}$ haloalkyl), aminoalkyl, cycloalkyl, heterocyclyl and aryl, wherein $R^9$ is optionally substituted by one or more D where such an optional substitution is chemically feasible; and A, B and D are independently selected from halo, nitro, cyano, hydroxy, hydroxyalkyl, haloalkyl, haloalkoxy, amino, azido, carboxyl, carbamoyl, mercapto, oxo, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N—($C_{1-10}$ alkyl)amino, N,N—($C_{1-10}$ alkyl)$_2$amino, $C_{1-10}$ alkanoylamino, N—($C_{1-10}$ alkyl)carbamoyl, N,N—($C_{1-10}$ alkyl)$_2$carbamoyl, $C_{1-10}$ alkyl-S(O)$_a$ wherein a is 0, 1 or 2, $C_{1-10}$ alkoxycarbonyl, N—($C_{1-10}$ alkyl)sulphamoyl, N,N—($C_{1-10}$ alkyl)$_2$sulphamoyl, H$_2$NS(O)$_2$NH—, N—($C_{1-10}$ alkyl)NHS(O)$_2$NH—, N,N—($C_{1-10}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

In various embodiments, the substitution with —NH$_2$ or —OH on aryl or heteroaryl of $R^8$ is adjacent to the attachment of the X—C(O)NH— group to the aryl or heteroaryl.

In an embodiment, $R^8$ is hydroxy and the compounds are characterized as hydroxamates. In another embodiment, $R^8$ is substituted aryl or heteroaryl and the compounds are characterized as arylamides.

In an embodiment, $R^9$ is H.

In an embodiment, X is phenyl. In various embodiments, the N—$R^9$ linker and —C(O)NH—$R^8$ groups are disposed on the phenyl in a 1,4-configuration, where the N—$R^9$ linker is considered as the 1-position.

In an embodiment, X is thiophene. In various embodiments, the N—$R^9$ linker and —C(O)NH—$R^8$ groups are disposed on the thiophene in a 2,5-configuration, where the linker is considered as the 2-position (with the S atom of the thiophene ring taken as the 1-position).

In an embodiment, X is pyridine. In various embodiments, the N—$R^9$ linker and —C(O)NH—$R^8$ groups are disposed on the pyridine in a 2,5-configuration, where the linker is considered as the 2-position, or in a 3,6-configuration, where the linker is considered as the 3-position (in all cases, the N atom of the pyridine ring is taken as the 1-position).

In an embodiment, X is thiazole. In various embodiments, the N—$R^9$ linker and —C(O)NH—$R^8$ groups are disposed on the thiazole in a 2,4- or 2,5-configuration, where the linker is considered as the 2-position (with the S atom of the thiazole ring taken as the 1-position).

In an embodiment, the 6-membered nitrogen containing heteroaryl is pyrimidine, with $U^1$ and $U^4$ being ring nitrogens. In various embodiments, the pyrimidine is substituted with a fused imidazole ring which itself is optionally substituted with one or more $R^1$.

In the Formulae herein, non-limiting examples of A and B include halo, alkyl, nitro, cyano, hydroxy, cycloalkyl, trifluoromethoxy, trifluoromethyl, trifluoroethyl, amino, carboxyl, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, oxo, aryl, heterocyclyl and cycloalkyl.

In the definitions herein of $R^1$, $R^6$, $R^7$, A and B, the carbon ranges for the groups alkyl, alkenyl, alkynyl, alkoxy, alkanoyl, alkanoyloxy, alkanoylamino, and the like include all ranges encompassed in the recited ranges $C_{1-10}$ and $C_{2-10}$. For example, in non-limiting fashion $C_{1-10}$ and $C_{2-10}$ include a disclosure of $C_{1-6}$, $C_{1-3}$, $C_{2-6}$, and $C_{2-3}$. In various embodiments, $C_{1-10}$ carbon-chain containing groups such as $C_{1-10}$ alkyl, $C_{2-10}$ alkenyl, $C_{2-10}$ alkynyl and so forth include the respective $C_{1-6}$ and $C_{1-3}$ shorter carbon-chains such as $C_{1-6}$ alkyl, $C_{1-3}$ alkyl, $C_{2-6}$ alkenyl, $C_{2-3}$ alkenyl, $C_{2-6}$ alkynyl and $C_{2-3}$ alkynyl.

In the Tables that follow, examples are given with n=0 or n=1. When n=0, the entry in the $R^7$ column reads H (hydrogen atom) to indicate that all substituents are hydrogen. When n=1, the entry in the $R^7$ column gives the identity and position of the single non-hydrogen substituent.

Pharmaceutical compositions comprise an HDAC and/or CDK-inhibitory effective amount of one or more compounds described herein and a pharmaceutically-acceptable carrier.

Methods of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

DETAILED DESCRIPTION

The following description is merely exemplary in nature and is not intended to limit the present disclosure, application, or uses.

DEFINITIONS

"Alkenyl" refers to a straight or branched hydrocarbyl group with at least one site of unsaturation, i.e. a carbon-carbon, $sp^2$ double bond. In an embodiment, alkenyl has from 2 to 12 carbon atoms. In some embodiments, alkenyl is a $C_2-C_{10}$ alkenyl group or a $C_2-C_6$ alkenyl group. Examples of alkenyl group include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkanoyl" is the group RC(O)—; "alkanoyloxy" is RC(O)O—; and "alkanoylamino" is RC(O)NR'—; where R is an alkyl group as defined herein, and R' is hydrogen or alkyl. In various embodiments, R is a $C_1-C_{10}$ alkyl group or a $C_1-C_6$ alkyl group.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1-C_{10}$ alkyl group or a $C_1-C_6$ alkyl group.

"Alkyl" refers to a straight or branched chain saturated hydrocarbyl group. In an embodiment, alkyl has from 1 to 12 carbon atoms. In some embodiments, alkyl is a $C_1-C_{10}$ alkyl group or a $C_1-C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RNH— and "N,N-(alkyl)$_2$amino" is $R_2N$—, where the R groups are alkyl as defined herein and are the same or different. In various embodiments, R is a $C_1-C_{10}$ alkyl group or a $C_1-C_6$ alkyl group. Examples of alkylamino groups include methylamino, ethylamino, propylamino, butylamino, dimethylamino, diethylamino, and methylethylamino.

"Alkylaminoalkyl" refers to an alkyl moiety substituted with an alkylamino group, wherein alkylamino is as defined herein. Examples of alkylaminoalkyl groups include methylaminomethyl and ethylaminomethyl.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2-C_{10}$ alkynyl group or a $C_2-C_6$ alkynyl group. Examples of alkynyl groups include acetylenic (—C≡CH) and propargyl (—$CH_2$C≡CH).

"Aryl" refers to a monocyclic, bicyclic, or tricyclic carbon ring, wherein at least one ring is aromatic. In various embodiments, aryl encompasses a ring system of up to 14 carbon atoms. Aryl includes a carbocyclic aromatic ring fused with a 5- or 6-membered cycloalkyl group. Examples of aryl groups include, but are not limited to, phenyl, naphthyl, tetrahydronaphthyl and indanyl.

"Aryloxy" is RO—, where R is aryl. "Arylthio" is RS—, where R is aryl.

"Carbamoyl" is the group $NH_2$—C(O)—; the nitrogen can be substituted with alkyl groups. N-(alkyl)carbamoyl is RNH—C(O)— and N,N-(alkyl)$_2$ carbamoyl is $R_2N$—C(O)—, where the R groups are alkyl as defined herein and are the same or different. In various embodiments, R is a $C_1-C_{10}$ alkyl group or a $C_1-C_6$ alkyl group.

"Cycloalkyl" is a hydrocarbyl group containing at least one saturated or partially unsaturated ring structure, and attached via a ring carbon. In various embodiments, it refers to a saturated or a partially unsaturated $C_3-C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkyloxy" is RO—, where R is cycloalkyl.

"Cycloalkylalkyl" refers to an alkyl moiety substituted with a cycloalkyl group, wherein cycloalkyl is as defined herein. Examples of cycloalkylalkyl groups include cyclopropylmethyl, cyclobutylmethyl, cyclopentylethyl and cyclohexylmethyl.

"Dialkylamino" refers to an RR'N— group where R and R' are independently alkyl as defined herein. Examples of dialkylamino groups include, but are not limited to, dimethylamino, diethylamino, methylethylamino and methylpropylamino. In various embodiments, R and R' are independently a $C_1-C_{10}$ alkyl group or a $C_1-C_6$ alkyl group.

"Dialkylaminoalkyl" refers to an alkyl moiety substituted with a dialkylamino group, wherein dialkylamino is as defined herein. Examples of dialkylaminoalkyl groups include, but are not limited to, dimethylaminomethyl and diethylaminomethyl.

"Feasible" refers to a structure or process that is capable of being accomplished; one that is possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use. Chemically feasible structures are bound by the rules of electron bonding, whereby bonds can only be formed between atoms that are capable of forming bonds with one another. Likewise, chemically feasible processes can only produce structures that are chemically feasible.

"Halo" refers to chloro (—Cl), bromo (—Br), fluoro (—F) or iodo (—I).

"Haloalkoxy" refers to an alkoxy group substituted with one or more halo groups. Examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, imidazopyridyl, pyranyl, pyrazolyl, pyrrolopyridyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroaryloxy" is RO—, where R is heteroaryl.

"Heterocyclyl" includes the heteroaryls defined below and refers to an unsaturated, saturated or partially unsaturated monocyclic, bicyclic or tricyclic group of 2 to 14 ring-carbon atoms and, in addition to ring-carbon atoms, 1 or more heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, isoindolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclyloxy" is RO—, where R is heterocyclyl.
"Heterocyclylthio" is RS—, where R is heterocyclyl.

"Hydroxyalkoxy" refers to an alkoxy group substituted with a hydroxyl group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxy group. Examples of hydroxyalkyl groups include, but are not limited to, hydroxymethyl, hydroxyethyl, hydroxypropyl and hydroxybutyl.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

"Sulphamoyl" is NH$_2$—S(O)$_2$—; "N-(alkyl)sulphamoyl" is RNH—S(O)$_2$—; and "N,N-(alkyl)$_2$ sulphamoyl" is R$_2$N—S(O)$_2$—, where the R groups are alkyl as defined herein and are the same or different. In various embodiments, R is a $C_1$-$C_{10}$ alkyl group or a $C_1$-$C_6$ alkyl group.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, other ingredient, or combination of ingredients that alone or together provide a carrier or vehicle with which a compound or compounds of the invention is formulated and/or administered, and in which every ingredient or the carrier as a whole is pharmaceutically acceptable.

"Pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease.

"Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, the invention provides a compound of Formula (I) or a pharmaceutically acceptable salt thereof:

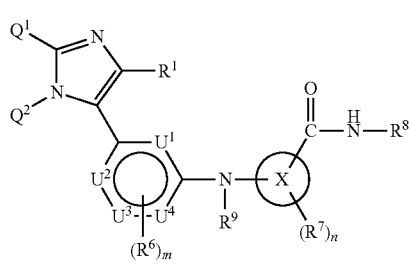

Formula (I)

wherein $Q^1, Q^2, U^1, U^2, U^3, U^4, R^1, R^6, R^7, R^8, R^9$ and X are as defined above.

In particular embodiments, the variables are further exemplified as follows:

$R^1$ is independently selected from the group consisting of H, halo, nitro, cyano, hydroxy, hydroxyalkyl, haloalkyl, haloalkoxy, amino, azido, carboxyl, carbamoyl, mercapto, sulphamoyl, alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, NH$_2$—S(O)$_2$NH—, N—($C_{1-6}$ alkyl)sulphamoyl, N,N—($C_{1-6}$ alkyl)$_2$sulphamoyl, aryl, aryloxy, arylthio, heteroaryl, heteroaryloxy, cycloalkyl, cycloalkyloxy, heterocyclyl, heterocyclyl(C═O)—, heterocyclyloxy and heterocyclylthio; wherein $R^1$ is optionally substituted by one or more A where such an optional substitution is chemically feasible;

$Q^1$ and $Q^2$ together form a cyclic moiety to make a fused ring along with the imidazole moiety, wherein the cyclic moiety is substituted by one or more substituents selected from $R^1$ groups, each of which is optionally substituted by one or more A where such an optional substitution is chemically feasible;

$U^1, U^2, U^3$ and $U^4$ are as defined above;

m is 0, 1 or 2;

$R^6$ is halo, hydroxy, nitro, cyano, trifluoromethyl, trifluoromethoxy, amino, carboxyl, carbamoyl, sulphamoyl, $C_{1-3}$ alkyl, $C_{2-3}$ alkenyl, $C_{2-3}$ alkynyl, $C_{1-3}$ alkoxy, $C_{1-3}$ alkanoyl, N—($C_{1-3}$ alkyl)amino, N,N—($C_{1-2}$ alkyl)$_2$ amino, $C_{1-3}$ alkanoylamino, N—($C_{1-3}$ alkyl)carbamoyl, N,N—($C_{1-2}$ alkyl)$_2$ carbamoyl, $C_{1-3}$ alkyl-S(O)$_a$ wherein a is 0, 1 or 2, NH$_2$—S(O)$_2$NH—, N—($C_{1-3}$ alkyl)sulphamoyl or N,N—($C_{1-3}$ alkyl)$_2$sulphamoyl; wherein $R^6$ is optionally substituted by one or more B where such an optional substitution is chemically feasible;

X is phenyl, 5-membered heteroaryl, or 6-membered heteroaryl, wherein the heteroaryl contains one or more heteroatoms selected from N, S and O;

$R^7$ and n are as defined above;

$R^8$ is hydroxy, aryl or heteroaryl, wherein aryl or heteroaryl are substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^9$ is H, alkyl, haloalkyl, aminoalkyl, cycloalkyl, heterocyclyl or aryl, wherein $R^9$ is optionally substituted by one or more D where such an optional substitution is chemically feasible; and A, B and D are independently selected from halo, nitro, cyano, hydroxy, oxo, hydroxyalkyl, haloalkyl, haloalkoxy, amino, azido, carboxyl, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N—($C_{1-6}$ alkyl)amino, N,N—($C_{1-6}$ alkyl)$_2$amino, $C_{1-6}$ alkanoylamino, N—($C_{1-6}$ alkyl)carbamoyl, N,N—($C_{1-6}$ alkyl)$_2$carbamoyl, $C_{1-6}$ alkyl-S(O)$_a$ wherein a is 0, 1 or 2, $C_{1-6}$ alkoxycarbonyl, N—($C_{1-6}$ alkyl)sulphamoyl, N,N—($C_{1-6}$ alkyl)$_2$sulphamoyl, H$_2$NS(O)$_2$NH—, N—($C_{1-6}$ alkyl)NHS(O)$_2$NH—, N,N—($C_{1-6}$ alkyl)$_2$NS(O)$_2$NH—, aryl, aryloxy, arylthio, cycloalkyl, cycloalkyloxy, heterocyclyl, heterocyclyl(C═O)—, heterocyclyloxy and heterocyclylthio.

In particular embodiments, compounds are selected from those of Formulae (I$^a$), (I$^b$), and (I$^c$), with substituents defined as in Formula (I):

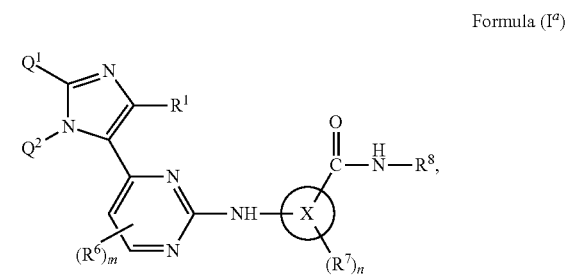

Formula (I$^a$)

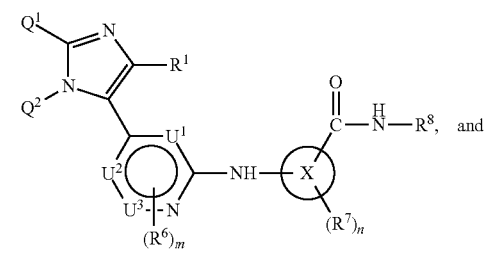

Formula (I$^b$), and

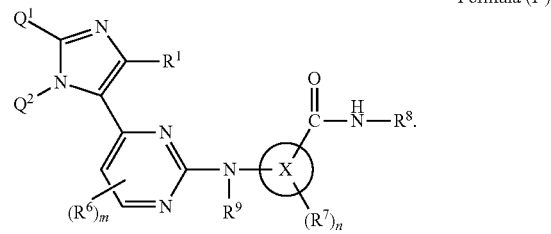

Formula (I$^c$).

Formula (I$^a$) represents pyrimidine compounds, while Formula (I$^b$) represents inhibitors where at least $U^4$ is nitrogen. Formula (I) represents pyridine compounds when $U^1, U^2$, and $U^3$ all comprise ring carbons. In various embodiments, $U^1, U^2$ and $U^3$ are selected to be any of (a) $U^1, U^2$ and $U^3$ are —CH— or —CR$^6$—; (b) $U^1$ and $U^2$ are —CH— or —CR$^6$— and $U^3$ is —N—; (c) $U^1$ and $U^3$ are —CH— or —$CR^6$— and $U^2$ is —N—; and (d) $U^1$ and $U^2$ are —N— and $U^3$ is —CH— or —$CR^6$—; and e) $U^1$ and $U^3$ are —N— and $U^2$ is —CH— or —$CR^6$—. Formula ($I^c$) represents pyrimidine compounds containing —$NR^9$— linker where $R^9$ is a non-hydrogen substituent selected from alkyl, haloalkyl, aminoalkyl, cycloalkyl, heterocyclyl, aryl, haloaryl, and haloheterocyclyl, and $R^9$ can be optionally substituted as described herein.

In various embodiments, compounds defined above are useful to inhibit HDACs and/or CDKs. In a particular embodiment, a compound of the invention inhibits both HDAC and CDK. In one embodiment, therefore, a compound of the invention is used in inhibiting HDAC and/or CDK enzymes such as, for example, mammalian HDAC and/or CDK. More specifically, a compound of the invention can be used to treat or inhibit HDAC and/or CDK-mediated diseases or abnormalities.

In an embodiment of the compounds, one or more (including all) of the substituents $R^1$, $R^6$, $R^7$, $R^8$, $R^9$, $U^1$, $U^2$, $U^3$, $U^4$, $Q^1$, $Q^2$, and X are further limited as follows:

$R^1$ is selected from the group consisting of H, chloro, fluoro, bromo, methyl, ethyl, propyl, isopropyl, methoxy, ethoxy, acetyl, carboxyl, methylcarboxyl, cyano, methoxyethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, methylcarboxyl, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methylthiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

$Q^1$ and $Q^2$ together with the imidazole ring to which they are attached form a cyclic moiety to form a two ring fused aromatic ring system that connects to the 6-membered heteroaryl. Examples of the ring system include, but are not limited to:

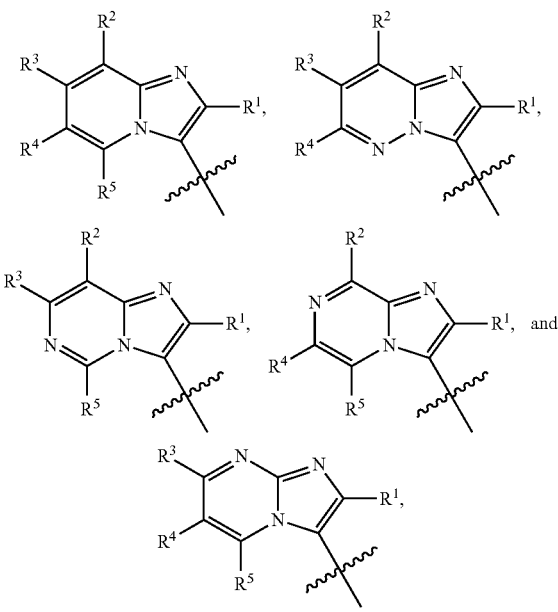

wherein the wavy line shows the point of attachment to the 6-membered nitrogen containing heteroaryl, and $R^2$, $R^3$, $R^4$, and $R^5$ are independently selected from the groups $R^1$ optionally substituted with A;

$U^1$, $U^2$, $U^3$ and $U^4$ are selected to form any of the following 6-membered heteroaryl moieties:

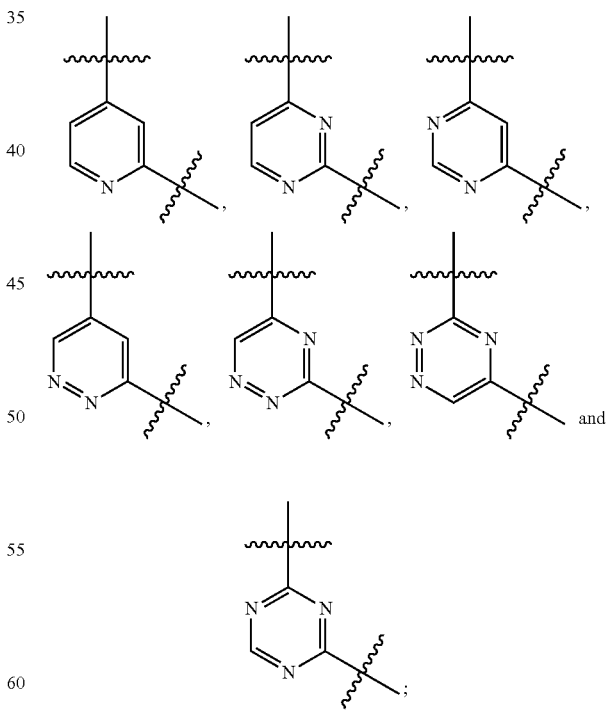

optionally the 6-membered nitrogen containing heteroaryls are substituted with one or more $R^6$;

$R^6$ is methyl, ethyl, hydroxy, fluoro, bromo or trifluoromethyl and m is 0 or 1;

X is phenyl or 5- or 6-membered heteroaryl selected from the group consisting of:

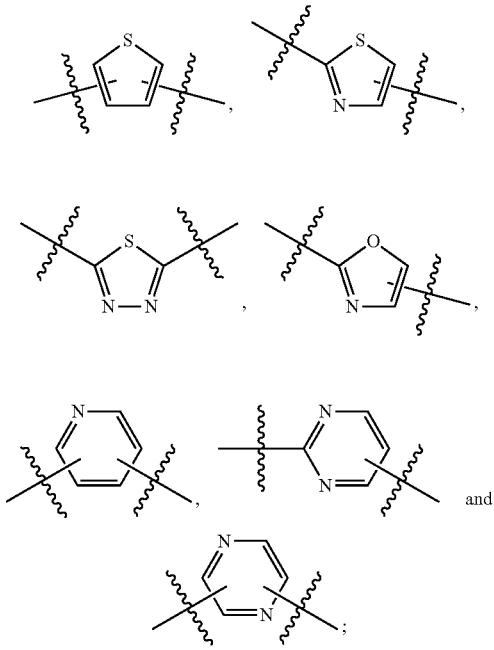

$R^7$ is independently fluoro, chloro, bromo, or methyl and n is 0, 1 or 2; and $R^8$ is hydroxyl, aryl or heteroaryl, wherein aryl or heteroaryl are substituted with —NH$_2$ or —OH at a ring position adjacent to attachment of the —CONH-moiety, and $R^8$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

In particular embodiments, $R^8$ is hydroxy,

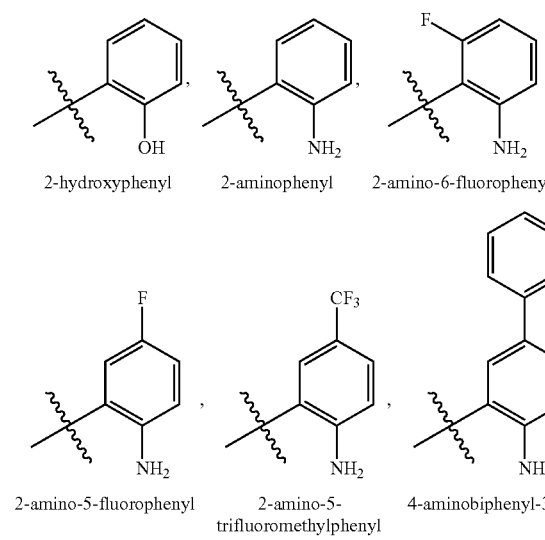

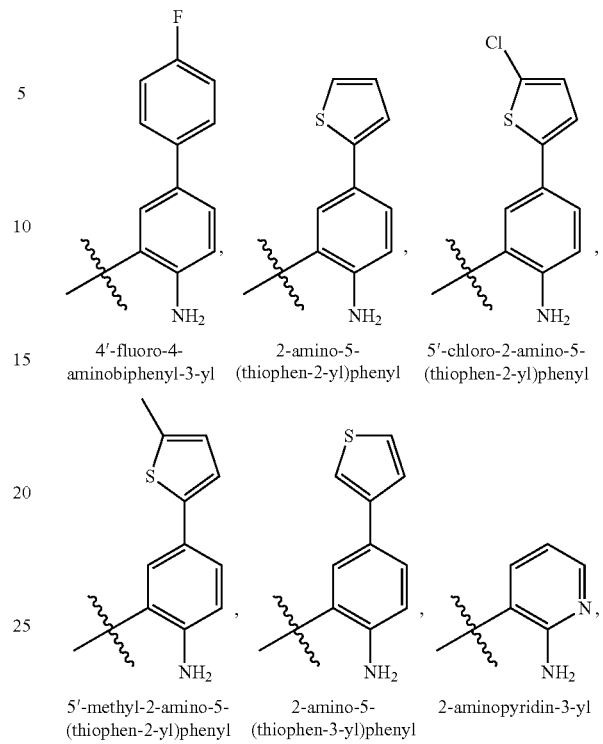

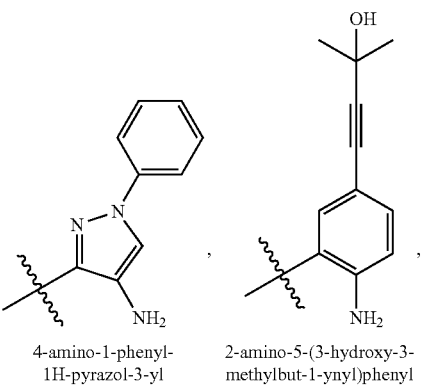

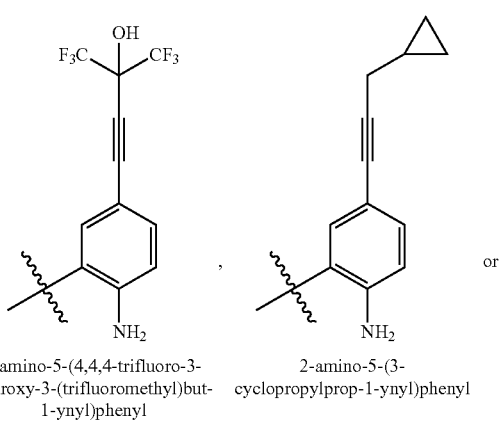

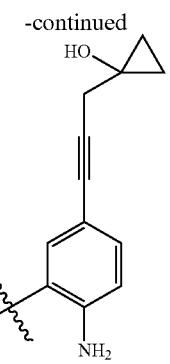

2-amino-5-(3-
(1-hydroxycyclopropyl)prop-1-ynyl)phenyl

In various embodiments, X is a phenyl ring and the NH or —NR$^9$— linker and —CONHR$^8$ moiety are disposed about the phenyl ring of Formula (I$^a$), (I$^b$), or (I$^c$) in either a 1,3-(meta) or a 1,4-(para) configuration. R$^7$ can be attached to any ring position of the phenyl ring not occupied by the linker and —CONHR$^8$ moiety and such attachment includes 1,2-(ortho), 1,3-(meta) and 1,4-(para) configurations wherein the linker is at position 1. In the Tables that follow, ortho-, meta- and para-configurations of R$^7$ mean attachment to positions 2, 3 and 4 of the phenyl ring as shown in Formulas (I-a) and (1-b), respectively. Where R$^7$ is an ortho-substitution (i.e., position 2), meta-CONHR$^8$ moiety is intended to be at position 5.

In one embodiment, the invention provides a compound of Formula (I$^a$-a) and a pharmaceutically acceptable salt thereof:

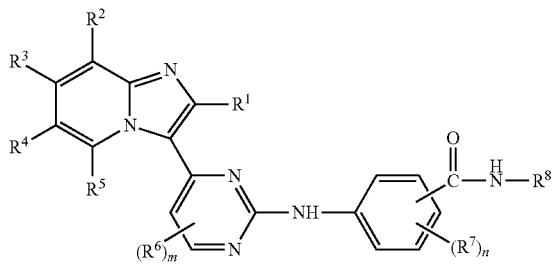

Formula (I$^a$-a)

wherein R$^1$, R$^6$, R$^7$ and R$^8$ are as defined above for various aspects of Formula I; and R$^2$, R$^3$, R$^4$ and R$^5$ are independently selected from R$^1$ groups optionally substituted by one or more A. In Formula (I$^a$-a), an imidazopyridine ring is substituted on a pyrimidine. The compounds are hydroxamates when R$^8$ is hydroxyl, and arylamides when R$^8$ is substituted aryl or substituted heteroaryl.

In an embodiment of Formula (I$^a$-a), at least two of R$^1$, R$^2$, R$^3$, R$^4$ and R$^5$ are H, and each non-hydrogen R$^1$, R$^2$, R$^3$, R$^4$ and R$^5$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, methylcarboxyl, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methylthiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy; R$^6$ if present is halo, hydroxy, alkyl or haloalkyl; m is 0 or 1; R$^7$ if present is fluoro, chloro, bromo, or methyl; n is 0, 1 or 2; and R$^8$ is hydroxy, aryl or heteroaryl, wherein aryl or heteroaryl are substituted with —NH$_2$ or —OH at a ring position adjacent to attachment of the —CONH-moiety, and R$^8$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

Non-limiting examples of such compounds include those selected from the following structure and pharmaceutically acceptable salts thereof, where R$^{6'}$ is H or R$^6$ and R$^{7'}$ is H or R$^7$. The substitution pattern of various embodiments is given in Table 1.

TABLE 1

Examples of Formula (I<sup>a</sup>-a)

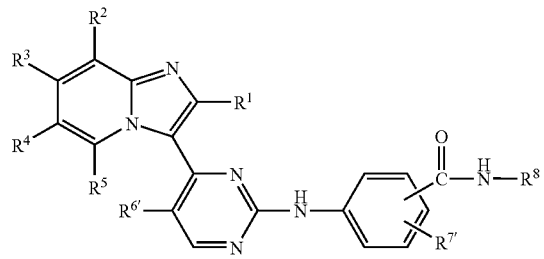

| Compound No. | R¹ | R² | R³ | R⁴ | R⁵ | R⁶' | R⁷' | —CONHR¹ attachment | R⁸ |
|---|---|---|---|---|---|---|---|---|---|
| a-01 | H | H | H | H | H | H | H | para | —OH |
| a-02 | H | H | H | H | H | H | H | meta | —OH |
| a-03 | H | H | H | H | H | —CH₃ | H | para | —OH |
| a-04 | H | H | H | H | H | —CH₃ | H | meta | —OH |
| a-05 | H | H | H | H | H | H | H | para | 2-aminophenyl |
| a-06 | H | H | H | H | H | H | H | meta | 2-aminophenyl |
| a-07 | H | H | H | H | H | —CH₃ | H | para | 2-aminophenyl |
| a-08 | H | H | H | H | H | —CH₃ | H | meta | 2-aminophenyl |
| a-09 | H | H | H | H | H | H | H | para | 2-aminopyridin-3-yl |
| a-10 | H | H | H | H | H | H | H | meta | 2-aminopyridin-3-yl |
| a-11 | H | H | H | H | H | —CH₃ | H | para | 2-aminopyridin-3-yl |
| a-12 | H | H | H | H | H | —CH₃ | H | meta | 2-aminopyridin-3-yl |
| a-13 | H | H | H | H | H | H | H | para | ![pyrazole-NH2] |
| a-14 | H | H | H | H | H | H | H | meta | ![pyrazole-NH2] |
| a-15 | H | H | H | H | H | —CH₃ | H | para | ![pyrazole-NH2] |
| a-16 | H | H | H | H | H | —CH₃ | H | meta | ![pyrazole-NH2] |
| a-17 | H | H | H | H | H | H | H | para | 2-amino-6-fluorophenyl |
| a-18 | H | H | H | H | H | H | H | meta | 2-amino-6-fluorophenyl |
| a-19 | H | H | H | H | H | —CH₃ | H | para | 2-amino-6-fluorophenyl |

TABLE 1-continued

Examples of Formula (I$^a$-a)

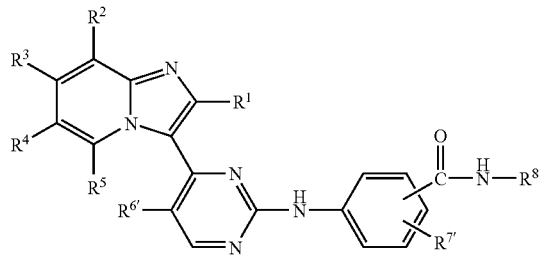

| Compound No. | R$^1$ | R$^2$ | R$^3$ | R$^4$ | R$^5$ | R$^{6'}$ | R$^{7'}$ | —CONHR$^1$ attachment | R$^8$ |
|---|---|---|---|---|---|---|---|---|---|
| a-20 | H | H | H | H | H | —CH$_3$ | H | meta | 2-amino-6-fluorophenyl |
| a-21 | H | H | H | H | H | H | ortho-F | para | 2-amino-6-fluorophenyl |
| a-22 | H | H | H | H | H | H | ortho-F | meta | 2-amino-6-fluorophenyl |
| a-23 | H | H | H | H | H | —CH$_3$ | ortho-F | para | 2-amino-6-fluorophenyl |
| a-24 | H | H | H | H | H | —CH$_3$ | ortho-F | meta | 2-amino-6-fluorophenyl |
| a-25 | —CH$_3$ | H | H | H | H | H | H | para | —OH |
| a-26 | —CH$_3$ | H | H | H | H | H | H | meta | —OH |
| a-27 | —CH$_3$ | H | H | H | H | —CH$_3$ | H | para | —OH |
| a-28 | —CH$_3$ | H | H | H | H | —CH$_3$ | H | meta | —OH |
| a-29 | —CH$_3$ | H | H | H | H | H | H | para | 2-aminophenyl |
| a-30 | —CH$_3$ | H | H | H | H | H | H | meta | 2-aminophenyl |
| a-31 | —CH$_3$ | H | H | H | H | —CH$_3$ | H | para | 2-aminophenyl |
| a-32 | —CH$_3$ | H | H | H | H | —CH$_3$ | H | meta | 2-aminophenyl |
| a-33 | —CH$_3$ | H | H | H | H | H | H | para | 2-aminopyridin-3-yl |
| a-34 | —CH$_3$ | H | H | H | H | H | H | meta | 2-aminopyridin-3-yl |
| a-35 | —CH$_3$ | H | H | H | H | —CH$_3$ | H | para | 2-aminopyridin-3-yl |
| a-36 | —CH$_3$ | H | H | H | H | —CH$_3$ | H | meta | 2-aminopyridin-3-yl |
| a-37 | —CH$_3$ | H | H | H | H | H | H | para | 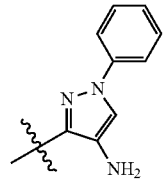 |
| a-38 | —CH$_3$ | H | H | H | H | H | H | meta | 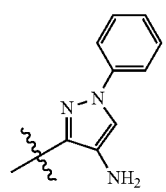 |
| a-39 | —CH$_3$ | H | H | H | H | —CH$_3$ | H | para | 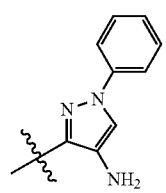 |

TABLE 1-continued

Examples of Formula (Iᵃ-a)

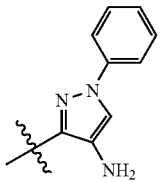

| Compound No. | R¹ | R² | R³ | R⁴ | R⁵ | R⁶' | R⁷' | —CONHR¹ attachment | R⁸ |
|---|---|---|---|---|---|---|---|---|---|
| a-40 | —CH₃ | H | H | H | H | —CH₃ | H | meta | |
| a-41 | —CH₃ | H | H | H | H | H | H | para | 2-amino-6-fluorophenyl |
| a-42 | —CH₃ | H | H | H | H | H | H | meta | 2-amino-6-fluorophenyl |
| a-43 | —CH₃ | H | H | H | H | —CH₃ | H | para | 2-amino-6-fluorophenyl |
| a-44 | —CH₃ | H | H | H | H | —CH₃ | H | meta | 2-amino-6-fluorophenyl |
| a-45 | —CH₃ | H | H | H | H | H | ortho-F | para | 2-amino-6-fluorophenyl |
| a-46 | —CH₃ | H | H | H | H | H | ortho-F | meta | 2-amino-6-fluorophenyl |
| a-47 | —CH₃ | H | H | H | H | —CH₃ | ortho-F | para | 2-amino-6-fluorophenyl |
| a-48 | —CH₃ | H | H | H | H | —CH₃ | ortho-F | meta | 2-amino-6-fluorophenyl |
| a-45 | —CH₃ | —Cl | H | H | H | H | H | para | —OH |
| a-46 | —CH₃ | H | —Cl | H | H | H | H | para | —OH |
| a-47 | —CH₃ | H | H | —Cl | H | H | H | para | —OH |
| a-48 | —CH₃ | H | H | H | —Cl | H | H | para | —OH |
| a-49 | —CH₃ | —Cl | H | H | H | H | H | meta | —OH |
| a-50 | —CH₃ | H | —Cl | H | H | H | H | meta | —OH |
| a-51 | —CH₃ | H | H | —Cl | H | H | H | meta | —OH |
| a-52 | —CH₃ | H | H | H | —Cl | H | H | meta | —OH |
| a-53 | —CH₃ | —Cl | H | H | H | H | H | para | 2-aminophenyl |
| a-54 | —CH₃ | H | —Cl | H | H | H | H | para | 2-aminophenyl |
| a-55 | —CH₃ | H | H | —Cl | H | H | H | para | 2-aminophenyl |
| a-56 | —CH₃ | H | H | H | —Cl | H | H | para | 2-aminophenyl |
| a-57 | —CH₃ | —Cl | H | H | H | H | H | para | 2-aminophenyl |
| a-58 | —CH₃ | H | —Cl | H | H | H | H | para | 2-aminophenyl |
| a-59 | —CH₃ | H | H | —Cl | H | H | H | para | 2-aminophenyl |
| a-60 | —CH₃ | H | H | H | —Cl | H | H | para | 2-aminophenyl |
| a-61 | —CH₃ | —Cl | H | H | H | H | H | para | 2-aminopyridin-3-yl |
| a-62 | —CH₃ | H | —Cl | H | H | H | H | para | 2-aminopyridin-3-yl |
| a-63 | —CH₃ | H | H | —Cl | H | H | H | para | 2-aminopyridin-3-yl |
| a-64 | —CH₃ | H | H | H | —Cl | H | H | para | 2-aminopyridin-3-yl |
| a-65 | —CH₃ | —Cl | H | H | H | H | H | para | 2-aminopyridin-3-yl |
| a-66 | —CH₃ | H | —Cl | H | H | H | H | para | 2-aminopyridin-3-yl |
| a-67 | —CH₃ | H | H | —Cl | H | H | H | para | 2-aminopyridin-3-yl |
| a-68 | —CH₃ | H | H | H | —Cl | H | H | para | 2-aminopyridin-3-yl |
| a-69 | —CH₃ | —CF₃ | H | H | H | H | H | para | —OH |
| a-70 | —CH₃ | H | —CF₃ | H | H | H | H | para | —OH |
| a-71 | —CH₃ | H | H | —CF₃ | H | H | H | para | —OH |

TABLE 1-continued

Examples of Formula (I$^a$-a)

| Compound No. | R$^1$ | R$^2$ | R$^3$ | R$^4$ | R$^5$ | R$^{6'}$ | R$^{7'}$ | —CONHR$^1$ attachment | R$^8$ |
|---|---|---|---|---|---|---|---|---|---|
| a-72 | —CH$_3$ | H | H | H | —CF$_3$ | H | H | para | —OH |
| a-73 | —CH$_3$ | —CF$_3$ | H | H | H | H | H | para | 2-aminophenyl |
| a-74 | —CH$_3$ | H | —CF$_3$ | H | H | H | H | para | 2-aminophenyl |
| a-75 | —CH$_3$ | H | H | —CF$_3$ | H | H | H | para | 2-aminophenyl |
| a-76 | —CH$_3$ | H | H | H | —CF$_3$ | H | H | para | 2-aminophenyl |
| a-77 | —CH$_3$ | —OCH$_3$ | H | H | H | H | H | para | —OH |
| a-78 | —CH$_3$ | H | —OCH$_3$ | H | H | H | H | para | —OH |
| a-79 | —CH$_3$ | H | H | —OCH$_3$ | H | H | H | para | —OH |
| a-80 | —CH$_3$ | H | H | H | —OCH$_3$ | H | H | para | —OH |
| a-81 | —CH$_3$ | —OCH$_3$ | H | H | H | H | H | para | 2-aminophenyl |
| a-82 | —CH$_3$ | H | —OCH$_3$ | H | H | H | H | para | 2-aminophenyl |
| a-83 | —CH$_3$ | H | H | —OCH$_3$ | H | H | H | para | 2-aminophenyl |
| a-84 | —CH$_3$ | H | H | H | —OCH$_3$ | H | H | para | 2-aminophenyl |
| a-85 | —CH$_3$ | -CH$_2$N(CH$_3$)$_2$ | H | H | H | H | H | para | —OH |
| a-86 | —CH$_3$ | H | -CH$_2$N(CH$_3$)$_2$ | H | H | H | H | para | —OH |
| a-87 | —CH$_3$ | H | H | -CH$_2$N(CH$_3$)$_2$ | H | H | H | para | —OH |
| a-88 | —CH$_3$ | H | H | H | -CH$_2$N(CH$_3$)$_2$ | H | H | para | —OH |
| a-89 | —CH$_3$ | -CH$_2$N(CH$_3$)$_2$ | H | H | H | H | H | para | 2-aminophenyl |
| a-90 | —CH$_3$ | H | -CH$_2$N(CH$_3$)$_2$ | H | H | H | H | para | 2-aminophenyl |

TABLE 1-continued

Examples of Formula (I<sup>a</sup>-a)

[Structure: imidazo[1,2-a]pyridine with R2, R3, R4, R5 substituents on pyridine ring and R1 at 2-position; 3-position connected to pyrimidine (with R6') linked via NH to phenyl bearing R7 and CONHR8]

| Compound No. | R¹ | R² | R³ | R⁴ | R⁵ | R⁶' | R⁷ | —CONHR¹ attachment | R⁸ |
|---|---|---|---|---|---|---|---|---|---|
| a-91 | —CH₃ | H | H | —CH₂N(CH₃)₂ | H | H | H | para | 2-aminophenyl |
| a-92 | —CH₃ | H | H | H | —CH₂N(CH₃)₂ | H | H | para | 2-aminophenyl |
| a-93 | —CH₃ | —CH₂N(CH₃)₂ | H | H | H | H | ortho-F | para | 2-aminophenyl |
| a-94 | —CH₃ | H | —CH₂N(CH₃)₂ | H | H | H | ortho-F | para | 2-aminophenyl |
| a-95 | —CH₃ | H | H | —CH₂N(CH₃)₂ | H | H | ortho-F | para | 2-aminophenyl |
| a-96 | —CH₃ | H | H | H | —CH₂N(CH₃)₂ | H | ortho-F | para | 2-aminophenyl |
| a-97 | —CH₃ | —CH₂N(CH₃)₂ | H | H | H | H | ortho-F | para | 2-amino-6-fluorophenyl |
| a-98 | —CH₃ | H | —CH₂N(CH₃)₂ | H | H | H | ortho-F | para | 2-amino-6-fluorophenyl |

TABLE 1-continued

Examples of Formula (Iᵃ-a)

| Compound No. | R¹ | R² | R³ | R⁴ | R⁵ | R⁶' | R⁷' | —CONHR¹ attachment | R⁸ |
|---|---|---|---|---|---|---|---|---|---|
| a-99 | —CH₃ | H | H | -N(CH₃)CH₂- | H | H | ortho-F | para | 2-amino-6-fluorophenyl |
| a-100 | —CH₃ | H | H | H | -N(CH₃)CH₂- | H | ortho-F | para | 2-amino-6-fluorophenyl |
| a-101 | —CH₃ | -N(CH₃)CH₂- | H | H | H | H | ortho-F | para | —OH |
| a-102 | —CH₃ | H | -N(CH₃)CH₂- | H | H | H | ortho-F | para | —OH |
| a-103 | —CH₃ | H | H | -N(CH₃)CH₂- | H | H | ortho-F | para | —OH |
| a-104 | —CH₃ | H | H | H | -N(CH₃)CH₂- | H | ortho-F | para | —OH |
| a-105 | —CH₃ | pyrrolidinyl-CH₂- | H | H | H | H | H | para | 2-aminophenyl |
| a-106 | —CH₃ | H | pyrrolidinyl-CH₂- | H | H | H | H | para | 2-aminophenyl |

TABLE 1-continued

Examples of Formula (I*ᵃ*-a)

| Compound No. | R¹ | R² | R³ | R⁴ | R⁵ | R⁶' | R⁷ | —CONHR¹ attachment | R⁸ |
|---|---|---|---|---|---|---|---|---|---|
| a-107 | —CH₃ | H | H | pyrrolidin-1-ylmethyl | H | H | H | para | 2-aminophenyl |
| a-108 | —CH₃ | H | H | H | pyrrolidin-1-ylmethyl | H | H | para | 2-aminophenyl |
| a-109 | —CH₃ | pyrrolidin-1-ylmethyl | H | H | H | H | ortho-F | para | 2-amino-6-fluorophenyl |
| a-110 | —CH₃ | H | pyrrolidin-1-ylmethyl | H | H | H | ortho-F | para | 2-amino-6-fluorophenyl |
| a-111 | —CH₃ | H | H | pyrrolidin-1-ylmethyl | H | H | ortho-F | para | 2-amino-6-fluorophenyl |
| a-112 | —CH₃ | H | H | H | pyrrolidin-1-ylmethyl | H | ortho-F | para | 2-amino-6-fluorophenyl |
| a-113 | —CH₃ | morpholin-4-yl | H | H | H | H | H | para | 2-aminophenyl |
| a-114 | —CH₃ | H | morpholin-4-yl | H | H | H | H | para | 2-aminophenyl |

TABLE 1-continued

Examples of Formula (Iᵃ-a)

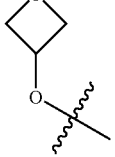

| Compound No. | R¹ | R² | R³ | R⁴ | R⁵ | R⁶' | R⁷' | —CONHR¹ attachment | R⁸ |
|---|---|---|---|---|---|---|---|---|---|
| a-115 | —CH₃ | H | H | morpholin-4-yl | H | H | H | para | 2-aminophenyl |
| a-116 | —CH₃ | H | H | H | morpholin-4-yl | H | H | para | 2-aminophenyl |
| a-117 | —CH₃ | morpholin-4-yl | H | H | H | H | ortho-F | para | 2-amino-6-fluorophenyl |
| a-118 | —CH₃ | H | morpholin-4-yl | H | H | H | ortho-F | para | 2-amino-6-fluorophenyl |
| a-119 | —CH₃ | H | H | morpholin-4-yl | H | H | ortho-F | para | 2-amino-6-fluorophenyl |
| a-120 | —CH₃ | H | H | H | morpholin-4-yl | H | ortho-F | para | 2-amino-6-fluorophenyl |
| a-121 | —CH₃ | 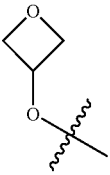 | H | H | H | H | H | para | 2-aminophenyl |
| a-122 | —CH₃ | H | 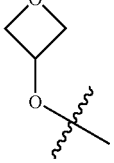 | H | H | H | H | para | 2-aminophenyl |
| a-123 | —CH₃ | H | H | 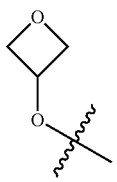 | H | H | H | para | 2-aminophenyl |
| a-124 | —CH₃ | H | H | H | 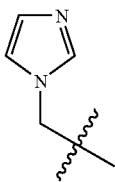 | H | H | para | 2-aminophenyl |
| a-125 | —CH₃ | [imidazolyl group] | H | H | H | H | H | para | 2-aminophenyl |

TABLE 1-continued
Examples of Formula (I<sup>a</sup>-a)
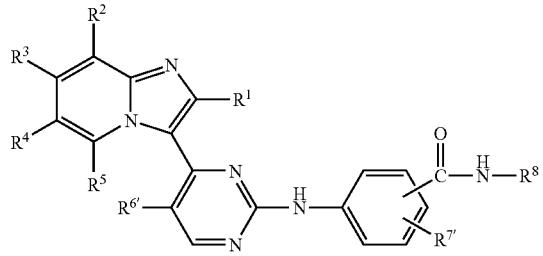
| Compound No. | R¹ | R² | R³ | R⁴ | R⁵ | R⁶' | R⁷' | —CONHR¹ attachment | R⁸ |
|---|---|---|---|---|---|---|---|---|---|
| a-126 | —CH₃ | H | 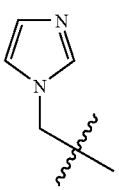 | H | H | H | H | para | 2-aminophenyl |
| a-127 | —CH₃ | H | H | 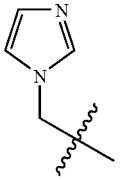 | H | H | H | para | 2-aminophenyl |
| a-128 | —CH₃ | H | H | H | 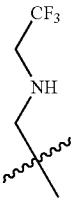 | H | H | para | 2-aminophenyl |
| a-129 | —CH₃ | 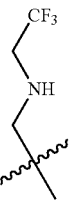 | H | H | H | H | H | para | 2-aminophenyl |
| a-130 | —CH₃ | H | 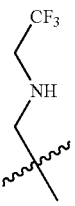 | H | H | H | H | para | 2-aminophenyl |
| a-131 | —CH₃ | H | H |  | H | H | H | para | 2-aminophenyl |

TABLE 1-continued

Examples of Formula (I$^a$-a)

| Compound No. | R$^1$ | R$^2$ | R$^3$ | R$^4$ | R$^5$ | R$^{6'}$ | R$^{7'}$ | —CONHR$^1$ attachment | R$^8$ |
|---|---|---|---|---|---|---|---|---|---|
| a-132 | —CH$_3$ | H | H | H | ![CF3-CH-NH-CH(CH3)- group] | H | H | para | 2-aminophenyl |
| a-133 | —CH$_3$ | ![CH3-O-CH2-CH2-N(CH3)-CH(CH3)- group] | H | H | H | H | H | para | 2-aminophenyl |
| a-134 | —CH$_3$ | H | ![CH3-O-CH2-CH2-N(CH3)-CH(CH3)- group] | H | H | H | H | para | 2-aminophenyl |
| a-135 | —CH$_3$ | H | H | ![CH3-O-CH2-CH2-N(CH3)-CH(CH3)- group] | H | H | H | para | 2-aminophenyl |

TABLE 1-continued
Examples of Formula (I<sup>a</sup>-a)
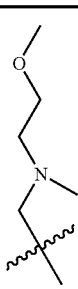
| Compound No. | R¹ | R² | R³ | R⁴ | R⁵ | R⁶' | R⁷ | —CONHR¹ attachment | R⁸ |
|---|---|---|---|---|---|---|---|---|---|
| a-136 | —CH₃ | H | H | H | 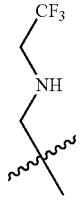 | H | H | para | 2-aminophenyl |
| a-137 | —CH₃ | 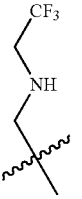 | H | H | H | H | H | para | —OH |
| a-138 | —CH₃ | H | 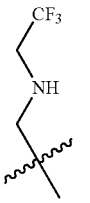 | H | H | H | H | para | —OH |
| a-139 | —CH₃ | H | H | 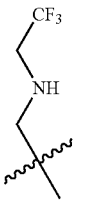 | H | H | H | para | —OH |
| a-140 | —CH₃ | H | H | H | 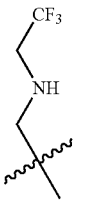 | H | H | para | —OH |

TABLE 1-continued

Examples of Formula (Iᵃ-a)

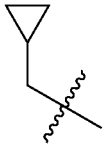

| Compound No. | R¹ | R² | R³ | R⁴ | R⁵ | R⁶' | R⁷' | —CONHR¹ attachment | R⁸ |
|---|---|---|---|---|---|---|---|---|---|
| a-141 | —CH₃ | 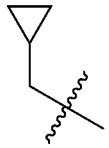 | H | H | H | H | H | para | 2-aminophenyl |
| a-142 | —CH₃ | H | 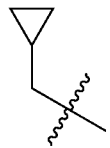 | H | H | H | H | para | 2-aminophenyl |
| a-143 | —CH₃ | H | H | 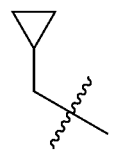 | H | H | H | para | 2-aminophenyl |
| a-144 | —CH₃ | H | H | H | 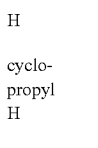 | H | H | para | 2-aminophenyl |
| a-145 | —CH₃ | cyclopropyl | H | H | H | H | H | para | 2-aminophenyl |
| a-146 | —CH₃ | H | cyclopropyl | H | H | H | H | para | 2-aminophenyl |
| a-147 | —CH₃ | H | H | cyclopropyl | H | H | H | para | 2-aminophenyl |
| a-148 | —CH₃ | H | H | H | cyclopropyl | H | H | para | 2-aminophenyl |
| a-149 | —CH₃ | 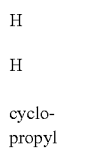 | H | H | H | H | H | para | 2-aminophenyl |
| a-150 | —CH₃ | H | 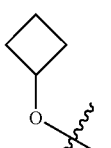 | H | H | H | H | para | 2-aminophenyl |

TABLE 1-continued
Examples of Formula (I$^a$-a)
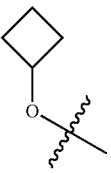
| Compound No. | R$^1$ | R$^2$ | R$^3$ | R$^4$ | R$^5$ | R$^{6'}$ | R$^7$ | —CONHR$^1$ attachment | R$^8$ |
|---|---|---|---|---|---|---|---|---|---|
| a-151 | —CH$_3$ | H | H | 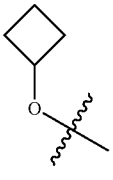 | H | H | H | para | 2-aminophenyl |
| a-152 | —CH$_3$ | H | H | H | 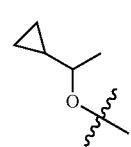 | H | H | para | 2-aminophenyl |
| a-153 | —CH$_3$ | 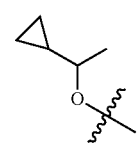 | H | H | H | H | H | para | 2-aminophenyl |
| a-154 | —CH$_3$ | H | 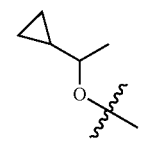 | H | H | H | H | para | 2-aminophenyl |
| a-155 | —CH$_3$ | H | H | 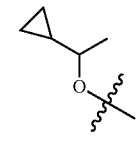 | H | H | H | para | 2-aminophenyl |
| a-156 | —CH$_3$ | H | H | H | 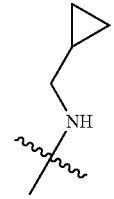 | H | H | para | 2-aminophenyl |
| a-157 | —CH$_3$ |  | H | H | H | H | H | para | 2-aminophenyl |

TABLE 1-continued
Examples of Formula (I$^a$-a)
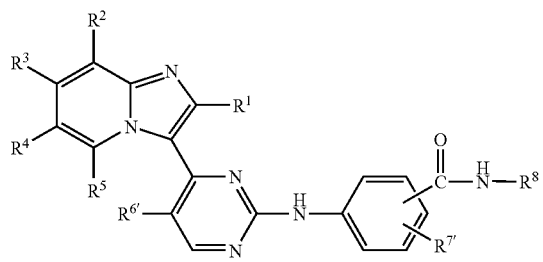
| Compound No. | R$^1$ | R$^2$ | R$^3$ | R$^4$ | R$^5$ | R$^6'$ | R$^7'$ | —CONHR$^1$ attachment | R$^8$ |
|---|---|---|---|---|---|---|---|---|---|
| a-158 | —CH$_3$ | H | 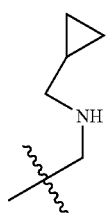 | H | H | H | H | para | 2-aminophenyl |
| a-159 | —CH$_3$ | H | H | 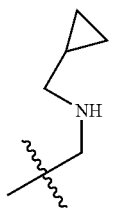 | H | H | H | para | 2-aminophenyl |
| a-160 | —CH$_3$ | H | H | H | 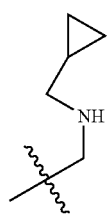 | H | H | para | 2-aminophenyl |
| a-161 | —CH$_3$ | 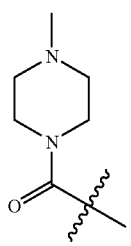 | H | H | H | H | H | para | 2-aminophenyl |
| a-162 | —CH$_3$ | H | 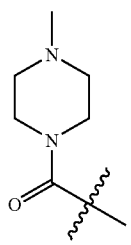 | H | H | H | H | para | 2-aminophenyl |

TABLE 1-continued
Examples of Formula (I^a-a)
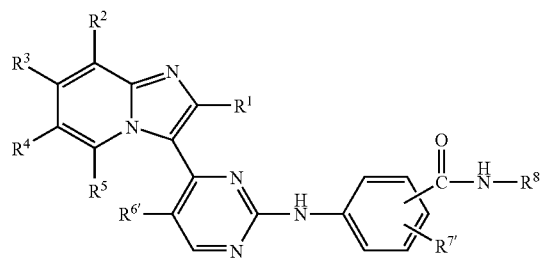
| Compound No. | R¹ | R² | R³ | R⁴ | R⁵ | R⁶' | R⁷' | —CONHR¹ attachment | R⁸ |
|---|---|---|---|---|---|---|---|---|---|
| a-163 | —CH₃ | H | H | 4-methylpiperazinyl-C(O)C(CH₃)₂– | H | H | H | para | 2-aminophenyl |
| a-164 | —CH₃ | H | H | H | 4-methylpiperazinyl-C(O)C(CH₃)₂– | H | H | para | 2-aminophenyl |
| a-165 | —CH₃ | isoindolin-2-yl | H | H | H | H | H | para | 2-aminophenyl |
| a-166 | —CH₃ | H | isoindolin-2-yl | H | H | H | H | para | 2-aminophenyl |
| a-167 | —CH₃ | H | H | isoindolin-2-yl | H | H | H | para | 2-aminophenyl |

TABLE 1-continued
Examples of Formula (I<sup>a</sup>-a)
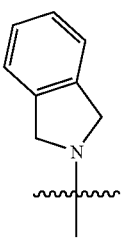
| Compound No. | R¹ | R² | R³ | R⁴ | R⁵ | R⁶' | R⁷' | —CONHR¹ attachment | R⁸ |
|---|---|---|---|---|---|---|---|---|---|
| a-168 | —CH₃ | H | H | H | 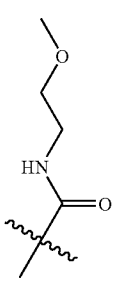 | H | H | para | 2-aminophenyl |
| a-169 | —CH₃ | —F | H | H | H | H | H | para | —OH |
| a-170 | —CH₃ | —F | H | H | H | H | H | para | 2-aminophenyl |
| a-171 | —CH₃ | H | H | —Br | H | H | H | para | —OH |
| a-172 | —CH₃ | H | H | —Br | H | H | H | para | 2-aminophenyl |
| a-173 | —CH₃ | H | 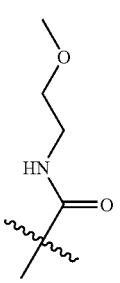 | H | H | H | H | para | —OH |
| a-174 | —CH₃ | H | 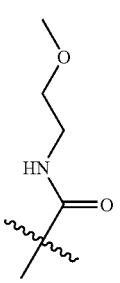 | H | H | H | H | para | 2-aminophenyl |
| a-175 | —CH₃ | H | H | 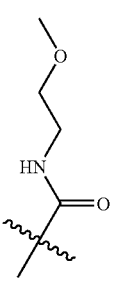 | H | H | H | para | —OH |

TABLE 1-continued
Examples of Formula (I^a-a)
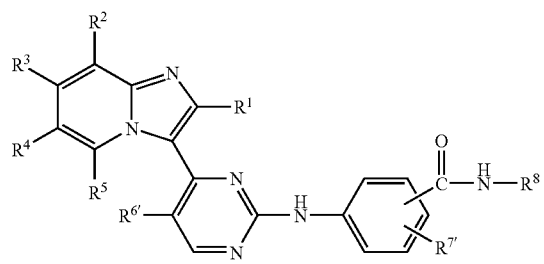
| Compound No. | R¹ | R² | R³ | R⁴ | R⁵ | R⁶' | R⁷ | —CONHR¹ attachment | R⁸ |
|---|---|---|---|---|---|---|---|---|---|
| a-176 | —CH₃ | H | H | 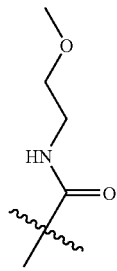 | H | H | H | para | 2-aminophenyl |
| a-177 | —CH₃ | H | 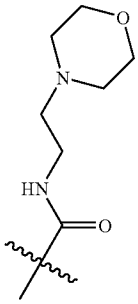 | H | H | H | H | para | —OH |
| a-178 | —CH₃ | H | 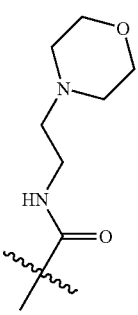 | H | H | H | H | para | 2-aminophenyl |
| a-179 | —CH₃ | H | H | 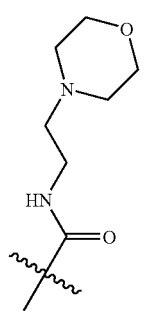 | H | H | H | para | —OH |

TABLE 1-continued

Examples of Formula (Iᵃ-a)

| Compound No. | R¹ | R² | R³ | R⁴ | R⁵ | R⁶' | R⁷ | —CONHR¹ attachment | R⁸ |
|---|---|---|---|---|---|---|---|---|---|
| a-180 | —CH₃ | H | H | ![morpholinoethylamide] | H | H | H | para | 2-aminophenyl |
| a-181 | —CH₃ | H | ![N-methylpiperazinyl carbonyl isopropyl] | H | H | H | H | para | —OH |
| a-182 | —CH₃ | H | H | ![N-methylpiperazinyl carbonyl isopropyl] | H | H | H | para | 2-aminophenyl |
| a-183 | —CH₃ | H | H | H | ![N-methylpiperazinyl carbonyl isopropyl] | H | H | para | —OH |

TABLE 1-continued

Examples of Formula (I^a-a)

| Compound No. | R¹ | R² | R³ | R⁴ | R⁵ | R⁶' | R⁷' | —CONHR¹ attachment | R⁸ |
|---|---|---|---|---|---|---|---|---|---|
| a-184 | —CH₃ | H | H | 4-methylpiperazin-1-yl-carbonyl-C(CH₃)₂— | H | H | H | para | 2-aminophenyl |
| a-185 | —CH₃ | H | morpholinoethoxy-C(CH₃)₂— | H | H | H | H | para | —OH |
| a-186 | —CH₃ | H | H | morpholinoethoxy-C(CH₃)₂— | H | H | H | para | 2-aminophenyl |
| a-187 | —CH₃ | H | (dimethylamino)ethoxy-C(CH₃)₂— | H | H | H | H | para | —OH |
| a-188 | —CH₃ | H | H | (dimethylamino)ethoxy-C(CH₃)₂— | H | H | H | para | 2-aminophenyl |

TABLE 1-continued
Examples of Formula (I$^a$-a)
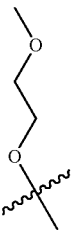
| Compound No. | R$^1$ | R$^2$ | R$^3$ | R$^4$ | R$^5$ | R$^{6'}$ | R$^{7'}$ | —CONHR$^1$ attachment | R$^8$ |
|---|---|---|---|---|---|---|---|---|---|
| a-189 | —CH$_3$ | H | 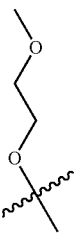 | H | H | H | H | para | —OH |
| a-190 | —CH$_3$ | H | 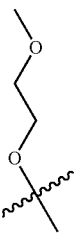 | H | H | H | H | para | 2-aminophenyl |
| a-191 | —CH$_3$ | H | H |  | H | H | H | para | —OH |
| a-192 | —CH$_3$ | H | H |  | H | H | H | para | 2-aminophenyl |
| a-193 | —CH$_3$ | H |  | H | H | H | H | para | —OH |

TABLE 1-continued

Examples of Formula (Iᵃ-a)

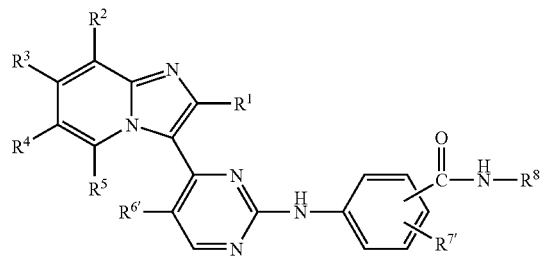

| Compound No. | R¹ | R² | R³ | R⁴ | R⁵ | R⁶' | R⁷' | —CONHR¹ attachment | R⁸ |
|---|---|---|---|---|---|---|---|---|---|
| a-194 | —CH₃ | H | ![Me₂N-CH₂CH₂-NH-] | H | H | H | H | para | 2-aminophenyl |
| a-195 | —CH₃ | H | H | —OCH₃ | H | H | H | para | —OH |
| a-196 | —CH₃ | H | H | —OCH₃ | H | H | H | para | 2-aminophenyl |
| a-197 | H | H | —OCH₃ | H | H | H | H | para | —OH |
| a-198 | H | H | —OCH₃ | H | H | H | H | para | 2-aminophenyl |
| a-199 | —CH₃ | H | ![Me₂N-CH₂-] | H | H | H | H | para | —OH |
| a-200 | —CH₃ | H | ![Me₂N-CH₂-] | H | H | H | H | para | 2-aminophenyl |
| a-201 | —CF₃ | H | H | H | H | H | H | para | —OH |
| a-202 | —CF₃ | H | H | H | H | H | H | para | 2-aminophenyl |
| a-203 | —CF₃ | H | —OCH₃ | H | H | H | H | para | —OH |
| a-204 | —CF₃ | H | —OCH₃ | H | H | H | H | para | 2-aminophenyl |
| a-205 | —CH₃ | H | —CN | H | H | H | H | para | —OH |
| a-206 | —CH₃ | H | —CN | H | H | H | H | para | 2-aminophenyl |
| a-207 | —CH₃ | H | —COOCH₃ | H | H | H | H | para | —OH |
| a-208 | —CH₃ | H | —COOCH₃ | H | H | H | H | para | 2-aminophenyl |
| a-209 | —CH₃ | H | —COOH | H | H | H | H | para | —OH |
| a-210 | —CH₃ | H | —COOH | H | H | H | H | para | 2-aminophenyl |
| a-211 | —CH₃ | H | H | H | H | H | ortho-F | para | —OH |
| a-212 | —CH₃ | H | H | H | H | H | meta-F | para | —OH |

TABLE 1-continued

Examples of Formula (I$^a$-a)

| Compound No. | R$^1$ | R$^2$ | R$^3$ | R$^4$ | R$^5$ | R$^6'$ | R$^7'$ | —CONHR$^1$ attachment | R$^8$ |
|---|---|---|---|---|---|---|---|---|---|
| a-213 | —CH$_3$ | H | H | H | H | H | ortho-F | para | 2-aminophenyl |
| a-214 | —CH$_3$ | H | H | H | H | H | meta-F | para | 2-aminophenyl |
| a-215 | —CH$_3$ | H | (CH$_3$)$_2$NCH$_2$CH$_2$NHC(O)C(CH$_3$)$_2$– | H | H | H | H | para | —OH |
| a-216 | —CH$_3$ | H | (CH$_3$)$_2$NCH$_2$CH$_2$NHC(O)C(CH$_3$)$_2$– | H | H | H | H | para | 2-aminophenyl |
| a-217 | —CH$_3$ | H | H | (CH$_3$)$_2$NCH$_2$CH$_2$NHC(O)C(CH$_3$)$_2$– | H | H | H | para | —OH |

TABLE 1-continued

Examples of Formula (I<sup>a</sup>-a)

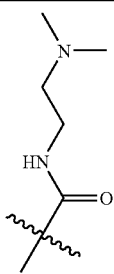

| Compound No. | R¹ | R² | R³ | R⁴ | R⁵ | R⁶' | R⁷ | —CONHR¹ attachment | R⁸ |
|---|---|---|---|---|---|---|---|---|---|
| a-218 | —CH₃ | H | H | 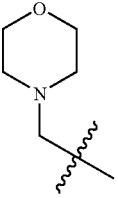 | H | H | H | para | 2-aminophenyl |
| a-219 | H | H | H | H | H | F | H | para | —OH |
| a-220 | H | H | H | H | H | F | H | para | 2-aminophenyl |
| a-221 | —CH₃ | H | 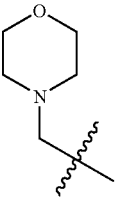 | H | H | H | H | para | —OH |
| a-222 | —CH₃ | H | 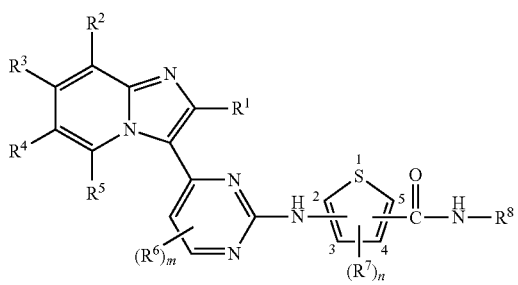 | H | H | H | H | para | 2-aminophenyl |

In another embodiment where the ring X is a thiophene, the invention provides a compound of Formula (I$^a$-b) and a pharmaceutically acceptable salt thereof.

Formula (I$^a$-b)

where m, n, and the groups R¹, R⁶, R⁷ and R⁸ are as defined for various aspects of Formula (I) and (I$^a$-a) above, and wherein R², R³, and R⁴ are independently selected from groups R¹.

In some embodiments, the NH containing moiety and —CONH—R⁸ are attached to the thiophene ring in a 2,5-configuration, where the NH linker is considered as the 2-position (with the S atom of the thiophene ring taken as the 1-position). Non-limiting examples of such compounds include those selected from the following structure (Formula I$^a$-b0) and pharmaceutically acceptable salts thereof, where R$^{6'}$ is H or R⁶. The substitution pattern of various embodiments is given in Table 2 for compounds b0-01 through b0-150.

TABLE 2

Examples of Formula (Iᵃ-b0)

Formula (Iᵃ-b0)

| Compound No. | $R^1$ | $R^2$ | $R^3$ | $R^4$ | $R^5$ | $R^{6'}$ | $R^8$ |
|---|---|---|---|---|---|---|---|
| b0-01 | H | H | H | H | H | H | —OH |
| b0-02 | H | H | H | H | H | —CH₃ | —OH |
| b0-03 | H | H | H | H | H | H | 2-aminophenyl |
| b0-04 | H | H | H | H | H | —CH₃ | 2-aminophenyl |
| b0-05 | —CH₃ | H | H | H | H | H | —OH |
| b0-06 | —CH₃ | H | H | H | H | —CH₃ | —OH |
| b0-07 | —CH₃ | H | H | H | H | H | 2-aminophenyl |
| b0-08 | —CH₃ | H | H | H | H | —CH₃ | 2-aminophenyl |
| b0-09 | —CH₃ | —Cl | H | H | H | H | —OH |
| b0-10 | —CH₃ | H | —Cl | H | H | H | —OH |
| b0-11 | —CH₃ | H | H | —Cl | H | H | —OH |
| b0-12 | —CH₃ | H | H | H | —Cl | H | —OH |
| b0-13 | —CH₃ | —Cl | H | H | H | H | 2-aminophenyl |
| b0-14 | —CH₃ | H | —Cl | H | H | H | 2-aminophenyl |
| b0-15 | —CH₃ | H | H | —Cl | H | H | 2-aminophenyl |
| b0-16 | —CH₃ | H | H | H | —Cl | H | 2-aminophenyl |
| b0-17 | —CH₃ | —Cl | H | H | H | H | 2-amino-6-fluorophenyl |
| b0-18 | —CH₃ | H | —Cl | H | H | H | 2-amino-6-fluorophenyl |
| b0-19 | —CH₃ | H | H | —Cl | H | H | 2-amino-6-fluorophenyl |
| b0-20 | —CH₃ | H | H | H | —Cl | H | 2-amino-6-fluorophenyl |
| b0-21 | —CH₃ | —CF₃ | H | H | H | H | —OH |
| b0-22 | —CH₃ | H | —CF₃ | H | H | H | —OH |
| b0-23 | —CH₃ | H | H | —CF₃ | H | H | —OH |
| b0-24 | —CH₃ | H | H | H | —CF₃ | H | —OH |
| b0-25 | —CH₃ | —CF₃ | H | H | H | H | 2-aminophenyl |
| b0-26 | —CH₃ | H | —CF₃ | H | H | H | 2-aminophenyl |
| b0-27 | —CH₃ | H | H | —CF₃ | H | H | 2-aminophenyl |
| b0-28 | —CH₃ | H | H | H | —CF₃ | H | 2-aminophenyl |
| b0-29 | —CH₃ | —OCH₃ | H | H | H | H | —OH |
| b0-30 | —CH₃ | H | —OCH₃ | H | H | H | —OH |
| b0-31 | —CH₃ | H | H | —OCH₃ | H | H | —OH |
| b0-32 | —CH₃ | H | H | H | —OCH₃ | H | —OH |
| b0-33 | —CH₃ | —OCH₃ | H | H | H | H | 2-aminophenyl |
| b0-34 | —CH₃ | H | —OCH₃ | H | H | H | 2-aminophenyl |
| b0-35 | —CH₃ | H | H | —OCH₃ | H | H | 2-aminophenyl |
| b0-36 | —CH₃ | H | H | H | —OCH₃ | H | 2-aminophenyl |
| b0-37 | —CH₃ | CH₃-N(CH₃)-CH(−)− | H | H | H | H | —OH |
| b0-38 | —CH₃ | H | CH₃-N(CH₃)-CH(−)− | H | H | H | —OH |

TABLE 2-continued
Examples of Formula (Iª-b0)
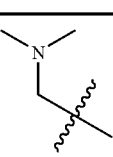
Formula (Iª-b0)
| Compound No. | R¹ | R² | R³ | R⁴ | R⁵ | R⁶' | R⁸ |
|---|---|---|---|---|---|---|---|
| b0-39 | —CH₃ | H | H | 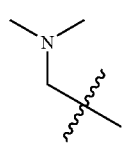 | H | H | —OH |
| b0-40 | —CH₃ | H | H | H | 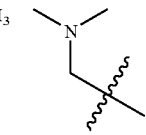 | H | —OH |
| b0-41 | —CH₃ | 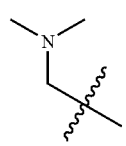 | H | H | H | H | 2-aminophenyl |
| b0-42 | —CH₃ | H | 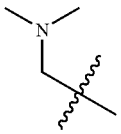 | H | H | H | 2-aminophenyl |
| b0-43 | —CH₃ | H | H | 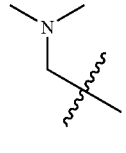 | H | H | 2-aminophenyl |
| b0-44 | —CH₃ | H | H | H | 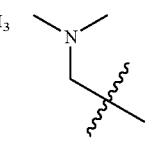 | H | 2-aminophenyl |
| b0-45 | —CH₃ | 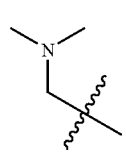 | H | H | H | H | 2-amino-6-fluorophenyl |
| b0-46 | —CH₃ | H |  | H | H | H | 2-amino-6-fluorophenyl |

TABLE 2-continued

Examples of Formula (Iª-b0)

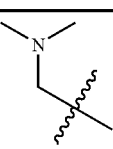

Formula (Iª-b0)

| Compound No. | R¹ | R² | R³ | R⁴ | R⁵ | R⁶' | R⁸ |
|---|---|---|---|---|---|---|---|
| b0-47 | —CH₃ | H | H | 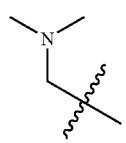 | H | H | 2-amino-6-fluorophenyl |
| b0-48 | —CH₃ | H | H | H | 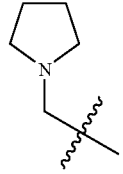 | H | 2-amino-6-fluorophenyl |
| b0-49 | —CH₃ | 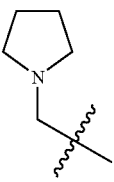 | H | H | H | H | 2-aminophenyl |
| b0-50 | —CH₃ | H | 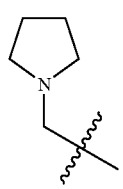 | H | H | H | 2-aminophenyl |
| b0-51 | —CH₃ | H | H | 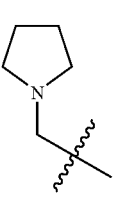 | H | H | 2-aminophenyl |
| b0-52 | —CH₃ | H | H | H |  | H | 2-aminophenyl |
| b0-53 | —CH₃ | morpholin-4-yl | H | H | H | H | 2-aminophenyl |
| b0-54 | —CH₃ | H | morpholin-4-yl | H | H | H | 2-aminophenyl |
| b0-55 | —CH₃ | H | H | morpholin-4-yl | H | H | 2-aminophenyl |
| b0-56 | —CH₃ | H | H | H | morpholin-4-yl | H | 2-aminophenyl |

TABLE 2-continued

Examples of Formula (I<sup>a</sup>-b0)

Formula (I<sup>a</sup>-b0)

| Compound No. | R¹ | R² | R³ | R⁴ | R⁵ | R⁶' | R⁸ |
| --- | --- | --- | --- | --- | --- | --- | --- |
| b0-57 | —CH₃ | oxetan-3-yloxymethyl | H | H | H | H | 2-aminophenyl |
| b0-58 | —CH₃ | H | oxetan-3-yloxymethyl | H | H | H | 2-aminophenyl |
| b0-59 | —CH₃ | H | H | oxetan-3-yloxymethyl | H | H | 2-aminophenyl |
| b0-60 | —CH₃ | H | H | H | oxetan-3-yloxymethyl | H | 2-aminophenyl |
| b0-61 | —CH₃ | (1H-imidazol-1-yl)-2-methylpropyl | H | H | H | H | 2-aminophenyl |
| b0-62 | —CH₃ | H | (1H-imidazol-1-yl)-2-methylpropyl | H | H | H | 2-aminophenyl |

TABLE 2-continued

Examples of Formula (I$^a$-b0)

Formula (I$^a$-b0)

| Compound No. | R$^1$ | R$^2$ | R$^3$ | R$^4$ | R$^5$ | R$^6'$ | R$^8$ |
|---|---|---|---|---|---|---|---|
| b0-63 | —CH$_3$ | H | H | 1-imidazolyl-CH$_2$-C(CH$_3$)- | H | H | 2-aminophenyl |
| b0-64 | —CH$_3$ | H | H | H | 1-imidazolyl-CH$_2$-C(CH$_3$)- | H | 2-aminophenyl |
| b0-65 | —CH$_3$ | CF$_3$CH$_2$NH-CH$_2$-C(CH$_3$)- | H | H | H | H | 2-aminophenyl |
| b0-66 | —CH$_3$ | H | CF$_3$CH$_2$NH-CH$_2$-C(CH$_3$)- | H | H | H | 2-aminophenyl |
| b0-67 | —CH$_3$ | H | H | CF$_3$CH$_2$NH-CH$_2$-C(CH$_3$)- | H | H | 2-aminophenyl |
| b0-68 | —CH$_3$ | H | H | H | CF$_3$CH$_2$NH-CH$_2$-C(CH$_3$)- | H | 2-aminophenyl |

TABLE 2-continued
Examples of Formula (Iᵃ-b0)
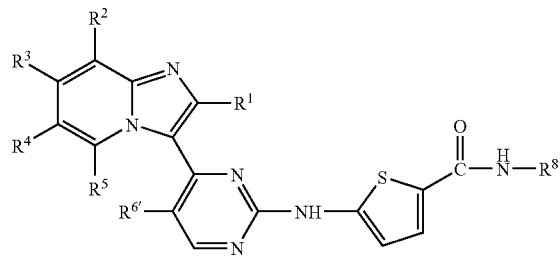
Formula (Iᵃ-b0)
| Compound No. | R¹ | R² | R³ | R⁴ | R⁵ | R⁶' | R⁸ |
|---|---|---|---|---|---|---|---|
| b0-69 | —CH₃ | CH₃OCH₂CH₂N(CH₃)CH(CH₃)– | H | H | H | H | 2-aminophenyl |
| b0-70 | —CH₃ | H | CH₃OCH₂CH₂N(CH₃)CH(CH₃)– | H | H | H | 2-aminophenyl |
| b0-71 | —CH₃ | H | H | CH₃OCH₂CH₂N(CH₃)CH(CH₃)– | H | H | 2-aminophenyl |
| b0-72 | —CH₃ | H | H | H | CH₃OCH₂CH₂N(CH₃)CH(CH₃)– | H | 2-aminophenyl |

TABLE 2-continued
Examples of Formula (Iª-b0)
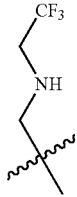
Formula (Iª-b0)
| Compound No. | R¹ | R² | R³ | R⁴ | R⁵ | R⁶' | R⁸ |
|---|---|---|---|---|---|---|---|
| b0-73 | —CH₃ | 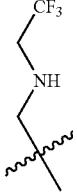 | H | H | H | H | —OH |
| b0-74 | —CH₃ | H | 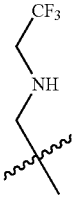 | H | H | H | —OH |
| b0-75 | —CH₃ | H | H | 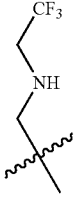 | H | H | —OH |
| b0-76 | —CH₃ | H | H | H | 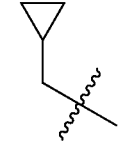 | H | —OH |
| b0-77 | —CH₃ | 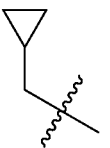 | H | H | H | H | 2-aminophenyl |
| b0-78 | —CH₃ | H |  | H | H | H | 2-aminophenyl |

TABLE 2-continued

Examples of Formula (I^a-b0)

Formula (I^a-b0)

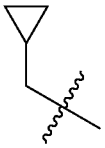

| Compound No. | R^1 | R^2 | R^3 | R^4 | R^5 | R^6' | R^8 |
|---|---|---|---|---|---|---|---|
| b0-79 | —CH$_3$ | H | H | 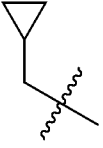 | H | H | 2-aminophenyl |
| b0-80 | —CH$_3$ | H | H | H | 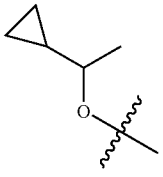 | H | 2-aminophenyl |
| b0-81 | —CH$_3$ | cyclo-propyl | H | H | H | H | 2-aminophenyl |
| b0-82 | —CH$_3$ | H | cyclo-propyl | H | H | H | 2-aminophenyl |
| b0-83 | —CH$_3$ | H | H | cyclo-propyl | H | H | 2-aminophenyl |
| b0-84 | —CH$_3$ | H | H | H | cyclo-propyl | H | 2-aminophenyl |
| b0-85 | —CH$_3$ | cyclo-butyloxy | H | H | H | H | 2-aminophenyl |
| b0-86 | —CH$_3$ | H | cyclo-butyloxy | H | H | H | 2-aminophenyl |
| b0-87 | —CH$_3$ | H | H | cyclo-butyloxy | H | H | 2-aminophenyl |
| b0-88 | —CH$_3$ | H | H | H | cyclo-butyloxy | H | 2-aminophenyl |
| b0-89 | —CH$_3$ | 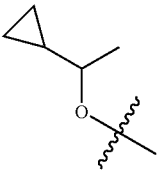 | H | H | H | H | 2-aminophenyl |
| b0-90 | —CH$_3$ | H | 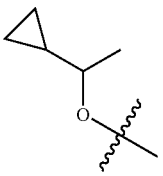 | H | H | H | 2-aminophenyl |
| b0-91 | —CH$_3$ | H | H |  | H | H | 2-aminophenyl |

TABLE 2-continued
Examples of Formula (I$^a$-b0)
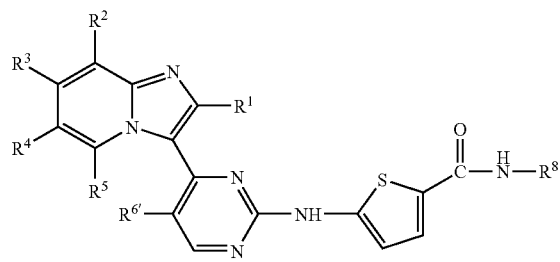
Formula (I$^a$-b0)
| Compound No. | R$^1$ | R$^2$ | R$^3$ | R$^4$ | R$^5$ | R$^6'$ | R$^8$ |
|---|---|---|---|---|---|---|---|
| b0-92 | —CH$_3$ | H | H | H | 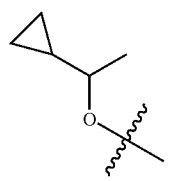 | H | 2-aminophenyl |
| b0-93 | —CH$_3$ | 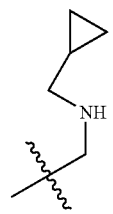 | H | H | H | H | 2-aminophenyl |
| b0-94 | —CH$_3$ | H |  | H | H | H | 2-aminophenyl |
| b0-95 | —CH$_3$ | H | H | 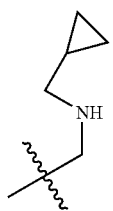 | H | H | 2-aminophenyl |
| b9-96 | —CH$_3$ | H | H | H | 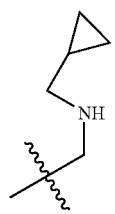 | H | 2-aminophenyl |

TABLE 2-continued

Examples of Formula (Iᵃ-b0)

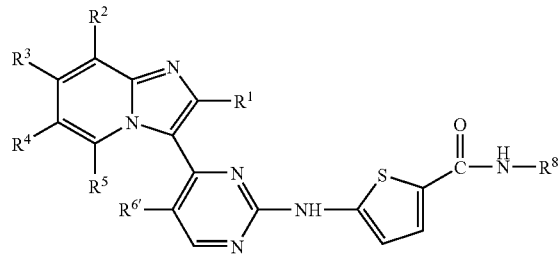

Formula (Iᵃ-b0)

| Compound No. | R¹ | R² | R³ | R⁴ | R⁵ | R⁶' | R⁸ |
|---|---|---|---|---|---|---|---|
| b0-97 | —CH₃ | (4-methylpiperazinyl carbonyl isopropyl) | H | H | H | H | 2-aminophenyl |
| b0-98 | —CH₃ | H | (4-methylpiperazinyl carbonyl isopropyl) | H | H | H | 2-aminophenyl |
| b0-99 | —CH₃ | H | H | (4-methylpiperazinyl carbonyl isopropyl) | H | H | 2-aminophenyl |
| b0-100 | —CH₃ | H | H | H | (4-methylpiperazinyl carbonyl isopropyl) | H | 2-aminophenyl |
| b0-101 | —CH₃ | (isoindolinyl ethyl) | H | H | H | H | 2-aminophenyl |

TABLE 2-continued
Examples of Formula (Iª-b0)
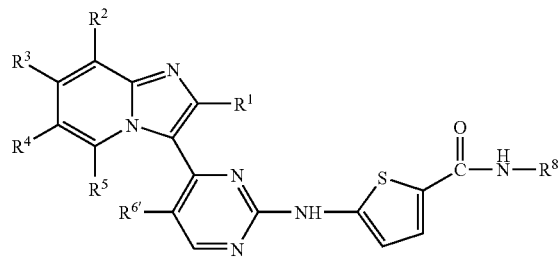
Formula (Iª-b0)
| Compound No. | R¹ | R² | R³ | R⁴ | R⁵ | R⁶' | R⁸ |
|---|---|---|---|---|---|---|---|
| b0-102 | —CH₃ | H | 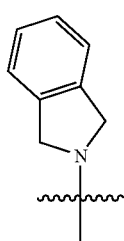 | H | H | H | 2-aminophenyl |
| b0-103 | —CH₃ | H | H | 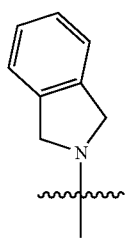 | H | H | 2-aminophenyl |
| b0-104 | —CH₃ | H | H | H | 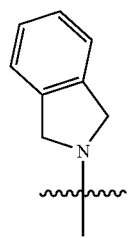 | H | 2-aminophenyl |
| b0-105 | —CH₃ | —F | H | H | H | H | —OH |
| b0-106 | —CH₃ | —F | H | H | H | H | 2-aminophenyl |
| b0-107 | —CH₃ | H | H | —Br | H | H | —OH |
| b0-108 | —CH₃ | H | H | —Br | H | H | 2-aminophenyl |
| b0-109 | —CH₃ | H | 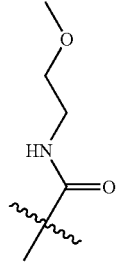 | H | H | H | —OH |

TABLE 2-continued
Examples of Formula (I$^a$-b0)
Formula (I$^a$-b0)
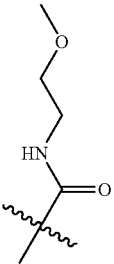
| Compound No. | R$^1$ | R$^2$ | R$^3$ | R$^4$ | R$^5$ | R$^6$ | R$^8$ |
|---|---|---|---|---|---|---|---|
| b0-110 | —CH$_3$ | H | 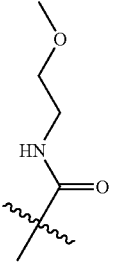 | H | H | H | 2-aminophenyl |
| b0-111 | —CH$_3$ | H | H | 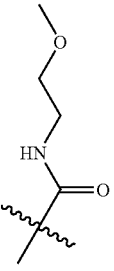 | H | H | —OH |
| b0-112 | —CH$_3$ | H | H | 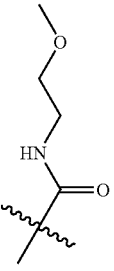 | H | H | 2-aminophenyl |
| b0-113 | —CH$_3$ | H | 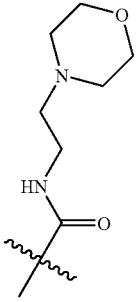 | H | H | H | —OH |

TABLE 2-continued
Examples of Formula (Iᵃ-b0)
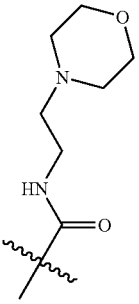
Formula (Iᵃ-b0)
| Compound No. | R¹ | R² | R³ | R⁴ | R⁵ | R⁶' | R⁸ |
|---|---|---|---|---|---|---|---|
| b0-114 | —CH₃ | H | 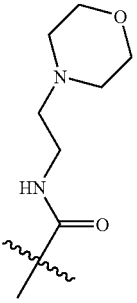 | H | H | H | 2-aminophenyl |
| b0-115 | —CH₃ | H | H | 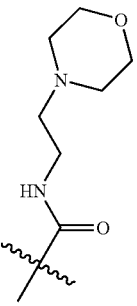 | H | H | —OH |
| b0-116 | —CH₃ | H | H | 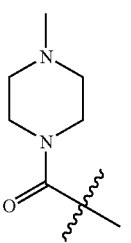 | H | H | 2-aminophenyl |
| b0-117 | —CH₃ | H | (structure) | H | H | H | —OH |

TABLE 2-continued

Examples of Formula (I$^a$-b0)

Formula (I$^a$-b0)

| Compound No. | R$^1$ | R$^2$ | R$^3$ | R$^4$ | R$^5$ | R$^6'$ | R$^8$ |
|---|---|---|---|---|---|---|---|
| b0-118 | —CH$_3$ | H | 4-methylpiperazin-1-yl-carbonyl-isopropyl | H | H | H | 2-aminophenyl |
| b0-119 | —CH$_3$ | H | H | 4-methylpiperazin-1-yl-carbonyl-isopropyl | H | H | —OH |
| b0-120 | —CH$_3$ | H | H | 4-methylpiperazin-1-yl-carbonyl-isopropyl | H | H | 2-aminophenyl |
| b0-121 | —CH$_3$ | H | 2-(morpholin-4-yl)ethoxy-isopropyl | H | H | H | —OH |

TABLE 2-continued
Examples of Formula (I$^a$-b0)
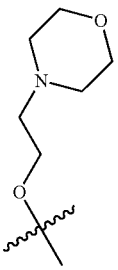
Formula (I$^a$-b0)
| Compound No. | R$^1$ | R$^2$ | R$^3$ | R$^4$ | R$^5$ | R$^{6'}$ | R$^8$ |
|---|---|---|---|---|---|---|---|
| b0-122 | —CH$_3$ | H | 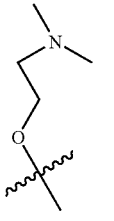 | H | H | H | 2-aminophenyl |
| b0-123 | —CH$_3$ | H | 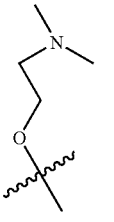 | H | H | H | —OH |
| b0-124 | —CH$_3$ | H | 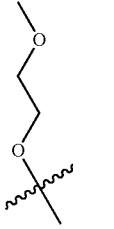 | H | H | H | 2-aminophenyl |
| b0-125 | —CH$_3$ | H | 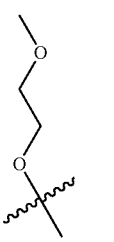 | H | H | H | —OH |
| b0-126 | —CH$_3$ | H | 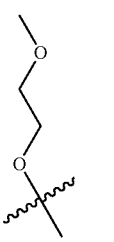 | H | H | H | 2-aminophenyl |

TABLE 2-continued

Examples of Formula (I$^a$-b0)

Formula (I$^a$-b0)

| Compound No. | R$^1$ | R$^2$ | R$^3$ | R$^4$ | R$^5$ | R$^{6'}$ | R$^8$ |
|---|---|---|---|---|---|---|---|
| b0-127 | —CH$_3$ | H | H | -OCH$_2$CH$_2$OC(CH$_3$)$_2$- | H | H | —OH |
| b0-128 | —CH$_3$ | H | H | -OCH$_2$CH$_2$OC(CH$_3$)$_2$- | H | H | 2-aminophenyl |
| b0-129 | —CH$_3$ | H | -NHC(CH$_3$)$_2$CH$_2$N(CH$_3$)$_2$ | H | H | H | —OH |
| b0-130 | —CH$_3$ | H | -NHC(CH$_3$)$_2$CH$_2$N(CH$_3$)$_2$ | H | H | H | 2-aminophenyl |
| b0-131 | —CH$_3$ | H | H | —OCH$_3$ | H | H | —OH |
| b0-132 | —CH$_3$ | H | H | —OCH$_3$ | H | H | 2-aminophenyl |
| b0-133 | —CF$_3$ | H | H | —OCH$_3$ | H | H | —OH |
| b0-134 | —CF$_3$ | H | H | —OCH$_3$ | H | H | 2-aminophenyl |
| b0-135 | —CH$_3$ | H | -C(CH$_3$)$_2$CH$_2$N(CH$_3$)$_2$ | H | H | H | —OH |

TABLE 2-continued

Examples of Formula (Iª-b0)

Formula (Iª-b0)

| Compound No. | R¹ | R² | R³ | R⁴ | R⁵ | R⁶' | R⁸ |
|---|---|---|---|---|---|---|---|
| b0-136 | —CH₃ | H | (dimethylaminomethyl with gem-dimethyl) | H | H | H | 2-aminophenyl |
| b0-137 | —CF₃ | H | H | H | H | H | —OH |
| b0-138 | —CF₃ | H | H | H | H | H | 2-aminophenyl |
| b0-139 | —CH₃ | H | —CN | H | H | H | —OH |
| b0-140 | —CH₃ | H | —CN | H | H | H | 2-aminophenyl |
| b0-141 | —CH₃ | H | —COOCH₃ | H | H | H | —OH |
| b0-142 | —CH₃ | H | —COOCH₃ | H | H | H | 2-aminophenyl |
| b0-143 | —CH₃ | H | —COOH | H | H | H | —OH |
| b0-144 | —CH₃ | H | —COOH | H | H | H | 2-aminophenyl |
| b0-145 | —CH₃ | H | (N,N-dimethylaminoethyl-NH-C(O)- with gem-dimethyl) | H | H | H | —OH |
| b0-146 | —CH₃ | H | (N,N-dimethylaminoethyl-NH-C(O)- with gem-dimethyl) | H | H | H | 2-aminophenyl |
| b0-147 | H | H | H | H | H | F | —OH |
| b0-148 | H | H | H | H | H | F | 2-aminophenyl |
| b0-149 | —CH₃ | H | (morpholinomethyl with gem-dimethyl) | H | H | H | —OH |

TABLE 2-continued

Examples of Formula (I$^a$-b0)

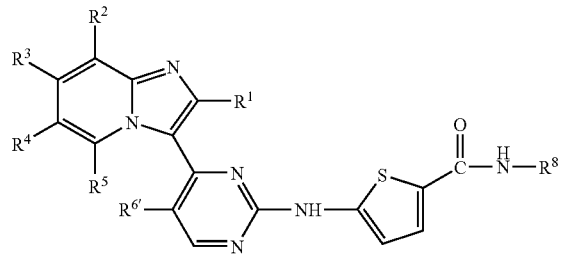

Formula (I$^a$-b0)

| Compound No. | R$^1$ | R$^2$ | R$^3$ | R$^4$ | R$^5$ | R$^6$' | R$^8$ |
|---|---|---|---|---|---|---|---|
| b0-150 | —CH$_3$ | H | morpholinomethyl | H | H | H | 2-aminophenyl |

In other embodiments, the NH containing moiety and —CONH—R$^8$ are attached to the thiophene ring in a 2,4-configuration, where the NH linker is considered as the 2-position (with the S atom of the thiophene ring taken as the 1-position). Non-limiting examples of such compounds include those selected from the following structure (Formula I$^a$-b1) and pharmaceutically acceptable salts thereof, where R$^6$' is H or R$^6$. In specific examples b1-01 to b1-148, the substituents R$^1$, R$^3$, R$^4$, R$^5$, R$^6$' and R$^8$ take on the respective values given in the table for Compounds b0-01 to b0-150.

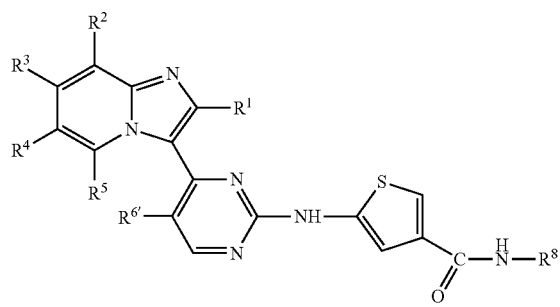

Formula (I$^a$-b1)

In yet other embodiments, the NH containing moiety and —CONH—R$^8$ are attached to the thiophene ring in a 2,4-configuration, where the NH linker is considered as the 2-position (with the S atom of the thiophene ring taken as the 1-position). Non-limiting examples of such compounds include those selected from the following structure (Formula I$^a$-b2) and pharmaceutically acceptable salts thereof, where R$^6$' is H or R$^6$. In specific examples b2-01 to b2-148, the substituents R$^1$, R$^3$, R$^4$, R$^5$, R$^6$' and R$^8$ take on the respective values given in the table for Compounds b0-01 to b0-150.

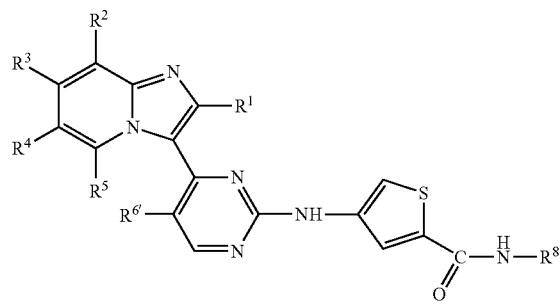

Formula (I$^a$-b2)

In a further embodiment, the invention provides a compound selected from those of Formula (I$^a$-c) and a pharmaceutically acceptable salt thereof, where Q$^1$ and Q$^2$ together form a pyridazine ring fused to imidazole.

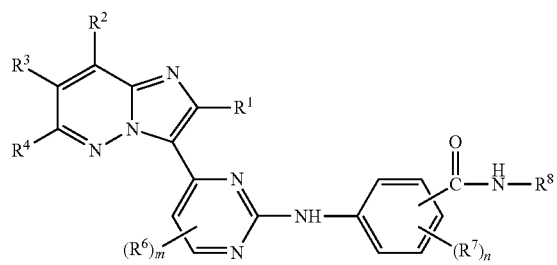

Formula (I$^a$-c)

wherein m, n, R$^1$, R$^6$, R$^7$ and R$^8$ are as defined for various aspects of Formulae (I) and (I$^a$-a) above, and wherein R$^2$, R$^3$, and R$^4$ are independently selected from groups R$^1$. In various embodiments, —CONH—R$^8$ is attached to the phenyl ring at a position para to the NH linker.

Non-limiting examples of such compounds include those of the following structure and pharmaceutically acceptable salts thereof:

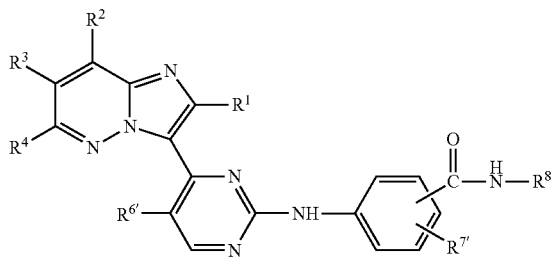

wherein R$^{6'}$ is H or R$^6$ and R$^{7'}$ is H or R$^7$. In specific examples c-01 to c-222, the substituents R$^1$, R$^2$, R$^3$, R$^4$, R$^{6'}$, R$^{7'}$, and R$^8$ are selected according to those given in the table for Compounds a-01 to a-222. That is, for examples c-01 through c-222, the R$^5$ column of Table 1 is not taken into account since compounds of Formula (I$^a$-c) do not have the R$^5$ substituent.

In a further embodiment, the invention provides a compound selected from those of Formula (I$^a$-d) and a pharmaceutically acceptable salt thereof:

Formula (1$^a$-d)

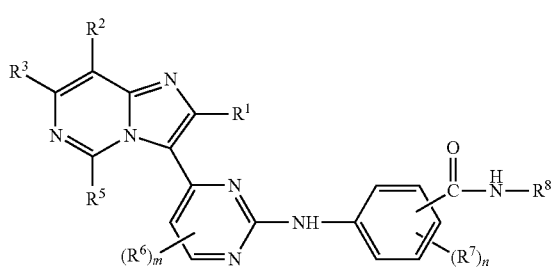

wherein m, n, R$^1$, R$^6$, R$^7$ and R$^8$ are as defined for various aspects of Formulae (I) and (I$^a$-a) above, and wherein R$^2$, R$^3$, and R$^5$ are independently selected from groups R$^1$. In various embodiments, —CONH—R$^8$ is attached to the phenyl ring at a position para to the NH linker.

Non-limiting examples of such compounds include those of the following structure and pharmaceutically acceptable salts thereof:

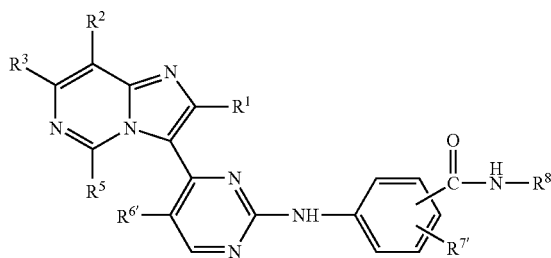

wherein R$^{6'}$ is H or R$^6$ and R$^{7'}$ is H or R$^7$. In specific examples d-01 to d-222, the substituents R$^1$, R$^2$, R$^3$, R$^5$, R$^{6'}$, R$^{7'}$ and R$^8$ are selected according to the pattern of substituents given in the table for Compounds a-01 to a-222. That is, for examples d-01 through d-222, the R$^4$ column of Table 1 is not considered as the compounds have not group R$^4$.

In another embodiment where Q$^1$ and Q$^2$ form a fused pyrazine ring, the invention provides a compound selected from those of Formula (I$^a$-e) and a pharmaceutically acceptable salt thereof.

Formula (1$^a$-e)

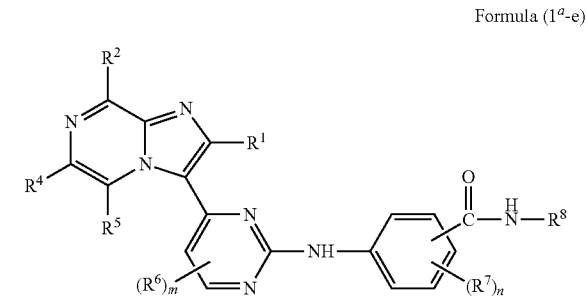

wherein m, n, R$^1$, R$^6$, R$^7$ and R$^8$ are as defined for various aspects of Formulas (I) and (I$^a$-a) above, and wherein R$^2$, R$^4$, and R$^5$ are independently selected from groups R$^1$. In various embodiments, —CONH—R$^8$ is attached to the phenyl ring at a position para to the NH linker.

Non-limiting examples of such compounds include those of the following structure and pharmaceutically acceptable salts thereof:

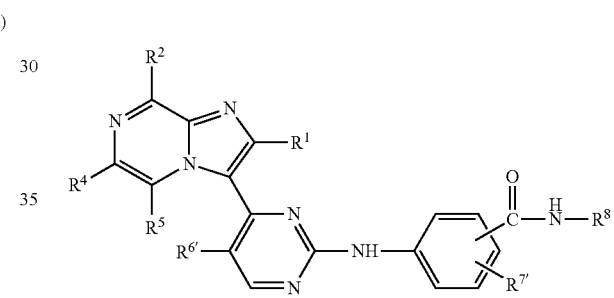

wherein R$^{6'}$ is H or R$^6$ and R$^{7'}$ is H or R$^7$. In specific examples e-01 to e-222, the substitutents R$^1$, R$^2$, R$^4$, R$^5$, R$^{6'}$, R$^{7'}$ and R$^8$ show the respective substitution patterns given in the table for Compounds a-01 to a-222 wherein in analogous fashion the R$^3$ column of Table 1 is not considered.

In another embodiment where Q$^1$ and Q$^2$ together form a fused pyrimidine ring, the invention provides a compound selected from those of Formula (I$^a$-f) and a pharmaceutically acceptable salt thereof Formula (1$^a$-f)

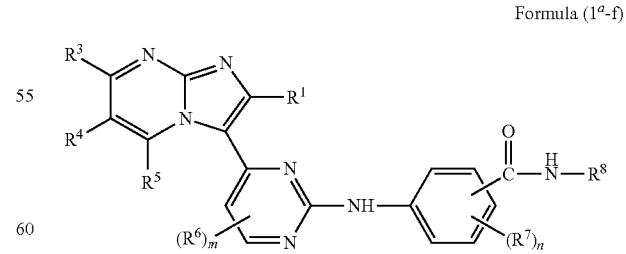

wherein m, n, R$^1$, R$^6$, R$^7$ and R$^8$ are as defined for various aspects of Formulae (I) and (I$^a$-a) above, and wherein R$^3$, R$^4$, and R$^5$ are independently selected from groups R$^1$. In various embodiments, —CONH—R$^8$ is attached to the phenyl ring at a position para to the NH linker.

Non-limiting examples of such compounds include those of the following structure and pharmaceutically acceptable salts thereof:

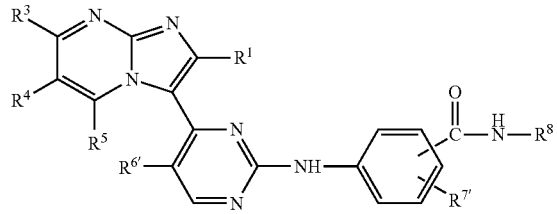

wherein R⁶' is H or R⁶ and R⁷' is H or R⁷. In specific examples f-01 to f-222, the substituents $R^1$, $R^3$, $R^4$, $R^5$, $R^{6'}$, $R^{7'}$ and $R^8$ take on the respective values given in the table for Compounds a-01 to a-222, ignoring the $R^2$ column.

In another embodiment where $Q^1$ and $Q^2$ together form a fused pyridine ring and the ring X is a 6-membered heteroaryl, the invention provides a compound selected from those of Formula ($I^a$-g) and a pharmaceutically acceptable salt thereof Formula (1$^a$-g)

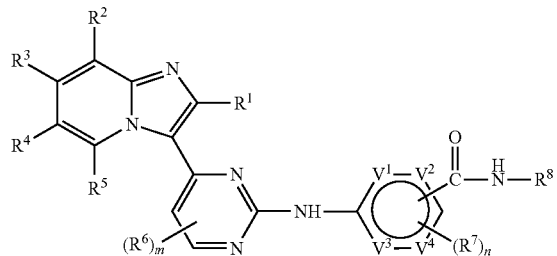

wherein m, n, $R^1$, $R^6$, $R^7$ and $R^8$ are as defined for various aspects of Formulae (I) and ($I^a$-a) above, wherein $R^2$, $R^3$, $R^4$, and $R^5$ are independently selected from groups $R^1$, and wherein $V^1$, $V^2$, $V^3$, and $V^4$ are ring atoms independently selected from N, O, S, and C and at least one of $V^1$, $V^2$, $V^3$, and $V^4$ is a non-carbon atom. In particular embodiments, —CONH—$R^8$ is attached to the heteroaryl ring X at a position para to the NH linker.

Non-limiting examples of such compounds include those of the following structures and pharmaceutically acceptable salts thereof:

Formula ($I^a$-g0)

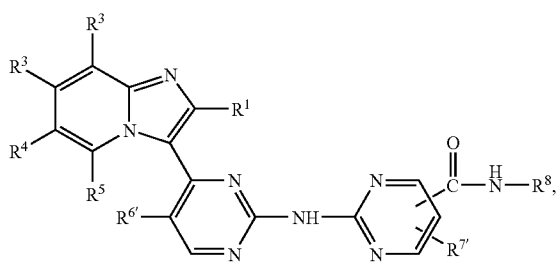

Formula ($I^a$-g1)

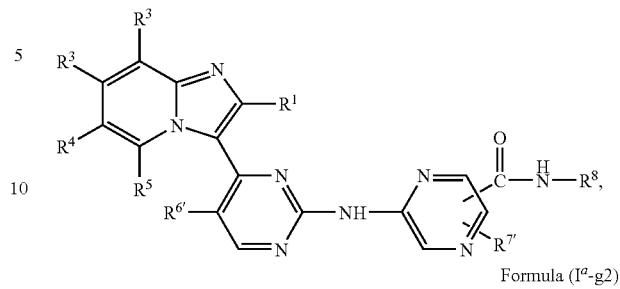

Formula ($I^a$-g2)

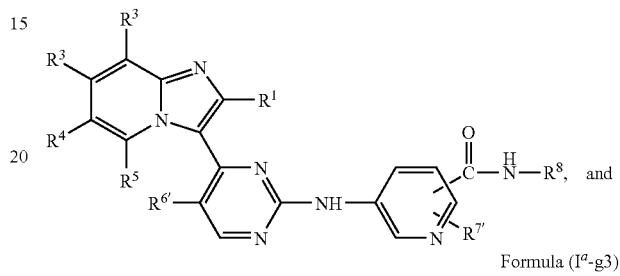

Formula ($I^a$-g3)

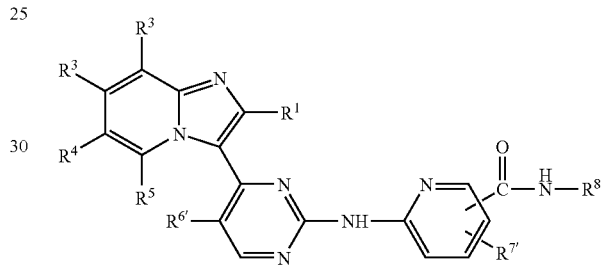

wherein R⁶' is H or R⁶ and R⁷' is H or R⁷. In specific examples, the substituents $R^1$, $R^3$, $R^4$, $R^5$, $R^{6'}$, $R^{7'}$ and $R^8$ of compounds of Formulae ($I^a$-g0), ($I^a$-g1), ($I^a$-g2), and ($I^a$-g3) take on values having the same combination or pattern of substituents given in the table for Compounds a-01 to a-222.

In another embodiment where $Q^1$ and $Q^2$ together form a fused pyridine and X is a 5-membered heteroaryl, the invention provides a compound selected from those of Formula ($I^a$-h) and a pharmaceutically acceptable salt thereof Formula (1$^a$-h)

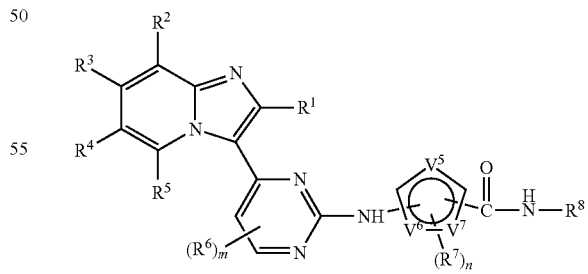

wherein m, n, $R^1$, $R^6$, $R^7$ and $R^8$ are as defined for various aspects of Formulae (I) and ($I^a$-a) above, wherein $R^2$, $R^3$, $R^4$, and $R^5$ are independently selected from groups $R^1$, and wherein $V^5$, $V^6$, and $V^7$ are ring atoms independently selected from N, O, S, and C and at least one of $V^5$, $V^6$, and $V^7$ is a non-carbon atom.

Non-limiting examples of such compounds include those of the following structures and pharmaceutically acceptable salts thereof:

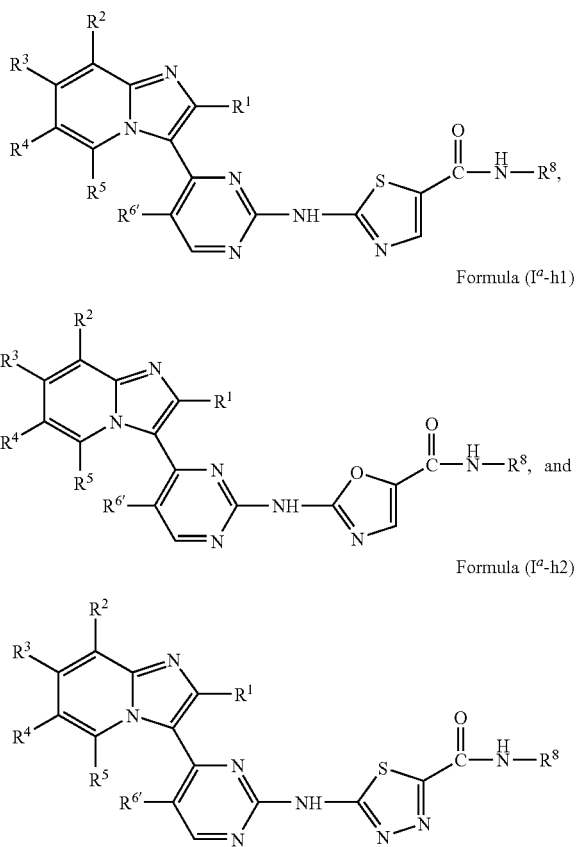

Formula (I<sup>a</sup>-h0)

Formula (I<sup>a</sup>-h1)

Formula (I<sup>a</sup>-h2)

wherein $R^{6'}$ is H or $R^6$. In specific examples, the substituents $R^1$, $R^3$, $R^4$, $R^5$, $R^{6'}$ and $R^8$ of compounds of Formulae (I$^a$-h0), (I$^a$-h1), and (I$^a$-h2) take on values having the same combination or pattern of substituents given in the table for Compounds b0-01 to b0-150.

In another embodiment, the invention provides a compound of Formula (I$^b$) and a pharmaceutically acceptable salt thereof:

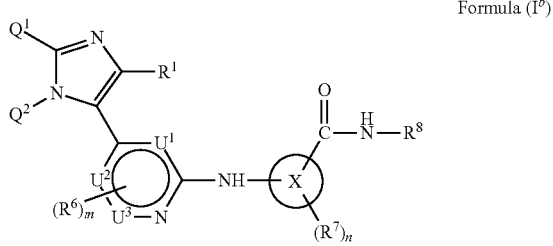

Formula (I$^b$)

wherein $Q^1$, $Q^2$, $R^1$, $R^6$, $R^7$, $R^8$, $U^1$, $U^2$, $U^3$, and X are as defined above for various aspects of Formula (I). In one aspect, Formula (I$^b$) represents compounds of Formula (I) where at least $U^4$ is a nitrogen.

In an embodiment of Formula (I$^b$), $R^1$ and substituents on the cyclic moiety formed by $Q^1$ and $Q^2$ are independently selected from the group consisting of H, methyl, ethyl, propyl, chloro, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, morpholinylmethyl, morpholinylethoxy, imidazolylmethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidinylmethyl and pyrrolidinylethoxy; $R^6$ is halo, hydroxy, alkyl or haloalkyl; m is 0 or 1; $R^7$ is fluoro, chloro, bromo, or methyl; n is 0, 1 or 2; and $R^8$ is hydroxy, aryl or heteroaryl, wherein aryl or heteroaryl are substituted with —NH$_2$ or —OH at a ring position adjacent to attachment of the —CONH-moiety, and $R^8$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

In one embodiment, the invention provides a compound of Formula (I$^b$-a) and a pharmaceutically acceptable salt thereof.

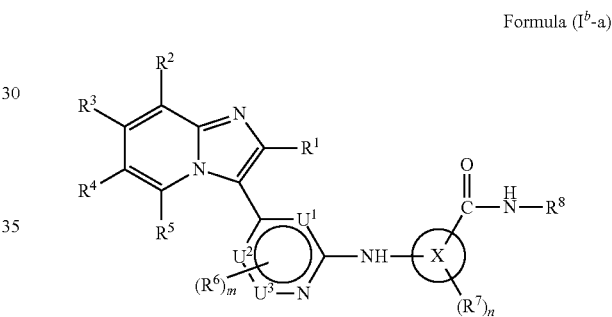

Formula (I$^b$-a)

wherein m, n, $U^1$, $U^2$, $U^3$, $R^1$, $R^6$, $R^7$, $R^8$, and X are as defined for various aspects of Formulae (I) and (I$^b$) above, and wherein $R^2$, $R^3$, $R^4$, and $R^5$ are independently selected from groups $R^1$. In various embodiments, X is phenyl and —CONH—$R^8$ is attached to the phenyl ring at a position para to the NH linker. Compounds of Formula (I$^b$-a) contain an imidazopyridine group substituted on the 6-membered nitrogen containing heteroaryl. In various embodiments, the nitrogen heteroaryl is a pyridine, a pyrimidine, a pyridazine, or a triazine as discussed below.

Imidazopyridine substituted nitrogen heteroaryls are shown in Formulae (I$^b$-a1), (I$^b$-a2), (I$^b$-a3), and (I$^b$-a4), where $R^{6'}$ is H or $R^6$, and $R^{7'}$ is H or $R^7$:

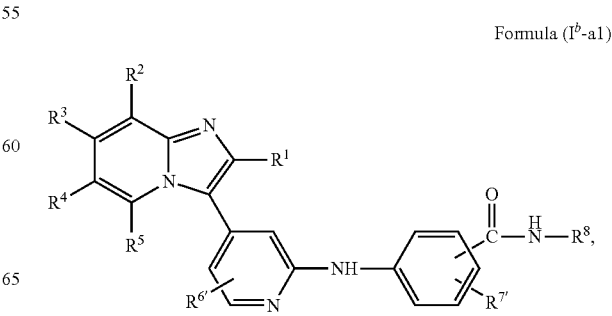

Formula (I$^b$-a1)

-continued

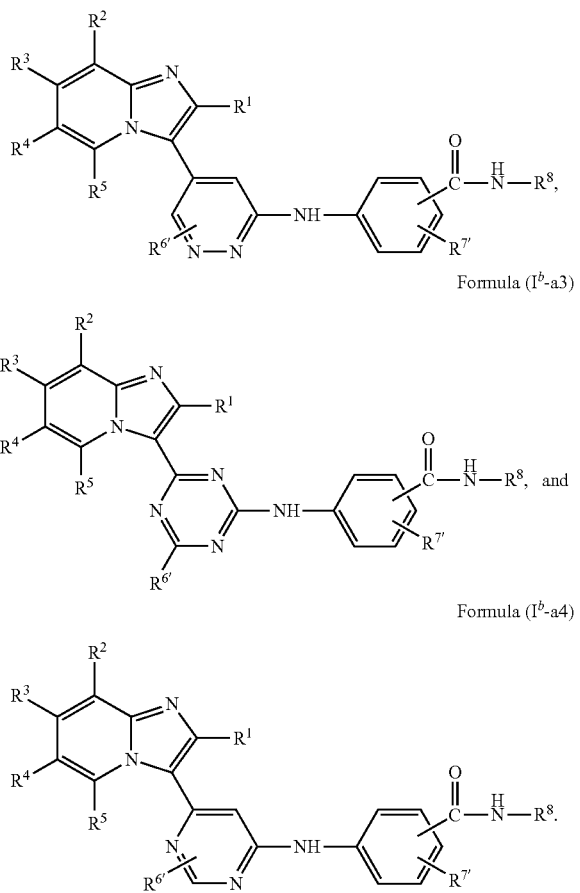

Formula (I<sup>b</sup>-a2)

Formula (I<sup>b</sup>-a3)

Formula (I<sup>b</sup>-a4)

In Formulae (I$^b$-a1), (I$^b$-a2), (I$^b$-a3), and (I$^b$-a4), the identity of groups R$^1$, R$^2$, R$^3$, R$^4$, R$^5$, R$^{6'}$, R$^{7'}$ and R$^8$ can be any of those described for the pyrimidine compounds of Formula (I$^a$-a). In particular, examples of compounds of Formulae (I$^b$-a1), (I$^b$-a2), (I$^b$-a3), and (I$^b$-a4) include those having the same combination or pattern of substituents given in the table for Compounds a-01 to a-222.

In many embodiments described, the substituent R$^9$ of Formula (I) is hydrogen. In other embodiments where R$^9$ is non-hydrogen, the invention provides a compound of Formula (I$^c$) and a pharmaceutically acceptable salt thereof:

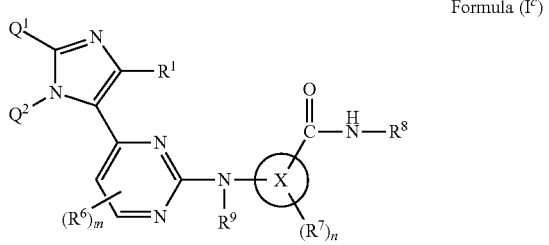

Formula (I$^c$)

wherein m, n, Q$^1$, Q$^2$, R$^1$, R$^6$, R$^7$, R$^8$, and X are as defined above for various aspects of Formula (I); and R$^9$ is a non-hydrogen substitutent selected from alkyl, haloalkyl, aminoalkyl, cycloalkyl, heterocyclyl, and aryl, wherein R$^9$ is optionally substituted by one or more D where such an optional substitution is chemically feasible.

In an embodiment of Formula (I$^c$), R$^1$ and substituents on the cyclic moiety formed by Q$^1$ and Q$^2$ are independently selected from the group consisting of H, methyl, ethyl, propyl, chloro, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, morpholinylmethyl, morpholinylethoxy, imidazolylmethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidinylmethyl and pyrrolidinylethoxy; R$^6$ is halo, hydroxy, alkyl or haloalkyl; m is 0 or 1; R$^7$ is fluoro, chloro, bromo, or methyl; n is 0, 1 or 2; R$^8$ is hydroxy, aryl or heteroaryl, wherein aryl or heteroaryl are substituted with —NH$_2$ or —OH at a ring position adjacent to attachment of the —CONH-moiety, and R$^8$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl; and R$^9$ is alkyl, haloalkyl, aminoalkyl, cycloalkyl, heterocyclyl, or aryl, wherein R$^9$ is optionally substituted by one or more D where such an optional substitution is chemically feasible.

Compounds of Formula I$^c$ include, but are not limited to, the following formulae:

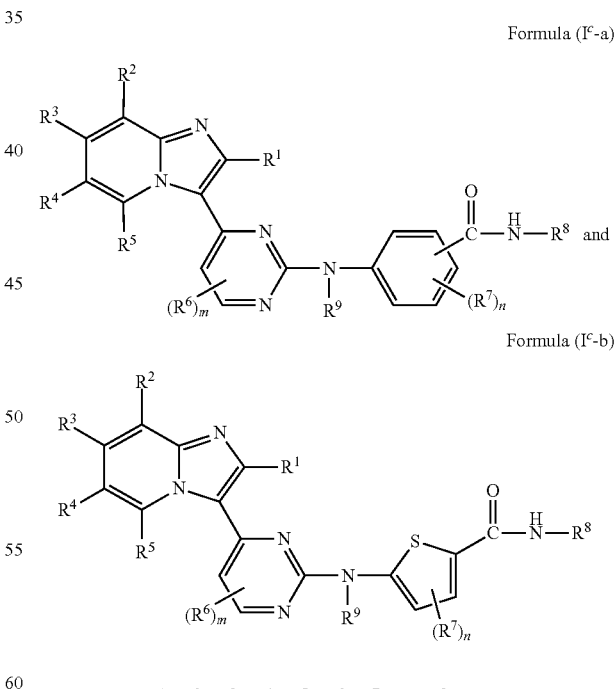

Formula (I$^c$-a)

Formula (I$^c$-b)

wherein n, R$^1$, R$^2$, R$^3$, R$^4$, R$^5$, R$^6$, R$^7$ and R$^8$ are as defined for various aspects of Formulae (I), (I$^a$) and (I$^b$) above, and wherein R$^2$, R$^3$, R$^4$, and R$^5$ are independently selected from groups R$^1$. Compounds of Formulae (I$^c$-a) and (I$^c$-b) contain an imidazopyridine group substituted on the 6-membered nitrogen containing heteroaryl, while X is phenyl and thiophene, respectively.

In Formulae (I^c-a) and (I^c-b), the identity of groups $R^1$, $R^2$, $R^3$, $R^4$, $R^5$, $R^6$, $R^7$ and $R^8$ can be any of those described for the pyrimidine compounds of Formula (I^a-a); and $R^9$ is alkyl, haloalkyl or aminoalkyl. In particular, examples of compounds of Formulae (I^c-a) and (I^c-b) include those having the same combination or pattern of substituents given in the table for Compounds a-01 to a-220 wherein in addition $R^9$ can be methyl, ethyl, trifluoromethyl or trifluoroethyl for each combination. Non-limiting examples include but are not limited to N-Hydroxy-4-[(4-imidazo[1,2-a]pyridin-3-yl-pyrimidin-2-yl)-(2,2,2-trifluoro-ethyl)-amino]-benzamide; and N-(2-Amino-phenyl)-4-[(4-imidazo[1,2-a]pyridin-3-yl-pyrimidin-2-yl)-(2,2,2-trifluoro-ethyl)-amino]-benzamide.

Compound Preparation

A compound of the present invention such as those of Formulae (I), (I^a), (I^b), and (I^c) can be prepared according to the schemes described below, but it shall be appreciated that modifications of the illustrated process or other process can also be used. Schemes A, B, and C illustrate a method to prepare a compound of Formula I from ketone compound 1 and guanidine compound 2.

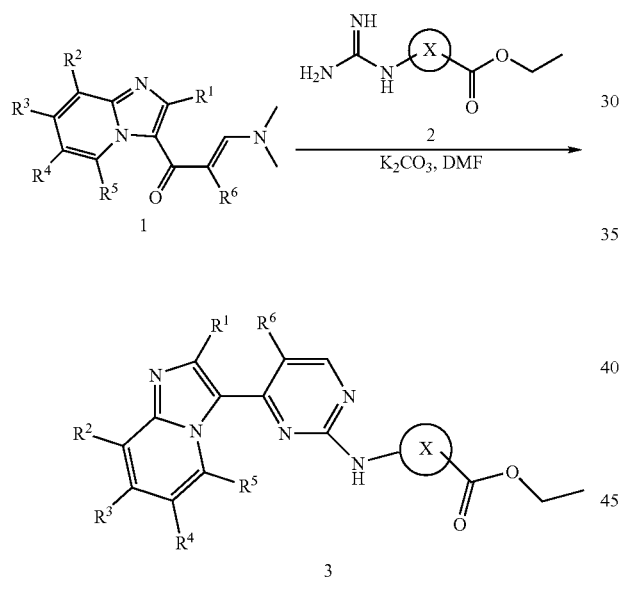

Scheme A

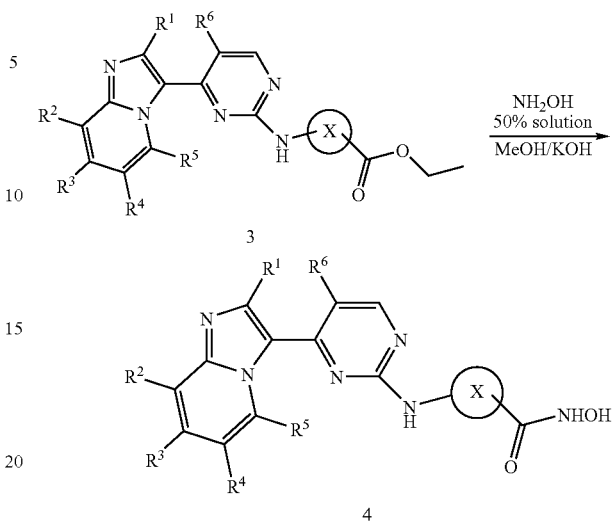

Scheme B

Ketone compound 1 is dissolved in a solvent such as dimethylformamide (DMF) to prepare a solution. Guanidine compound 2 containing an X aromatic group (for clarity the group X in the synthetic schemes is given without the $R^7$ group that is optionally attached in the compounds) is added to the solution, and the mixture is refluxed. The solid product is recovered and dried to yield compound 3, containing the pyrimidine ring formed from the reaction of compound 1 and compound 2.

In various embodiments, compound 3 is converted to hydroxamates or arylamides of Formula I. Scheme B below illustrates synthesis of hydroxamates and scheme C illustrates synthesis of arylamides (where the group $R^8$ is a substituted aryl ring) from intermediate compound 3.

In an illustrative synthesis, compound 3 is dissolved in a solvent such as a mixture of methanol and dichloromethane and the mixture is stirred to prepare a solution. $NH_2OH$ is added to the stirred solution slowly. After stirring, NaOH is added dropwise and brought to room temperature and stirred. The volatiles are evaporated under vacuum, diluted with water, and cooled. The pH of the solution is adjusted to about 7 using HCl and stirred. The resulting solid is filtered, washed with water and dried under vacuum to afford compound 4 containing a hydroxamate group —NHOH.

In Scheme C, the intermediate ester compound 3 is converted to an arylamide compound, illustrated by compound 5, wherein T stands for $NH_2$ or OH (attached to the phenyl ring at a position adjacent to the —NHC(O)—X— moiety) and $R^{10}$ is selected from amino, halo, alkyl, cycloalkyl, heterocyclyl, aryl, haloaryl and haloheterocyclyl.

Scheme C

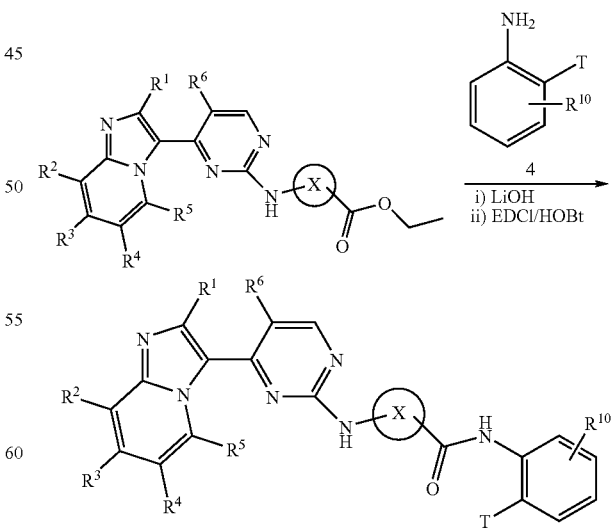

Ester compound 3 is converted to the free carboxylic acid, and is then reacted with substituted aniline compound 4 to yield an arylamide of formula 5. For example, LiOH is added to a stirred solution of 3 in a mixture of solvents. The volatiles are removed under vacuum, and the residue is diluted with water and acidified to about pH 3. The resulting solids are filtered, washed with water and dried under vacuum to furnish a carboxylic acid intermediate. The intermediate is dissolved in a solvent such as DMF and the mixture is stirred to prepare a solution. To the stirred solution is added 1-ethyl-3-(3'-dimethylaminopropyl)carbodiimide hydrochloride (EDCI) followed by hydroxybenzotriazole (HOBt). After stirring, diisopropyl ethyl amine is added and stirred. Then substituted aniline 4 (representative of substituted aryl or heteroaryl) is added, and the reaction mixture is stirred. The solvent is removed under vacuum. The residue is diluted with water and stirred. The resulting solids are filtered and purified through column chromatography to provide benzamide compound 5.

Ketone compound 1 can be synthesized by several pathways, depending on the substitution pattern of $R^1$, $R^2$, $R^3$, $R^4$, $R^5$, and $R^6$ and the availability of starting materials.

A first synthetic route begins with the reaction of an aminopyridine compound 2' with a chlorodiketone compound 1' to make an acyl imidazopyridine compound 3', which is condensed with a suitable reagent such as dimethylformamide dimethyl acetal (DMFDMA) to yield ketone compound 1. Typical starting materials and reaction conditions are illustrated in Scheme D.

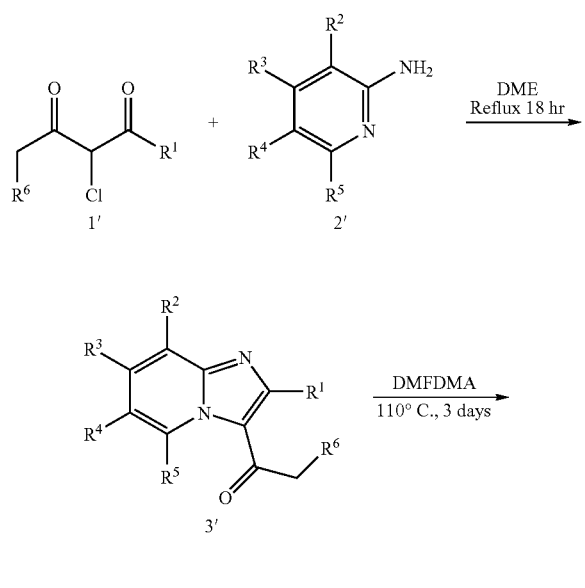

A second route to ketone compound 1 is given in Scheme E, where the imidazopyridine is formed first and is then acylated to give intermediate 3', which is converted to ketone compound 1 as shown in Scheme D.

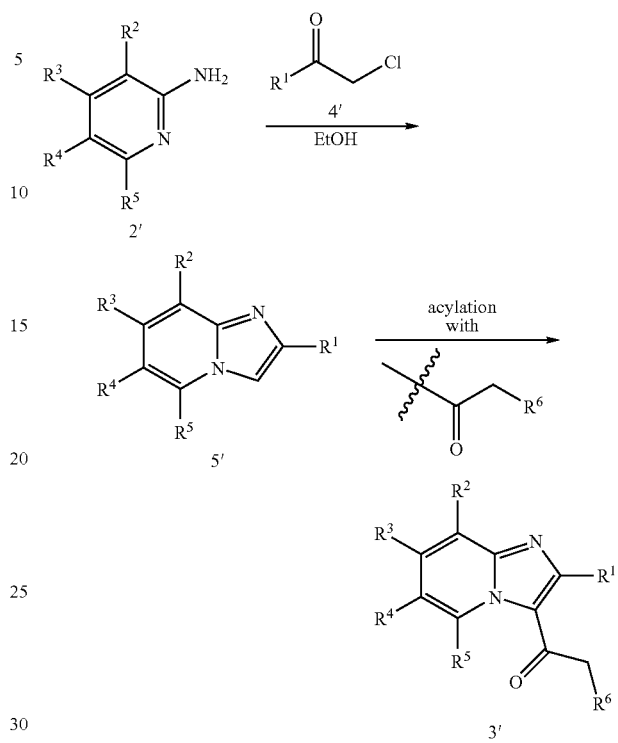

In Scheme E, the imidazo ring is elaborated first, and then subjected to acylation to add the ketone side chain and group $R^6$, both of which will become part of the pyrimidine in subsequent synthetic steps. In one sense, this affords more flexibility in the choices of $R^1$ and $R^6$ than does Scheme D. At the same time, the reaction of aminopyridine compound 2' with chloroketone or chloroaldehyde compound 4' occurs under similar conditions as in Scheme D, and is permissive of the same broad range of substituents $R^2$, $R^3$, $R^4$, and $R^5$ on the aminopyridine starting material compound 2'.

The reactions and starting materials for Schemes A, B, C, D, and E are generally known from the literature or represent applications of well known chemical transformations, such as Friedel-Crafts type acylation and the like. Illustrative conditions are also given in the Examples.

Guanidine intermediate compound 2 can be made according to Scheme F, illustrated for X as a phenyl ring and as a generic heteroaryl.

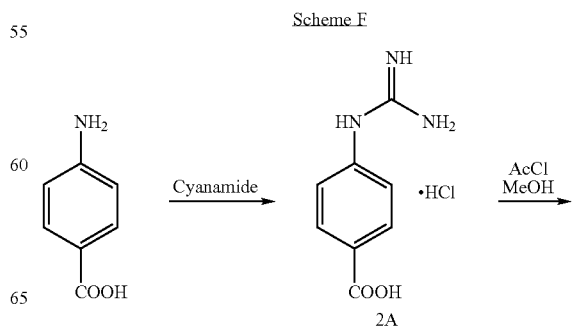

-continued

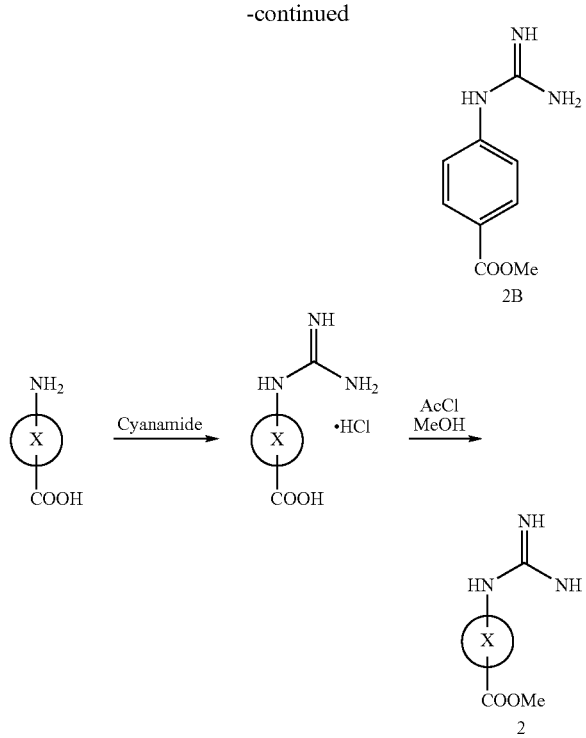

The compounds of the present invention inhibit histone deacetylase and/or CDK and are useful to treat or ameliorate diseases mediated directly or indirectly by HDAC and/or CDK. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, a pharmaceutically acceptable carrier. In various embodiments, the carrier comprises a diluent, adjuvant, excipient, other additive, or a combination of additive that separately or together provide a carrier in which the compositions can be formulated or administered. The composition can take any suitable form for the desired route of administration. Where the composition is to be administered orally, any suitable orally deliverable dosage form can be used, including, without limitation, tablets, capsules (solid- or liquid-filled), powders, granules, syrups and other liquids, elixirs, inhalants, troches, lozenges, and solutions. Injectable compositions or iv infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC and/or CDK. Examples of such active ingredients are, without limitation, agents to treat or inhibit cancer, Huntington's disease, cystic fibrosis, liver fibrosis, renal fibrosis, pulmonary fibrosis, skin fibrosis, Rheumatoid arthritis, diabetes, stroke, amyotrophic lateral sclerosis, cardiac hypertrophy, heart failure or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitor such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase 9 inhibitors, histone deacetylase 10 inhibitors, and histone deacetylase 11 inhibitors.

Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC and/or CDK since the compounds of the present invention have inhibitory activity against those molecules. In some embodiments, therefore, a method of the present invention is used in inhibiting or treating HDAC- and/or CDK-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as Rheumatoid arthritis, diabetes, acute and chronic neurological diseases such as stroke, amyotrophic lateral sclerosis, hypertrophy such as cardiac hypertrophy, heart failure including congestive heart failure, and Alzheimer's disease.

In an embodiment, a method according to the present invention is applied to a patient with cancer, cystic fibrosis, or pulmonary fibrosis. In some embodiments, a method using a compound according to the present invention is used to treat or inhibit fibrosis selected from the group consisting of cystic fibrosis, injection fibrosis, endomyocardial fibrosis, pulmonary fibrosis, mediastinal fibrosis, myelofibrosis, retroperitoneal fibrosis, progressive massive fibrosis and renal fibrosis. In some other embodiments, a method using a compound according to the present invention is used to treat or inhibit a cancer selected from bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES
The following examples further illustrate the invention.
Examples 1 and 2
Example 1
N-Hydroxy-4-(4-(2-methylimidazo[1,2-a]pyridin-3-yl)-pyrimidin-2-ylamino)-benzamide
Example 2
N-(2-Amino-phenyl)-4-(4-(2-methylimidazo[1,2-a]pyridin-3-yl)-pyrimidin-2-ylamino)-benzamide
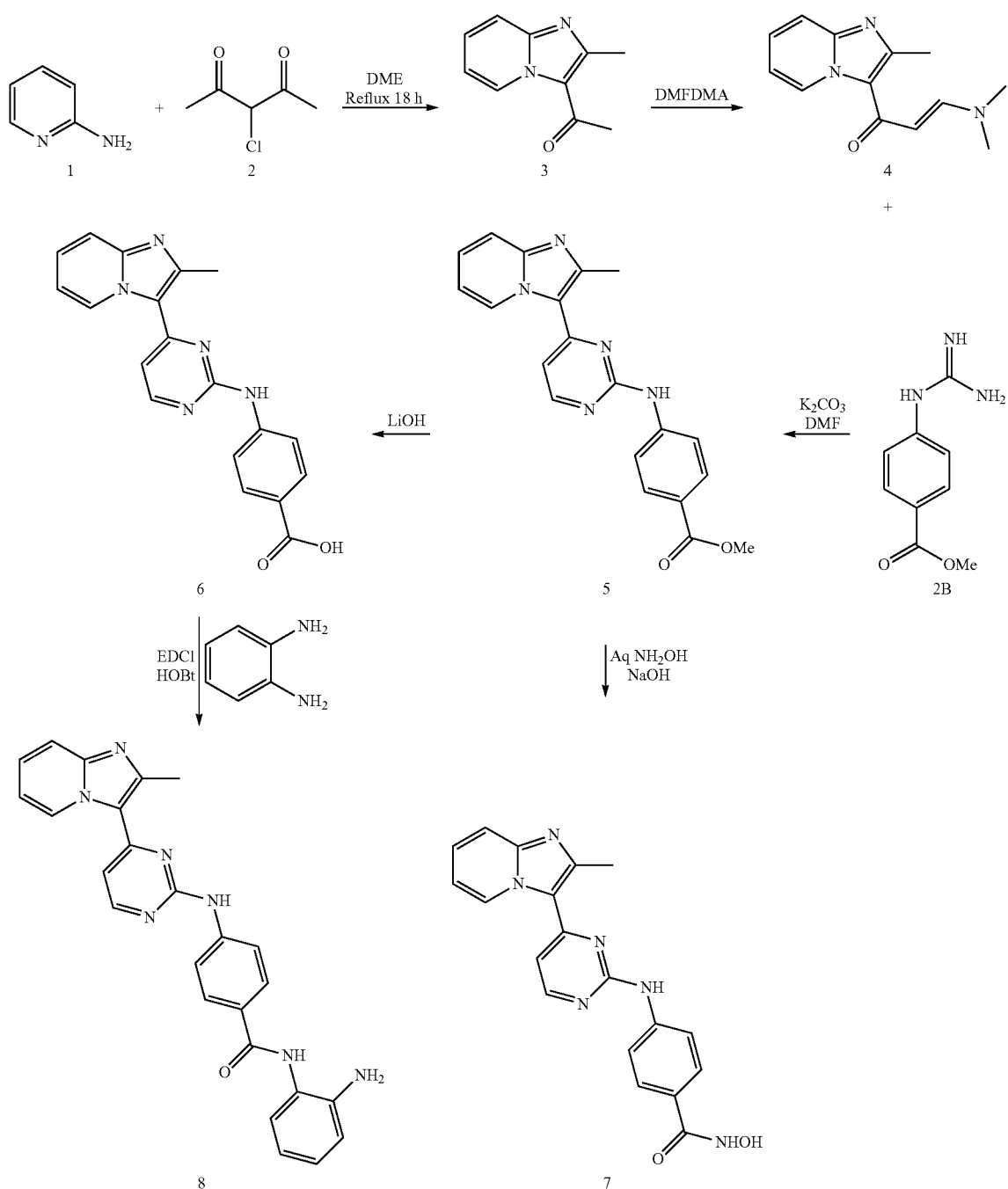
Example 2 (Compound I<sup>a</sup>-a-29)    Example 1 (Compound I<sup>a</sup>-a-25)

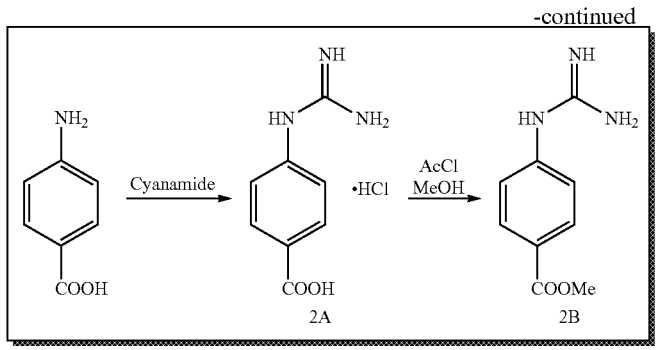

Preparation of Intermediate (hereinafter "Int") 4: Int-3 (2.0 g, 11.4 mmol) in DMFDMA (8 mL) was stirred at 110° C. for 3 days under inert condition. The reaction mixture was cooled to room temperature, diluted with ether (25 mL) and stirred for 30 minutes. The precipitated solid was filtered, washed with ether (2×10 mL), and dried under vacuum to obtain pure Int-4 (1.0 g, 36%).

Preparation of Int-2B: To a stirred suspension of 4-aminobenzoic acid (50 g, 0.364 mole) in a mixture of concentrated HCl/water (46 mL/283 mL) was added cyanamide (35 g, 0.839 mole) at room temperature. The reaction mixture was heated at 100° C. for 6 hours. The reaction mixture was then allowed stand at room temperature (without stirring) for 16 hours. The precipitated solid was filtered and washed with water (100 mL). The solid was taken in aqueous $K_2CO_3$ solution (30 g in 400 mL of water) and stirred for 30 minutes. The solid was filtered, washed with water (2×50 mL) and dried under vacuum to provide Int-2A (35 g, 53%) as white solid. $^1$H NMR (200 MHz, dmso-$d_6$): δ 8.40-8.21 (bs, 2H), 7.93 (d, J=8.4 Hz, 2H), 7.18 (d, J=8.4 Hz, 2H). Mass (m/z): 180.1 [M$^+$+1]. To a stirred suspension of Int-2A (35 g, 195.5 mmol) in methanol (350 mL) was added acetyl chloride (35 mL, 490 mmol) dropwise at 0° C. under inert atmosphere over a period of 20 minutes. The reaction mixture was stirred at room temperature for 16 hours. After consumption of starting material (by thin layer chromatography (TLC)), the reaction mixture was neutralized using solid $NaHCO_3$ at 0° C. Solid (excess $NaHCO_3$) was filtered and filtrate was evaporated under vacuum to get crude compound. The crude compound was washed with EtOAc (100 mL) to afford pure Int-2B (35 g, 92%) as white solid. $^1$H NMR (200 MHz, dmso-$d_6$): δ 8.45-8.23 (bs, 2H), 7.98 (d, J=8.4 Hz, 2H), 7.34 (d, J=8.8 Hz, 2H), 3.83 (s, 3H). Mass (m/z): 194.1 [M$^+$+1].

Preparation of Int-5: To a stirred solution of Int-4 (1.2 g, 5.2 mmol) and Int-2B (3.0 g, 15 mmol) in DMF (12 mL) under inert condition was added $K_2CO_3$ (2.16 g, 15 mmol) and the mixture was stirred overnight at 100° C. The reaction mixture was cooled to room temperature, diluted with water (50 mL) and stirred for 30 minutes. The precipitated solid was filtered, washed with water and dried under vacuum to obtain crude compound which was purified by column chromatography using MeOH:dichloromethane (DCM) (2:98) to afford pure Int-5 (0.8 g, 44%).

Preparation of Compound 7: To a stirred solution of Int-5 (0.6 g, 1.67 mmol) in MeOH: DCM (42 mL, 5:2) was slowly added aqueous hydroxylamine (50 wt % solution) (12 mL) at 0° C. and stirred for 10 minutes. Then aqueous NaOH solution (0.48 g in 3 mL water) was added and stirring continued at room temperature for 3 hours. The reaction mixture was concentrated under reduced pressure. The residue was diluted with water (10 mL) and pH was adjusted to about 7.0 using 2 N HCl at 0° C. The precipitated solid was filtered, washed with water (2×5 mL) and dried under vacuum to afford pure Compound 7 (0.32 g, 53%). $^1$H NMR (200 MHz, dmso-$d_6$): δ 11.0 (brs, 1H), 9.95 (s, 1H), 9.77 (d, J=6.6 Hz, 1H) 8.89 (brs, 1H), 8.56 (d, J=5.6 Hz, 1H), 7.82-7.47 (m, 5H), 7.44 (t, J=7.0 Hz, 1H), 7.15 (d, J=5.6 Hz, 1H), 7.0 (t, J=7.0 Hz, 1H), 2.65 (s, 3H); $^{13}$C NMR (125 MHz, dmso-$d_6$): 164.1, 159.1, 157.8, 156.7, 147.1, 145.4, 143.1, 128.4, 127.5, 126.7, 125.2, 118.1, 117.4, 116.1, 112.9, 109.6, 16.8. Mass (m/z): 361 (M$^+$+1), (MP: 201° C.).

Preparation of Compound 8: To a stirred suspension of Int-5 (0.6 g, 1.6 mmol) in methanol:tetrahydrofuran (THF): water (2:2:1) (15 mL) was added LiOH, $H_2O$ (0.21 g, 5 mmol) and stirred at room temperature for 18 hours. The reaction mixture was concentrated under reduced pressure, diluted with water (10 mL) and acidified with 3 N HCl to about pH 6 and stirred for 30 minutes. The precipitated solid was filtered, washed with water (2×10 mL) and dried under vacuum to afford pure Int-6 (0.45 g, 78%). $^1$H NMR (200 MHz, dmso-$d_6$): δ 2.72 (s, 3H), 7.24 (b, J=5.0 Hz, 1H), 7.33 (t, J=6.7 Hz, 1H), 7.77-7.89 (m, 6H), 8.68 (d, J=5.6 Hz, 1H), 9.81 (d, J=6.8 Hz, 1H) and 10.2 (s, 1H). Mass (m/z): 345 (M$^+$+1). To a stirred solution of Int-6 (0.6 g, 1.7 mmol) in DMF at 0° C. were added HOBt (0.23 g, 1.7 mmol), EDCI (0.73 g, 3.8 mmol), N,N-diisopropylethylamine (DIPEA) (0.8 mL, 4.3 mmol) and o-phenylene diamine (0.187 g, 1.7 mmol) sequentially. The mixture was stirred under inert atmosphere at room temperature for 16 hours. The reaction mixture was poured into ice water (80 mL) and stirred for 10 minutes. The precipitated solid was filtered and washed with water (3×10 mL), dried under vacuum, and finally purified by column chromatography using MeOH:DCM (5:95) to afford pure Compound 8 (0.25 g, 33%). $^1$H NMR (200 MHz, dmso-$d_6$): 2.67 (s, 3H), 4.87 (bs, 2H), 6.63 (t, J=7.6 Hz, 1H), 6.77 (m, 1H), 6.94 (m, 1H), 7.05 (m, 1H), 7.15 (m, 2H), 7.45 (m, 1H), 7.65 (m, 1H), 7.88-7.93 (m, 4H), 8.59 (d, J=5.4 Hz, 1H), 9.53 (s, 1H), 9.80 (d, J=7.0 Hz, 1H) and 10.0 (s, 1H). $^{13}$C NMR (125 MHz, dmso-$d_6$): δ 16.6, 109.7 112.8, 116.1, 116.2, 116.2 117.5, 117.8, 123.6, 126.1, 126.5, 126.6, 127.0, 128.2, 128.4, 142.9 143.3, 145.5, 147.1, 156.8, 157.9, 159.2 and 164.7. Mass (m/z): 435 (M$^+$+1), MP: 262.1° C.

Examples 3 and 4

Example 3

N-Hydroxy-3-[4-(2-methyl-imidazo[1,2-a]pyridin-3-yl)-pyrimidin-2-ylamino]-benzamide

Example 4

N-(2-Amino-phenyl)-3-[4-(2-methyl-imidazo[1,2-a]pyridin-3-yl)-pyrimidin-2-ylamino]-benzamide

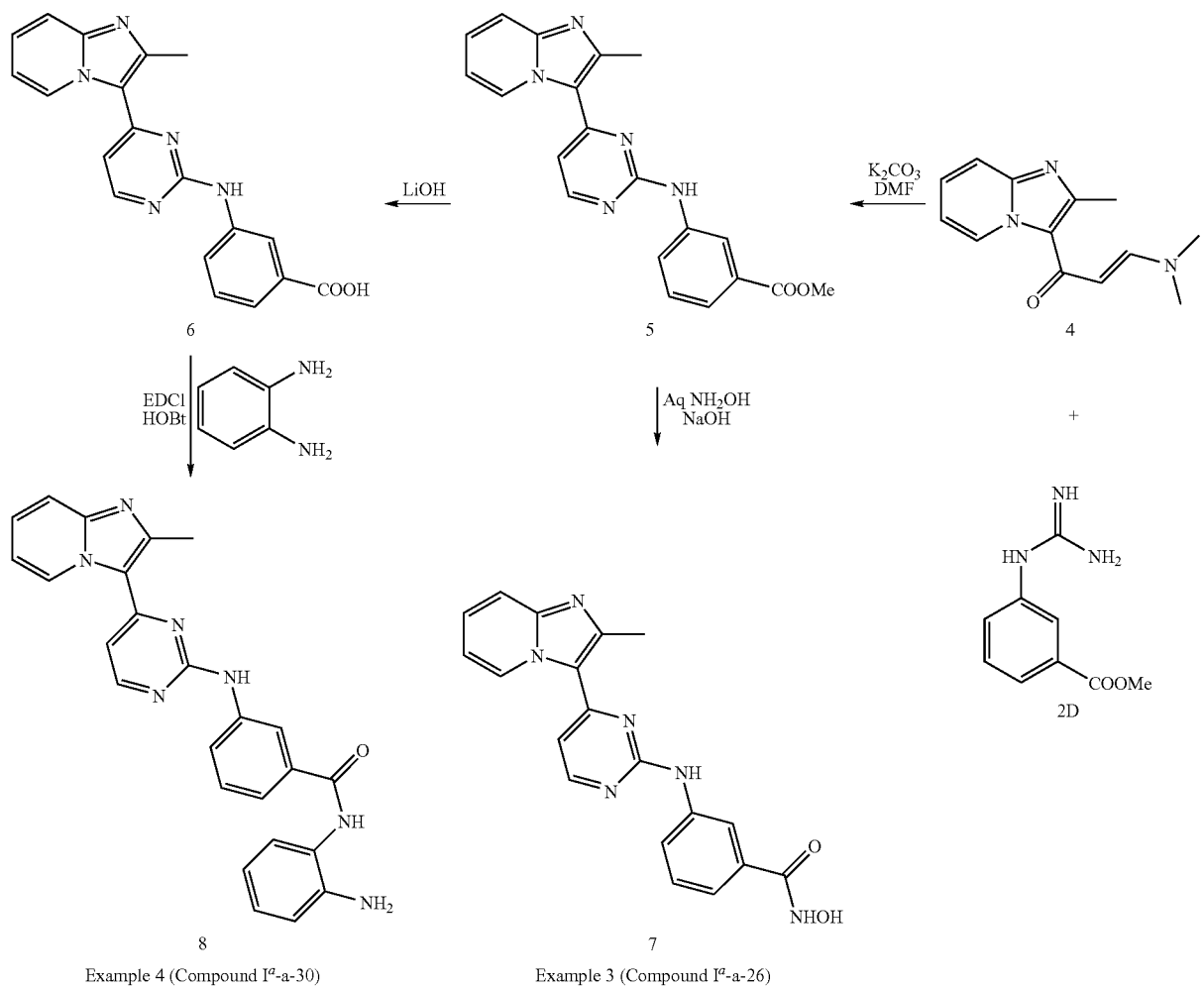

Example 4 (Compound I$^a$-a-30)    Example 3 (Compound I$^a$-a-26)

Preparation of Compound 7: To a stirred solution of Int-4 of Example 1 (1.2 g, 5.2 mmol) and Int-2B (3.0 g, 15 mmol) in DMF (12 mL) under inert condition was added $K_2CO_3$ (2.16 g, 15 mmol) and the mixture was stirred overnight at 100° C. The reaction mixture was then cooled to room temperature, diluted with water (60 mL), and stirred for 15 minutes. The precipitated solid was filtered, washed with water, and dried under vacuum to obtain crude compound, which was purified by column chromatography using MeOH:DCM (2:98) to afford pure Int-5 (0.7 g, 38%). To a stirred solution of Int-5 (0.6 g, 1.67 mmol) in MeOH:DCM (42 mL, 5:2) was added aqueous hydroxyl amine (50 wt % solution) (12 mL) slowly at 0° C. and stirred for 10 minutes. Then aqueous NaOH solution (0.48 g in 3 mL water) was added and stirring continued at room temperature for 5 hours. The reaction mixture was concentrated under reduced pressure. The residue was diluted with water (10 mL) and the pH was adjusted to about 7.0 using 2 N HCl at 0° C. The precipitated solid was filtered, washed with water (2×5 mL) and dried under vacuum to afford pure Compound 7 (Example 3, 0.28 g, 46%). $^1$H NMR (200 MHz, dmso-d$_6$): δ 11.2 (brs, 1H), 9.80-9.75 (m, 2H), 9.18 (brs, 1H), 8.53 (d, J=5.2 Hz, 1H), 8.10 (s, 1H), 7.90-7.89 (m, 1H), 7.64-7.60 (m, 1H), 7.45-7.33 (m, 3H), 7.11 (d, J=5.0 Hz, 1H), 7.01 (t, J=7.0 Hz, 1H), 2.65 (s, 3H); $^{13}$C NMR (125 MHz, dmso-d$_6$): 164.3, 159.4, 157.8, 156.8, 147.1, 145.4, 140.4, 133.4, 128.4, 126.7, 121.9, 119.8, 118.5, 117.3, 116.0, 112.9, 109.1 and 16.9; Mass (m/z): 361 (M$^+$+1), MP: 191.9° C.

Preparation of Compound 8: To a stirred suspension of Int-5 (1.6 g, 4.45 mmol) in methanol:THF:water (40 ml, 2:2:1) was added LiOH, H$_2$O (0.561 g, 13.3 mmol) and stirred at room temperature for 18 hours. The reaction mixture was concentrated under reduced pressure, diluted with water (20 mL), acidified with 3N HCl to about pH 6, and stirred for 30 minutes. The precipitated solid was filtered, washed with water (2×20 mL), and dried under vacuum to afford pure Int-6 (1.2 g, 80%). To a stirred solution of Int-6 (0.4 g, 1.1 mmol) in DMF (8 mL) at 0° C. were added HOBt (0.155 g, 1.15 mmol), EDCI (0.488 g, 2.55 mmol), DIPEA (0.5 mL, 2.7 mmol) and o-phenylene diamine (0.125 g, 1.15 mmol) sequentially. The mixture was stirred under inert atmosphere at room temperature for 16 hours. The reaction mixture was poured into ice water (60 mL) and stirred for 10 minutes. The precipitated solid was filtered and washed with water (3×10 mL) and dried under vacuum. The resulting material was finally purified by column chromatography using MeOH: DCM (5:95) to afford pure Compound 8 (Example 4, 0.23 g, 45%). $^1$H NMR (200 MHz, dmso-d$_6$): δ 2.66 (s, 3H), 4.87 (bs, 2H), 6.59 (t, J=6.8 Hz, 1H), 6.77 (d, J=6.6 Hz, 1H), 6.96 (q, 2H), 7.14 (m, 2H), 7.44 (m, 2H), 7.62 (m, 2H), 7.99 (d, J=8.0 Hz, 1H), 8.27 (s, 1H), 8.55 (d, J=5.5 Hz, 1H), 9.62 (s, 1H), 9.82 (m, 2H). $^{13}$C NMR (125 MHz, dmso-d$_6$): δ 16.8, 109.1, 112.8, 116.1, 116.2, 116.3, 117.4, 119.2, 120.7, 122.2, 123.4, 126.2, 126.3, 126.6, 128.3, 135.3, 140.4, 142.8, 145.5, 147.1, 156.8, 157.9, 159.5 and 165.5. Mass (m/z): 436.0 (M$^+$+1), MP: 234° C.

Examples 5 and 6

Example 5

N-Hydroxy-4-(4-imidazo[1,2-a]pyridin-3-yl-pyrimidin-2-ylamino)-benzamide

Example 6

N-(2-Amino-phenyl)-4-(4-imidazo[1,2-a]pyridin-3-yl-pyrimidin-2-ylamino)-benzamide Preparation of Compound 5: To a solution of imidazo[1,2-a]pyridine (8.0 g, 67.7 mmol) in carbon disulfide (80 mL), was added powdered anhydrous AlCl$_3$ (22.4 g, 169.4 mmol) carefully at 0° C. under inert atmosphere. After being stirred for 30 minutes at room temperature, the reaction mixture was refluxed gently and acetic anhydride (6.8 mL, 67.7 mmol) was added to the reaction mixture drop wise over a period of 30 minutes (at reflux temperature). The reaction mixture was continued at reflux temperature for 5 hours. Carbon disulfide was removed under vacuum. The residue was quenched with ice water (200 mL). The aqueous layer was extracted with DCM (2×200 mL). The organic extracts were washed with saturated NaHCO$_3$ solution (2×100 mL), water (100 mL), and brine (100 mL). The organic layer was dried over anhydrous Na$_2$SO$_4$ and evaporated under vacuum to afford Int-1 (2.3 g, 22%) as brown solid. $^1$H NMR (200 MHz, CDCl$_3$): δ 9.67 (d, J=7 Hz, 1H), 8.36 (bs, 1H), 7.79 (d, J=8.8 Hz, 1H), 7.54-7.46 (m, 1H), 7.13-7.06 (m, 1H), 2.61 (s, 3H). Mass (m/z): 148 [M$^+$+1]. A solution of Int-1 (5 g, 31.2 mmol) in DMFDMA (25 mL) was stirred at reflux temperature for 36 hours under N$_2$ atmosphere. After consumption of starting material as monitored by TLC, the reaction mixture was cooled to room temperature and diluted with ether (100 mL) and stirred for 15 minutes. The precipitated solid was filtered, washed with ether (2×10 mL) and dried under vacuum to provide Int-2 (4.7 g, 70%) as brown solid. $^1$H NMR (200 MHz, CDCl$_3$): δ 9.82 (d, J=6.8 Hz, 1H), 8.22 (s, 1H), 7.81 (d, J=12.2 Hz, 1H), 7.71 (d, J=8.8 Hz, 1H), 7.37 (t, J=7.4 Hz, 1H), 6.97 (t, J=6.2 Hz,

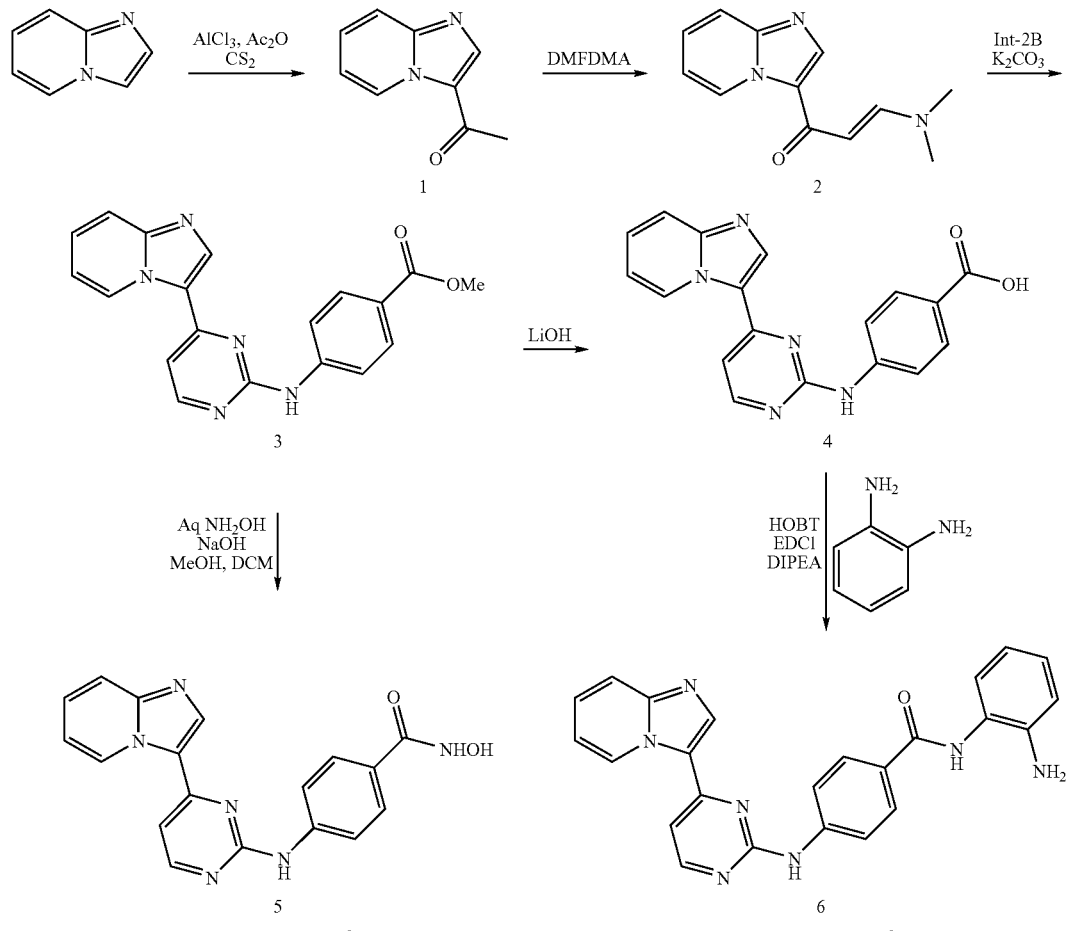

Example 5 (Compound I$^a$-a-01)     Example 6 (Compound I$^a$-a-05)

1H), 5.71 (d, J=12.2 Hz, 1H), 3.06 (bs, 6H). Mass (m/z): 216.0 [M⁺+1]. To a solution of Int-2 (1.3 g, 6.0 mmol) in DMF (10 mL) was added Int-2B (3.5 g, 18.1 mmol) followed by K$_2$CO$_3$ (2.5 g, 18.1 mmol) at room temperature under inert atmosphere. Resulting mixture was heated at 100° C. for 16 hours. Reaction mixture was cooled to room temperature, poured into ice water (70 mL) and stirred for 15 minutes. The precipitated solid was filtered, washed with water (10 mL) and dried under vacuum to afford Int-3 (1.1 g, 55%) as light brown solid. $^1$H NMR (200 MHz, dmso-d$_6$): δ 10.11-10.05 (m, 2H), 8.64 (s, 1H), 8.52 (d, J=5.5 Hz, 1H), 7.85-7.63 (m, 5H), 7.46 (t, J=7.0 Hz, 1H), 7.32 (d, J=5.3 Hz, 1H), 7.07 (d, J=6.2 Hz, 1H), 3.75 (s, 3H). Mass (m/z): 345.9 [M⁺+1]. To a solution of Int-3 (0.7 g, 2 mmol) in methanol (35 mL) and DCM (14 mL) was added hydroxylamine 50 wt % solution in water (14 mL) at 0° C. After being stirred for 10 minutes at same temperature, NaOH solution (0.56 g in 3.5 mL of water) was added to reaction mixture at 0° C. The reaction mixture was allowed to warm up to room temperature and stirred for 5 hours. Volatiles were evaporated under vacuum, resulting residue was neutralized (about pH 7) using 2 N HCl at 0° C. and stirred for 10 min. The precipitated solid was filtered, washed with water (2×5 mL) and dried under vacuum. This crude material was purified by preparative high performance liquid chromatography (HPLC) (acetonitrile (ACN):Water: 0.1% trifluoroacetic acid (TFA)) to afford pure Compound 5 (0.22 g, 31%) as its TFA salt as an off white solid. $^1$H NMR (200 MHz, dmso-d$_6$): δ 11.05 (bs, 1H), 10.2 (d, J=6.6 Hz, 1H), 10.07 (s, 1H), 8.92 (bs, 1H), 8.59 (d, J=5.6 Hz, 1H), 7.96 (d, J=8.8 Hz, 1H), 7.86-7.72 (m, 5H), 7.52 (d, J=5.2 Hz, 1H), 7.39 (t, J=6.6 Hz, 1H). $^{13}$C NMR (120 MHz, dmso-d$_6$): δ 164.4, 159.0, 158.5, 158.2, 158.0, 156.0, 142.7, 132.1, 131.0, 130.2, 127.6, 125.7, 121.7, 118.4, 115.9, 114.9, 108.2. Mass (m/z): 347.2 [M⁺+1].

Preparation of Compound 6: To a solution of Int-3 (0.5 g, 1.4 mmol) in methanol (6 mL) and THF (6 mL) was added lithium hydroxide (0.18 g, 4.3 mmol) at room temperature followed by water (3 mL). The resulting mixture was stirred at room temperature for 16 hours. Solvent was evaporated under vacuum. The resulting mixture was diluted with water (10 mL) and acidified to about pH 6 using 3 N HCl at 0° C. The precipitated solid was filtered, washed with water (2×5 mL), and dried under vacuum to provide Int-4 (0.42 g, 89%) as solid. $^1$H NMR (200 MHz, dmso-d$_6$): δ 10.3 (d, J=6.6 Hz, 1H), 10.2 (s, 1H), 9.00 (bs, 1H), 8.62 (d, J=5.0 Hz, 1H), 8.01-7.77 (m, 7H), 7.55 (d, J=5.2 Hz, 1H), 7.44 (d, J=7.0 Hz, 1H). Mass (m/z): 332.1 [M⁺+1]. MP: 218.6° C. To a solution of Int-4 (0.45 g, 1.3 mmol) in DMF (5 mL) were added HOBt (0.18 g, 1.3 mmol), EDCI (0.57 g, 2.9 mmol), DIPEA (0.6 mL, 3.3 mmol) at 0° C. under inert atmosphere. After being stirred for 10 minutes at same temperature, o-phenylenediamine (0.14 g, 1.3 mmol) was added to the reaction mixture. The reaction mixture was allowed to warm to room temperature and stirring was continued for 16 hours. Reaction mixture was poured into ice water (50 mL) and stirred for 10 minutes. The resulting precipitated solid was filtered, washed with water (3×5 mL) and dried under vacuum. Crude material was purified over silica gel column chromatography eluting with 4% MeOH/DCM to afford Compound 6 (0.19 g, 33%) as off white solid. $^1$H NMR (200 MHz, dmso-d$_6$): δ 10.1 (d, J=7.0 Hz, 1H), 10.0 (s, 1H), 9.54 (s, 1H), 8.64 (s, 1H), 8.52 (d, J=5.4 Hz, 1H), 8.01-7.88 (m, 4H), 7.80 (d, J=9.2 Hz, 1H), 7.55-7.47 (m, 2H), 7.19 (d, J=6.8 Hz, 2H), 6.96 (t, J=7.47.0 Hz, 1H), 6.80 (d, J=7.6 Hz, 1H), 6.60 (t, J=7.2 Hz, 1H), 4.88 (bs, 2H). $^{13}$C NMR (200 MHz, dmso-d$_6$): δ 164.8, 159.1, 157.2, 156.9, 147.9, 143.3, 143.0, 138.7, 129.3, 128.5, 127.1, 126.9, 126.5, 126.4, 126.1, 123.6, 120.9, 117.9, 117.3, 116.2, 116.0, 113.7, 107.8. Mass (m/z): 314.0 [M⁺+1]. MP: 238.5° C.

Examples 7 and 8

Example 7

N-Hydroxy-3-(4-imidazo[1,2-a]pyridin-3-yl-pyrimidin-2-ylamino)-benzamide

Example 8

N-(2-Amino-phenyl)-3-(4-imidazo[1,2-a]pyridin-3-yl-pyrimidin-2-ylamino)-benzamide

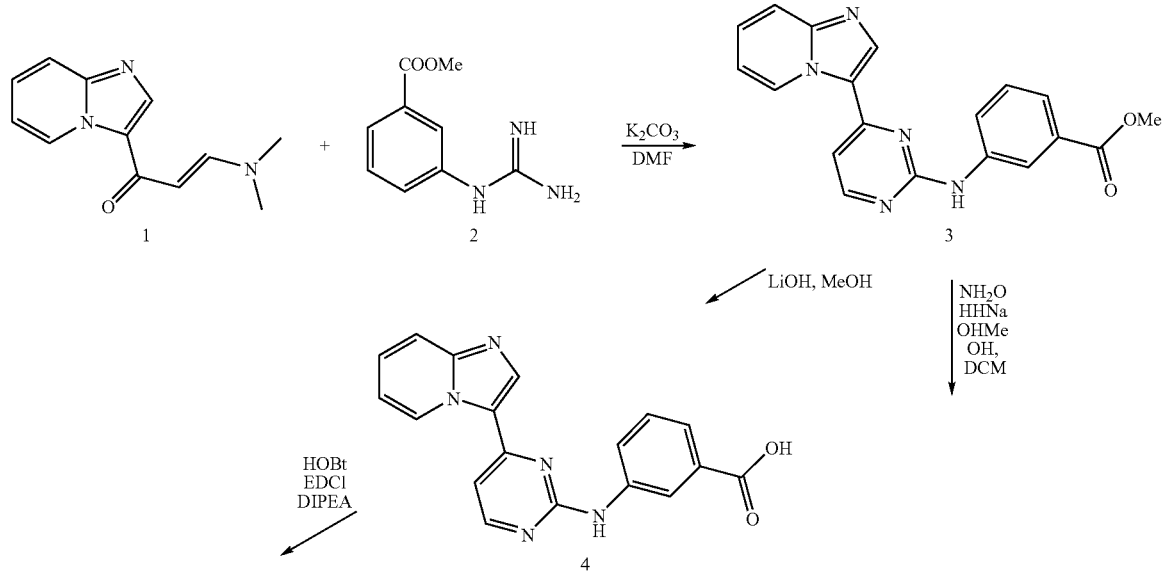

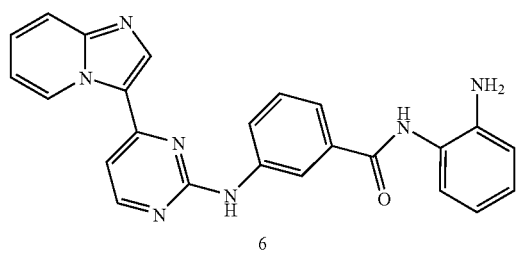

Example 8 (Compound I$^a$-a-06)

Example 7 (Compound I$^a$-a-02)

Preparation of Compound 5: To a solution of Int-1 (2.5 g, 11.6 mmol) in DMF (20 mL) was added Int-2 (6.7 g, 34.8 mmol) followed by K$_2$CO$_3$ (4.8 g, 34.8 mmol) at room temperature under inert atmosphere. The resulting mixture was heated at 100° C. for 16 hours. After consumption of starting precursor (by TLC), the reaction mixture was cooled to room temperature, poured into ice water (200 mL), and stirred for 15 minutes. The precipitated solid was filtered, washed with water (3×10 mL), dried under vacuum and purified by column chromatography (SiO$_2$) using 3% MeOH:DCM to afford Int-3 (1.2 g, 30%) as light brown solid. $^1$H NMR (200 MHz, dmso-d$_6$): δ 10.1 (d, J=6.6 Hz, 1H), 9.93 (s, 1H), 8.64 (s, 1H), 8.49 (d, J=5.2 Hz, 1H), 8.39 (s, 1H), 8.09 (d, J=8.8 Hz, 1H), 7.80 (d, J=9.0 Hz, 1H), 7.61 (m, 4H), 7.10 (t, J=7.0 Hz, 1H), 3.84 (s, 3H). Mass (m/z): 346 [M$^+$+1]. To a solution of Int-3 (0.6 g, 1.7 mmol) in methanol (10 mL) and THF (10 mL) was added LiOH (0.21 g, 5.2 mmol) at room temperature followed by water (5 mL). The resulting mixture was stirred at room temperature for 16 hours. Upon completion of starting material, solvent was evaporated under vacuum, diluted with water (10 mL) and acidified to about pH 6 using 3N HCl at 0° C. The precipitated solid was filtered, washed with water (2×5 mL) and dried under vacuum to provide Int-4 (0.50 g, 87%) as solid. $^1$H NMR (200 MHz, dmso-d$_6$): δ 10.1 (d, J=7.2 Hz, 1H), 9.98 (s, 1H), 8.68 (s, 1H), 8.49 (d, J=5.6 Hz, 1H), 8.33 (s, 1H), 7.92-7.80 (m, 3H), 7.71-7.57 (m, 2H), 7.50-7.38 (m, 2H), 7.23 (t, J=7.0 Hz, 1H). Mass (m/z): 332 [M$^+$+1]. To a solution of Int-3 (0.3 g, 0.86 mmol) in methanol (3.0 mL) and DCM (12 mL) was added hydroxylamine 50 wt % solution in water (9.0 mL) at 0° C. After being stirred for 10 minutes at the same temperature, aqueous NaOH solution (0.14 g, 3.4 mmol) in water (1.5 mL) was added to reaction mixture at 0° C. The reaction mixture was allowed to warm up to room temperature and was stirred for 24 hours. The volatiles were evaporated under vacuum. The resulting residue was neutralized using 2N HCl at 0° C. and stirred for 10 minutes. The precipitated solid was filtered, washed with water (2×5 mL) and dried under vacuum. Crude solid material was washed with 10% MeOH/DCM (10 mL) which afforded pure Compound 5 (0.18 g, 60%) as off white solid. $^1$H NMR (200 MHz, dmso-d$_6$): δ 10.1 (d, J=6.6 Hz, 1H), 9.75 (s, 1H), 8.62 (s, 1H), 8.45 (d, J=5.6 Hz, 1H), 8.07 (s, 1H), 7.84-7.73 (2H), 7.51-7.30 (m, 4H), 7.10 (t, J=7.0 Hz, 1H). $^{13}$C NMR (125 MHz, dmso-d$_6$): δ 163.9, 159.6, 157.3, 156.8, 147.8, 140.8, 138.5, 135.6, 129.4, 128.0, 126.8, 121.0, 120.8, 119.8, 118.3, 117.0, 113.7, 107.09, 107.05. Mass (m/z): 347 [M$^+$+1]. MP: 186.4° C.

Preparation of Compound 6: To a stirred suspension of Int-4 (0.50 g, 1.5 mmol) in DMF (8 mL) were added HOBt (0.2 g, 1.5 mmol), EDCI.HCl (0.63 g, 3.3 mmol) and DIPEA (0.65 mL, 3.7 mmol) at 0° C. under inert atmosphere. After being stirred for 10 minutes at the same temperature, o-phenylenediamine (0.16 g, 1.5 mmol) was added to the reaction mixture and stirring continued for 16 hours at room temperature. The reaction mixture was poured into ice water (50 mL) and stirred for 15 minutes at 0° C. The precipitated solid was filtered, washed with water (3×5 mL) and dried under vacuum. Crude material was purified over silica gel column chromatography eluting with 3% MeOH/DCM to afford Compound 6 (0.26 g, 41%) as off white solid. $^1$H NMR (200 MHz, dmso-d$_6$): δ 10.1 (d, J=6.6 Hz, 1H), 9.87 (s, 1H), 9.62 (s, 1H), 8.64 (s, 1H), 8.45 (d, J=5.4 Hz, 1H), 8.27 (s, 1H), 8.01 (d, J=7.4 Hz, 1H), 7.78 (d, J=9.2 Hz, 1H), 7.65 (d, J=7.6 Hz, 1H), 7.51-7.43 (m, 3H), 7.18-7.07 (m, 2H), 6.96 (t, J=8.0 Hz, 1H), 6.79 (d, J=8.0 Hz, 1H), 6.59 (t, J=7.8 Hz, 1H), 4.88 (bs, 2H). 13 NMR (125 MHz, dmso-d$_6$): 165.4, 159.4, 157.3, 156.8, 147.8, 142.8, 140.4, 138.6, 135.2, 129.3, 128.4, 126.8, 126.3, 126.2, 123.4, 122.2, 120.9, 120.8, 119.1, 117.2, 116.2, 116.1, 113.6, 107.3. Mass (m/z): 422.3 [M$^+$+1]. MP: 232.1° C.

Examples 9 and 10

Example 9

N-Hydroxy-4-[4-(2-methyl-7-trifluoromethyl-imidazo[1,2-a]pyridin-3-yl)-pyrimidin-2-ylamino]-benzamide Example 10

N-(2-Amino-phenyl)-4-[4-(2-methyl-7-trifluoromethyl-imidazo[1,2-a]pyridin-3-yl)-pyrimidin-2-ylamino]-benzamide

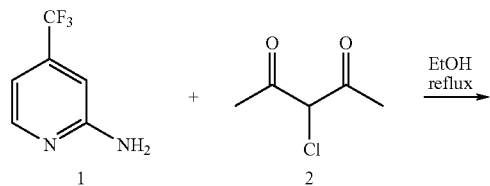

-continued

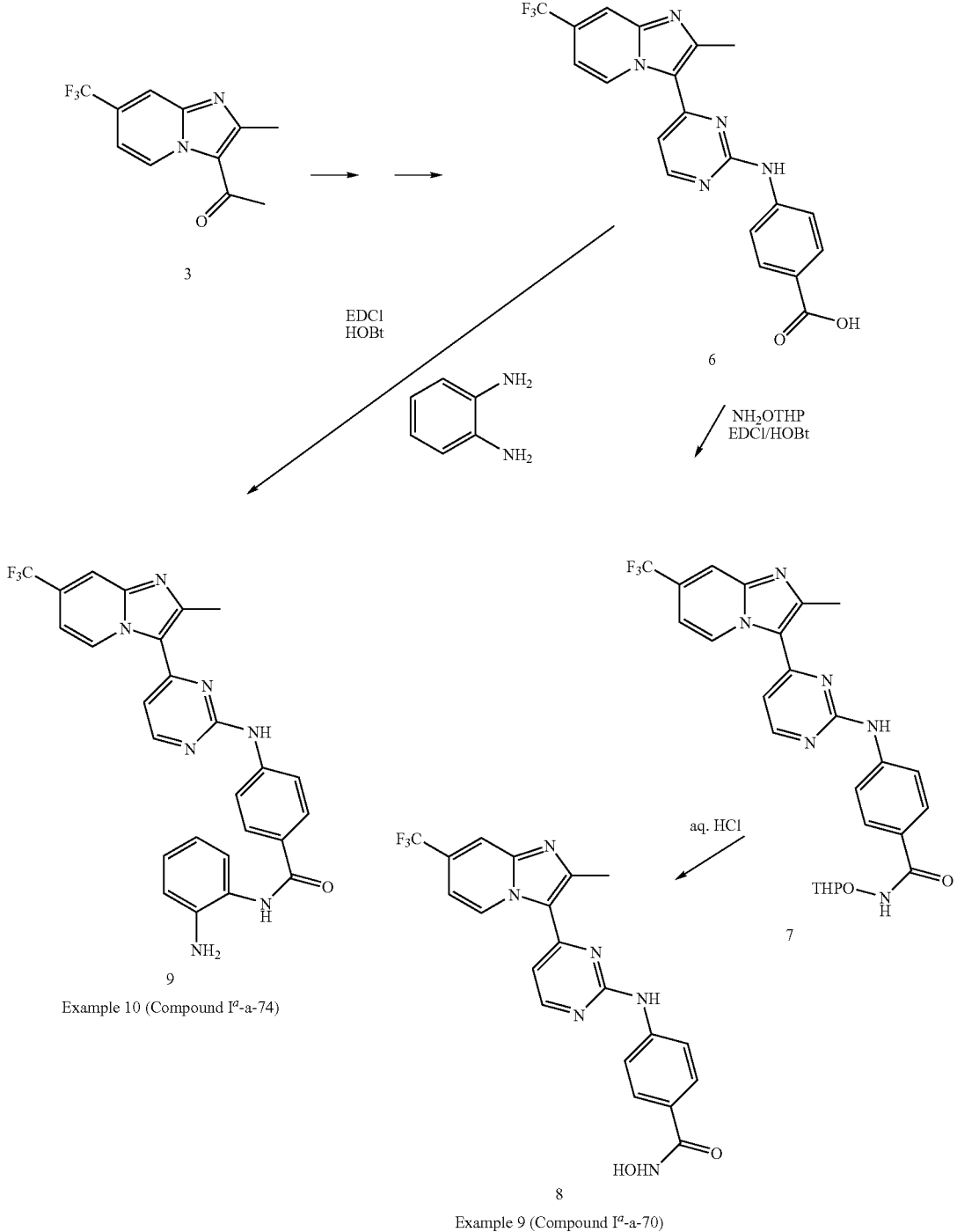

Example 10 (Compound I<sup>a</sup>-a-74)

Example 9 (Compound I<sup>a</sup>-a-70)

To a solution of Int-1 (1.4 g, 8.6 mmol) in ethanol (14 mL) was added Int-2 (1.15 mL, 10.37 mmol) at room temperature under inert atmosphere, and the reaction mixture was stirred at 80° C. for 16 hours. The reaction mixture was cooled to room temperature and concentrated under reduced pressure. The resulting residue was diluted with EtOAc and washed with 0.5 N HCl (10 mL) and water (10 mL). The organic layer was dried over $Na_2SO_4$, filtered, evaporated under reduced pressure, and purified by column chromatography using ethyl acetate/hexane (2:8) to afford Int-3 (0.42 g, 21%). A solution of Int-3 (0.42 g, 1.73 mmol) in DMFDMA (5 mL) was stirred at reflux temperature for 24 hours under inert atmosphere. The reaction mixture was cooled to room temperature and diluted with ether, and then stirred for 30 minutes. The precipitated solid was filtered, washed with ether, and dried under vacuum to afford Int-4 (0.40 g, 77%). To a stirred solution of Int-4 (0.70 g, 2.3 mmol) and Int-2B (1.3 g, 6.7 mmol) in DMF was added $K_2CO_3$ (0.92 g, 6.7 mmol) and the mixture was stirred at 100° C. for 18 hours. The reaction mixture was cooled to room temperature, diluted with water (70 mL) and stirred for 30 minutes. The precipitated solid was filtered, washed with water and dried under vacuum to afford pure Int-5 (0.70 g, 70%). Int-5 (0.70 g, 1.6 mmol) was refluxed in 4 N HCl (30 mL) for 4 hours. After complete consumption of starting precursor (by TLC), the reaction mixture was cooled to 0° C. The precipitated solid was filtered, washed with water and dried under vacuum to afford pure Int-6 (0.50 g, 73%). To a stirred solution of Int-6 (0.5 g, 1.2 mmol) in DMF (5 mL) were added HOBt (0.163 g, 1.22 mmol), EDCI (0.51 g, 2.66 mmol), DIPEA (0.5 mL, 2.71 mmol) and tetrahydro-2H-pyran-2-amine ($NH_2OTHP$) (0.28 g, 2.42 mmol) at 0° C. under inert atmosphere. The reaction mixture was stirred at room temperature for 18 hours. After consumption of starting precursor (by TLC), the reaction mixture was diluted with water and stirred for 30 minutes. The precipitated solid was filtered, washed with water, dried under vacuum and purified by column chromatography using EtOAc/hexane (6:4) to afford Int-7 (0.4 g, 63%).

Preparation of Compound 8: To a stirred solution of Int-7 (0.4 g, 0.76 mmol) in MeOH (5 mL) was added concentrated HCl (2 mL) slowly at 0° C. The mixture was stirred overnight at room temperature. The precipitated solid was filtered, washed with water and dried under vacuum to afford pure Compound 8 (0.3 g, 92%). $^1$H-NMR (dmso-$d_6$, 200 MHz) δ 11.05 (bs, 1H), 10.06 (s, 1H), 9.8-9.85 (m, 1H), 8.65-8.66 (m, 1H), 8.17 (s, 1H), 7.9 (d, J=6.4 Hz, 1H), 7.82 (d, J=3.4 Hz, 1H), 7.72 (d, J=3.4 Hz, 1H), 7.32 (d, J=2 Hz, 1H), 7.235-7.246 (m, 1H), 2.71 (s, 3H); $^{13}$C-NMR (dmso-$d_6$, 125 MHz) δ 167.06, 159.23, 159.12, 158.63, 155.97, 147.2, 144.48, 142.82, 130.28, 129.68, 127.59, 126.97, 126.7, 125.5, 124.3, 123.39, 122.14, 119.32, 118.19, 117.9, 113.6, 110.63, 110.37, 108.6, 15.92; MS (M+1) 428; MP: 253.8° C.

Preparation of Compound 9: To a stirred solution of Int-7 (0.42 g, 1.01 mmol) in DMF (5 mL) were added HOBt (0.137 g, 1.01 mmol), EDCI (0.408 g, 2.12 mmol), DIPEA (0.35 g, 2.7 mmol) and o-phenylene diamine (0.131 g, 1.21 mmol) sequentially. The mixture was stirred under inert atmosphere at room temperature for 18 hours. Water was added to the reaction mixture and stirred for 30 minutes. The precipitated solid was filtered, washed with water, dried under vacuum and purified by column chromatography using MeOH:DCM (2:98) to afford pure Compound 9 (0.3 g, 58%). $^1$H-NMR (dmso-$d_6$, 200 MHz) δ 10.08 (bs, 1H), 9.85 (d, J=7.2 Hz, 1H), 9.54 (bs, 1H), 8.67 (d, J=5.2 Hz, 1H), 8.14 (s, 1H), 7.88-7.96 (m, 4H), 7.15-7.32 (m, 3H), 6.94-6.97 (m, 1H), 6.79 (d, J=8 Hz, 1H), 6.6-6.64 (m, 1H), 4.88 (bs, 1H), 2.71 (s, 3H) $^{13}$C-NMR (125 MHz, dmso-$d_6$): δ 164.7, 159.27, 158.56, 148.54, 143.49, 143.22, 143.04, 129.26, 128.55, 127.17, 126.54, 126.21, 126.07, 125.8, 124.44, 123.63, 122.27, 119.24, 117.89, 116.26, 116.12, 114.18, 110.35, 107.9, 16.47; Mass: 503 (M$^+$+1); MP: 267° C.

Examples 11 and 12

Example 11

N-Hydroxy-4-[4-(2-methyl-6-trifluoromethyl-imidazo[1,2-a]pyridin-3-yl)-pyrimidin-2-ylamino]-benzamide Example 12

N-(2-Amino-phenyl)-4-[4-(2-methyl-6-trifluoromethyl-imidazo[1,2-a]pyridin-3-yl)-pyrimidin-2-ylamino]-benzamide

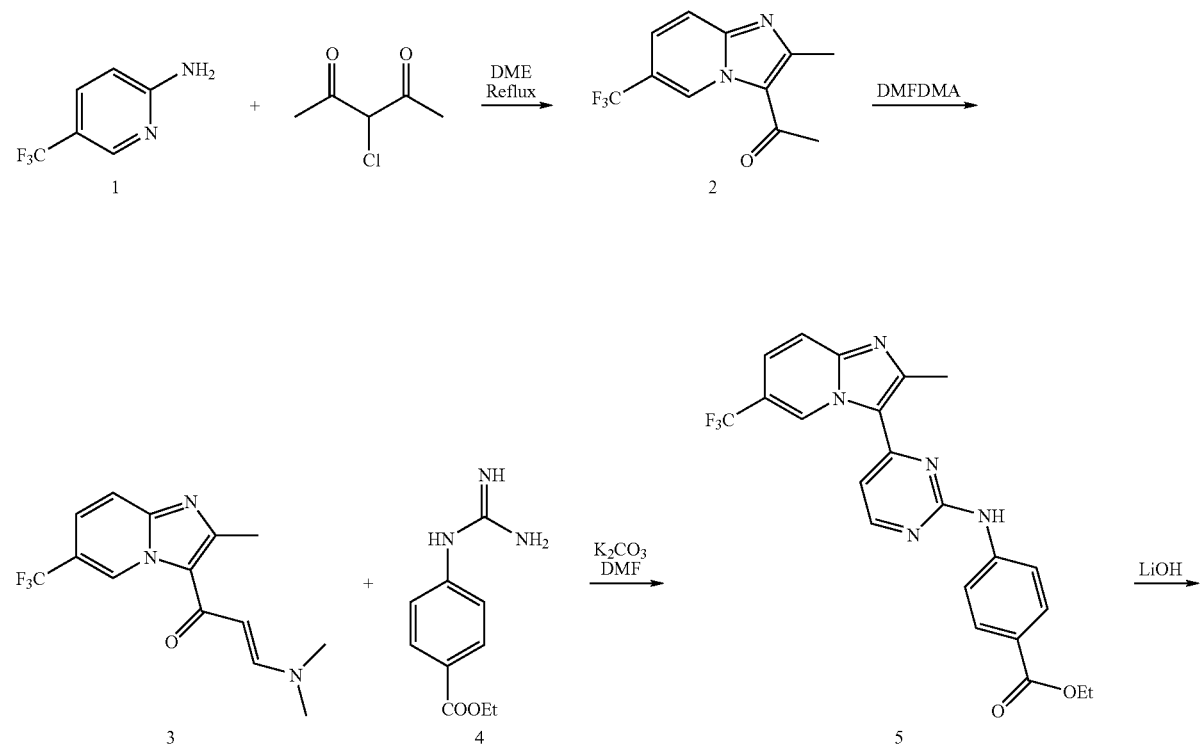

-continued

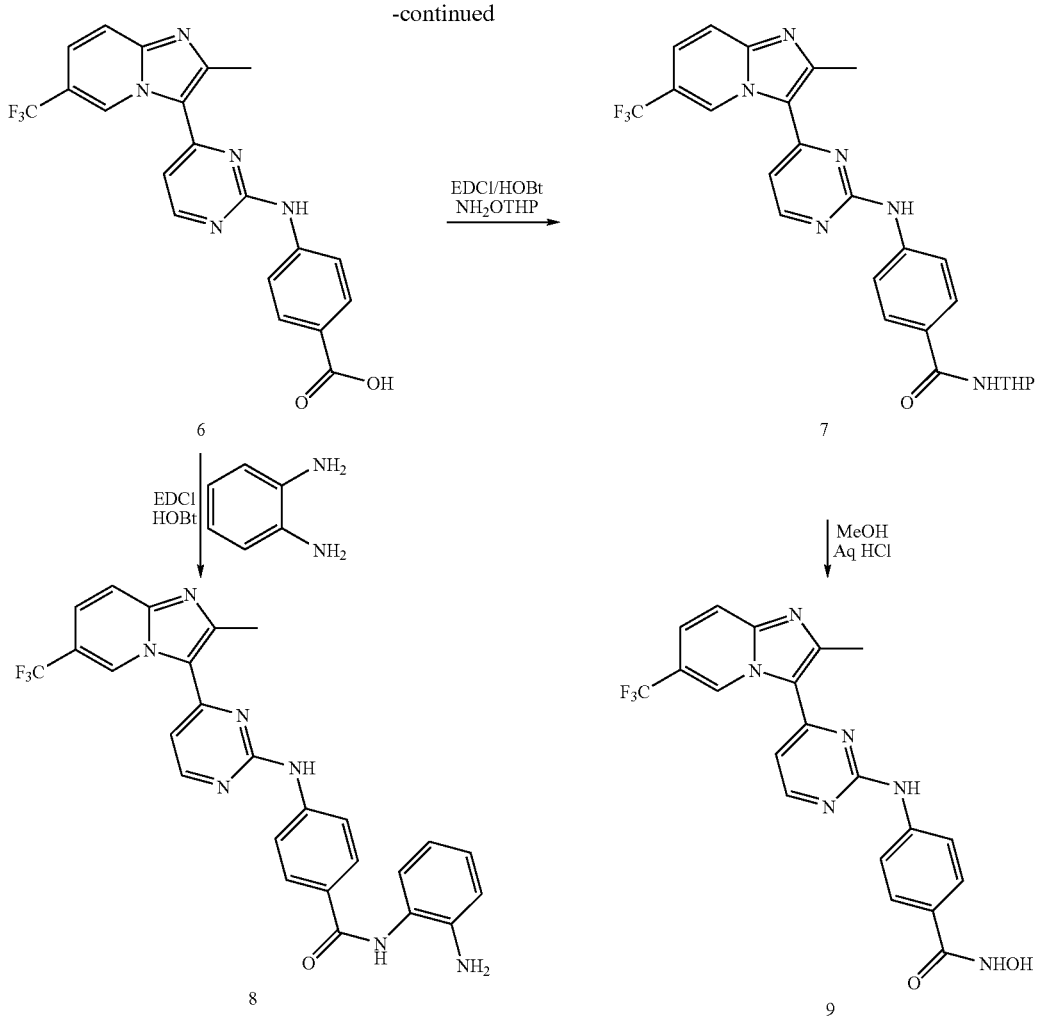

Example 12 (Compound I$^a$-a-75)

Example 11 (Compound I$^a$-a-71)

A stirred solution of Int-1 (5.0 g, 30.86 mmol) and 3-chloropentane-2,4-dione (4.96 g, 37.03 mmol) in DME (75 mL) under $N_2$ atmosphere was stirred for 24 hours at 90° C. After complete consumption of starting precursor (by TLC), the reaction mixture was concentrated under vacuum. The residue was purified by column chromatography using EtOAc to afford Int-2 (1.7 g, 22%). $^1$H NMR (200 MHz, dmso-d$_6$): δ 2.49 (s, 1H), 2.75 (s, 3H), 7.85 (d, J=5.4 Hz, 2H), 9.96 (s, 1H). Mass (M/z): 242.9 [M$^+$+1]. A solution of Int-2 (2.0 g, 8.2 mmole) in DMFDMA (5.5 mL) was stirred at reflux temperature for 16 hours. After complete consumption of starting material (by TLC), the reaction mixture was cooled to room temperature and diluted with ether (20 mL) and stirred for 30 minutes. The precipitated solid was filtered, washed with ether and dried under vacuum to provide Int-3 (1.6 g, 62%) as brown solid. $^1$H NMR (200 MHz, dmso-d$_6$): δ2.69 (s, 3H), 2.91 (s, 3H), 3.17 (s, 3H), 5.50 (d, J=12 Hz, 1H), 7.63 (d, J=9.6 Hz, 1H), 7.78 (d, J=12.2 Hz, 2H), 10.04 (s, 1H). Mass (M/z): 297.9 [M$^+$+1]. To a solution of Int-3 (2.0 g, 6.7 mmol) in DMF (15 mL) was added Int-4 (2.61 g, 13.4 mmol) followed by $K_2CO_3$ (2.32 g, 16.8 mmol) at room temperature under inert atmosphere and the mixture was stirred at 110° C. for 20 hours. The reaction mixture was cooled to room temperature, diluted with water (100 mL) and stirred for 30 minutes and extracted with EtOAc (3×150 mL). The combined organic extracts was dried over anhydrous $Na_2SO_4$ and evaporated under reduced pressure to provide Int-5 (1.96 g, 68%) as brown solid. $^1$H NMR (200 MHz, dmso-d$_6$): δ 2.66 (s, 3H), 3.80 (s, 3H), 7.21 (d, J=5.6 Hz, 1H), 7.66 (m, 1H), 7.84 (m, 5H), 8.65 (d, J=5.2 Hz, 1H), 9.85 (s, 1H), 10.22 (s, 1H). Mass (M/z): 427.7 [M$^+$+1]. To a stirred solution of Int-5 (2.0 gm, 4.6 mmol) in MeOH:THF:water (29 mL, 10:12:7) was stirred at room temperature under nitrogen atmosphere. LiOH, $H_2O$ (588 mg, 14.0 mmol) was added and the mixture was stirred for 48 hours. The solvent was removed under vacuum. The crude product was acidified with 1N HCl (about pH 5) and stirred for 30 minutes. The resulting solids were filtered and dried under high vacuum to give Int-6 (1.68 g, 87%). $^1$H NMR (200 MHz, dmso-d$_6$): δ 2.66 (s, 3H); 7.21 (d, J=5.2 Hz, 1H), 7.65 (d, J=9.8 Hz, 1H) 7.83 (s, 5H); 8.65 (d, J=5.2 Hz, 1H); 9.86 (s, 1H); 10.16 (s, 1H). Mass (M/z): 413.6 [M$^+$+1]. To a stirred solution of Int-6 (900 mg, 2.17 mmol) in DMF (10 ml) at 0° C. under nitrogen atmosphere was added EDCI (919 mg, 4.7 mmol) and HOBt (294 mg, 2.17 mmol). After 10 minutes $NH_2$OTHP (509 mg, 4.3 mmol) was added. After another 15 minutes DIPEA (0.95 ml, 5.44 mmol) was added and the stirring continued overnight at room temperature. Water (50 ml) was added to the reaction mass and stirred for 30 minutes. The precipitated solid was filtered, dried under vacuum, and purified by column chromatography (SiO$_2$) using 3% MeOH in DCM to give Int-7 as a pale yellow solid (600 mg, 53%). $^1$H NMR (200 MHz, dmso-d$_6$): δ 1.53 (s, 3H); 1.71 (s, 3H); 2.66 (s, 3H); 3.50 (d, J=11.2 Hz, 1H); 4.05 (m, 1H); 4.96 (s, 1H); 7.19 (d, J=5.2 Hz, 1H); 7.85-7.62 (m, 6H); 8.64 (d, J=5.2 Hz, 1H); 9.85 (s, 1H); 10.07 (s, 1H); 11.44 (s, 1H). Mass (M/z): 512.6 [M$^+$+1].

Preparation of Compound 8: To a stirred solution of Int-7 (340 mg, 0.66 mmol) in methanol (15 ml) under nitrogen atmosphere was added concentrated HCl (1.5 ml) and the contents were stirred for 16 hours at room temperature. The resulting solids were filtered and dried under vacuum to afford the final compound as its HCl salt which was neutralized using saturated NaHCO$_3$ and stirred for 30 minutes. The product was filtered and dried under vacuum to furnish Compound 8 (190 mg, 66%). $^1$H NMR (500 MHz, dmso-d$_6$): δ 2.66 (s, 3H); 7.14 (d, J=5, Hz, 1H); 7.79-7.61 (m, 6H); 8.58 (d, J=5, Hz, 1H); 9.82 (s, 1H); $^{13}$C NMR (125 MHz, dmso-d$_6$) 163.9, 159.3, 158.8, 156.1, 148.0, 145.1, 142.6, 127.4, 126.7, 125.7, 124.7, 122.6, 121.9, 119.3, 118.2, 117.3, 115.3, 115.1, 110.5, 16.1. Mass (M/z): 428.6 [M$^+$+1]. M.P.: 165.6° C.

Preparation of Compound 9: To a stirred solution of Int-6 (800 mg, 1.93 mmol) in DMF (8 ml) at 0° C. under nitrogen was added EDCI (817 mg, 4.26 mmol) and HOBt (261 mg, 1.93 mmol). After stirring for 15 minutes, o-phenylenediamine (209 mg, 1.93 mmol) was added. Again after 15 minutes, DIPEA (0.84 ml, 4.84 mmol) was added to the mixture and stirring continued overnight at room temperature. Water (40 ml) was added and the reaction mass was stirred for 30 minutes. The precipitated solid was filtered, dried under high vacuum, and purified by column chromatography using 2% MeOH:DCM to afford the final Compound 9 (470 mg, 48%) as pale yellow solid. $^1$H NMR (200 MHz, dmso-d$_6$): δ 2.67 (s, 3H); 4.86 (bs, 2H); 6.63-6.60 (t, 1H); 6.78 (d, J=1.4 Hz, 1H); 6.96-6.92 (t, 1H), 7.22-7.13 (m, 2H), 7.66 (d, J=8 Hz, 1H), 7.95-7.82 (q, 5H); 8.66 (d, J=5 Hz, 1H); 9.51 (s, 1H); 9.88 (s, 1H); 10.11 (s, 1H). $^{13}$C NMR (125 MHz, dmso-d$_6$) 164.7, 159.3, 158.8, 156.1, 148.0, 145.1, 143.1, 143.0, 128.5, 127.2, 126.7, 126.5, 126.2, 123.6, 121.9, 119.3, 118.1, 117.3, 116.3, 116.1, 115.3, 115.1, 110.7, 16.0. Mass (M/z): 503.7 [M$^+$+1]. M.P.: 238.1° C.

Examples 13 and 14

Example 13

N-Hydroxy-4-[4-(7-methoxy-2-methyl-imidazo[1,2-a]pyridin-3-yl)-pyrimidin-2-ylamino]-benzamide Example 14

N-(2-Amino-phenyl)-4-[4-(7-methoxy-2-methyl-imidazo[1,2-a]pyridin-3-yl)-pyrimidin-2-ylamino]-benzamide

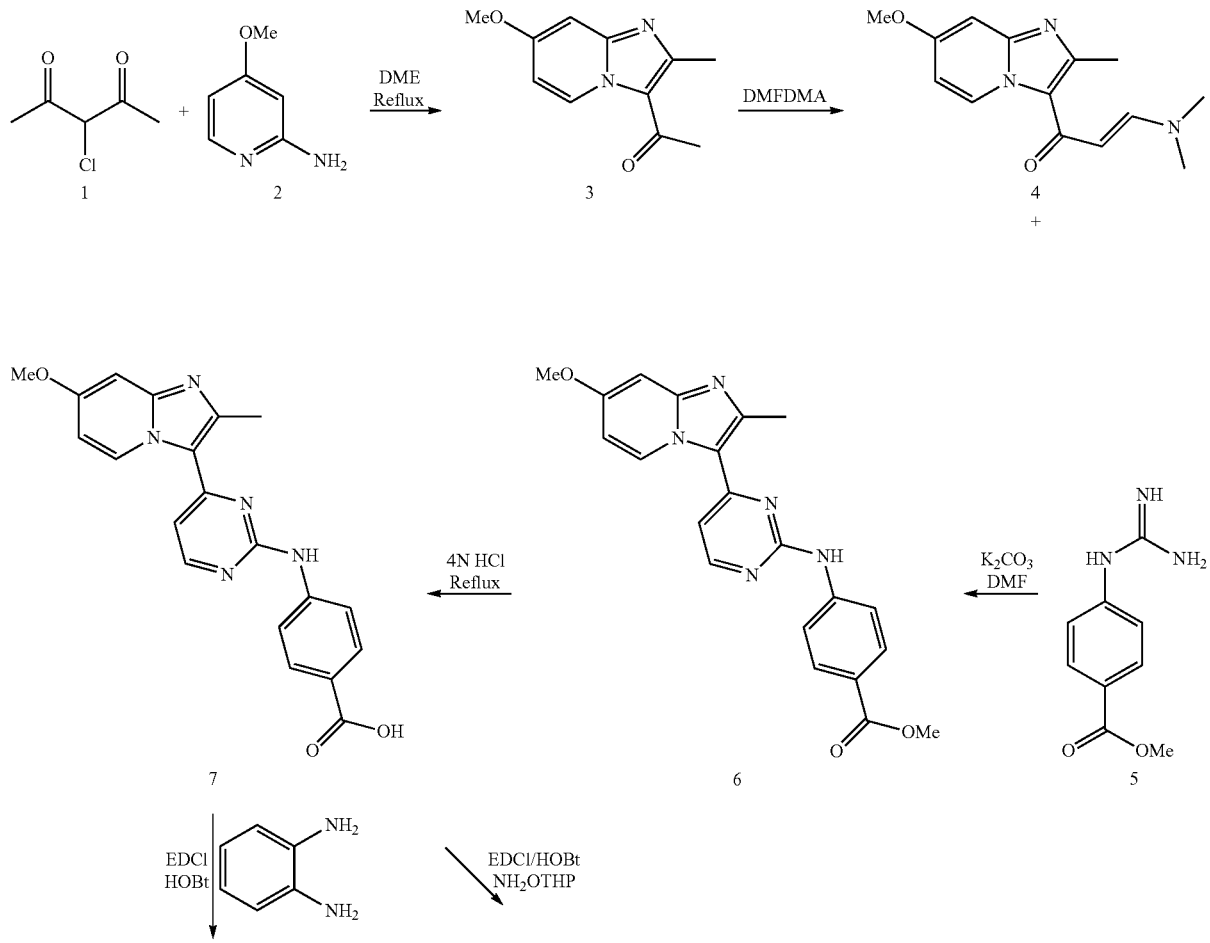

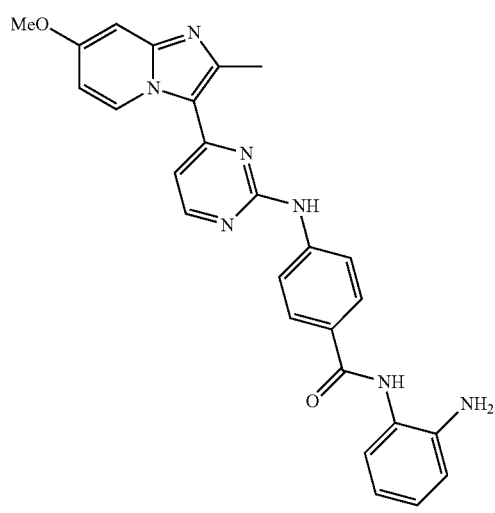

9

Example 14 (Compound I$^a$-a-82)

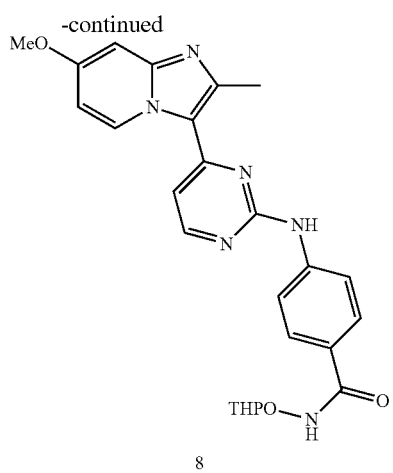

8

↓ MeOH, Aq HCl

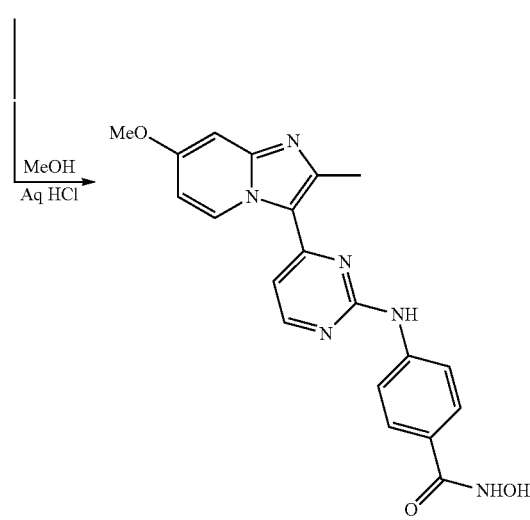

10

Example 13 (Compound I$^a$-a-78)

To a solution of Int-1 (2.5 g, 20.16 mmol) in DME (25 mL) was added Int-2 (3.5 g, 26.2 mmol) and stirred under reflux for 24 hours. The reaction mixture was concentrated under vacuum to obtain crude mass which was purified by column chromatography eluting pure compound using ethyl acetate to afford Int-3 (2.0 g, 49%). $^1$H NMR (200 MHz, CDCl$_3$): δ 9.56 (d, J=7.2 Hz, 1H), 7.07 (d, J=2.6 Hz, 1H), 6.73 (dd, J=2.6, 7.6 Hz, 1H), 3.92 (s, 3H), 2.59 (s, 3H). Mass (m/z): 205 (M$^+$+1). To a solution of Int-3 (2.0 g, 9.8 mmol) in DMFDMA (20 mL) was heated to 100° C. for 24 hours. The reaction mixture was concentrated under vacuum and the residue was diluted with diethyl ether (30 mL). The precipitated solids were filtered, washed with diethyl ether (2×10 mL), and dried under vacuum to afford Int-4 (2.2 g, 87%) as brown solid. $^1$H NMR (200 MHz, CDCl$_3$): δ 9.52 (d, J=8 Hz, 1H), 7.76 (d, J=12.4 Hz, 1H), 6.84 (d, J=2.6 Hz, 1H), 6.58 (dd, J=2.6, 7.6 Hz, 1H), 5.53 (d, J=12.4 Hz, 1H), 3.86 (s, 3H), 3.03 (bs, 6H), 2.72 (s, 3H). Mass (m/z): 259.9 (M$^+$+1). To a stirred solution of Int-4 (2.2 g, 8.49 mmol) in DMF (22 mL) was added Int-5 (3.3 g, 17.0 mmol) and K$_2$CO$_3$ (2.93 g, 21.22 mmol). The reaction mixture was heated to 100° C. for 24 hours. The reaction mixture was diluted with water (200 mL) and stirred for 30 minutes. The precipitated solid was filtered, washed with water (2×50 mL), and dried under vacuum to afford Int-6 (2.2 g, 66%). $^1$H NMR (200 MHz, dmso-d$_6$): δ 10.05 (s, 1H), 9.70 (d, J=8 Hz, 1H), 8.53 (d, J=5.6 Hz, 1H), 7.91 (s, 4H), 7.12 (d, J=5.4 Hz, 1H), 7.04 (s, 1H), 6.71 (s, J=7.4 Hz, 1H), 3.88 (s, 3H), 3.81 (s, 3H), 2.61 (s, 3H). Mass (m/z): 389.9 (M$^+$+1). Int-6 (2.2 g, 5.65 mmol) in 4N HCl (40 mL) was heated to reflux for 4 hours. The reaction mixture was cooled to room temperature, diluted with water (50 mL), and stirred for 15 minutes. The precipitated solid was filtered, washed with water (20 mL), and dried under vacuum to afford Int-7 (1.7 g, 81%) as brown solid. $^1$H NMR (200 MHz, dmso-d$_6$): δ 10.30 (s, 1H), 9.66 (d, J=7.8 Hz, 1H), 8.72 (d, J=5.2 Hz, 1H), 7.88 (s, 4H), 7.29-7.16 (m, 3H), 4.0 (s, 3H), 2.71 (s, 3H). Mass (m/z): 375.8 (M$^+$+1). To a stirred solution of Int-7 (800 mg, 2.13 mmol) in DMF (8 mL) were added EDCI (818 mg, 4.26 mmol), HOBt (286 mg, 2.13 mmol) and DIPEA (688 mg, 5.33 mol), followed by NH$_2$—OTHP (500 mg, 4.27 mmol) at 0° C. The reaction mixture was stirred at room temperature for 16 hours. The reaction mixture was diluted with water (100 mL). The precipitated solid was filtered, washed with water (30 mL), and dried under vacuum to obtain crude compound which was purified by column chromatography eluting pure compound using MeOH:DCM (2:98) to afford THP protected final Int-8 (650 mg, 64%) as pale yellow solid. $^1$H NMR (200 MHz, dmso-d$_6$): δ 11.47 (s, 1H), 9.92 (s, 1H), 9.70

(d, J=7.8 Hz, 1H), 8.52 (d, J=5.4 Hz, 1H), 7.86 (d, J=8.8 Hz, 2H), 7.74 (d, J=8.8 Hz, 2H), 7.10 (d, J=5.6 Hz, 1H), 7.05 (d, J=2.2 Hz, 1H), 6.73 (dd, J=2.6, 7.8 Hz, 1H), 4.98 (s, 1H), 4.10-4.07 (m, 1H), 3.89 (s, 3H), 3.54-3.49 (m, 1H), 2.61 (s, 3H), 1.72-1.55 (m, 6H). Mass (m/z): 474.8 (M⁺+1).

Preparation of Compound 10: To a stirred suspension of Int-8 (650 mg, 1.37 mmol) in MeOH (7 mL) was added concentrated HCl (1.5 mL) at 0° C. The reaction mixture was stirred at room temperature for 16 hours. The precipitated solid was filtered, washed with methanol (10 mL), and dried under vacuum. The solid was neutralized using NaHCO₃ solution The precipitated solid was filtered, washed with water (10 mL), and dried under vacuum to afford the free hydroxamic acid Compound 10 (350 mg, 65%) as pale yellow solid. ¹H NMR (200 MHz, dmso-d₆): δ 11.0 (bs, 1H), 9.85 (s, 1H), 9.68 (d, J=7.8 Hz, 1H), 9.0 (bs, 1H), 8.5 (d, J=5.6 Hz, 1H), 7.8 (d, J=8.8 Hz, 2H), 7.7 (d, J=8.8 Hz, 2H), 7.09-7.03 (m, 3H), 6.71 (dd, J=2.6, 8.0 Hz, 1H), 3.88 (s, 3H), 2.60 (s, 3H). ¹³C NMR (125 MHz, dmso-d₆): δ 164.2, 159.18, 158.54, 157.58, 156.76, 147.59, 143.05, 129.30, 127.46, 125.45, 118.10, 116.46, 106.55, 94.61, 55.70, 16.93; Mass (m/z): 390.9 (M⁺+1); Melting Point: 209° C.

Preparation of Compound 9: To a stirred solution of Int-7 (800 mg, 2.13 mmol) in DMF (8 mL) was added EDCI (818 mg, 4.26 mmol), HOBt (286 mg, 2.13 mmol), DIPEA (688 mg, 4.26 mmol) and o-phenylene diamine (231 mg, 2.13 mmol) at 0° C. The reaction mixture was stirred at room temperature for 16 hours, and diluted with water (100 mL). The precipitated solid was filtered, washed with water (2×25 mL), dried under vacuum and finally purified by column chromatography using MeOH:DCM (3:97) to furnish Compound 9 (400 mg, 40%) as pale yellow solid. ¹H NMR (200 MHz, dmso-d₆): δ 9.94 (s, 1H), 9.73 (d, J=7.8 Hz, 1H), 9.53 (s, 1H), 8.53 (d, J=5.6 Hz, 1H), 7.94 (d, J=8.8 Hz, 2H), 7.88 (d, J=8.8 Hz, 2H), 7.18-7.05 (m, 3H), 7.0-6.93 (m, 1H), 6.80-6.74 (m, 2H), 6.64-6.56 (m, 1H), 4.89 (bs, 2H), 3.89 (s, 3H), 2.62 (s, 3H). ¹³C NMR (125 MHz, dmso-d₆): δ 164.82, 159.16, 158.59, 157.60, 156.77, 147.59, 143.48, 143.08, 129.32, 128.53, 126.96, 126.59, 126.25, 123.67, 117.83, 116.49, 116.30, 116.14, 109.13, 106.63, 94.61, 55.7, 16.90; Mass (m/z): 465.7 (M⁺+1); Melting Point: 241.5° C.

Examples 15 and 16

Example 15

N-Hydroxy-4-[4-(2-trifluoromethyl-imidazo[1,2-a]pyridin-3-yl)-pyrimidin-2-ylamino]-benzamide Example 16

N-(2-Amino-phenyl)-4-[4-(2-trifluoromethyl-imidazo[1,2-a]pyridin-3-yl)-pyrimidin-2-ylamino]-benzamide

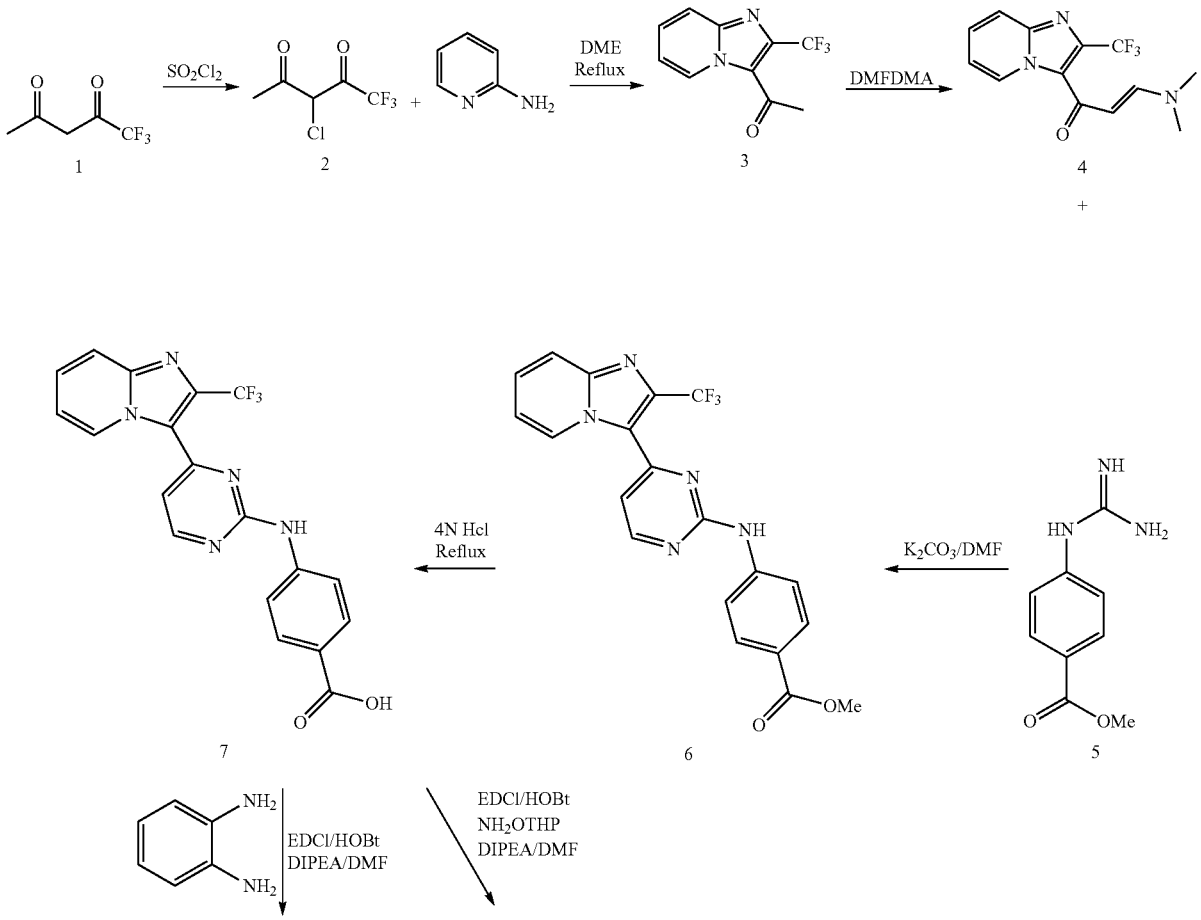

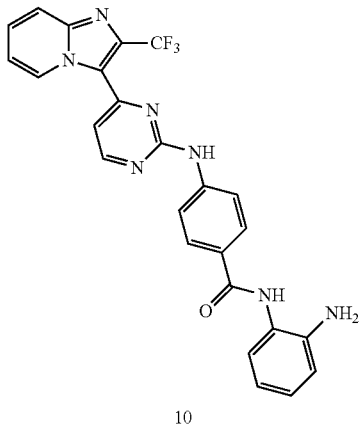

10

Example 16 (Compound I$^a$- a-202)

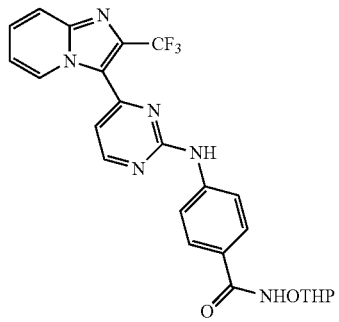

8

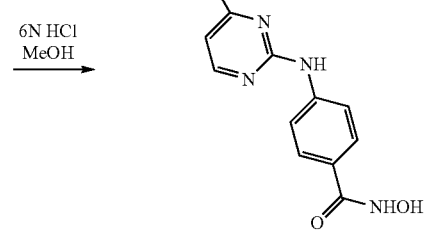

9

Example 15 (Compound I$^a$- a-201)

To a stirred solution of Int-1 (7 g, 45.4 mmol) in benzene (7 ml) was added sulfuryl chloride (3.6 ml, 45.4 mmol) slowly over a period of 2 hours. After addition of SO$_2$Cl$_2$, the mixture was stirred at room temperature for 2 hours. The reaction mixture was quenched with 7 ml of water followed by ethyl acetate (10 ml). The organic phase was separated, dried over anhydrous sodium sulphate, filtered and concentrated under reduced pressure at 25° C. to a volume of about 10 mL which was used for the next step without any purification. $^1$H NMR (200 MHz, CDCl$_3$): δ 2.44 (s, 3H), 4.49 (s, 1H). To a solution of 2-amino-pyridine (3.65 g, 38.8 mmol) in DME (40 ml) was added Int-2 at room temperature. The reaction mixture was refluxed for 3 hours. After disappearance of starting material the volatiles were removed under reduced pressure and the crude mass was purified by silica gel column chromatography using EtOAc:Hexane as eluent to provide Int-3 (2 g, 22%) as white solid. $^1$H NMR (200 MHz, CDCl$_3$): δ 2.75 (s, 3H), 7.16-7.26 (m, 1H), 7.55-7.63 (t, 1H), 7.85 (d, J=9.2 Hz, 1H), 9.77 (d, J=7 Hz, 1H); Mass (M$^+$): 228. Int-3 (2.9 g, 12.7 mmol) in DMFDMA (30 ml) and one drop of DMF were refluxed for 16 hours. The volatiles were removed under reduced pressure and the crude was triturated with hexane (40 ml) to afford Int-4 (3 g, 83%) as a solid. $^1$H NMR (200 MHz, CDCl$_3$): δ 2.95 (s, 3H), 3.20 (s, 2H), 5.68 (d, J=12.4 Hz, 1H), 6.96-7.03 (t, 1H), 7.35-7.39 (t, 1H), 7.72 (d, J=8.8 Hz, 1H), 7.82 (d, J=12.4 Hz, 1H), 9.30 (d, J=7.2 Hz, 1H); Mass (M$^+$): 283. To a stirred solution of Int-4 (2 g, 7.06 mol) in DMF (30 ml) was added Int-5 (4.09 g, 21.2 mmol), potassium carbonate (2.9 g, 21.2 mmol) and the mixture was stirred at 110° C. for 18 hours. After disappearance of starting material, the reaction mixture was cooled to room temperature and diluted with water (300 ml), and stirred for 30 minutes. The resulting precipitate was filtered, washed with water (50 ml) and dried under vacuum to furnish critical cyclized Int-6 (1.8 g, 62%) as a brown solid. $^1$H NMR (200 MHz, CDCl$_3$): δ 3.91 (s, 3H), 6.99-7.0 (t, 1H), 7.21-7.26 (m, 1H), 7.46-7.50 (m, 2H), 7.71-7.84 (m, 3H), 8.02 (d, J=8.8 Hz, 2H), 8.63 (d, J=5 Hz, 1H), 9.17 (d, J=7.4 Hz, 1H); Mass (M$^+$): 413. Int-6 (1.2 g, 2.9 mmol) in 4 N HCl (50 ml) was refluxed for 3 hours. The progress of reaction was monitored by TLC. After complete disappearance of starting material, heating was removed and the reaction mixture was cooled to room temperature. The resulting precipitate was filtered, washed with water (50 ml) and dried under vacuum to provide Int-7 (0.9 g, 78%) as yellow solid. $^1$H NMR (200 MHz, dmso-d$_6$): δ 7.17-7.23 (m, 2H), 7.57-7.64 (t, 1H), 7.84-7.92 (m, 5H), 8.76 (d, J=5.2 Hz, 1H), 9.12 (d, J=7.4 Hz, 1H), 10.29 (s, 1H); Mass (M$^+$): 399. To a solution of Int-7 (1 g, 2.5 mmol) in DMF (15 ml) was added EDCI (1.05 g, 5.5 mmol), HOBt (0.33 g, 2.5 mmol) and DIPEA (1.1 ml, 6.2 mmol) at 0° C. followed by NH$_2$—OTHP (0.43 g, 3.7 mmol) at 0° C. The reaction mixture was stirred at room temperature for 16 hours, diluted with water (40 ml), and stirred for another 30 minutes. The precipitated solid was filtered, washed with water (20 ml), dried under vacuum and purified by silica gel column chromatography using (EtOAc:Hexane, 7:3) to give Int-8 (0.7 g, 56%) as a brown solid. $^1$H NMR (200 MHz, dmso-d$_6$): δ 1.53-1.70 (m, 6H), 4.33-4.35 (m, 1H), 4.85-4.89 (m, 1H), 4.96 (s, 1H) 7.14-7.20 (m, 2H), 7.61-7.64 (t, 1H), 7.69 (d, J=8.8 Hz, 2H), 7.85 (d, J=8.8 Hz, 3H), 10.19 (s, 1H), 11.45 (s, 1H); Mass (M$^+$): 498.

Preparation of Compound 9: To a suspension of Int-8 (0.7 g, 1.4 mmol) in methanol (10 ml) was added 6N HCl (1.4 ml) at 0° C. The mixture was stirred overnight at room temperature. The precipitated solid was then filtered, washed with methanol (5 ml), and dried under vacuum to provide Compound 9 (0.45 g, 77%) as yellow solid. $^1$H NMR (200 MHz, dmso-d$_6$): δ 7.14-7.24 (m, 2H), 7.56-7.70 (m, 3H), 7.80-7.88 (m, 3H), 8.74 (d, J=5.2 Hz, 1H), 9.10 (d, J=7 Hz, 1H), 10.16 (s, 1H), 11.04 (brs, 1H); $^{13}$CNMR (125 MHz, dmso-d$_6$): δ 112.74, 114.94, 117.94, 118.17, 120.72, 120.79, 122.93, 125.08, 125.64, 127.32, 127.53, 128.65, 133.25, 133.55, 142.74, 144.72, 154.40, 159.54, 159.6, 164.07; Mass (M$^+$): 414; Melting Point: 230.8° C.

Preparation of Compound 10: To a solution of Int-7 (0.59 g, 1.47 mmol) in DMF (10 ml) was added EDCI (0.62 g, 3.2 mmol), HOBt (0.19 g, 1.47 mmol) and DIPEA (0.68 ml, 3.6 mmol) at 0° C. followed by O-phenylene diamine (0.15 g, 1.47 mmol). The reaction mixture was stirred overnight at room temperature. After disappearance of starting acid (by TLC), the reaction was diluted with water (60 ml), and stirred for 30 minutes. The resulting precipitates were filtered and washed with water (20 ml) and dried under vacuum. The crude material was purified by column chromatography (SiO$_2$) using (1% MeOH:DCM) to furnish Compound 10 (0.34 g, 47%) as pale yellow solid. $^1$H NMR (200 MHz, dmso-d$_6$): δ 4.86 (brs, 2H), 6.55-6.62 (t, 1H), 6.76 (d, J=6.6 Hz, 1H), 6.92-6.99 (t, 1H), 7.12-7.25 (m, 3H), 7.56-7.64 (t, 1H), 7.84-7.96 (m, 5H), 8.76 (d, J=5.2 Hz, 1H), 9.12 (d, J=6.8 Hz, 1H), 9.51 (s, 1H), 10.22 (s, 1H); $^{13}$C NMR (125 MHz, dmso-d$_6$): δ 112.85, 114.96, 116.17, 116.32, 117.96, 120.75, 120.80, 122.95, 123.64, 126.28, 126.6, 127.35, 128.54, 128.68, 133.26, 133.56, 143.06, 144.74, 154.44, 159.61, 164.79; Mass (M$^+$): 489. Melting Point: 150.7° C.

Examples 17 and 18
Example 17
N-Hydroxy-4-[4-(2-methyl-imidazo[1,2-b]pyridazin-3-yl)-pyrimidin-2-ylamino]-benzamide
Example 18
N-(2-Amino-phenyl)-4-[4-(2-methyl-imidazo[1,2-b]pyridazin-3-yl)-pyrimidin-2-ylamino]-benzamide
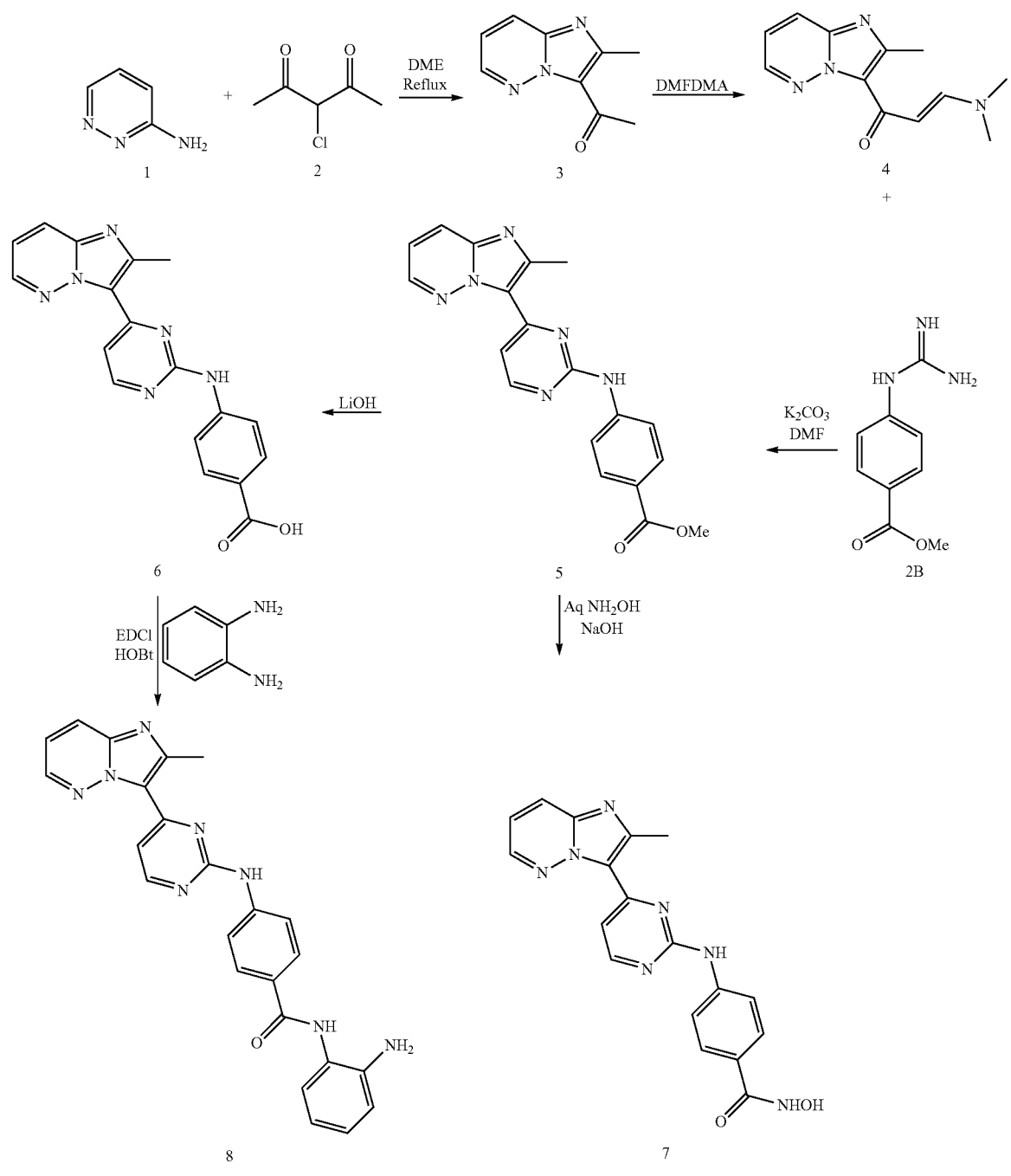
Example 18 (Compound I*a*- c-29)　　　　Example 17 (Compound I*a*- c-25)

To a stirred solution of Int-1 (10 g, 76 mmol) in DME was added Int-2 (10 mL, 90 mmol) dropwise under inert condition at room temperature. The mixture was refluxed overnight and cooled to room temperature. Volatiles were evaporated under reduced pressure. The obtained residue was purified by column chromatography using 50% EtOAc/Hexane to afford Int-3 (3 g, 22%). Int-3 (1.2 g, 6.8 mmol) in DMFDMA (12 mL) was stirred at 100° C. for 36 hours under inert condition. The reaction mixture was cooled to room temperature, diluted with ether (50 mL) and stirred for 30 minutes. The precipitated solid was filtered and washed with ether and dried under vacuum to obtain Int-4 (1.0 g, 63%). To a stirred solution of Int-4 (1.0 g, 4.3 mmol) and Int-2B (2.5 g, 13 mmol) in DMF (10 mL) under inert condition was added $K_2CO_3$ (1.79 g, 13 mmol) at room temperature and the mixture was stirred overnight at 110° C. The reaction mixture was then cooled to room temperature, diluted with water, and stirred for 30 minutes. The precipitated solid was filtered, washed with water, and dried under vacuum to obtain Int-5 (0.85 g, 56%).

Preparation of Compound 7: To a cooled solution of Int-5 (0.6 g, 1.6 mmol) in MeOH:DCM (42 mL, 5:2) was slowly added aqueous hydroxyl amine (12 mL, 50% solution). After stirring for 15 minutes, aqueous NaOH (0.48 g, 12 mmol in 3 mL water) was added and stirring continued overnight at room temperature. The reaction mixture was concentrated under reduced pressure. The residue was diluted with water (30 mL), and pH was adjusted to about 7.0 using 2 N HCl at 0° C. The precipitated solid was filtered, and dried under vacuum to afford the product which was further washed with 20% MeOH:DCM to obtain pure Compound 7 (0.35 g, 58%). $^1$H NMR (200 MHz, dmso-$d_6$): δ 11.0 (bs, 1H), 9.84 (s, 1H), 9.0 (bs, 1H), 8.68-8.62 (m, 2H), 8.17 (d, J=9.2 Hz, 1H), 7.88-7.84 (m, 3H), 7.70 (d, J=8.4 Hz, 2H), 7.42-7.37 (m, 1H), 2.80 (s, 3H). $^{13}$C NMR (125 MHz, dmso-$d_6$): δ 164.0, 159.4, 158.4, 155.6, 147.0, 143.4, 143.0, 139.4, 127.3, 125.0, 121.2, 118.5, 118.0, 110.0, 17.0. Mass (m/z): 261.9 ($M^+$+1). MP: 198.4° C.

Preparation of Compound 8: To a stirred solution of Int-5 (1.2 g, 3.3 mmol) in a mixture of MeOH:THF:$H_2O$ (30 mL, 2:2:1) was added LiOH (0.699 g, 1.6 mmol) and the mixture was stirred at room temperature for 18 hours. The reaction mixture was concentrated under reduced pressure, diluted with water (20 mL) and acidified with 2N HCl to about pH 6 and stirred for 10 minutes. The precipitated solid was filtered, washed with water (2×10 mL) and dried under vacuum to afford Int-6 (0.87 g, 75%). To a stirred solution of Int-6 (0.5 g, 1.4 mmol) in DMF (8 mL) at 0° C. were added HOBt (0.189 g, 1.4 mmol), EDCI (0.59 g, 3.0 mmol), DIPEA (0.42 g, 3.2 mmol) and o-phenylenediamine (0.187 g, 1.7 mmol) sequentially. The mixture was stirred under inert atmosphere at room temperature for 16 hours. Water was added to the reaction mixture and stirred for 30 minutes. The precipitated solid was filtered, washed with water, and dried under vacuum and purified by column chromatography using 5% MeOH/DCM (0.32 g, 50%). $^1$H NMR (200 MHz, dmso-$d_6$): δ 9.90 (s, 1H), 9.50 (s, 1H), 8.70-8.65 (m, 2H), 8.20 (d, J=7.8 Hz, 1H), 7.98-7.89 (m, 5H), 7.42-7.35 (m, 1H), 7.18 (d, J=6.8 Hz, 1H), 6.95 (t, J=6.6 Hz, 1H), 6.79 (d, J=7.0 Hz, 1H), 6.58 (t, J=9.2 Hz, 1H), 4.86 (bs, 2H), 2.83 (s, 3H). $^{13}$C NMR (125 MHz, dmso-$d_6$): δ 164.8, 159.4, 158.4, 155.6, 147.0, 143.5, 143.4, 143.0, 139.4, 128.4, 126.8, 126.6, 126.2, 125.0, 123.6, 121.2, 118.5, 117.8, 116.2, 115.1, 110.1, 17.1. Mass (m/z): 436.8 ($M^+$+1). MP: 214.4° C.

Examples 19 and 20

Example 19

N-Hydroxy-4-[4-(2-methyl-imidazo[1,2-a]pyrazin-3-yl)-pyrimidin-2-ylamino]-benzamide Example 20

N-(2-Amino-phenyl)-4-[4-(2-methyl-imidazo[1,2-a]pyrazin-3-yl)-pyrimidin-2-ylamino]-benzamide

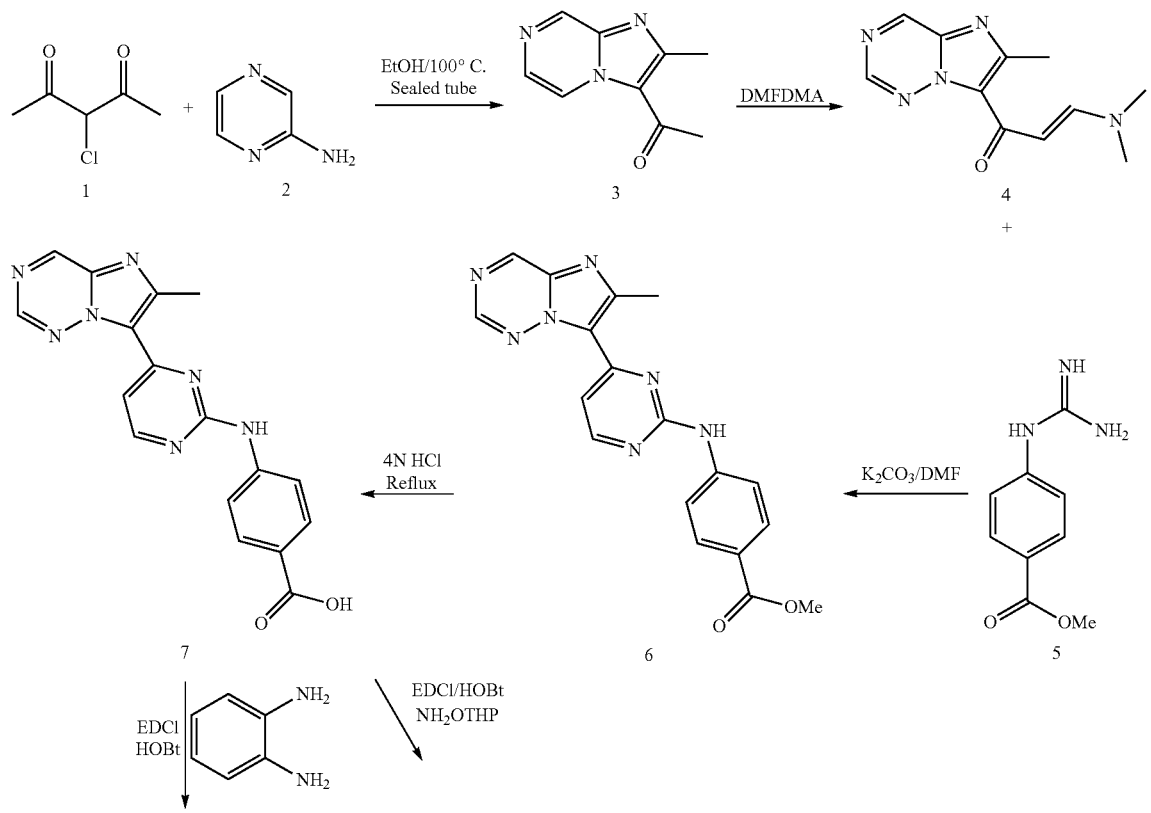

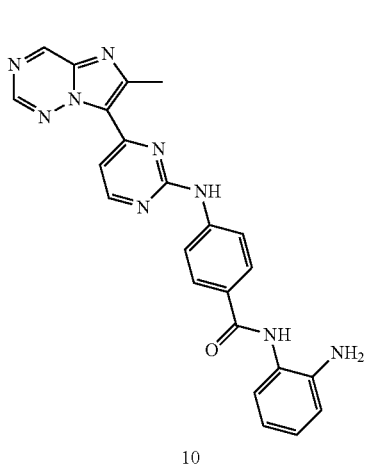

Example 20 (Compound I$^a$-e-29)

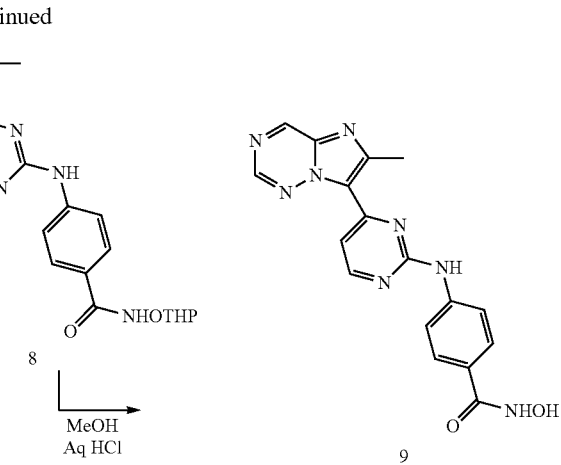

Example 19 (Compound 1$^a$-e-25)

Preparation of Int-8: To a solution of Int-1 (6 g, 63.08 mmol) in ethanol (20 mL) in a sealed tube was added Int-2 (11.0 g, 82.0 mmol). The mixture was stirred at 100° C. for 24 hours. The reaction mixture was diluted with DCM (150 mL). The solid material was filtered and the residue was washed with DCM (2×50 mL). The combined filtrate was concentrated under vacuum and purified by column chromatography using ethyl acetate to afford Int-3 (0.35 g, 3%). $^1$H NMR (200 MHz, CDCl$_3$): δ 9.52 (dd, J=1.4, 4.6 Hz, 1H), 9.15 (d, J=1.4 Hz, 1H), 8.14 (d, J=4.4 Hz, 1H), 2.86 (s, 3H), 2.67 (s, 3H). Mass (m/z): 176 [M$^+$+1]. A solution of Int-3 (0.55 g, 3.14 mmol)) in DMFDMA (6 mL) was heated at 110° C. for 16 hours. After cooling to room temperature, the volatiles were removed under vacuum, and the residue was diluted with ether (15 mL). The precipitated solid was filtered, washed with ether (2×2.5 mL), and dried under vacuum to afford Int-4 (0.55 g, 76%). $^1$H NMR (200 MHz, CDCl$_3$): δ 9.44 (dd, J=1.6, 4.8 Hz, 1H), 9.05 (s, 1H), 7.98 (d, J=4.8 Hz, 1H), 7.85 (d, J=12 Hz, 1H), 5.56 (d, J=12 Hz, 1H), 3.19 (bs, 3H), 2.96 (bs, 3H), 2.80 (s, 3H). Mass (m/z): 231 [M$^+$+1]. To a stirred solution of Int-4 (0.5 g, 2.17 mmol)) in DMF (5 mL) were added Int-5 (1.05 g, 5.4 mmol) and K$_2$CO$_3$ (0.78 g, 5.64 mmol). The mixture was stirred at 100° C. for 16 hours and diluted with water (40 mL). The precipitated solid was filtered, washed water (20 mL) and dried under vacuum to afford Int-6 (0.51 g, 65%) as brown solid. $^1$H NMR (200 MHz, dmso-d$_6$): δ 10.21 (s, 1H), 9.67 (d, J=4.8 Hz, 1H), 9.14 (s, 1H), 8.68 (d, J=5.6 Hz, 1H), 8.07 (d, J=12 Hz, 1H), 7.92 (s, 4H), 7.30 (d, J=5.4 Hz, 1H), 3.81 (s, 3H), 2.74 (s, 3H). Mass (m/z): 360.9 [M$^+$+1]. A suspension of Int-6 (0.5 g, 1.38 mmol) in 4N HCl (35 mL) was refluxed for 3 hours. The reaction mixture was cooled to room temperature. The precipitated solid was filtered, washed with water (30 mL) and dried under vacuum to afford Int-7 (0.41 g, 85%) as brown solid. $^1$H NMR (200 MHz, dmso-d$_6$): δ 10.24 (s, 1H), 9.72 (d, J=4.8 Hz, 1H), 9.23 (s, 1H), 8.7 (d, J=5.6 Hz, 1H), 8.12 (d, J=4.8 Hz, 1H), 7.9 (s, 4H), 7.31 (d, J=5.2 Hz, 1H), 2.75 (s, 3H). Mass (m/z): 346.9 [M$^+$+1]. To a stirred solution of Int-7 (0.4 g, 1.156 mmol) in DMF (5 mL) at 0° C. were added EDCI (0.443 g, 2.31 mmol), HOBt (0.156 g, 1.156 mmol) and DIPEA (0.373 g, 2.9 mmol) followed by NH$_2$—OTHP (0.224 g, 1.73 mmol). The mixture was stirred overnight at room temperature after which the product was purified directly by column chromatography using (1:25) MeOH:DCM to afford the THP protected Int-8 (0.37 g, 72%) as off white solid. $^1$H NMR (200 MHz, dmso-d$_6$): δ 11.5 (s, 1H), 10.15 (s, 1H), 9.55 (d, J=4.4 Hz, 1H), 9.03 (s, 1H), 8.58 (d, J=5.4 Hz, 1H), 8.0 (d, J=4.8 Hz, 1H), 7.8-7.64 (m, 4H), 7.22 (d, J=5.6 Hz, 1H), 4.93 (bs, 1H), 4.20 (m, 1H), 3.5 (m, 1H), 2.66 (s, 3H), 1.69-1.5 (m, 5H). Mass (m/z): 458 [M$^+$+1].

Preparation of Compound 9: To Int-8 (0.35 g, 0.786 mmol)) in MeOH (4 mL) was added 6 N HCl (1 mL) at 0° C. and stirred overnight at room temperature. The precipitated solid was filtered, washed with MeOH (2 mL) and dried under vacuum to afford the title compound (0.25 g, 88%) as pale yellow solid. $^1$H NMR (200 MHz, dmso-d$_6$): δ 11.06 (s, 1H), 10.04 (s, 1H), 9.64 (d, J=3.8 Hz, 1H), 9.13 (d, J=1.25 Hz, 1H), 8.90 (bs, 1H), 8.65 (d, J=5.6 Hz, 1H), 8.06 (d, J=4.4 Hz, 1H), 7.84 (d, J=8.8 Hz, 2H), 7.73 (d, J=8.8 Hz, 2H), 7.26 (d, J=5.4 Hz, 1H), 2.73 (s, 3H). $^{13}$C NMR (125 MHz, dmso-d$_6$): δ 162.1, 157.2, 156.7, 154.2, 146.0, 140.9, 140.2, 138.0, 128.1, 125.5, 123.5, 118.0, 116.8, 116.2, 108.1, 14.6; Mass (m/z): 361.9 [M$^+$+1]; Melting Point: 240.5° C.

Preparation of Compound 10: To a stirred solution of Int-7 (0.4 g, 1.156 mmol) in DMF (4 mL) at 0° C. EDCI (0.443 g, 2.31 mmol), HOBt (0.156 g, 1.156 mmol), DIPEA (0.373 g, 2.89 mmol) at 0° C. followed by o-phenylene-diamine (0.125 g, 1.156 mmol). The reaction mixture was stirred overnight at room temperature and diluted with water (30 mL). The precipitated solid was filtered, washed with water (2×10 mL) and dried under vacuum. It was finally purified by column chromatography using (5:95, MeOH:DCM) to provide the title compound (0.20 g, 40%) as pale yellow solid. $^1$H NMR (200 MHz, dmso-d$_6$): δ 10.11 (s, 1H), 9.68 (d, J=4.0 Hz, 1H), 9.54 (s, 1H), 9.14 (s, 1H), 8.68 (d, J=5.4 Hz, 1H), 8.10 (d, J=4.6 Hz, 1H), 7.96-7.88 (d, J=7.0 Hz, 2H), 7.80 (d, J=7.0 Hz, 2H), 7.28 (d, J=5.6 Hz, 1H), 7.16 (d, J=7.6 Hz, 1H), 7.0-6.96 (m, 1H), 6.78 (d, J=7 Hz, 1H), 6.63-6.56 (m, 1H), 4.88 (bs, 2H), 2.74 (s, 3H). $^{13}$C-NMR (125 MHz, dmso-d$_6$): δ 164.7, 159.2, 158.7, 156.2, 148.1, 143.2, 143.1, 142.2, 140.1, 130.2, 128.5, 127.2, 126.6, 126.2, 123.6, 120.8, 118.8, 117.9, 116.2, 116.1, 110.2, 16.6; Mass (m/z): 436.9 [M$^+$+1]; Melting Point: 247.9° C.

Examples 21 and 22

Example 21

N-Hydroxy-4-[4-(2-methyl-imidazo[1,2-a]pyrimidin-3-yl)-pyrimidin-2-ylamino]-benzamide

Example 22

N-(2-Amino-phenyl)-4-[4-(2-methyl-imidazo[1,2-a]pyrimidin-3-yl)-pyrimidin-2-ylamino]-benzamide To a solution of Int-1 (1 g, 10.5 mmol) in ethanol (10 ml) was added 2-chloro-pentanedione (1.6 g, 12.6 mmol) at room temperature. The reaction mixture was refluxed for 48 hours. After disappearance of starting material, the volatiles were removed under reduced pressure and the crude mass was purified by column chromatography using ethyl acetate as eluent to provide Int-2 (0.25 g, 13%). $^1$H NMR (200 MHz, CDCl$_3$): δ 9.97 (dd, J=1.8 Hz, 1H), 8.73-8.7 (m, 1H), 7.11-7.06 (m, 1H), 2.86 (s, 3H), 2.65 (s, 3H); Mass (M$^+$): 175. Int-2 (0.7 g, 4.0 mmoles) in DMFDMA (10 ml) was refluxed at 110° C. for 16 hours. Ether was added at room temperature and stirred for 20 minutes. The precipitated solid was filtered

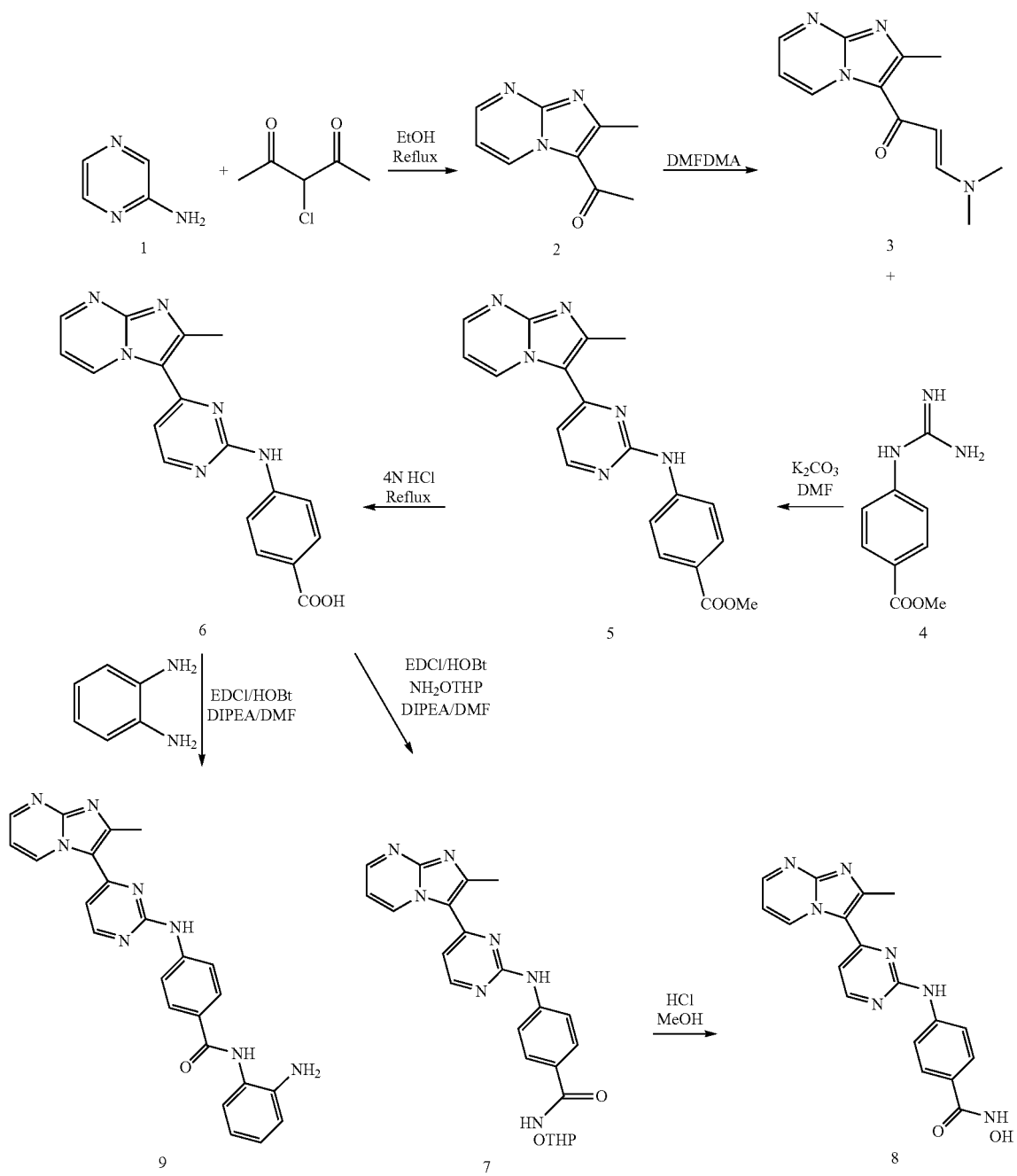

to afford Int-3 (0.7 g, 76%). ¹H NMR (200 MHz, CDCl₃): δ 9.93-9.98 (dd, J=1.8, 7.0 Hz, 1H), 8.57-8.6 (m, 1H), 7.82 (d, J=12.4 Hz, 1H), 6.92-6.98 (m, 1H), 5.56 (d, J=12.4 Hz, 1H), 3.17 (bs, 3H), 2.99 (bs, 3H), 2.82 (s, 3H). Mass (M⁺): 230. To a stirred solution of Int-3 (0.7 g, 3.04 mmol) in DMF (10 ml) were added Int-4 (1.7 g, 9.0 mmol) and potassium carbonate (1.2 g, 9.0 mmol). The reaction mixture was stirred overnight at 80° C. After disappearance of starting material, the reaction mixture was cooled to room temperature, diluted with water (50 ml), and stirred for 30 minutes. The resulting precipitate was filtered, washed with water (10 ml) and dried under vacuum to furnish critical cyclized Int-5 (along with some impurity) (0.4 g, 40%). ¹H NMR (200 MHz, dmso-d₆): δ 10.14 (bs, 1H), 9.02-9.04 (d, J=5.4 Hz, 1H), 8.68-8.7 (d, J=5 Hz, 1H), 7.92 (s, 4H), 7.63-7.66 (d, J=5.2 Hz, 1H), 7.33-7.39 (m, 1H), 3.82 (s, 3H), 3.0 (s, 3H); Mass (M⁺): 360. Int-5 (1.5 g) in 4N HCl (75 ml) was refluxed for 3 hours, and cooled to room temperature. The pH was adjusted to about 5 using saturated NaHCO₃ solution. The resulting precipitate was filtered and dried to provide Int-6 (1 g, 71%). ¹H NMR (200 MHz, dmso-d₆): δ 10.14 (bs, 1H), 9.05-9.08 (d, J=6.0 Hz, 1H), 8.68-8.7 (t, J=5.2 Hz, 1H), 7.92 (s, 4H), 7.64-7.66 (d, J=5.4 Hz, 1H), 7.37-7.43 (m, 1H), 3.0 (s, 3H); Mass (M⁺): 346.

Preparation of Compound 9: To a cooled solution of Int-6 (1 g, 2.8 mmol) in DMF (8 ml) was added HOBt (0.378 g, 2.8 mmol), EDCI (1.17 g, 6.16 mmol), o-phenylenediamine (0.312 g, 2.8 mmol) and DIPEA (1.2 ml, 7.0 mmol) sequentially. The reaction mixture was stirred overnight at room temperature. The reaction mixture was diluted with water (70 ml), and stirred for 30 minutes. The resulting precipitates were filtered and washed with water (20 ml) to get crude product, which was purified by preparative HPLC (ACN:Water) which furnished Compound 9 (0.28 g, 23%). ¹H NMR (200 MHz, dmso-d₆): δ 9.9 (bs, 1H), 9.53 (bs, 1H), 9.61-9.63 (m, 2H), 8.83-8.87 (d, J=7 Hz, 1H), 7.94 (s, 4H), 7.63-7.65 (d, J=5 Hz, 1H), 7.11-7.18 (m, 2H), 6.94 (t, J=6.6 Hz, 1H), 6.75-6.79 (d, J=8.0 Hz, 1H), 6.61 (t, J=7.4 Hz, 1H), 4.87 (bs, 2H), 3.0 (s, 3H). ¹³C NMR (125 MHz, dmso-d₆): δ 164.86, 161.7, 159.4, 158.58, 150.96, 146.6, 143.45, 143.06, 137.76, 133.2, 128.46, 126.95, 126.57, 126.24, 123.7, 120.84, 117.9, 116.3, 116.15, 110.15, 108.9, 9.6. Mass: (M⁺) 436, Melting point 255.1° C.

Preparation of Compound 8: To a cooled solution of Int-6 (1.2 g, 3.46 mmol) in DMF were added HOBt (0.467 g; 3.46 mmol), EDCI (1.65 g; 8.65 mmol), NH₂OTHP (0.811 g; 6.93 mmoles), and DIPEA (1.5 mL; 8.65 mmoles). The reaction mixture was stirred overnight at room temperature. The reaction mixture was diluted with water (60 ml) and extracted with DCM (3×30 ml). The organic layer was dried over anhydrous sodium sulphate, and concentrated. The resulting crude was purified by preparative HPLC (ACN:water) to get pure Int-7 (0.5 g, 33%). ¹H NMR (200 MHz, dmso-d₆): δ 11.47 (s, 1H), 9.87 (s, 1H), 8.87-8.82 (d, J=7 Hz, 1H), 8.62-8.59 (d, J=5.2 Hz, 1H), 7.86-7.9 (d, J=8.8 Hz, 2H), 7.72-7.77 (d, J=8.8 Hz, 2H), 7.61-7.64 (d, J=5 Hz, 2H), 7.11-7.16 (m, 1H), 4.98 (bs, 1H), 4.15 (bs, 1H), 3.5-3.6 (d, 1H), 2.99 (s, 3H), 1.55-1.72 (m, 6H); Mass: (M⁺) 445. To a suspension of Int-7 (0.5 g) in methanol (10 ml) at 0° C. was added concentrated HCl (1 ml). The reaction mixture was stirred overnight at room temperature. Methanol was evaporated under vacuum, and diluted with water (5 mL). The resulting precipitated solids were filtered and dried to afford Compound 8 (0.3 g, 74%). ¹H NMR (200 MHz, dmso-d6): δ 11.05 (bs, 1H), 9.88 (bs, 1H), 8.9-8.94 (d, J=7.4 Hz, 1H), 8.67 (bs, 1H), 8.61-8.64 (d, J=5 Hz, 1H), 7.83-7.87 (d, J=8.8 Hz, 2H), 7.7-7.75 (d, J=8.8 Hz, 2H), 7.59-7.62 (d, J=5.2 Hz, 1H), 7.23 (bs, 1H), 3.82 (bs, 1H), 3.0 (s, 3H). ¹³C NMR (125 MHz, dmso-d₆): δ 164.16, 160.73, 159.38, 158.68, 152.04, 146.16, 143.02, 136.32, 133.69, 127.48, 125.34, 121.24, 118.2, 110.09, 109.61, 9.53. Mass: (M⁺) 361, Melting point 211.9° C.

Example 23

N-(2-Amino-phenyl)-4-[4-(2-methyl-7-morpholin-4-yl-imidazo[1,2-a]pyridin-3-yl)-pyrimidin-2-ylamino]-benzamide (Compound Iᵃ-a-114)

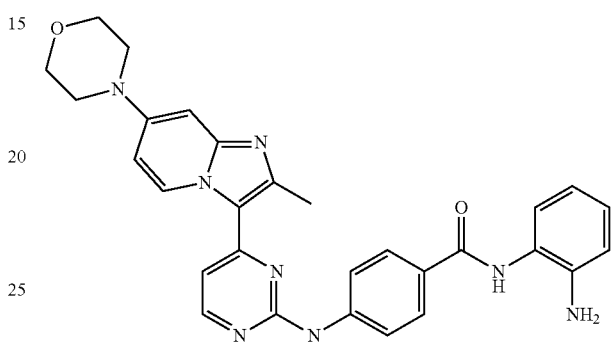

Example 23

A solution of 4-chloro-pyridin-2-ylamine (800 mg, 6.22 mmol) and morpholine (8.1 mL, 93.34 mmol) in N-methyl-2-pyrrolidone (NMP) (2 mL) was heated in a microwave (Emry's Optimizer) at 200° C. for 10 minutes. The resulting solution was directly purified by flash chromatography (SiO₂, 95:5:0.5/DCM:MeOH:NH₄OH) to give 4-morpholin-4-yl-pyridin-2-ylamine (Int-1). MS found for C₉H₁₃N₃O as (M+H)⁺ 180.39. A solution of Int-1 (418 mg, 2.34 mmol) and 3-chloro-pentane-2,4-dione (0.3 mL, 2.45 mmol) in NMP (2.5 mL) was added and heated in a microwave (Emry's Optimizer) at 150° C. for 30 minutes. The resulting solution was directly purified by flash chromatography (SiO₂, 96:4:/DCM:MeOH) to give 1-(2-methyl-7-morpholin-4-yl-imidazo[1,2-a]pyridin-3-yl)-ethanone (Int-2). MS found for C₁₄H₁₇N₃O₂ as (M+H)⁺ 260.39. A mixture of Int-2 (293 mg, 1.13 mmol) and DMF.DMA (2.3 mL) was heated at 150° C. for 10 hours. The mixture was concentrated and used further without purification. MS found for C₁₇H₂₂N₄O₂ as (M+H)⁺ 315.23. A solution of 1-(2-methyl-7-morpholin-4-yl-imidazo[1,2-a]pyridin-3-yl)-ethanone (263 mg, 0.84 mmol), 4-guanidinobenzoic acid hydrochloride (180 mg, 0.841) and 1,8-diazabicyclo[5.4.0]undec-7-ene (DBU) (0.25 mL, 1.67 mmol) in DMF (3 mL) was heated in a microwave (Emry's Optimizer) at 150° C. for 30 minutes. The reaction mixture was then diluted with water and acetonitrile and purified by preparative HPLC affording 4-[4-(2-methyl-7-morpholin-4-yl-imidazo[1,2-a]pyridin-3-yl)-pyrimidin-2-ylamino]-benzoic acid after lyophilization. MS found for C₂₃H₂₂N₆O₃ as (M+H)⁺ 431.46. To the above carboxylic acid (10 mg, 0.023 mmol) in DMF (1 mL), was added O-(7-azabenzotriazol-1-yl)-N,N,N',N'-tetramethyluronium hexafluorophosphate (HATU) (13 mg, 0.034 mmol), 1,2-phenylenediamine (5 mg, 0.046 mmol), DIPEA (0.01 mL, 0.068 mmol), and stirred at room temperature for 16 hours. The reaction mixture was diluted with water and acetonitrile and directly purified by preparative HPLC affording the title compound after lyophilization. MS found for C₂₉H₂₈N₈O₂ as (M+H)⁺ 521.28. ¹H NMR (400 MHz, dmso-d₆): δ 9.54 (d, J=8.0 Hz, 1H); 8.41 (d, J=5.6 Hz, 1H); 7.90 (d, J=8.4 Hz, 2H); 7.79 (d, J=8.4 Hz, 2H); 7.11 (d, J=7.6 Hz, 1H); 7.02-6.97 (m, 2H); 6.83 (d, J=7.6 Hz, 2H); 6.71-6.67 (m, 2H); 3.76 (m, 4H); 3.29 (m, 4H); 2.58 (s, 3H).

Example 24

N-(2-Amino-phenyl)-4-[4-(7-cyano-2-methyl-imidazo[1,2-a]pyridin-3-yl)-pyrimidin-2-ylamino]-benzamide (Compound I$^a$-a-206)

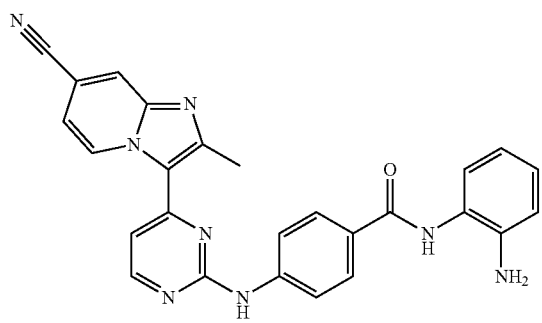

Example 24

Similar procedure from Example 26 was followed to obtain the title compound using 2-amino-isonicotinonitrile. MS found for $C_{26}H_{20}N_8O_1$ (M+H)$^+$ 461.18. $^1$H NMR (400 MHz, dmso-d$_6$): δ 10.07 (s, 1H), 9.77 (d, J=6.8 Hz, 1H), 9.49 (s, 1H), 8.63 (d, J=5.2 Hz, 1H), 8.36 (s, 1H), 7.94-7.84 (m, 4H), 7.33 (d, J=7.2 Hz, 1H), 7.21 (d, J=5.6 Hz, 1H), 7.12 (d, J=8.0 Hz, 1H), 6.92 (t, J=8.0 Hz, 1H), 6.74 (d, J=8.0 Hz, 1H), 6.56 (t, J=7.6 Hz, 1H), 4.83 (s, 2H), 2.67 (s, 3H).

Example 25

3-(2-(4-(2-aminophenylcarbamoyl)phenylamino)pyrimidin-4-yl)-2-methyl-N-(2-morpholinoethyl)imidazo[1,2-a]pyridine-7-carboxamide MS found for $C_{32}H_{33}N_9O_3$ as (M+H)$^+$ 592.27. $^1$H NMR (400 MHz, dmso-d$_6$): δ 10.0 (s, 1H), 9.74 (d, J=7.6 Hz, 1H), 9.49 (s, 1H), 8.60 (d, J=5.2 Hz, 1H), 8.11 (s, 1H), 7.94-7.86 (m, 4H), 7.41 (d, J=7.2 Hz, 1H), 7.19 (d, J=5.2 Hz, 1H), 7.12 (d, J=6.8 Hz, 1H), 6.92 (t, J=7.6 Hz, 1H), 6.74 (d, J=8.0 Hz, 1H), 6.56 (t, J=7.6 Hz, 1H), 4.83 (s, 2H), 3.56-3.50 (m, 4H), 3.42-3.35 (m, 2H), 2.66 (s, 3H), 2.40-2.35 (m, 2H).

Example 26

Methyl 3-(2-(4-(2-aminophenylcarbamoyl)phenylamino)pyrimidin-4-yl)-2-methylimidazo[1,2-a]pyridine-7-carboxylate

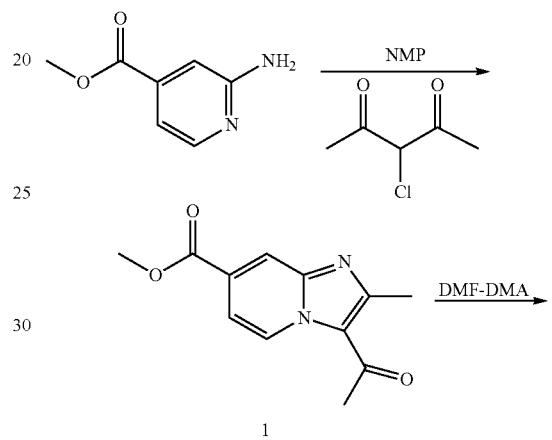

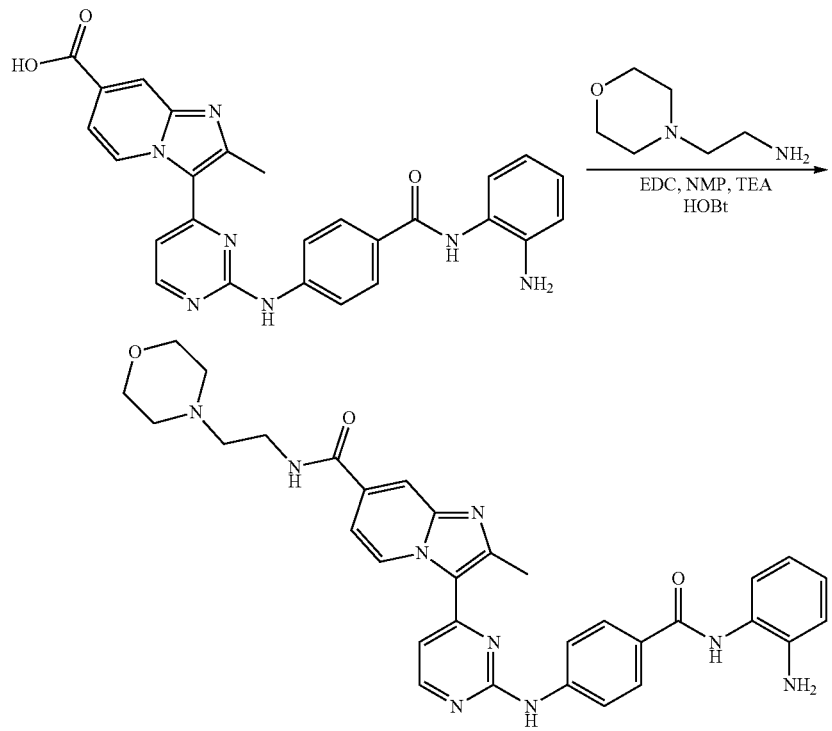

Example 25 (Compound 1$^a$-a-178)

-continued

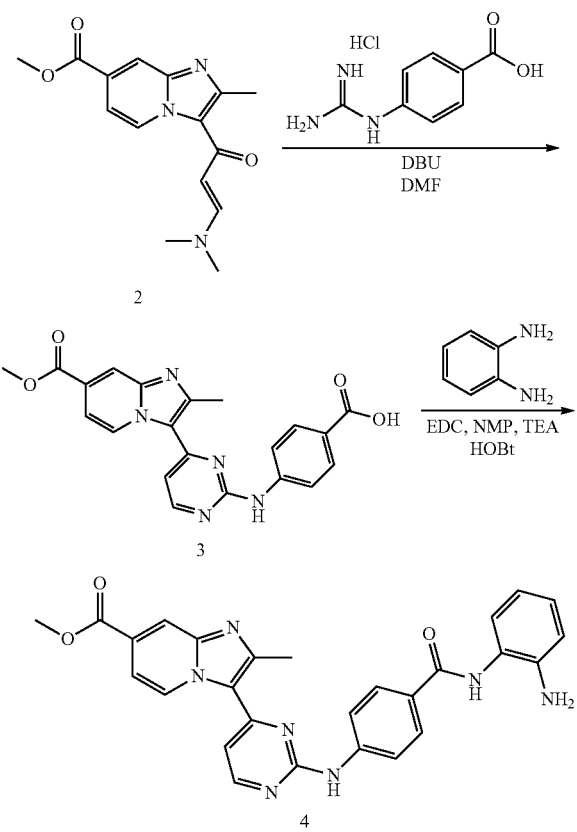

Example 26 (Compound 1ª-a-208)

2-amino-isonicotinic acid methyl ester (500 mg, 3.28 mmol) was dissolved in NMP (5 ml). 3-chloro-pentane-2,4-dione (0.42 ml, 1.5 eq) was added and the reaction mixture was heated in a microwave at 125° C. for 10 minutes. The reaction mixture was then diluted with saturated aqueous solution of $NaHCO_3$ and extracted with EtOAc. The organic phase was dried with $MgSO_4$ and evaporated. The solids were purified by silica gel chromatography (Hex:EtOAc 1:3) to give Int-1. Int-1 (200 mg, 0.86 mmol) was suspended in DMF-DMA (5 mL) and heated in a microwave at 160° C. for 30 minutes. The solid Int-2 was filtered out and used for next step without further purification. To Int-2 (100 mg, 0.348 mmol) in DMF, 4-guanidino-benzoic acid-HCl salt (150 mg, 2.0 eq) and DBU (0.14 ml, 3 eq) was added and the mixture was heated in the a microwave at 140° C. for 10 minutes. The reaction mixture was then diluted with 1N HCl and extracted with EtOAc. The organic phase was dried and evaporated to Int-3 which was used for next step without additional purifications. Int-3 (50 mg, 0.124 mmol), benzene-1,2-diamine (23.7 mg, 2.0 eq), HOBt (16.76 mg, 1.0 eq) and triethylamine (TEA) (0.02 mL, 2.0 eq) were mixed together in NMP at room temperature to have Compound 4. The reaction mixture was diluted with EtOAc and washed with water. The organic phase was dried, evaporated and purified by reverse phase chromatography. MS found for $C_{27}H_{23}N_7O_3$ as $(M+H)^+$ 494.32. $^1H$ NMR (400 MHz, dmso-$d_6$): δ 10.02 (s, 1H), 9.73 (d, J=7.6 Hz, 1H), 9.49 (s, 1H), 8.62 (d, J=5.2 Hz, 1H), 8.14 (s, 1H), 7.94-7.85 (m, 4H), 7.40 (dd, J=7.2, 5.6 Hz, 1H), 7.21 (d, J=5.6 Hz, 1H), 7.12 (d, J=7.6 Hz, 1H), 6.93 (dd, J=8.0, 1.6 Hz, 1H), 6.74 (d, J=8.0 Hz, 1H), 6.55 (d, J=8.0 Hz, 1H), 4.82 (s, 2H), 3.87 (s, 3H), 2.67 (s, 3H).

Example 27

N-(2-Amino-phenyl)-4-{4-[2-methyl-7-(4-methyl-piperazine-1-carbonyl)-imidazo[1,2-a]pyridin-3-yl]-pyrimidin-2-ylamino}-benzamide

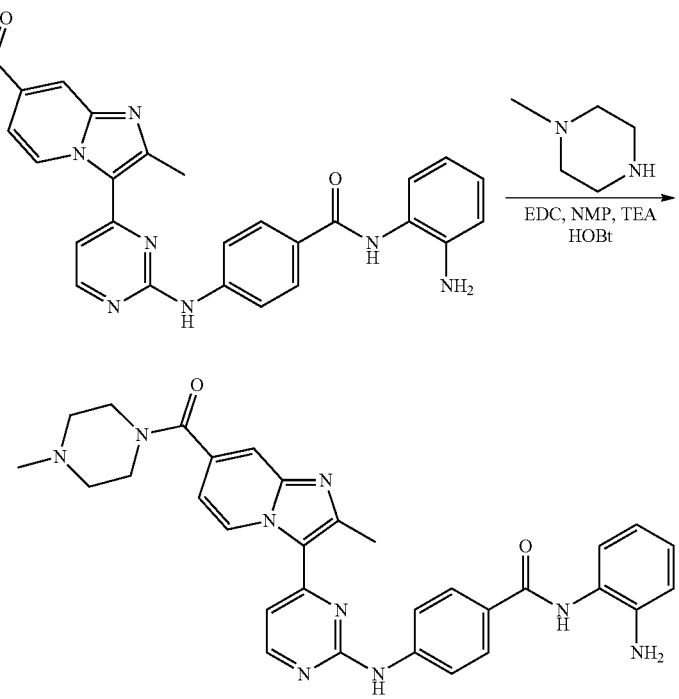

Example 27 (Compound 1ª-a-182)

MS found for $C_{31}H_{31}N_9O_2$ as $(M+H)^+$ 562.26. $^1H$ NMR (400 MHz, dmso-$d_6$): δ 9.95 (s, 1H), 9.75 (d, J=7.2 Hz, 1H), 9.48 (s, 1H), 8.59 (d, J=5.6 Hz, 1H), 7.93-7.85 (m, 4H), 7.18 (d, J=5.2 Hz, 1H), 7.12 (d, J=6.8 Hz, 1H), 7.01 (t, J=6.8 Hz, 1H), 6.92 (t, J=7.6 Hz, 1H), 6.74 (d, J=7.6 Hz, 1H), 6.56 (t, J=7.2 Hz, 1H), 4.82 (s, 2H), 3.62-3.25 (m, 4H), 2.65 (s, 3H), 2.62 (s, 3H), 2.40-2.12 (m, 4H).

Example 28

3-{2-[4-(2-Amino-phenylcarbamoyl)-phenylamino]-pyrimidin-4-yl}-2-methyl-imidazo[1,2-a]pyridine-7-carboxylic acid (Compound I$^a$-a-210)

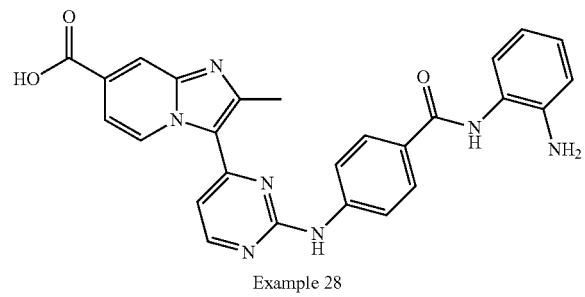

Example 28

Compound 3-{2-[4-(2-amino-phenylcarbamoyl)-phenylamino]-pyrimidin-4-yl}-2-methyl-imidazo[1,2-a]pyridine-7-carboxylic acid methyl ester (200 mg, 0.4 mmol) was dissolved in MeOH (5 mL) and then treated with 1N NaOH (1 mL). After 2 hours the reaction mixture was evaporated and the solids were re-suspended in water and 1N HCl was slowly added to precipitate the title compound. MS found for $C_{26}H_{21}N_7O_3$ as $(M+H)^+$ 480.53. $^1H$ NMR (400 MHz, dmso-$d_6$): δ 9.99 (s, 1H), 9.72 (d, J=5.6 Hz, 1H), 9.47 (s, 1H), 8.59 (d, J=5.5 Hz, 1H), 8.07 (s, 1H), 7.90-7.84 (m, 4H), 7.39 (dd, J=7.2, 6.0 Hz, 1H), 7.18-7.09 (m, 2H), 6.90 (t, J=6.0 Hz, 1H), 6.72 (d, J=7.6 Hz, 1H), 6.56-6.48 (m, 1H), 2.64 (s, 3H).

Example 29

N-(2-aminophenyl)-4-(4-(2-methyl-7-(2-morpholinoethoxy)imidazo[1,2-a]pyridin-3-yl)pyrimidin-2-ylamino)benzamide (Compound I$^a$-a-186)

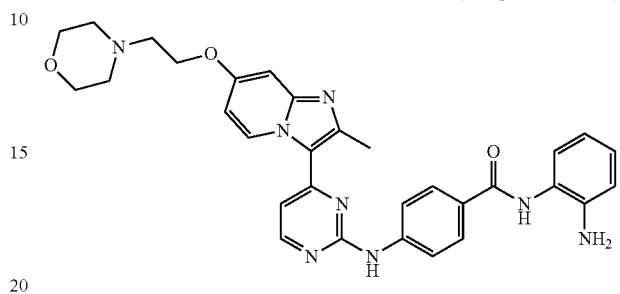

Example 29

To a mixture of methyl 4-(4-(7-chloro-2-methylH-imidazo[1,2-a]pyridin-3-yl)pyrimidin-2-ylamino)benzoate (100 mg, 0.25 mmol), KO$^t$Bu (86 mg, 0.76 mmol) in NMP (2 mL), and 2-morpholin-4-yl-ethanol (0.16 mL, 1.3 mmol) were added and heated in a microwave (Emry's Optimizer) at 170° C. for 10 minutes. The reaction mixture was then diluted with water and acetonitrile and purified by preparative HPLC affording 4-{4-[2-methyl-7-(2-morpholin-4-yl-ethoxy)-imidazo[1,2-a]pyridin-3-yl]-pyrimidin-2-ylamino}-benzoic acid after lyophilization. MS found for $C_{25}H_{26}N_6O_4$ as $(M+H)^+$ 475.05. To the above carboxylic acid (59 mg, 0.124 mmol) in DMF (3 mL), were added HATU (71 mg, 0.186 mmol), 1,2-phenylenediamine (27 mg, 0.25 mmol), and DIPEA (0.07 mL, 0.372 mmol) and stirred at room temperature for 16 hours. Additional 1,2-phenylenediamine (50 mg, 0.46 mmol), HATU (150 mg, 0.39 mmol) and DIPEA (0.2 mL) were added and stirred at room temperature for 4 hours. The reaction mixture was diluted with water and acetonitrile and directly purified by preparative HPLC affording the title compound, after lyophilization. MS found for $C_{31}H_{32}N_8O_3$ as $(M+H)^+$ 565.08. $^1H$ NMR (400 MHz, dmso-$d_6$): δ 10.04 (brs, 1H); 9.62 (m, 2H); 8.61 (d, J=4.8 Hz, 1H); 7.92 (d, J=8.8 Hz, 2H); 7.84 (d, J=8.8 Hz, 2H); 7.23 (s, 1H); 7.15 (d, J=6.0 Hz, 2H); 6.98-6.69 (m, 5H); 4.51 (m, 2H); 3.74-3.38 (m, 10H); 2.62 (s, 3H).

Example 30

N-(2-Amino-phenyl)-4-{4-[7-(2-dimethylamino-ethoxy)-2-methyl-imidazo[1,2-a]pyridin-3-yl]-pyrimidin-2-ylamino}-benzamide

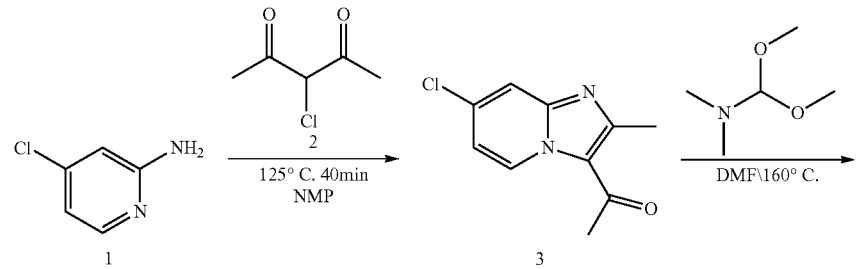

-continued

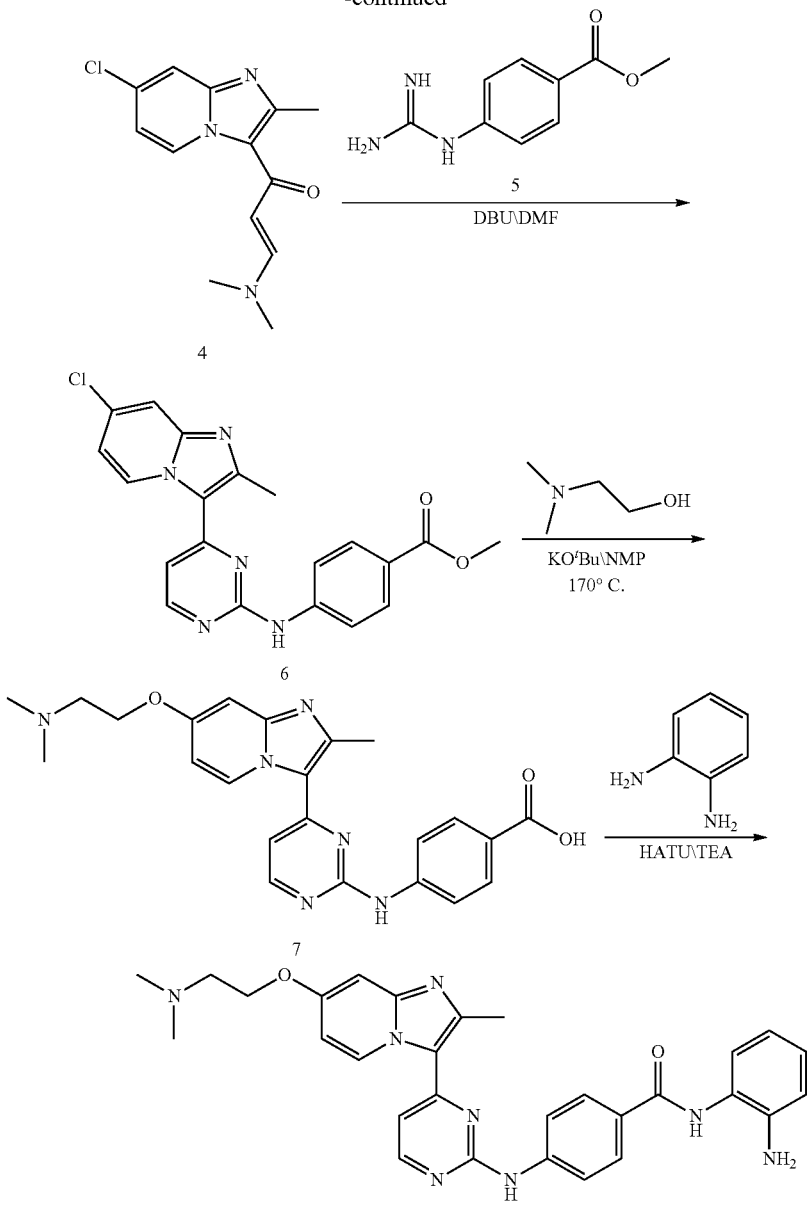

Example 30 (Compound I$^a$-a-188)

Int-1 (1.99 g, 0.016 mmol) and Int-2 (1.85 mL, 0.016 mol) were dissolved in NMP (15 mL) and the resulting mixture was heated under microwave condition with stirring at 125° C. for 40 minutes. It was then diluted with EtOAc and washed with saturated aqueous NaHCO$_3$ solution. The organic layers were then combined and dried with MgSO$_4$. Filtration and concentration gave Int-3 (2.92 g). MS m/z: 209 (MH$^+$). Crude Int-3 (2.92 g) and DMF-DMA (5 mL) were dissolved in DMF (10 mL), and heated under microwave condition with stirring at 160° C. for 20 minutes. The precipitate formed was then collected by filtration to afford Int-4 (1.53 g, 37% for two steps). MS m/z: 264 (MH$^+$). A mixture of Int-4 (1.53 g, 5.8 mmol), Int-5 (1.670 g, 8.6 mol) and DBU (1.72 mL, 11.6 mol) in DMF (15 mL) was heated under microwave condition with stirring at 160° C. After 30 minutes, water was added. The precipitate formed was collected by filtration and washed with water to afford Int-6 (1.20 g, 53%). MS m/z: 394 (MH$^+$).

A solution of Int-6 (0.15 g, 0.4 mmol) and dimethylaminoethanol (0.5 mL) in NMP (4 mL) was treated with KO$^t$Bu (0.200 g, 1.78 mmol) and heated under microwave condition with stirring at 170° C. After 10 minutes, water was added to the reaction mixture and acidified to about pH 4 with 1N HCl. The precipitate formed was collected by filtration to afford Int-7 (0.13 g, 80%). MS m/z: 433 (MH$^+$). Int-7 (0.13 g, 0.3 mmol) was coupled with phenylenediamine (0.035 g, 0.3 mmol) in the presence of HATU (0.15 g, 0.4 mmol) and triethylamine (0.12 mL, 0.9 mmol) in DMF (2 mL) and then purified by preparative HPLC to afford the title compound. MS (C$_{29}$H$_{30}$N$_8$O$_2$) m/z: 523 (MH$^+$). NMR $^1$H NMR (dmso-d$_6$): δ 10.12 (s, 1H), 9.74 (s, 1H), 9.64 (d, J=7.2 Hz, 1H), 8.67 (d, J=5.2 Hz, 1H), 7.94 (d, J=8.8 Hz, 2H), 7.86 (d, J=8.8 Hz, 2H), 7.25 (s, 1H), 7.20 (d, J=5.2 Hz, 2H), 7.05 (m, 2H), 6.95 (m, 1H), 6.82 (m, 1H), 4.54 (s, 2H), 3.57 (s, 2H), 2.85 (s, 6H), 2.66 (s, 3H), 2.49 (s, 2H).

Example 31

N-(2-Amino-phenyl)-4-{4-[7-(2-methoxy-ethoxy)-2-methyl-imidazo[1,2-a]pyridin-3-yl]-pyrimidin-2-ylamino}-benzamide

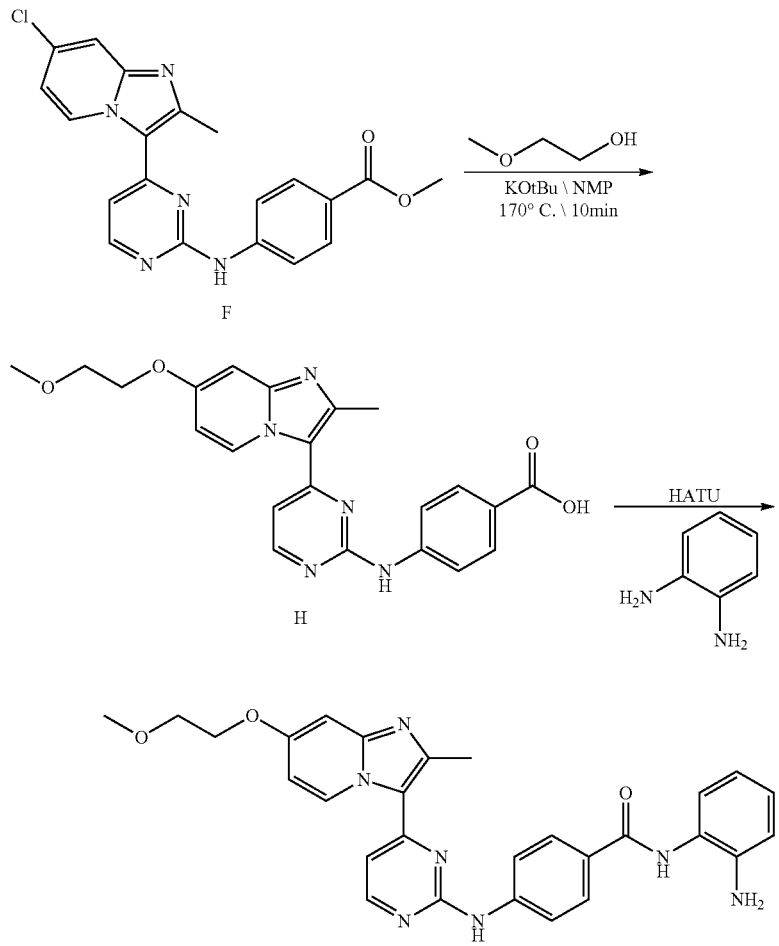

Example 31 (Compound I$^a$-a-190)

A solution of Int-F (0.16 g, 0.4 mmol) and 2-methoxyethanol (0.5 mL) in NMP (4 mL) was treated with KO$^t$Bu (0.30 g, 2.7 mmol). The resultant mixture was heated under microwave condition with stirring at 170° C. After 10 minutes, water was added to the reaction mixture and acidified to about pH 4 with 1N HCl. The formed precipitate was collected by filtration to afford Int-H (0.15 g, 84%). MS m/z: 420 (MH$^+$). Int-H (0.15 g, 0.4 mmol) was then coupled with phenylenediamine (0.076 g, 0.7 mmol) in the presence of HATU (0.3 g, 0.7 mmol) and triethylamine (0.3 mL, 1.8 mmol) in DMF (2 mL). The reaction mixture was then purified by preparative HPLC to afford the title compound. MS ($C_{28}H_{29}N_7O_3$) m/z: 510 (MH$^+$). NMR $^1$H NMR (dmso-d$_6$): δ 9.90 (s, 1H), 9.67 (d, J=7.6 Hz, 1H), 9.49 (s, 1H), 8.47 (d, J=5.6 Hz, 1H), 7.91 (d, J=8.8 Hz, 2H), 7.84 (d, J=8.8 Hz, 2H), 7.11 (d, J=7.2 Hz, 1H), 7.05 (d, J=5.6 Hz, 1H), 7.01 (s, 1H), 6.90 (t, J=8.0 Hz, 1H), 6.71 (m, 2H), 6.54 (t, J=7.6 Hz, 1H), 4.82 (s, 2H), 4.18 (m, 2H), 3.66 (m, 2H), 3.26 (s, 3H), 2.56 (s, 3H).

Example 32

N-(2-Amino-phenyl)-4-{4-[7-(2-dimethylamino-ethylamino)-2-methyl-imidazo[1,2-a]pyridin-3-yl]-pyrimidin-2-ylamino}-benzamide (Compound I$^a$-a-194)

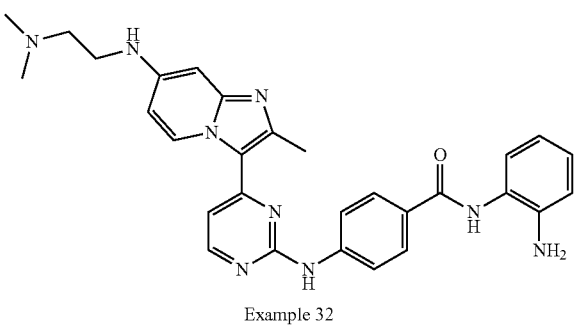

Example 32

A mixture of methyl 4-(4-(7-chloro-2-methylH-imidazo[1,2-a]pyridin-3-yl)pyrimidin-2-ylamino)benzoate (52 mg, 0.13 mmol), Pd(OAc)$_2$ (9 mg, 0.01 mmol), 2-Ditert-butylphosphine (6 mg, 0.02 mmol) and NaO$^t$Bu (19 mg, 0.2 mmol) in N$^1$,N$^1$-dimethylethane-1,2-diamine (3 mL) was heated in pressure vessel at 130° C. After 15 minutes, the reaction mixture was concentrated to give methyl 4-(4-(7-(2-(dimethylamino)ethylamino)-2-methyl-H-imidazo[1,2-a]pyridin-3-yl)pyrimidin-2-ylamino)benzoate (MS found for C$_{24}$H$_{27}$N$_7$O$_2$ as (M+H)$^+$ 446.25) and 4-(4-(7-(2-(dimethylamino)ethylamino)-2-methylH-imidazo[1,2-a]pyridin-3-yl)pyrimidin-2-ylamino)benzoic acid (MS found for C$_{23}$H$_{25}$N$_7$O$_2$ as (M+H)$^+$ 432.25) in a 1:2 ratio, respectively. The mixture was used further without purification. To the crude mixture in MeOH (5 mL) was added 1N NaOH (1 mL) and stirred at room temperature. After 16 hours, the reaction mixture was concentrated, diluted with water and washed with ether (3×). The aqueous phase was then neutralized with 6N HCl (1.5 mL) and purified by preparative HPLC giving 4-(4-(7-(2-(dimethylamino)ethylamino)-2-methylH-imidazo[1,2-a]pyridin-3-yl)pyrimidin-2-ylamino)benzoic acid. MS found for C$_{23}$H$_{25}$N$_7$O$_2$ as (M+H)$^+$ 432.28. To the acid in DMF (3 mL), were added HATU (80 mg, 0.21 mmol), 1,2-phenylenediamine (30 mg, 0.27 mmol) and DIPEA (0.1 mL). The reaction mixture was stirred at room temperature for 16 hours. The reaction mixture was then diluted with water and acetonitrile and directly purified by preparative HPLC, affording the title compound after lyophilization. MS found for C$_{29}$H$_{31}$N$_9$O as (M+H)$^+$ 522.21. $^1$H NMR (400 MHz, dmso-d$_6$): δ 10.04 (brs, 1H); 9.54 (m, 2H); 7.98 (d, J=8.8 Hz, 2H); 7.90 (d, J=8.8 Hz, 2H); 7.18 (m, 2H); 6.99 (t, J=7.2 Hz, 2H); 6.80 (d, J=8.4 Hz, 2H); 6.63-6.51 (m, 3H); 3.57 (m, 2H); 2.85 (s, 6H); 2.67 (m, 2H); 2.62 (s, 3H).

Examples 33 and 34

Example 33

3-Fluoro-N-hydroxy-4-[4-(2-methyl-imidazo[1,2-a]pyridin-3-yl)-pyrimidin-2-ylamino]-benzamide Example 34

N-(2-Amino-phenyl)-3-fluoro-4-[4-(2-methyl-imidazo[1,2-a]pyridin-3-yl)-pyrimidin-2-ylamino]-benzamide

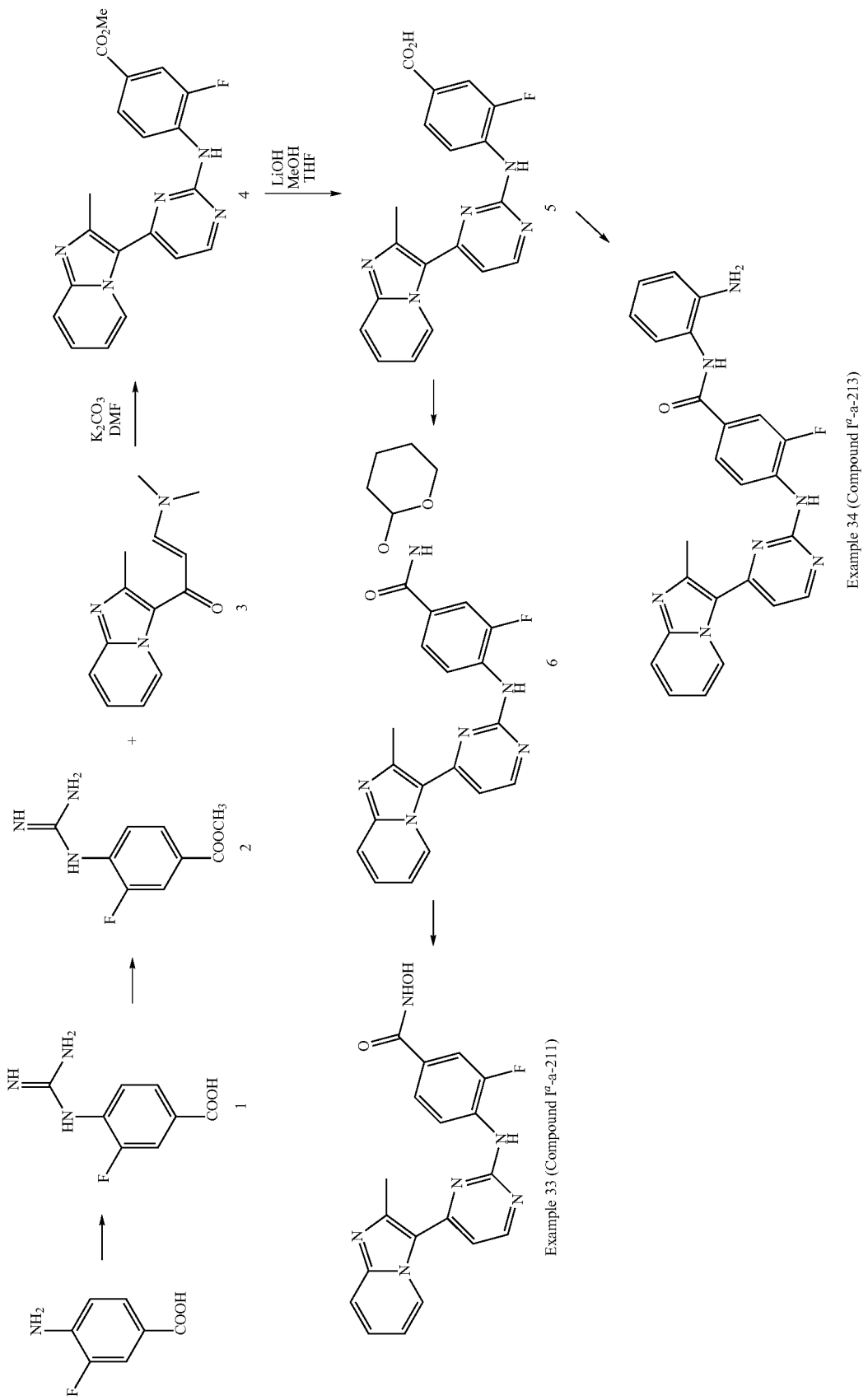

To a stirred solution of 4-amino-3-fluoro-benzoic acid (6.0 g, 38.6 mmol) in a mixture of concentrated HCl/water (5.4 mL/33 mL) was added cyanamide (3.7 g, 88.9 mmol) at room temperature. The reaction mixture was stirred at reflux temperature for 6 hours and then allowed to stand at room temperature (without stirring) for 16 hours. The precipitated solid was filtered off and dried under vacuum to provide Int-1 (5.0 g) as HCl salt. Mass (m/z): 199 [M$^+$+1]. To a stirred suspension of Int-1 (5.0 g, 195.5 mmol) in methanol (40 mL) was added acetyl chloride (10 mL) drop wise at 0° C. over a period of 10 minutes. The reaction mixture was warmed to room temperature and then stirred for 16 hours. The reaction mixture was neutralized (about pH 7) using NaHCO$_3$ at 0° C. The solids were filtered off and the filtrate was evaporated under vacuum to get crude compound. This crude compound was washed with EtOAc (10 mL) to afford Int-2 (5.0 g, 94%) as white solid. Mass (m/z): 212 [M$^+$+1]. To a stirred suspension of Int-3 (1.08 g, 4.7 mmol) in DMF (10 mL) was added Int-2 (2.5 g, 11.8 mmol), followed by K$_2$CO$_3$ (1.94 g, 14.0 mmol) at room temperature. The resulting mixture was heated to 100° C. and then stirred for 16 hours. The reaction mixture was cooled to room temperature, diluted with ice cold water (100 mL) and stirred for 15 minutes. The precipitated solid was filtered off, washed with water (3×10 mL) and dried under vacuum to afford Int-4 (0.7 g, 16%) as solid. Mass (m/z): 378 [M$^+$+1]. To a stirred solution of Int-4 (0.6 g, 1.6 mmol) in methanol (8 mL) and THF (8 mL) was added lithium hydroxide (0.33 g, 7.9 mmol) at room temperature, followed by water (4 mL). The resulting mixture was stirred at room temperature for 16 hours. The volatiles were concentrated under reduced pressure, diluted with water (10 mL) and acidified to about pH 5 using 3 N HCl at 0° C. The precipitated solid was filtered off, washed with water (2×5 mL) and dried under vacuum to provide Int-5 (0.46 g, 80%) as solid. Mass (m/z): 364 [M$^+$+1]. To a stirred solution Int-5 (0.6 g, 1.65 mmol) in DMF (10 mL) was added HOBt (0.22 g, 1.65 mmol), EDCI (0.78 g, 4.12 mmol), NH$_2$OTHP (0.38 g, 3.3 mmol) and N-ethyldiisopropylamine (0.7 mL, 4.12 mmol) at 0° C. The reaction mixture was warmed to room temperature and stirred for 16 hours. The reaction mixture was diluted with water, extracted with ethyl acetate (3×25 mL). The combined organic extracts were washed with brine, dried over anhydrous Na$_2$SO$_4$ and evaporated under vacuum. The crude material was purified over silica gel column chromatography eluting with 3% MeOH/DCM to afford Int-6 (0.35 g, 45.7%) as solid. Mass (m/z): 463 [M$^+$+1].

Preparation of Example 33: To a mixture of Int-6 (0.35 g, 0.75 mmol) in methanol (5.0 mL) was added concentrated HCl (1.0 mL) drop wise at 0° C. and the reaction mixture was stirred at room temperature for 16 hours. After reaction completion, the precipitated solid was filtered under vacuum to provide product as HCl salt. The HCl salt was neutralized using saturated NaHCO$_3$ solution to afford the title compound (0.28 g, 97%) as free hydroxamic acid solid. Mass (m/z): 379.1 [M$^+$+1]. $^1$H NMR (200 MHz, dmso-d$_6$): δ 9.61 (d, J=7 Hz, 1H), 9.20 (brs, 1H), 8.45 (d, J=5.6 Hz, 1H), 7.60-7.51 (m, 4H), 7.38 (t, J=5.8 Hz, 1H), 7.06 (d, J=5.6 Hz, 1H), 6.84 (t, 1H), 2.63 (s, 3H). $^{13}$C NMR (125 MHz, dmso-d$_6$): 162.5, 159.7, 158.2, 158.0, 156.9, 156.7, 147.3, 146.9, 145.5, 145.3, 128.5, 126.7, 126.3, 124.3, 122.6, 117.4, 117.2, 116.1, 116.0, 112.7, 109.5, 109.3, 107.4, 16.9.

Preparation of Example 34: To a stirred solution of Int-5 (0.53 g, 1.46 mmol) in DMF (10 mL) was added HOBt (0.19 g, 1.46 mmol), EDCI (0.61 g, 3.21 mmol), o-phenylenediamine (0.15 g, 1.46 mmol) and N-ethyldiisopropylamine (0.6 mL, 3.65 mmol) at 0° C. The reaction mixture was warmed to room temperature and stirred for 16 hours. The reaction mixture was diluted with water and stirred for 20 minutes. The precipitated solid was filtered off and dried under vacuum. The crude material was purified over silica gel column eluting with 2% MeOH/DCM to afford the title compound (0.3 g, 45%) as solid. Mass (m/z): 454 [M$^+$+1]. $^1$H NMR (200 MHz, dmso-d$_6$): δ 9.77 (d, J=7 Hz, 1H), 9.64 (s, 1H), 9.53 (s, 1H), 8.53 (d, J=5.4 Hz, 1H), 8.08 (t, J=8.6 Hz, 1H), 7.83 (t, J=9 Hz, 2H), 7.62 (d, J=9 Hz, 1H), 7.43 (t, J=6 Hz 1H), 7.19-7.14 (m, 2H), 6.98 (t, J=7.6 Hz, 2H), 6.78 (d, J=6.6 Hz, 1H), 6.6 (t, J=7.6 Hz, 1H), 4.92 (brs, 2H), 2.66 (s, 3H). $^{13}$C NMR (125 MHz, dmso-d$_6$): 179.5, 163.7, 159.5, 158.0, 157.0, 154.5, 152.6, 147.4, 145.5, 143.2, 130.7, 130.6, 130.0, 128.5, 126.8, 126.5, 123.9, 123.5, 123.0, 117.2, 116.1, 116.0, 115.0, 114.8, 112.8, 109.6, 16.97.

Examples 35 and 36

Example 35

2-Fluoro-N-hydroxy-4-[4-(2-methyl-imidazo[1,2-a]pyridin-3-yl)-pyrimidin-2-ylamino]-benzamide Example 36

N-(2-Amino-phenyl)-2-fluoro-4-[4-(2-methyl-imidazo[1,2-a]pyridin-3-yl)-pyrimidin-2-ylamino]-benzamide

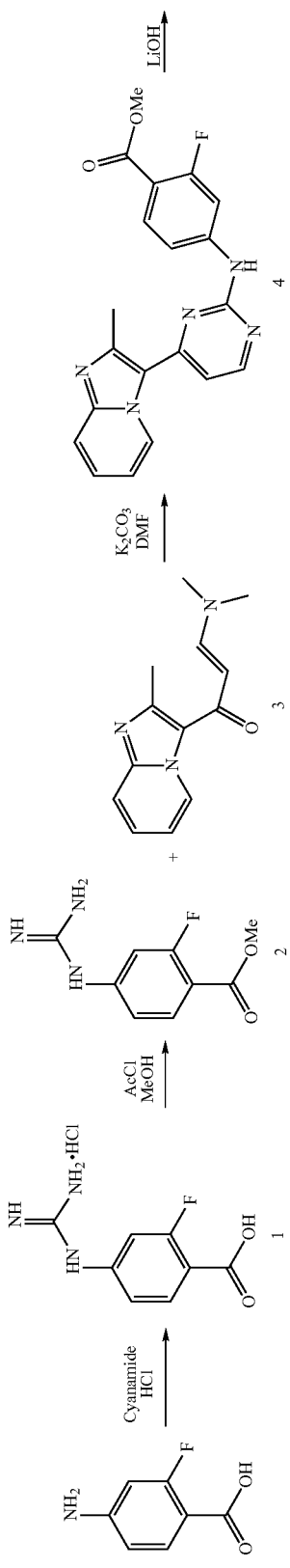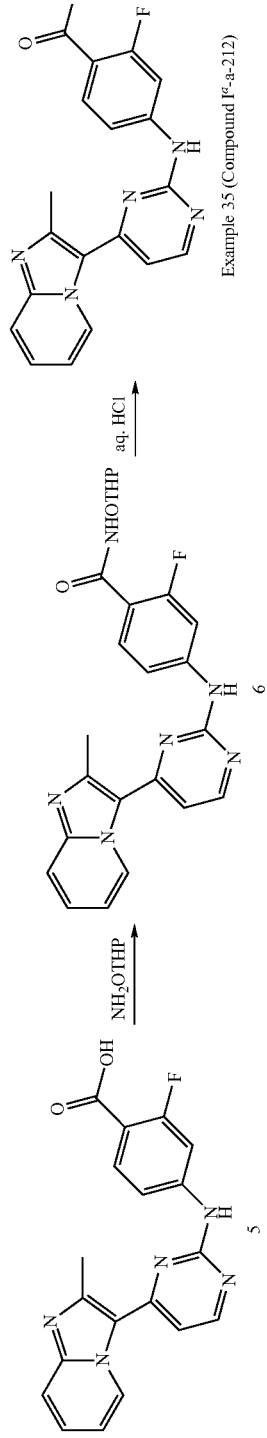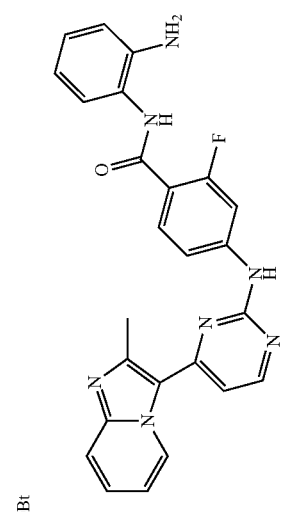

To a stirred suspension of 4-amino-2-fluoro benzoic acid (3.0 g, 19.30 mmol) and the mixture of conc. HCl/water (2.7 mL/16.5 mL) was added cyanamide (1.86 g, 44.4 mmol) at room temperature. The reaction mixture was heated at 100° C. for 7 hours and then allowed to stand at room temperature (without stirring) for 16 hours. The precipitated solid was filtered off, washed with water and dried under vacuum to afford Int-1 (3.0 g, 78%) as a salt. Mass (m/z): 198 [M$^+$+1]. $^1$H NMR (200 MHz, dmso-d$_6$): δ 7.99 (brs, 5H), 7.70 (t, J=8.4 Hz, 1H), 6.91-6.85 (m, 2H). To a stirred suspension of Int-1 (3.0 g, 15.2 mmol) in methanol (15 mL) was added acetyl chloride (16.2 mL, 22.8 mmol) drop wise at 0° C. over a period of 20 minutes. The reaction mixture was stirred at room temperature for 16 hours. The reaction mixture was neutralized using NaHCO$_3$ at 0° C. The precipitated solid was filtered off and the filtrate was concentrated under vacuum to get crude compound. The crude compound was washed with EtOAc (100 mL) to afford Int-2 (2.8 g, 87%) as white solid. Mass (m/z): 212 [M$^+$+1]. $^1$H NMR (200 MHz, dmso-d$_6$): δ 8.16 (brs, 5H), 7.89 (t, J=8.6 Hz, 1H), 7.23-7.12 (m, 2H), 3.8 (s, 3H). To a stirred solution of Int-3 (1.0 g, 4.30 mmol), guanidine ester-2 (2.0 g, 9.6 mmol) in DMF (7.0 mL) was added K$_2$CO$_3$ (1.5 g, 10.9 mmol) at room temperature. The reaction mixture was heated at 130° C. for 16 hours. After the reaction completion, the reaction mixture was allowed to room temperature, poured into ice cold water (40 mL) and stirred for 30 minutes. The precipitated solid was filtered off, washed with water (3×5 mL) and dried under vacuum to get crude product. The crude material was purified by silica gel column chromatography eluting with 1% MeOH/DCM to afford Int-4 (0.7 g, 42%) as solid. Mass (m/z): 378 [M$^+$+1]. $^1$H NMR (200 MHz, dmso-d$_6$): δ 10.31 (brs, 1H), 9.73 (d, J=6 Hz, 1H), 8.63 (d, J=5.6 Hz, 1H), 7.93-7.84 (m, 3H), 7.63-7.83 (m, 3H), 7.24 (d, J=5.4 Hz, 1H), 7.18-7.01 (m, 1H). To a stirred solution of Int-4 (0.7 g, 1.85 mmol) in methanol (5.0 mL), THF (5.0 mL) and water (3.0 mL) was added lithium hydroxide monohydrate (0.23 g, 5.57 mmol) at room temperature and then stirred for 16 hours. The volatiles were concentrated under vacuum. The residue was diluted with water (30 mL) and acidified to about pH 5 using 1 N HCl at 0° C. and stirred further for 30 minutes. The precipitated solid was filtered off, washed with water (2×30 mL) and dried under vacuum to afford Int-5 (0.559 g, 82%) as solid. Mass (m/z): 363 [M$^+$+1]. $^1$H NMR (200 MHz, dmso-d$_6$): δ 10.47 (brs, 1H), 9.79 (d, J=6.8 Hz, 1H), 8.76 (d, J=5.6 Hz, 1H), 7.96-7.78 (m, 4H), 7.55 (d, J=8.4 Hz, 1H), 7.46 (t, J=5.4 Hz, 1H), 7.33 (d, J=5.6 Hz, 1H). To a stirred suspension of Int-5 (0.6 g, 1.65 mmol) in DMF (8 mL) was added EDCI (0.697 g, 3.60 mmol), HOBt (0.222 g, 1.65 mmol) and N-ethyldiisopropylamine (0.74 mL, 4.1 mmol) at 0° C. under inert atmosphere. After being stirred for 15 minutes at the same temperature, NH$_2$OTHP (0.386 g, 3.3 mmol) was added to the reaction mixture at 0° C. The reaction mixture was allowed to warm to room temperature and stirred further for 16 hours. Reaction mixture was diluted with water (50 mL) and stirred for 30 minutes. The aqueous layer was extracted with DCM (3×50 mL) and the combined organic layer was dried over Na$_2$SO$_4$ and concentrated under reduced pressure. The crude material was purified over silica gel column chromatography eluting with 2.5% MeOH/DCM to afford Int-6 (0.395 g, 51%) as off-white solid.

Preparation of Example 35: To a mixture of Int-6 (0.595 g, 1.28 mmol) in methanol (25 mL) was added concentrated HCl (1.2 mL) drop wise at 0° C. and the reaction mixture was stirred at room temperature for 16 h under reduced pressure. The precipitated solid was filtered off, dried under vacuum to provide product as HCl salt. The salt was treated with saturated NaHCO$_3$ solution for 30 minutes, filtered and dried under vacuum to afford the title compound (0.29 g, 59%) as off white solid. MS (m/z): 379 [M$^+$+1]. $^1$H NMR (200 MHz, dmso-d$_6$): δ10.78 (s, 1H), 10.11 (s, 1H), 9.75 (d, J=6.8 Hz, 1H), 9.08 (s, 1H), 8.60 (d, J=5.6 Hz, 1H), 7.93-7.86 (m, 1H), 7.67-7.62 (m, 1H), 7.54-7.40 (m, 3H), 7.20 (d, J=5.4 Hz, 1H), 7.10-7.06 (m, 1H), 2.65 (s, 3H). $^{13}$C NMR (125 MHz, dmso-d$_6$): δ 161.48, 160.57, 159.02, 158.61, 158.0, 156.94, 147.35, 145.65, 144.33, 144.24, 130.23, 128.21, 126.90, 117.51, 116.32, 114.20, 114.07, 113.95, 113.03, 110.21, 105.35, 105.13, 16.74.

Preparation of Example 36: To a stirred solution Int-5 (0.55 g, 1.51 mmol) in DMF (9.0 mL) was added EDCI (0.638 g, 3.33 mmol), HOBt (0.203 g, 1.51 mmol) and N-ethyldiisopropylamine (0.676 mL, 3.77 mmol) at 0° C. under inert atmosphere. After being stirred for 15 minutes at the same temperature, o-phenylene diamine (0.163 g, 1.51 mmol) was added to the reaction mixture at 0° C. The reaction mixture was then allowed to room temperature, and stirred further for 16 hours. The reaction mixture was diluted with water (50 mL) and stirred for 30 minutes. The precipitated solid was filtered off, washed with water (2×10 mL) and dried under vacuum. The crude material was purified by column chromatography eluting with 3% MeOH/DCM to afford the title compound (0.31 g, 45%) as a white solid. Mass (m/z): 454.1 [M$^+$+1]. $^1$H NMR (200 MHz, dmso-d$_6$): δ10.18 (s, 1H), 9.77 (d, J=7.0 Hz, 1H), 9.28 (s, 1H), 8.62 (d, J=5.4 Hz, 1H), 8.02-7.95 (m, 1H), 7.73-7.56 (m, 3H), 7.49-7.46 (m, 1H), 7.33-7.29 (m, 1H), 7.22 (d, J=4.0 Hz, 1H), 7.08 (t, J=8.5 Hz, 1H), 6.94-6.90 (m, 1H), 6.78-6.75 (m, 1H), 6.59 (t, 1H), 4.90 (bs, 2H), 2.67 (s, 3H). $^{13}$C NMR (125 MHz, dmso-d$_6$): δ 162.15, 160.94, 158.95, 157.93, 156.91, 147.35, 145.63, 144.64, 144.55, 141.96, 130.77, 128.20, 126.86, 126.04, 125.43, 123.50, 117.45, 116.37, 116.27, 116.14, 115.88, 115.78, 114.08, 113.00, 110.19, 105.22, 104.99, 54.84, 16.73.

Example 37

3-(2-(4-(2-aminophenylcarbamoyl)phenylamino)pyrimidin-4-yl)-N-(2-(dimethylamino)ethyl)-2-methylimidazo[1,2-a]pyridine-6-carboxamide

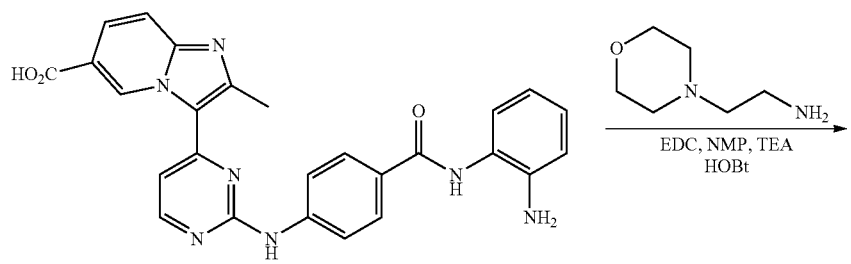

-continued

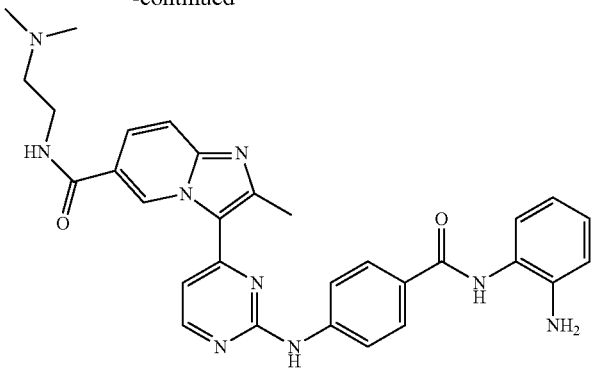

Example 37 (Compound I<sup>a</sup>-a-218)

Similar procedure from Example 26 was followed to obtain the title compound using 6-aminonicotinic acid methyl ester and 2-aminoethyldimethyl amine, MS found for $C_{30}H_{31}N_9O_2$ as (M+H)$^+$ 550.26. $^1$H NMR (400 MHz, dmso-d$_6$): δ 10.08 (s, 1H), 9.89 (s, 1H), 9.44 (s, 1H), 8.61 (d, J=5.8 Hz, 1H), 8.45-8.40 (m, 1H), 7.91-7.81 (m, 4H), 7.73 (d, J=7.2 Hz, 1H), 7.62 (d, J=7.4 Hz, 1H), 7.18-7.10 (m, 2H), 6.91 (t, J=6.2 Hz, 1H), 6.73 (d, J=5.4 Hz, 1H), 6.52 (t, J=6.4 Hz, 1H), 2.61 (s, 3H), 2.31-2.25 (m, 2H), 2.11 (s, 6H).

Example 38

3-(2-(4-(2-aminophenylcarbamoyl)phenylamino)pyrimidin-4-yl)-N-(2-methoxyethyl)-2-methylimidazo[1,2-a]pyridine-6-carboxamide

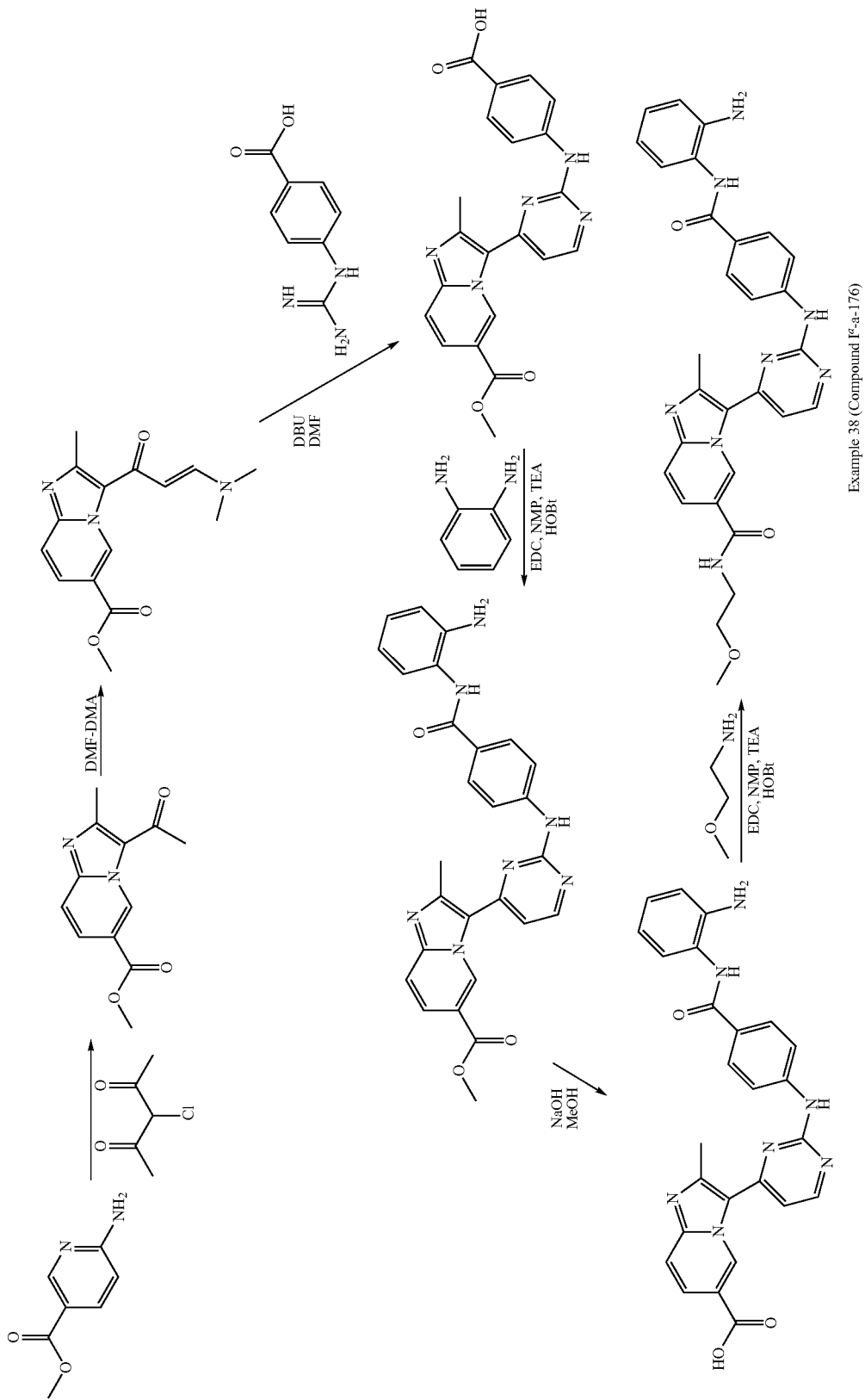

Similar procedure from Example 26 was followed to obtain the title compound using 6-Amino-nicotinic acid methyl ester and 2-methoxyethylamine. MS found for $C_{29}H_{28}N_8O_3$ as $(M+H)^+$ 537.23. $^1H$ NMR (400 MHz, dmso-$d_6$): δ 10.02 (s, 1H), 9.88 (s, 1H), 9.42 (s, 1H), 8.61-8.52 (m, 2H), 7.85-7.80 (m, 4H), 7.72 (d, J=8.2 Hz, 1H), 7.61 (d, J=8.4 Hz, 1H), 7.15-7.09 (m, 2H), 6.92 (t, J=6.4 Hz, 1H), 6.72 (d, J=7.2 Hz, 1H), 6.54 (t, J=6.4 Hz, 1H), 4.80 (s, 2H), 3.34-3.25 (m, 4H), 3.12 (s, 3H), 2.51 (s, 3H).

Example 39

N-(2-Amino-phenyl)-4-{4-[2-methyl-6-(4-methyl-piperazine-1-carbonyl)-imidazo[1,2-a]pyridin-3-yl]-pyrimidin-2-ylamino}-benzamide

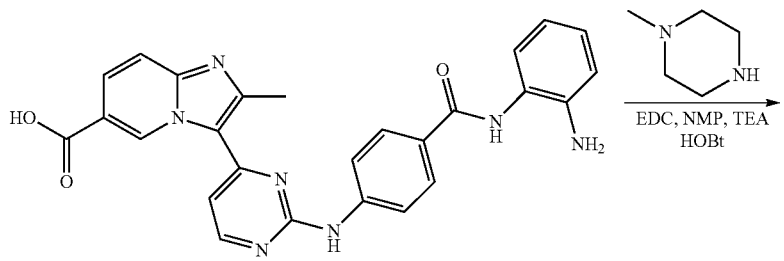

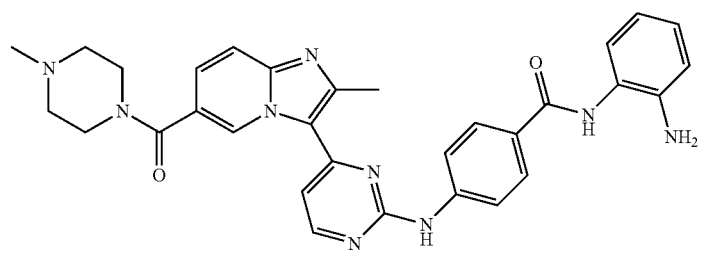

Example 39 (Compound I$^a$-a-184)

Similar procedure from Example 26 was followed to obtain the title compound using 6-amino-nicotinic acid methyl ester and 1-methylpiperazine MS found for $C_{31}H_{31}N_9O_2$ as $(M+H)^+$ 562.26. $^1H$ NMR (400 MHz, dmso-$d_6$): δ 10.05 (s, 1H), 9.73 (s, 1H), 9.45 (s, 1H), 8.51 (d, J=5.4 Hz, 1H), 8.16 (s, 1H), 7.92-7.79 (m, 4H), 7.65 (d, J=7.6 Hz, 1H), 7.41 (d, J=7.2 Hz, 1H), 7.20-7.11 (m, 2H), 6.92 (t, J=5.4 Hz, 1H), 6.73 (d, J=5.2 Hz, 1H), 6.53 (t, J=5.4 Hz, 1H), 4.80 (s, 2H), 2.62 (s, 3H), 2.21-2.12 (m, 4H), 2.02 (s, 3H).

Example 40

3-(2-(4-(2-aminophenylcarbamoyl)phenylamino) pyrimidin-4-yl)-2-methyl-N-(2-morpholinoethyl) imidazo[1,2-a]pyridine-6-carboxamide

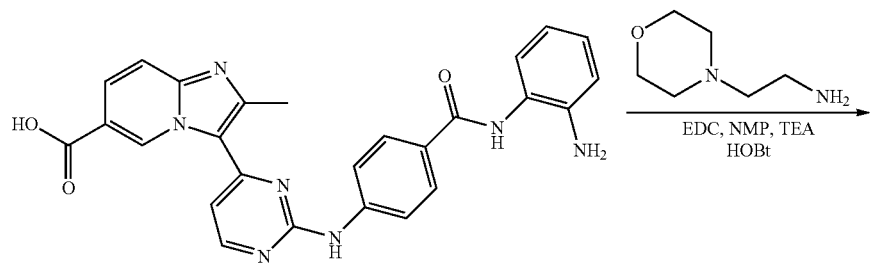

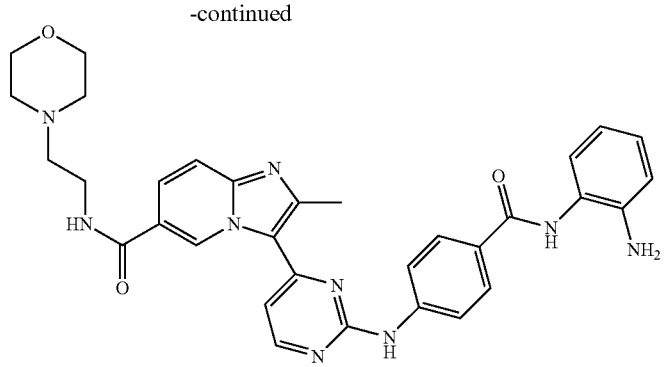

Example 40 (Compound I$^a$-a-180)

Similar procedure from Example 26 was followed to obtain the title compound using 6-amino-nicotinic acid methyl ester and 2-morpholin-4-yl-ethylamine. MS found for $C_{32}H_{33}N_9O_3$ as (M+H)$^+$ 592.27. $^1$H NMR (400 MHz, dmso-d$_6$): δ 10.02 (s, 1H), 9.88 (s, 1H), 9.42 (s, 1H), 8.60 (d, J=5.4 Hz, 1H), 8.40-8.36 (m, 1H), 7.36-7.31 (m, 4H), 7.70 (d, J=8.2 Hz, 1H), 7.61 (d, J=8.2 Hz, 1H), 7.17-7.08 (m, 2H), 6.89 (t, J=7.2 Hz, 1H), 6.71 (d, J=7.2 Hz, 1H), 6.55 (t, J=7.0 Hz, 1H), 4.81 (s, 2H), 3.45-3.40 (m, 4H), 2.58 (s, 3H), 2.31-2.23 (m, 6H).

Example 41

N-(2-Amino-phenyl)-4-{4-[6-(2-methoxy-ethoxy)-2-methyl-imidazo[1,2-a]pyridin-3-yl]-pyrimidin-2-ylamino}-benzamide

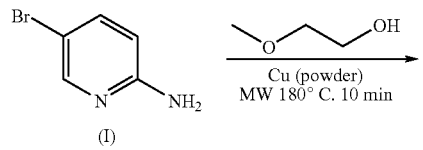

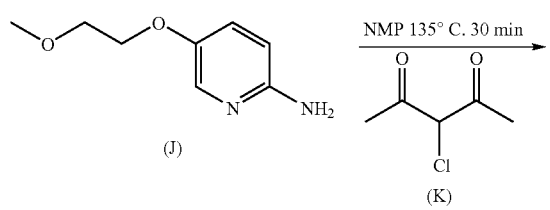

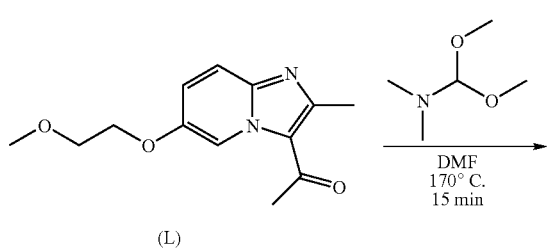

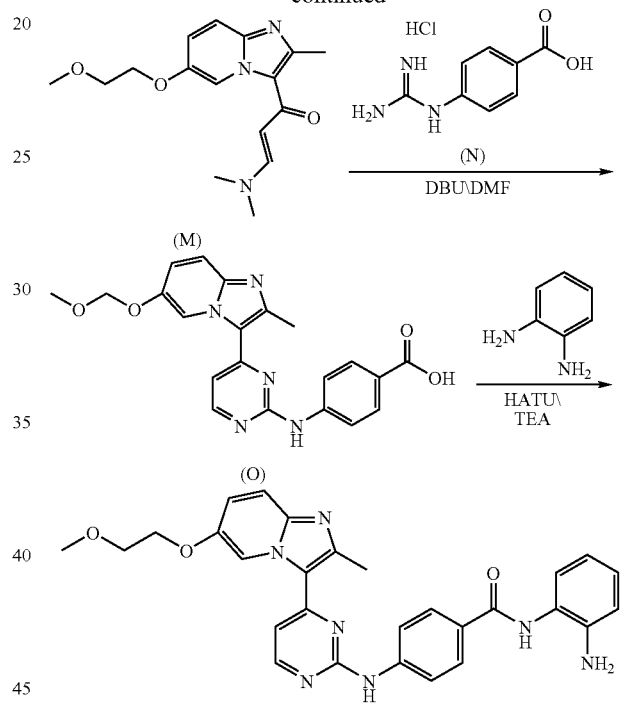

Example 41 (Compound I$^a$-a-192)

A mixture of Int-I (2.00 g, 0.012 mol), 2-methoxylethanol (10 mL), KO$^t$Bu (2.59 g, 0.023 mol) and Cu (dendritic, 3 u, 2.86 g) was heated under microwave condition with stirring at 180° C. for 3 hours. The solids were filtered and filtrate was concentrated, and purified with silica gel chromatography (5% MeOH/DCM) to afford Compound J (0.88 g, 45%). MS m/z: 169 (MH$^+$). A mixture of Int-J (0.88 g, 5.2 mmol) and Int-K (0.59 mL, 5.2 mmol) in NMP (6 mL) was heated under microwave condition at 135° C. for 30 minutes. The resultant mixture was then diluted with ethyl acetate and washed with saturated aqueous NaHCO$_3$ and dried (MgSO$_4$). Filtration followed by concentration gave Int-L (0.96 g, 74%). MS m/z: 249 (MH$^+$). Int-L (0.96 g, 3.9 mmol) and DMF-DMA (2 mL) in DMF (5 mL) was heated under microwave condition with stirring at 170° C. for 15 minutes. Water was then added and the precipitate formed was collected by filtration to afford Int-M (0.92 g, 78%). MS m/z: 304 (MH$^+$). Int-M (0.92 g, 3.0 mmol), Int-N (0.65 g, 3.0 mmol) and DBU (1.25 mL, 9.1 mmol) in DMF (5 mL) was heated under microwave condition with stirring at 170° C. After 20 minutes water was added to the reaction mixture and acidified to about pH 4 with 1N HCl. The precipitate formed was collected by filtration to afford Int-O (1.98 g). MS m/z: 420 (MH$^+$). Crude Int-O (0.25 g) was coupled with phenylenediamine (0.095 g, 0.9 mmol) in the presence of HATU (0.28 g, 0.7 mmol) and triethylamine (0.33 mL, 2.4 mmol) in DMF (2 mL) and then was purified by preparative HPLC to afford the title compound (0.033 g). MS ($C_{28}H_{27}N_7O_3$) m/z: 510 (MH$^+$). NMR $^1$H NMR (dmso-d$_6$): δ 9.90 (s, 1H), 9.51 (s, 1H), 9.17 (s, 1H), 8.57 (d, J=5.6 Hz, 1H), 7.94 (d, J=8.8 Hz, 2H), 7.83 (d, J=8.8 Hz, 2H), 7.53 (d, J=9.6 Hz, 1H), 7.21 (d, J=9.6 Hz, 1H), 7.12 (m, 2H), 6.94 (t, J=15.2 Hz, 1H), 6.76 (d, J=7.6 Hz, 1H), 6.58 (t, J=7.6 Hz, 1H), 4.84 (s, 2H), 3.90 (m, 2H), 3.53 (m, 2H), 3.21 (s, 3H), 2.59 (s, 3H).

Example 42

N-(2-Amino-phenyl)-4-[4-(6-methoxy-2-methyl-imidazo[1,2-a]pyridin-3-yl)-pyrimidin-2-ylamino]-benzamide

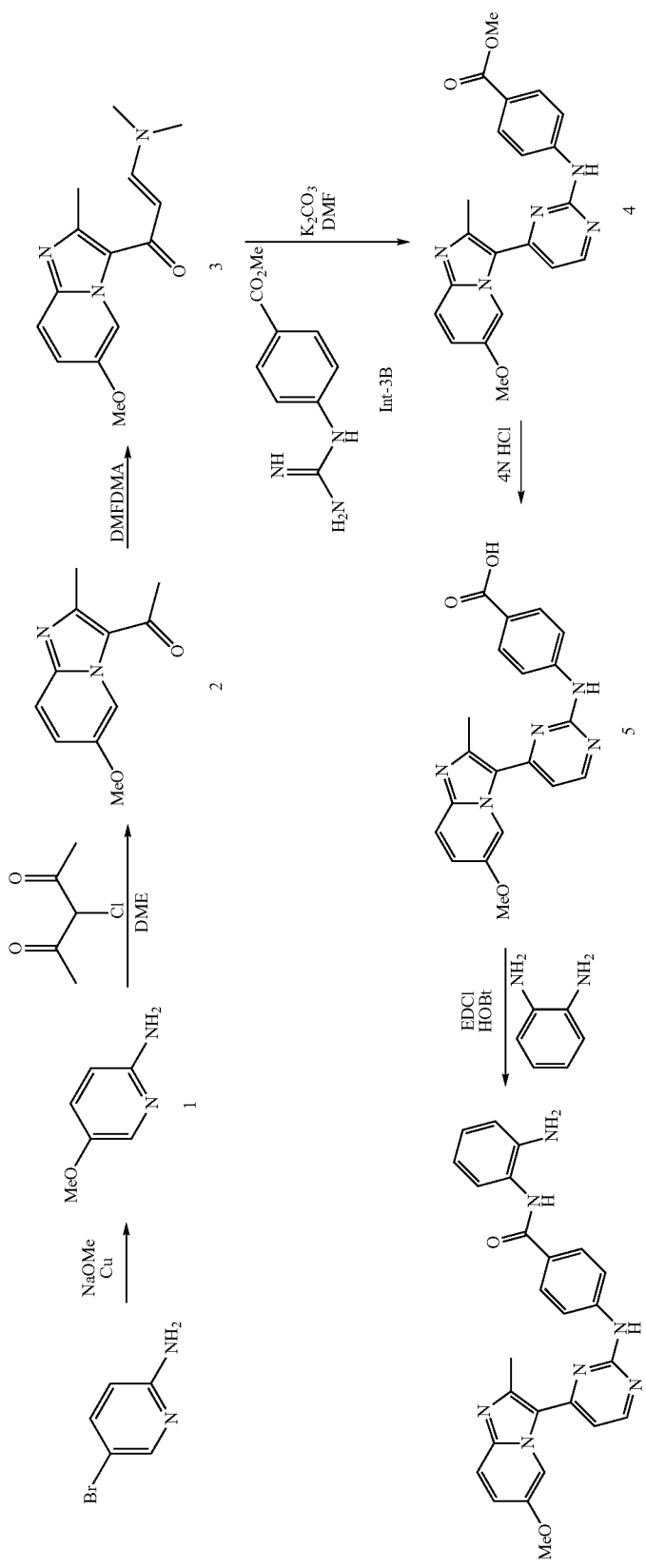

A mixture of 2-amino-5-bromopyridine (5.0 g, 28.9 mmol), sodium methoxide (6.3 g, 116.6 mmol) and copper powder (1.85 g, 28.9 mmol) in methanol (30 mL) was heated in sealed tube for 48 h at 100° C. The reaction mixture was cooled to room temperature, diluted with dichloromethane (50 mL), filtered through a pad of celite and the filtrate was concentrated under reduced pressure. The residue was diluted with water, extracted with dichloromethane (2×100 mL). The combined organic extracts were washed with water (50 mL) and brine (50 mL). The organic layer was dried over anhydrous Na$_2$SO$_4$ and concentrated under vacuum. The crude material was purified over silica gel column chromatography eluting with EtOAc:Hexane (6:4) to afford Int-1 (1.2 g, 34.3%) as brown color oil. To a solution of Int-1 (3.0 g, 24.2 mmol) in dimethoxy ethane (30 mL) was added 3-chloro-2,4-pentanedione (4.9 g, 36.4 mmol) at room temperature and the mixture was stirred at reflux temperature for 16 hours. The volatile was concentrated under reduced pressure. The residue was purified over silica gel column chromatography eluting with MeOH:DCM (1:9) to afford Int-2 (2.3 g, 46.6%) as brown color oil. A solution of Int-2 (1.5 g, 7.35 mmol) in DMF DMA (15 mL) was stirred at reflux temperature for 24 hours. The reaction mixture was cooled to room temperature and diluted with diethyl ether (15 mL) and stirred for 15 minutes. The precipitated solid was filtered, washed with ether (2×10 mL) and dried under vacuum to afford Int-3 (1.2 g, 63%) as brown solid. Mass (m/z): 260 [M$^+$+1]. $^1$H NMR (200 MHz, CDCl$_3$): δ 9.43 (d, J=2.2 Hz, 1H), 7.8 (d, J=12.4 Hz, 1H), 7.44 (d, J=9.8 Hz, 1H), 7.09 (dd, J=2.2, 9.6 Hz, 1H), 5.58 (d, J=12 Hz, 1H), 3.86 (s, 3H), 3.06 (brs, 6H), 2.75 (s, 3H). To a solution of Int-3 (1.6 g, 6.17 mmol) in DMF (25 mL) was added Int-3B (2.38 g, 12.3 mmol) followed by K$_2$CO$_3$ (2.13 g, 15.4 mmol) at room temperature under inert atmosphere and the reaction mixture was stirred at 100° C. for 16 hours. The reaction mixture was cooled to room temperature, poured into ice water (70 mL) and stirred for 15 minutes. The precipitated solid was filtered, washed with water (2×10 mL) and dried under vacuum to afford Int-4 (1.2 g, 50%) as brown solid. Mass (m/z): 390 [M$^+$+1]. $^1$H NMR (200 MHz, dmso-d$_6$): δ 10.13 (s, 1H), 9.17 (s, 1H), 8.59 (d, J=5.6 Hz, 1H), 8.-6.90 (m, 4H), 7.55 (d, J=10 Hz, 1H), 7.25-7.14 (m, 2H), 3.8 (s, 3H), 3.66 (s, 3H), 2.6 (s, 3H). A mixture of Int-4 (0.8 g, 2.05 mmol) and 4 N HCl (30 mL) was stirred at reflux temperature for 4 hours. The reaction mixture was cooled to room temperature and pH adjusted to about 5 using NaHCO$_3$ and stirred for 20 minutes. The precipitated solid was filtered, washed with water (2×10 mL) and dried under vacuum to afford Int-5 (0.7 g, 90.9% yield) as brown color solid. Mass (m/z): 376 [M$^+$+1]. $^1$H NMR (200 MHz, dmso-d$_6$): δ 10.29 (s, 1H), 9.18 (d, J=1.8 Hz, 1H), 8.72 (d, J=5.2 Hz, 1H), 8.-7.78 (m, 6H), 7.64 (dd, J=2.2, 10 Hz, 1H), 3.71 (s, 3H), 2.69 (s, 3H). To a stirred solution of Int-5 (0.7 g, 1.86 mmol) in DMF (10 mL) were added HOBt (0.25 g, 1.86 mmol), EDCI (0.71 g, 3.7 mmol), N-ethyldiisopropylamine (0.7 mL, 5.58 mmol) at 0° C. After being stirred for 10 minutes, and then added o-phenylenediamine (0.2 g, 1.86 mmol) to the reaction mixture at 0° C. The reaction mixture was warmed to room temperature and stirring was continued for 16 hours. The reaction mixture was poured into ice cold water (50 mL) and stirred for 10 minutes. The precipitated solid was filtered, washed with water (3×10 mL) and dried under vacuum. The crude material was purified over silica gel column chromatography eluting with 4% MeOH/DCM to afford the title compound (0.27 g, 31.1% yield) as off white solid. Mass (m/z): 465.2 [M$^+$+1]. $^1$H NMR (200 MHz, dmso-d$_6$): δ 10.02 (s, 1H), 9.53 (s, 1H), 9.18 (s, 1H), 8.59 (d, J=5.6 Hz, 1H), 7.86-7.98 (m, 4H), 7.60 (d, J=9.6 Hz, 1H), 7.13-7.25 (m, 3H), 6.85-7.0 (m, 1H), 6.75 (d, J=8.0 Hz, 1H), 6.45-6.61 (m, 1H), 4.86 (brs, 2H), 3.69 (s, 3H), 2.60 (s, 3H). $^{13}$C NMR (125 MHz, dmso-d$_6$): δ 164.69, 159.26, 158.17, 156.83, 148.74, 146.45, 143.33, 143.03, 142.42, 128.49, 127.05, 126.55, 126.21, 123.65, 120.66, 118.59, 118.10, 116.37, 116.29, 116.15, 110.27, 110.15, 55.90, 16.36.

Example 43

N-Hydroxy-4-[4-(6-methoxy-2-methyl-imidazo[1,2-a]pyridin-3-yl)-pyrimidin-2-ylamino]-benzamide

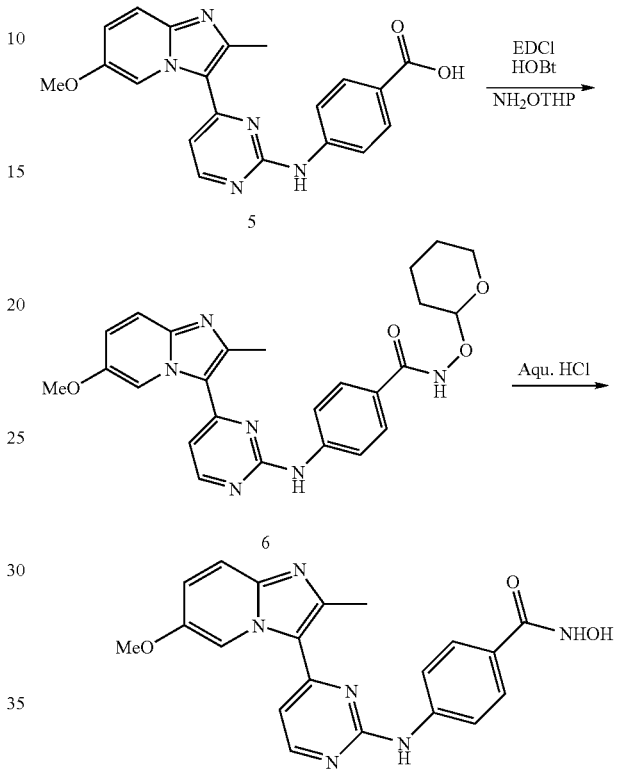

Example 43 (Compound I$^a$-a-79)

To a stirred solution of Int-5 (1.0 g, 2.66 mmol) in DMF (20 mL) were added HOBt (0.36 g, 2.66 mmol), EDCI (1.2 g, 5.32 mmol), N-ethyldiisopropylamine (1.0 mL, 7.98 mmol) at 0° C. After 10 minutes, then added NH$_2$OTHP (0.62 g, 5.32 mmol) was added to the reaction mixture at 0° C. The reaction mixture was warmed to room temperature and stirring was continued for 16 hours. The reaction mixture was poured into ice cold water (50 mL) and stirred for 10 minutes. The precipitated solid was filtered, washed with water (3×10 mL) and dried under vacuum. The crude material was purified over silica gel column chromatography eluting with 4% MeOH/DCM to afford Int-6 (0.95 g, 75.3%) as pale brown color solid. Mass (m/z): 475 [M$^+$+1]. $^1$H NMR (200 MHz, dmso-d$_6$): δ 10.44 (s, 1H), 9.17 (d, J=3.4 Hz, 1H), 8.66 (s, 1H), 8.5 (d, J=5.4 Hz, 1H), 7.9-7.65 (m, 4H), 7.49 (d, J=9.4 Hz, 1H), 7.10 (dd, J=2.2, 9.6 Hz, 1H) 7.02 (d, J=5.2 Hz, 1H), 5.09 (s, 1H), 4.2-4.0 (m, 1H), 3.7-3.5 (m, 1H), 3.59 (s, 3H), 2.7 (s, 3H), 1.9-1.5 (m, 6H). To a solution of Int-6 (1.0 g, 2.1 mmol) in methanol (15 mL) was added 2 N HCl (5.0 mL) at 0° C. and stirring was continued for 16 hours at room temperature. The precipitated solid was filtered, washed with methanol (5 mL) and water (5.0 mL), dried under vacuum to provide product as HCl salt. The salt was neutralized using saturated NaHCO$_3$ to afford the title compound as brown color solid (0.60 g, 73%). Mass (m/z): 390 [M$^+$+1]. $^1$H NMR (200 MHz, dmso-d$_6$): δ 11.1 (brs, 1H), 9.96 (s, 1H), 9.15 (s, 1H), 8.9 (brs, 1H), 8.57 (d, J=5.2 Hz, 1H), 7.53-7.82 (m, 5H), 7.10-7.24 (m, 2H), 3.62 (s, 3H), 2.60 (s, 3H). $^{13}$C NMR (125 MHz, dmso-d$_6$): δ 163.86, 159.18, 158.11, 156.71, 148.65, 146.33, 142.89, 142.33, 127.41, 125.37, 120.66, 118.55, 118.32, 116.31, 110.04, 55.81, 16.35.

Examples 44 and 45
Example 44
4-[4-(8-Fluoro-2-methyl-imidazo[1,2-a]pyridin-3-yl)-pyrimidin-2-ylamino]-N-hydroxy-benzamide
Example 45
N-(2-Amino-phenyl)-4-[4-(8-fluoro-2-methyl-imidazo[1,2-a]pyridin-3-yl)-pyrimidin-2-ylamino]-benzamide
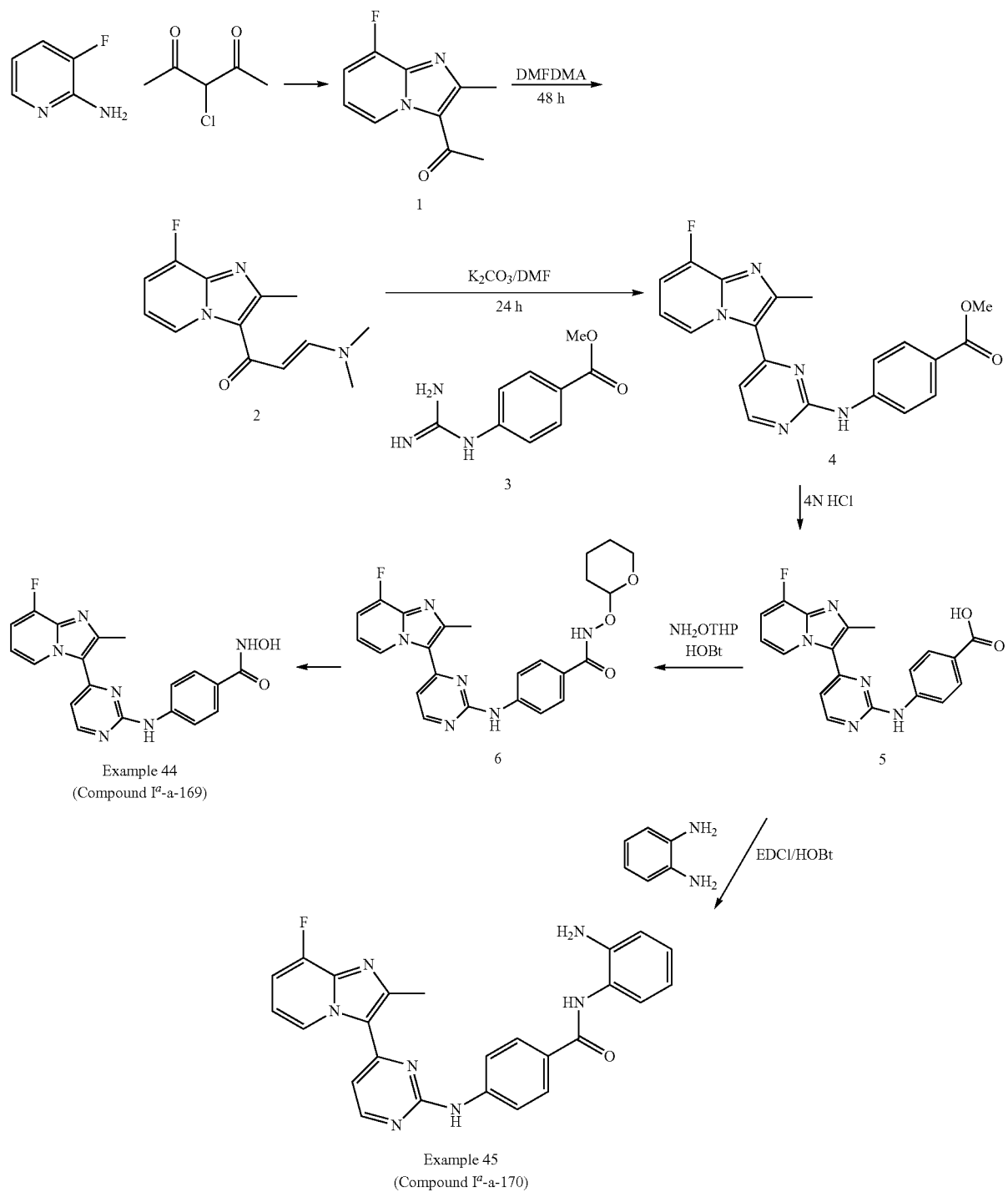

To a stirred solution of 3-fluoro-pyridin-2-ylamine (1.0 g, 8.92 mmol) in ethanol (20 mL) was added 3-chloro-pentane-2,4-dione (2.5 mL, 22.3 mmol) at room temperature. The reaction mixture was heated to reflux and then stirred for 48 hours. After the reaction completion, the volatiles were concentrated under reduced pressure and the residue was purified over silica gel column chromatography eluting with 2% MeOH/DCM to afford Int-1 (0.75 g, 44%) as off-white solid. Mass (m/z): 193 [M$^+$+1]. $^1$HNMR 200 MHz (CDCl$_3$): δ 9.54 (d, J=7 Hz, 1H), 7.18 (t, J=7 Hz, 1H), 6.99-6.89 (m, 1H), 2.83 (s, 3H). 2.65 (s, 3H). A solution of Int-1 (0.75 g, 3.9 mmol) in DMF-DMA (10 mL) was stirred at reflux temperature for 48 hours. The reaction mixture was allowed room temperature and diluted with hexane (25 mL) and stirred for 10 minutes. The precipitated solid was filtered off, dried under vacuum to afford Int-2 (0.75 g, 78%) as brown color solid. Mass (m/z): 248 [M$^+$+1]. $^1$HNMR 200 MHz (CDCl$_3$): δ 9.43 (d, J=6.2 Hz, 1H), 7.81 (d, J=12.4 Hz, 1H), 7.05 (t, J=7.6 Hz, 1H), 6.84-6.77 (m, 1H), 5.56 (d, J=12.2 Hz, 1H), 2.96 (s, 3H), 2.88 (s, 3H), 2.78 (s, 3H). Synthesis of Int-4: To a solution of Int-2 (1.5 g, 6.07 mmol) in DMF (25 mL) was added Int-3 (3.5 g, 18.2 mmol), followed by K$_2$CO$_3$ (2.5 g, 18.2 mmol) at room temperature and the reaction mixture was stirred at 110° C. for 16 hours. The reaction mixture was allowed to room temperature, poured in to ice-cold water (70 mL) and stirred further for 20 minutes. The precipitated solid was filtered off, washed with water (2×10 mL) and dried under vacuum to afford Int-4 (1.5 g, 68%) as brown solid. Mass (m/z): 364 [M$^+$+1]. $^1$HNMR 200 MHz (dmso-d$_6$): δ 10.29 (s, 1H), 9.63 (d, J=6.8 Hz, 1H), 8.69 (d, J=5.6 Hz, 1H), 7.88 (s, 3H), 7.70 (t, J=10.6 Hz, 1H), 7.29-7.23 (m, 2H), 4.83 (brs, 1H), 3.9 (s, 3H), 2.73 (s, 3H). A mixture of Int-4 (1.5 g, 3.97 mmol) and 4 N HCl (20 mL) was stirred at reflux temperature for 3 hours. The reaction mixture was cooled to 0° C. and stirred for 20 minutes. The precipitated solid was filtered off, washed with water (2×10 mL) and dried under vacuum to afford Int-5 (1.0 g, 71%) as pale yellow solid. Mass (m/z): 364 [M$^+$+1]. $^1$HNMR 200 MHz (dmso-d$_6$): δ 10.29 (s, 1H), 9.63 (d, J=6.8 Hz, 1H), 8.69 (d, J=5.6 Hz, 1H), 7.88 (s, 3H), 7.70 (t, J=10.6 Hz, 1H), 7.29-7.23 (m, 2H), 4.83 (brs, 1H), 2.73 (s, 3H). To a stirred suspension of Int-5 (0.8 g, 2.20 mmol) in DMF (10 mL) were added HOBt (0.29 g, 2.20 mmol), EDCI (1.05 g, 5.5 mmol), N-ethyldiisopropylamine (1.0 mL, 5.5 mmol) and NH$_2$OTHP (0.51 g, 4.40 mmol) at 0° C. The reaction mixture was warmed to room temperature and the stirring was continued for 16 hours. The reaction mixture was poured in to ice-cold water (50 mL) and stirred for 20 minutes. The precipitated solid was filtered off, washed with water (2×10 mL) and dried under vacuum. The crude material was purified over silica gel column chromatography eluting with 3% MeOH/DCM to afford Int-6 (0.45 g, 44%) as white solid. Mass (m/z): 463 [M$^+$+1].

Preparation of Example 44: To a solution of Int-6 (0.45 g, 0.97 mmol) in methanol (5 mL) was added concentrated HCl (1.0 mL) at 0° C. and the stirring was continued for 16 hours at room temperature. The precipitated solid was filtered off and dried under vacuum to provide product as HCl salt. The HCl salt was neutralized using saturated NaHCO$_3$ to afford free hydroxamic acid Example 44 as off-white solid (0.30 g, 81%). Mass (m/z): 378 [M$^+$+1]. $^1$H NMR (200 MHz, dmso-d$_6$): δ 9.80 (bs, 1H), 9.55 (d, J=7.0 Hz, 1H), 8.57 (d, J=5.6 Hz, 1H), 7.69 (s, 4H), 7.38-7.28 (m, 1H), 7.14 (d, J=5.0 Hz, 1H), 6.99-6.66 (t, 1H), 2.67 (s, 3H); $^{13}$C NMR (125 MHz, dmso-d$_6$): 163.9, 159.2, 158.2, 156.4, 152.2, 147.2, 146.7, 142.8, 137.8, 137.2, 127.4, 125.6, 124.8, 119.2, 118.1, 113.9, 112.0, 111.9, 109.9, 109.7, 109.4, 16.6.

Preparation of Example 45: To a stirred suspension of Int-5 (0.8 g, 2.20 mmol) in DMF (12 mL) were added HOBt (0.29 g, 2.20 mmol), EDCI (0.92 g, 4.84 mmol), N-ethyldiisopropylamine (1.0 mL, 5.5 mmol) and o-phenylenediamine (0.23 g, 2.20 mmol) at 0° C. The reaction mixture was warmed to room temperature and the stirring was continued for 16 hours. The reaction mixture was poured into ice-cold water (40 mL) and further stirred for 20 minutes. The precipitated solid was filtered off, washed with water (2×10 mL) and dried under vacuum. The crude material was purified over silica gel column chromatography eluting with 3% MeOH/DCM to afford the title compound (0.30 g, 30%) as off-white solid. Mass (m/z): 453 [M$^+$+1]. $^1$H NMR (200 MHz, dmso-d$_6$): δ 9.49 (s, 1H), 9.59-9.52 (m, 2H), 8.63 (d, J=5.4 Hz, 1H), 7.99-7.87 (m, 4H), 7.40-7.31 (m, 1H), 7.23-6.98 (m, 4H), 6.77 (d, J=7.0 Hz, 1H), 6.59 (t, J=7.4 Hz, 1H), 4.88 (brs, 2H), 2.68 (s, 3H). $^{13}$C NMR (125 MHz, dmso-d$_6$): 164.8, 159.2, 158.3, 156.5, 150.8, 148.8, 146.8, 143.3, 143.0, 137.7, 137.5, 128.5, 127.1, 126.5, 126.2, 124.8, 123.6, 119.3, 117.9, 116.3, 116.1, 112.0, 110.1, 109.5, 16.5.

Example 46

N-(2-Amino-phenyl)-4-[4-(7-dimethylaminomethyl-2-methyl-imidazo[1,2-a]pyridin-3-yl)-pyrimidin-2-ylamino]-benzamide

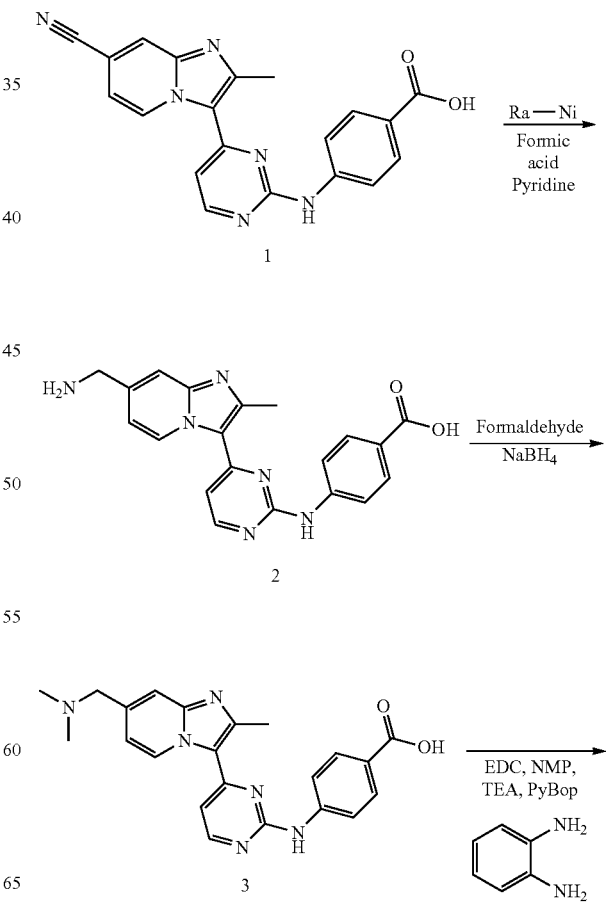

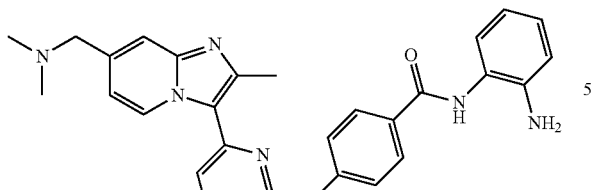

Example 46 (Compound I<sup>a</sup>-a-90)

A mixture of Int-1 (50 mg, 0.135 mmol), pyridine (1.2 mL), and acetic acid (0.6 mL) was stirred for at room temperature for 30 minutes and then excess Ra—Ni was added and stirred overnight. The mixture was then filtered through celite pad and washed several times with hot EtOH. The solution was evaporated and purified by reverse phase chromatography to have Int-2. Int-2 (24 mg, 0.064 mmol) was dissolved in acetonitrile (5 mL), p-formaldehyde (2 eq) and NaBH(OAc)$_3$ (2 eq) were added and stirred at room temperature for 30 minutes. The mixture was quenched with 1N HCl and then evaporated and extracted with EtOAc. The organic phase was dried and evaporated to have Int-3. Similar procedure from Example 26 was followed to obtain the title compound using 4-[4-(7-Dimethylaminomethyl-2-methyl-imidazo[1,2a]pyridin-3-yl)-pyrimidin-2-ylamino]-benzoic acid. MS found for $C_{28}H_{28}N_8O$ as (M+H)$^+$ 493.24. $^1$H NMR (400 MHz, dmso-d$_6$): δ 9.91 (s, 1H), 9.65 (d, J=5.4 Hz, 1H), 9.45 (s, 1H), 8.52 (d, J=4.6 Hz, 1H), 7.92-7.83 (m, 4H), 7.43 (s, 1H), 7.11 (d, J=5.2 Hz, 2H), 6.97-6.86 (m, 2H), 6.72 (d, J=5.6 Hz, 1H), 6.53 (t, J=5.2 Hz, 1H), 4.81 (s, 2H), 3.43 (s, 2H), 2.58 (s, 3H), 2.12 (s, 6H).

Example 47

N-(2-Amino-phenyl)-4-[4-(6-bromo-2-methyl-imidazo[1,2-a]pyridin-3-yl)-pyrimidin-2-ylamino]-benzamide (Compound I<sup>a</sup>-a-172)

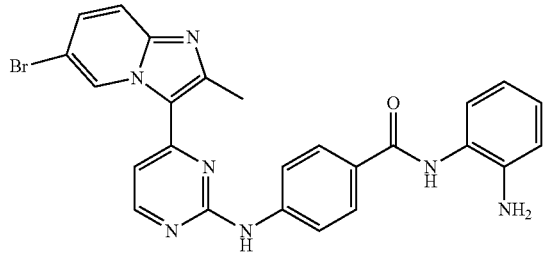

Example 47

Similar procedure from Example 26 was followed to obtain the title compound using 2-amino-5-bromopyridine. $^1$H NMR (400 MHz, dmso-d$_6$): δ 10.07 (brs, 1H); 9.76 (s, 1H); 9.50 (s, 1H); 8.59 (d, J=5.2 Hz, 1H); 7.94 (d, J=8.8 Hz, 2H); 7.85 (d, J=8.8 Hz, 2H); 7.61 (d, J=59.2 Hz, 1H); 7.52 (d, J=9.2 Hz, 1H); 7.15 (m, 2H); 6.93 (t, J=8.0 Hz, 1H); 6.76 (d, J=8.0 Hz, 1H); 6.57 (t, J=7.6 Hz, 1H); 4.83 (s, 2H); 2.63 (s, 3H).

Examples 48 and 49

Example 48

N-(2-Amino-phenyl)-4-[4-(7-methoxy-2-trifluoromethyl-imidazo[1,2-a]pyridin-3-yl)-pyrimidin-2-ylamino]-benzamide Example 49

N-Hydroxy-4-[4-(7-methoxy-2-trifluoromethyl-imidazo[1,2-a]pyridin-3-yl)-pyrimidin-2-ylamino]-benzamide

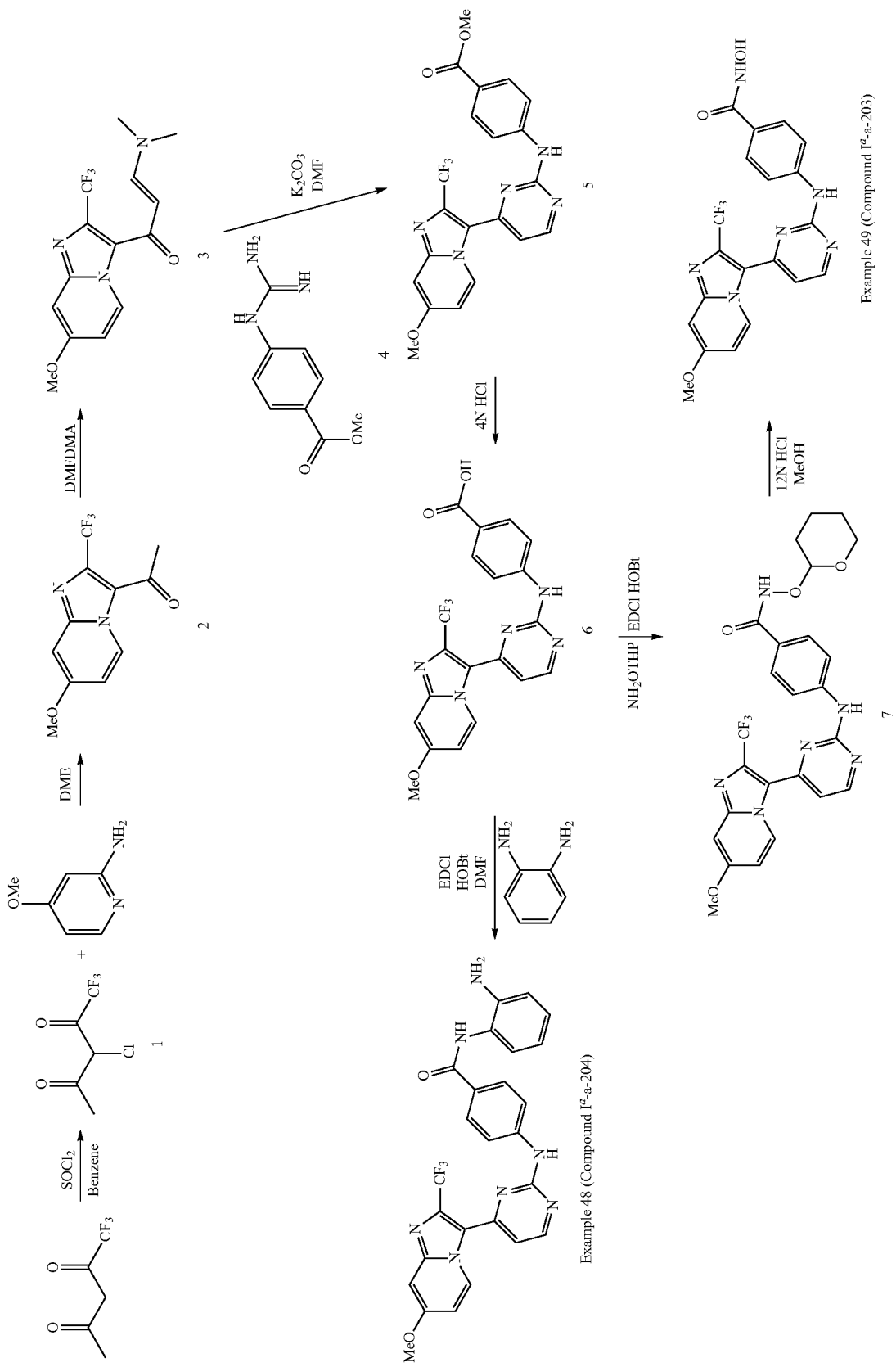

To a stirred solution of 1,1,1-trifluoro-2,4-pentane-dione (7 g, 45.4 mmol) in benzene (7 mL) was added sulfuryl chloride (3.6 mL, 45.4 mmol) slowly over a period of 2 hours at room temperature and then stirred for 2 hours at the same temperature. The reaction mixture was quenched with 7 mL water, followed by addition of ethyl acetate (20 mL) slowly. The organic phase was separated, dried over anhydrous $Na_2SO_4$ and concentrated under reduced pressure at 25° C. to afford crude Int-1 (11 g, contains trace amount of EtOAc) as liquid. The crude compound was used in the next step without purification. Mass (m/z): 189 [M$^+$+1]. To a stirred solution of 4-methoxypyridin-2-amine (2.0 g, 16.1 mmol) in DME (20 ml) was added Int-1 (6.0 g, 32.2 mmol) at room temperature and the reaction mixture was stirred at reflux temperature for 3 hours. The volatiles were concentrated under reduced pressure. The crude material was purified by silica gel column chromatography eluting with EtOAc/hexane (15:85) to afford Int-2 (0.5 g, 12%). Mass (m/z): 259 [M$^+$+1]. $^1$H NMR (200 MHz, dmso-d$_6$): δ 9.23 (d, J=6.2 Hz, 1H), 6.78 (t, J=7.4 Hz, 1H), 6.61 (d, J=7.8 Hz, 1H), 4.01 (s, 3H), 2.77 (s, 3H). A solution of Int-2 (0.4 g, 1.56 mmol) in DMF-DMA (10 mL) was stirred at reflux temperature for 16 hours. After the reaction, the volatiles were concentrated under reduced pressure. The crude material was washed with hexane (2×15 mL) to afford Int-3 (0.4 g, 81%) as brown color solid. Mass (m/z): 314 [M$^+$+1]. $^1$H NMR (200 MHz, dmso-d$_6$): δ 9.22 (d, J=8 Hz, 1H), 7.80 (d, J=12.2 Hz, 1H), 6.95 (s, 1H), 6.71-6.78 (dd, J=2.4, 2.6 Hz, 1H), 5.68 (d, J=12 Hz, 1H), 3.87 (s, 3H), 3.18 (s, 3H), 2.93 (s, 3H). To a solution of Int-3 (0.88 g, 2.81 mmol) in DMF (10 mL) was added Int-4 (1.3 g, 7.0 mmol) followed by $K_2CO_3$ (1.16 g, 8.4 mmol) at room temperature and the reaction mixture was stirred at 100° C. for 16 hours. The reaction mixture was cooled to room temperature, diluted with ice-water (80 mL) and further stirred for 20 minutes. The precipitated solid was filtered off, washed with water (2×10 mL) and dried under vacuum to afford Int-5 (0.8 g, 66%) as brown solid. Mass (m/z): 444 [M$^+$+1]. $^1$H NMR (200 MHz, dmso-d$_6$): δ 10.27 (brs, 1H), 9.03 (d, J=7.6 Hz, 1H), 8.72 (d, J=5.2 Hz, 1H), 7.93-7.89 (m, 4H), 7.22-7.13 (m, 2H), 6.84 (d, J=7 Hz, 1H), 3.91 (s, 3H), 3.82 (s, 3H). A mixture of Int-5 (0.9 g) and 4 N HCl (20 mL) was stirred at reflux temperature for 3 hours. The reaction mixture was cooled to room temperature to 0° C. and then stirred for 20 minutes. The precipitated solid was filtered off, washed with water (2×10 mL) and dried under vacuum to afford Int-6 (0.7 g, 90%) as solid. Mass (m/z): 432 [M$^+$+1]. $^1$H NMR (200 MHz, dmso-d$_6$): δ 10.27 (brs, 1H), 9.03 (d, J=7.6 Hz, 1H), 8.72 (d, J=5.2 Hz, 1H), 7.93-7.89 (m, 4H), 7.22-7.13 (m, 2H), 6.84 (d, J=7 Hz, 1H), 3.82 (s, 3H).

Preparation of Example 48: To a stirred suspension of Int-6 (0.6 g, 1.39 mmol) in DMF (10 mL) were added HOBt (0.18 g, 1.39 mmol), EDCI (0.58 g, 3.0 mmol), N-ethyldiisopropylamine (0.6 mL, 3.4 mmol) and o-phenylenediamine (0.15 g, 1.39 mmol) at 0° C. The reaction mixture was warmed to room temperature and the stirring was continued for 16 hours. The Reaction mixture was diluted with ice-cold water (80 mL) and stirred for 20 minutes. The precipitated solid was filtered off, washed with water (2×10 mL) and dried under vacuum. The crude material was purified over silica gel column chromatography eluting with 2% MeOH/DCM to afford the title compound (0.30 g, 41%) as off-white solid. Mass (m/z): 519.6 [M$^+$+1]. $^1$H NMR (200 MHz, dmso-d$_6$): δ 10.1 (brs, 1H), 9.51 (brs, 1H), 9.0 (d, J=7.6 Hz, 1H), 8.72 (d, J=5.0 Hz, 1H), 7.92-7.85 (m, 4H), 7.24-7.13 (m, 3H), 6.94-6.89 (m, 2H), 6.77 (d, J=6.6 Hz, 1H), 6.62 (t, 1H), 4.85 (brs, 2H), 3.90 (s, 3H). $^{13}$C NMR (125 MHz, dmso-d$_6$): 164.7, 159.5, 159.3, 154.4, 146.8, 143.1, 133.6, 133.3, 128.5, 128.1, 127.3, 126.6, 126.2, 123.6, 123.0, 120.8, 119.8, 117.9, 116.2, 116.1, 112.3, 109.5, 95.3, 56.0, 54.8.

Preparation of Example 49: To a stirred suspension of Int-6 (0.6 g, 1.39 mmol) in DMF (10 mL) was added HOBt (0.18 g, 1.4 mmol), EDCI (0.66 g, 3.4 mmol), N-ethyldiisopropylamine (0.6 mL, 3.4 mmol) and NH$_2$OTHP (0.24 g, 2.0 mmol) at 0° C. After the completion of addition, the reaction mixture was allowed to warm to room temperature and the stirring was continued for 16 hours. The reaction mixture was diluted with ice-cold water (80 mL) and further stirred for 20 minutes. The precipitated solid was filtered off, washed with water (2×10 mL) and dried under vacuum. The crude material was purified over silica gel column chromatography eluting with 2% MeOH/DCM to afford Int-7 (0.5 g, 68% yield) as solid. Mass (m/z): 529 [M$^+$+1]. To a solution of Int-7 (0.5 g, 0.97 mmol) in methanol (10 mL) was added concentrated HCl (1.0 mL) at 0° C. and the stirring was continued for 16 hours at room temperature. The precipitated solid was filtered and dried under vacuum to provide product as HCl salt. The HCl salt was neutralized using saturated NaHCO$_3$ to afford hydroxamic acid as off-white solid (0.34 g, 81%). Mass (m/z): 444 [M$^+$+1]. $^1$H NMR (200 MHz, dmso-d$_6$): δ 10.0 (brs, 1H), 9.0 (d, J=7.8 Hz, 1H), 8.68 (d, J=5.2 Hz, 1H), 7.80-7.65 (m, 4H), 7.23 (s, 1H), 7.08 (d, J=5.2 Hz, 1H), 6.91-6.86 (m, 1H), 3.90 (s, 3H). $^{13}$C NMR (125 MHz, dmso-d$_6$): 164.0, 159.5, 159.3, 154.4, 146.8, 142.5, 133.7, 133.4, 128.1, 127.4, 126.1, 123.0, 120.9, 119.8, 118.2, 112.2, 109.4, 95.3, 56.0.

Example 50

N-(2-Amino-phenyl)-4-(5-fluoro-4-imidazo[1,2-a]pyridin-3-yl-pyrimidin-2-ylamino)-benzamide (Compound I$^a$-a-220)

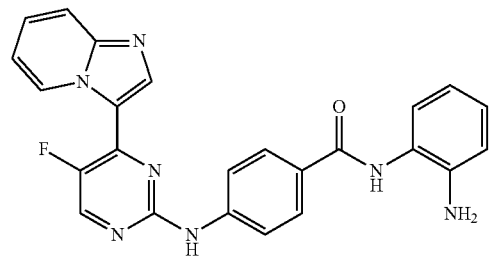

Example 50

Similar procedure from Example 51 was followed to obtain the title compound using 1,2-phenylenediamine. MS found for $C_{24}H_{18}FN_7O$ as (M+H)$^+$ 440.03. $^1$H NMR (400 MHz, dmso-d$_6$): δ 10.18 (d, J=7.6 Hz, 1H); 8.41 (d, J=3.6, Hz, 1H); 8.38 (d, J=4.0, Hz, 1H) 8.26 (brs, 1H); 7.92 (d, J=8.8 Hz, 2H); 7.81 (d, J=8.8 Hz, 2H); 7.69 (d, J=9.2, Hz, 1H); 7.54 (t, J=7.2 Hz, 1H); 7.15 (m, 2H); 7.01 (t, J=8.0 Hz, 1H); 6.84 (d, J=7.6, Hz, 1H); 6.72 (d, J=7.6 Hz, 1H); 4.45 (brs, 2H).

Example 51

4-(5-Fluoro-4-imidazo[1,2-a]pyridin-3-yl-pyrimidin-2-ylamino)-N-hydroxy-benzamide (Compound I$^a$-a-219)

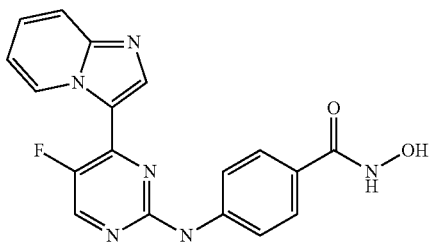

Example 51

To a solution of 3-bromo-imidazo[1,2-a]pyridine (1 g, 5.1 mmol) in dry THF (25 mL) under $N_2$ at −78° C. was added n-BuLi (1.6 M in hexanes, 3.8 mL, 6.12 mmol) and the reaction mixture was stirred at that temperature for 1 hour. Then freshly dried zinc bromide (1.7 g, 7.65 mmol) in dry THF (15 mL) was added slowly and the reaction mixture was slowly warmed up to room temperature and 2,4-dichloro-5-fluoro-pyrimidine (848 mg, 5.1 mmol) and Pd(PPh$_3$)$_4$ (294 mg, 0.26 mmol) was added. After 16 hours at 75° C., the reaction mixture was then concentrated and directly purified by purified by flash chromatography (SiO$_2$, 95:5:0.5/EtOAc: MeOH:TEA) to give 3-(2-chloro-5-fluoro-pyrimidin-4-yl)-imidazo[1,2-a]pyridine (Int-1) MS found for $C_{11}H_{16}ClN_4F$ as (M+H)$^+$ 249.51. $^1$H NMR (400 MHz, CDCl$_3$): δ 10.00 (d, J=6.8 Hz, 1H); 8.62 (s, 1H); 8.48 (d, J=3.2 Hz, 1H); 7.93 (d, J=9.2 Hz, 1H); 7.60 (t, J=7.2 Hz, 1H); 7.21 (t, J=7.2 Hz, 1H) To a solution of Int-1 (71 mg, 0.286 mmol), 4-amino-benzoic acid (47 mg, 0.344 mmol) in dioxane (3 mL), p-TSA (54 mg, 0.286 mmol) was added and heated in pressure vessel at 130° C. for 12 hours. Additional 4-amino-benzoic acid (23 mg, 0.172 mmol) and p-TSA (27 mg, 0.143 mmol) was added and heated at 130° C. After 12 hours, the reaction mixture was cooled to room temperature and diluted with dioxane gave 4-(5-Fluoro-4-imidazo[1,2-a]pyridin-3-yl-pyrimidin-2-ylamino)-benzoic acid (Int-2) as a tan solid which was filtered and dried. MS found for $C_{18}H_{12}FN_5O_2$ as (M+H)$^+$ 350.30. To Int-2 (100 mg, 0.29 mmol) in DMF (8 mL), was added HATU (163 mg, 0.43 mmol), O-(tert-butyldimethylsilyl)hydroxylamine (84 mg, 0.57 mmol) and DIPEA (0.15 mL, 0.86 mmol) and stirred at room temperature. After 16 hours, the reaction mixture was diluted with and 1N HCl (3 mL and stirred at room temperature for 12 hours. The reaction mixture was then directly purified by preparative HPLC affording the title compound as tan solid, after lyophilization. MS found for $C_{18}H_{13}FN_6O_2$ as (M+H)$^+$ 365.09. $^1$H NMR (400 MHz, dmso-d$_6$): δ 11.03 (brs, 1H); 10.16 (d, J=7.2 Hz, 1H); 10.05 (s, 1H); 8.64 (d, J=3.6 Hz, 1H); 8.46 (d, J=4.0 Hz, 1H); 7.87-7.74 (m, 5H); 7.62 (t, J=7.6 Hz, 1H); 7.24 (t, J=6.4 Hz, 1H).

Example 52

N-hydroxy-5-(4-(2-methylimidazo[1,2-a]pyridin-3-yl)pyrimidin-2-ylamino)thiophene-2-carboxamide

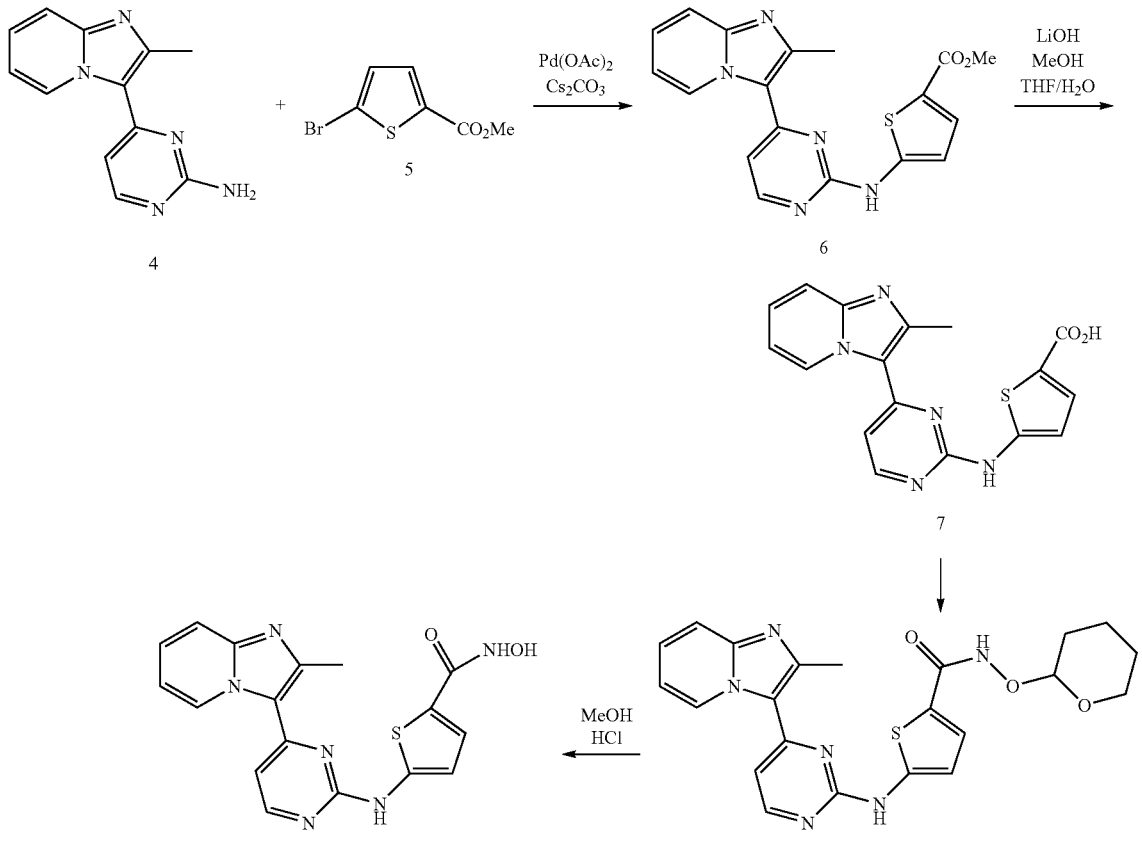

Example 52 (Compound I$^a$-b0-05)

To a stirred solution of Int-4 (1.0 g, 4.4 mmol) and methyl 5-bromothiophene-2-carboxylate-5 (1.17 g, 5.31 mmol) in dioxane (20 mL) were added Xanthophos (0.2 g, 0.34 mmol) and cesium carbonate (1.4 g, 4.4 mmol), followed by palladium (II) acetate (60 mg, 0.26 mmol) at room temperature and then degassed with $N_2$ bubbling for 30 minutes with vacuum. The reaction mixture was then heated to 100° C. and then stirred for 16 hours. The volatiles were concentrated under reduced pressure, and then the residue was diluted with EtOAc (100 mL). The organic layer was washed with water (30 mL), brine (30 mL), dried over anhydrous $Na_2SO_4$ and concentrated under vacuum. The crude material was purified by column chromatography eluting with 1% MeOH/DCM to afford Int-6 (0.2 g, 12%). Mass (m/z): 366 [M$^+$+1]. $^1$H NMR (200 MHz, dmso-d$_6$): δ 9.56 (d, J=9 Hz, 1H), 8.57 (d, J=5.6 Hz, 1H), 8.4 (brs, 1H), 7.68-7.62 (m, 2H), 7.36 (t, J=5.4 Hz, 1H), 7.07 (d, J=5.6 Hz, 1H), 6.9 (t, J=7.0 Hz, 1H), 6.64 (d, J=4 Hz, 1H), 3.85 (s, 3H) 2.75 (s, 3H). To a solution of Int-6 (0.5 g, 1.36 mmol) in methanol (10 mL) and THF (10 mL) was added lithium hydroxide (0.17 g, 4.0 mmol) at room temperature, followed by water (5 mL) and the reaction mixture was stirred at 60° C. for 16 hours. The volatiles were evaporated under vacuum, diluted with water (10 mL) and acidified to about pH 5 using 2 N HCl at 0° C. and stirred further for 30 minutes. The precipitated solid was filtered off, washed with water (2×5 mL) and dried under vacuum to afford Int-7 (0.25 g, 52%). Mass (m/z): 354 [M$^+$+1]. $^1$H NMR (200 MHz, dmso-d$_6$): δ 12.5 (brs, 1H), 11.31 (brs, 1H), 8.8 (brs, 1H), 8.66 (d, J=5.4 Hz, 1H), 7.69 (d, J=8.8 Hz, 1H), 7.54 (d, J=4.4 Hz, 2H), 7.2-7.16 (m, 2H), 6.76 (d, J=4.0 Hz, 1H). To a stirred solution of Int-7 (0.3 g, 0.85 mmol) in DMF (6.0 mL) was added HOBt (0.11 g, 0.85 mmol), EDCI (0.35 g, 1.87 mmol) and N-ethyldiisopropylamine (0.4 mL, 1.87 mmol) at 0° C. After being stirred for 15 minutes at the same temperature, $NH_2OTHP$ (0.21 g, 1.8 mmol) was added to the reaction mixture. The reaction mixture was warmed to room temperature and stirred further for 16 hours. The reaction mixture was diluted with water (20 mL), extracted with ethyl acetate (3×20 mL). The combined organic extracts were washed with brine, dried over anhydrous $Na_2SO_4$ and evaporated under vacuum. The crude material was purified over silica gel column chromatography eluting with 2% MeOH/DCM to afford Int-8 (0.2 g, 52%). Mass (m/z): 451 [M$^+$+1]. $^1$H NMR (200 MHz, dmso-d$_6$): δ 11.27 (brs, 1H), 11.18 (brs, 1H), 9.76 (brs, 1H), 8.63 (d, J=5.4 Hz, 1H), 7.65 (d, J=9.2 Hz, 1H), 7.42-7.46 (m, 2H), 7.17 (d, J=5.6 Hz, 1H), 7.07 (t, J=6.6 Hz, 1H), 6.71 (d, J=4.0 Hz, 1H), 4.9 (brs, 1H), 4.02 (brs, 1H), 3.49-3.46 (m, 1H), 2.66 (s, 3H), 1.68 (brs, 3H), 1.52 (brs, 3H). To a mixture of Int-8 (0.35 g, 7.7 mmol) in methanol (10 mL) was added 12 N HCl (1.0 mL) drop wise at 0° C. and the reaction mixture was stirred at room temperature for 16 hours. The precipitated solid was filtered off, dried under vacuum to provide product as HCl salt. The HCl salt was treated with saturated $NaHCO_3$ solution for 30 minutes, filtered and dried under vacuum to afford free hydroxamic acid Example 52 (0.25 g, 88%). Mass (m/z): 366.8 [M$^+$+1]. $^1$H NMR (200 MHz, dmso-d$_6$): δ 11.0 (bs, 1H), 9.80 (bs, 1H), 8.80 (bs, 1H), 8.62 (d, J=6.0 Hz, 1H), 7.65 (d, J=8.4 Hz, 1H), 7.42-7.45 (m, 2H), 7.15 (d, J=5.0 Hz, 1H), 7.06 (t, J=7 Hz, 1H), 6.69 (d, J=4.2 Hz, 1H), 2.66 (s, 3H). $^{13}$C NMR (125 MHz, dmso-d$_6$): 157.5, 157.0, 147.3, 146.5, 145.6, 128.7, 128.4, 126.9, 126.5, 126.2, 124.8, 117.5, 116.2, 112.9, 109.9, 109.7, 16.7.

Examples 53 and 54

Example 53

N-Hydroxy-4-[4-(2-methyl-imidazo[1,2-a]pyridin-3-yl)-pyridin-2-ylamino]-benzamide Example 54

N-(2-Amino-phenyl)-4-[4-(2-methyl-imidazo[1,2-a]pyridin-3-yl)-pyridin-2-ylamino]-benzamide

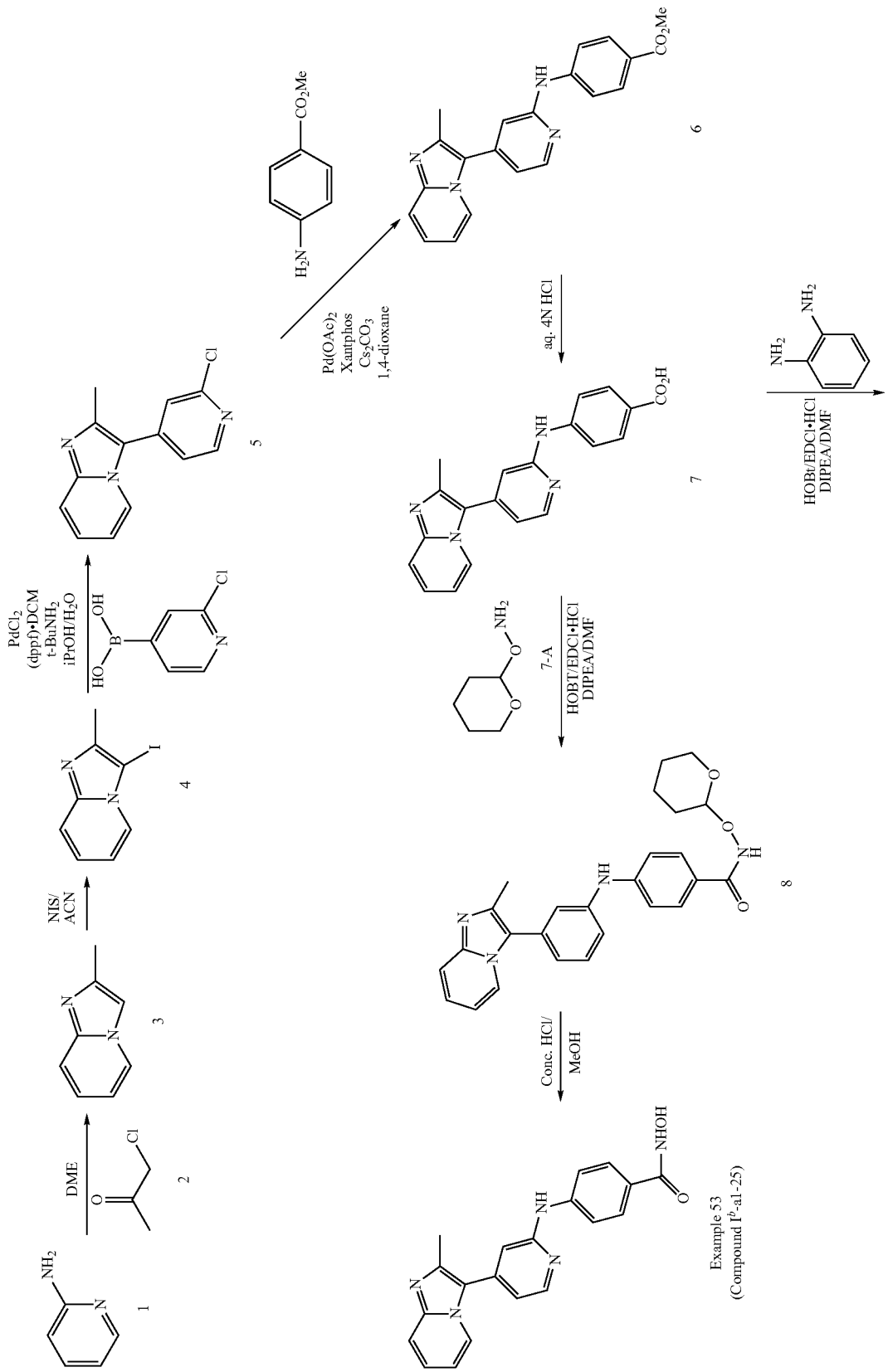

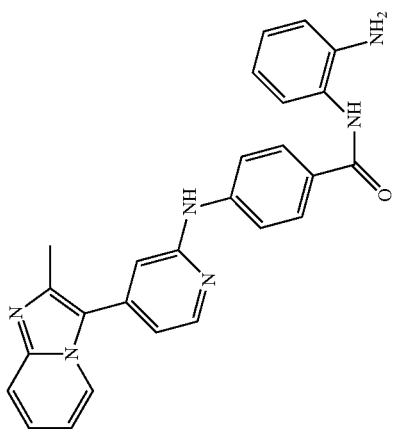
Example 54 (Compound I^b-a1-29)

To a stirred solution of Int-1 (20.0 g, 212 mmol) in DME (100 mL) was added Int-2 (25 mL, 318 mmol) at room temperature. The reaction mixture was heated to 85° C. and then stirred for 24 hours. After reaction completion, the volatiles were concentrated under reduced pressure and the residue was diluted with saturated NaHCO$_3$ solution. The aqueous layer was extracted with EtOAc (3×200 mL). The combined organic extracts were washed with water (50 mL), brine (2×75 mL), dried over anhydrous Na$_2$SO$_4$ and concentrated under vacuum to get crude compound. The obtained crude material was purified by column chromatography using 1% MeOH/DCM to afford Int-3 (6.0 g, 21%). Mass (m/z): 133 [M$^+$+1]. $^1$H NMR (200 MHz, dmso-d$_6$): δ 8.05 (d, J=8.2 Hz, 1H), 7.35 (s, 1H), 7.1 (t, J=6.8 Hz, 1H), 6.7 (t, J=6.8 Hz, 1H), 6.5 (d, J=8.2 Hz, 1H), 2.45 (s, 3H). To a stirred solution of Int-3 (5.0 g, 37.8 mmol) in CH$_3$CN (16 mL) was added NIS (10.2 g, 45.4 mmol) at room temperature and then stirred for 1 hour. After reaction completion, the volatiles were concentrated under reduced pressure and the residue was dissolved in EtOAc (150 mL). The organic layer was washed with water, dried over anhydrous Na$_2$SO$_4$ and concentrated under vacuum to afford Int-4 (4.5 g, 46%). Mass (m/z): 259 [M$^+$+1]. $^1$H NMR (200 MHz, dmso-d$_6$): δ 8.22 (d, J=8 Hz, 1H), 7.47 (d, J=7.2 Hz, 1H), 7.29 (t, J=7.0 Hz, 1H), 2.35 (s, 3H). Int-4 (3.0 g, 11.62 mmol) was dissolved in iPrOH—H$_2$O (50 mL, 1:1) and purged with N$_2$ for 5 minutes. Then PdCl$_2$ (dppf).DCM (1.89 g, 2.3 mmol) and t-BuNH$_2$ (1.8 mL) were added to the reaction mixture at room temperature. After being stirred for 15 minutes, 2-chloro pyridine 4-boronic acid (1.47 g, 9.3 mmol) was added to the reaction mixture and heated at 100° C. for 16 hours. After completion, the volatiles were concentrated under reduced pressure. The residue was diluted with water and extracted with EtOAc (3×50 mL). The combined organic extracts were dried over Na$_2$SO$_4$ and concentrated under reduced pressure to get crude product. The obtained crude material was purified by column chromatography eluting with 1% MeOH/DCM to afford Int-5 (0.6 g, 20%). Mass (m/z): 244 [M$^+$+1]. $^1$H NMR (200 MHz, dmso-d$_6$): δ 8.51 (t, J=5 Hz, 2H), 7.71 (s, 1H), 7.63-7.55 (m, 2H), 7.34 (t, J=7 Hz, 1H), 6.94 (t, J=7 Hz, 1H), 2.43 (s, 3H). To a stirred solution of Int-5 (1.0 g, 4.1 mmol) and methyl 4-aminobenzoate (0.24 g, 4.9 mmol) in 1,4-dioxane (15 mL) were added Pd(OAc)$_2$ (0.037 g, 0.163 mmol), xanthpos (0.142 g, 0.245 mmol) followed by Cs$_2$CO$_3$ (2.0 g, 6.1 mmol) were added to the reaction mixture under N$_2$ atmosphere. The resulting reaction mixture was heated at 100° C. for 16 hours. After reaction completion, the volatiles were concentrated under reduced pressure. The residue was diluted with water and extracted with EtOAc (2×50 mL). The combined organic layer was dried over Na$_2$SO$_4$ and concentrated under reduced pressure to get crude product. The obtained crude material was purified by column chromatography eluting with 1% MeOH/DCM to afford Int-6 (0.788 g, 54%). Mass (m/z): 359 [M$^+$+1]. $^1$H NMR (200 MHz, dmso-d$_6$): δ 8.4 (d, J=7.6 Hz, 1H), 8.2 (d, J=7.6 Hz, 1H), 8.0 (d, J=8.4 Hz, 2H), 7.6 (d, J=7.6 Hz, 1H), 7.5 (d, J=8.4 Hz, 2H), 7.2 (s, 1H), 6.96 (s, 2H), 6.85 (m, 2H), 3.8 (s, 3H), 2.7 (s, 3H). A mixture of Int-6 (0.8 g, 2.23 mmol) in 4 N HCl (16 mL) was stirred at 100° C. for 3 hours. The reaction mixture was allowed to room temperature and continued stirring for another 30 minutes. The precipitate solid was filtered off and dried under vacuum to afford Int-7 (0.613 g, 80%) as a solid. Mass (m/z): 345 [M$^+$+1]. $^1$H NMR (200 MHz, dmso-d$_6$): δ 8.4 (d, J=7.6 Hz, 1H), 8.2 (d, J=7.6 Hz, 1H), 8.0 (d, J=8.4 Hz, 2H), 7.6 (d, J=7.6 Hz, 1H), 7.5 (d, J=8.4 Hz, 2H), 7.2 (s, 1H), 6.96 (s, 2H), 6.85 (m, 2H), 2.7 (s, 3H). To a stirred solution Int-7 (0.5 g, 1.45 mmol) in DMF (10 mL) were added HOBt (0.195 g, 1.44 mmol), EDCI.HCl (0.605 g, 3.16 mmol) and DIPEA (0.65 mL) at 0° C. After 5 minutes, NH$_2$OTHP (0.37 g, 3.18 mmol) was added to the reaction mixture. The reaction mixture was warmed to room temperature and stirred for 16 hours. After the completion, the reaction mixture was diluted with water (20 mL) and stirred for 30 minutes. The precipitated solid was filtered off, washed with water and dried under vacuum. The crude material was purified over silica gel column chromatography eluting with 3% MeOH/DCM to afford Int-8 (0.4 g, 62%). Mass (m/z): 444 [M$^+$+1].

Preparation of Example 53: To a stirred solution of Int-8 (0.4 g, 0.90 mmol) in MeOH (10 mL) was added 4 N HCl (2 mL) at 0° C. and continued stirring for 16 hours at room temperature. After completion, the precipitated solid was filtered off, dried under vacuum to provide product as HCl salt. The salt was further treated with saturated NaHCO$_3$ solution for 30 minutes, filtered and dried under vacuum to afford the title compound (0.28 g, 81%) as a solid. Mass (m/z): 360 [M$^+$+1]. $^1$H NMR (200 MHz, dmso-d$_6$): δ 9.47 (brs, 1H), 8.47 (d, J=6.6 Hz, 1H), 8.34 (d, J=5.4 Hz, 1H), 7.75-7.67 (m, 5H), 7.57 (d, J=9.2 Hz, 1H), 7.30 (t, J=7 Hz, 1H), 7.0-6.90 (m, 4H), 2.45 (s, 3H); $^{13}$C NMR (125 MHz, dmso-d$_6$): 164.3, 156.1, 148.2, 144.5, 144.0, 141.9, 137.7, 127.7, 125.2, 124.5, 124.1, 118.7, 116.9, 116.5, 114.1, 112.6, 109.9.

Preparation of Example 54: To a stirred solution Int-7 (0.6 g, 1.7 mmol) in DMF (12 mL) were added HOBt (0.234 g, 1.7 mmol), EDCI.HCl (0.732 g, 3.8 mmol) and DIPEA (0.9 mL) at 0° C. under inert atmosphere. After being stirred for 5 minutes, and then added o-phenylenediamine (0.22 g, 2.0 mmol) to the reaction mixture. The reaction mixture was warmed to room temperature and further stirred for 16 hours. The reaction mass was diluted with water (20 mL) and stirred for 30 minutes. The precipitated solid was filtered off, washed with water and dried under vacuum. The crude material was purified over silica gel chromatography eluting with 4% MeOH/DCM to afford the title compound (0.32 g, 42%). Mass (m/z): 434.8 [M$^+$+1]. $^1$H NMR (200 MHz, dmso-d$_6$): δ 9.56 (brs, 1H), 9.48 (bs, 1H), 8.50 (d, J=7.0 Hz, 1H), 8.37 (d, J=4.88 Hz, 1H), 7.96-7.83 (m, 4H), 7.58 (d, J=9.2 Hz, 1H), 7.32 (t, J=8 Hz, 1H), 7.17 (d, J=6.0 Hz, 1H), 6.90-7.05 (m, 4H), 6.77 (d, J=8.0 Hz, 1H), 6.63-6.60 (m, 1H), 5.0 (bs, 2H), 2.50 (s, 3H). $^{13}$C NMR (125 MHz, dmso-d$_6$): 164.9, 156.0, 148.2, 144.5, 144.3, 142.9, 141.7, 137.7, 128.7, 126.4, 126.2, 125.9, 125.2, 124.1, 123.8, 118.7, 116.6, 116.4, 116.3, 116.2, 114.2, 112.6, 110.0, 14.

Example 55

N-(2-Amino-phenyl)-4-(6-imidazo[1,2-a]pyridin-3-yl-pyrimidin-4-ylamino)-benzamide (Compound I$^b$-a4-05)

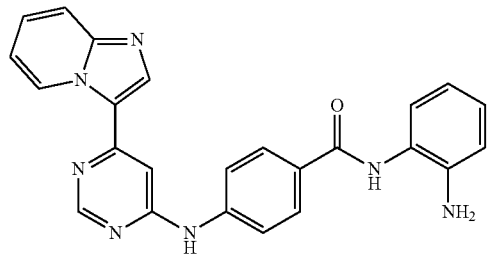

Example 55

To a solution of 3-bromo-imidazo[1,2-a]pyridine (1 g, 5.1 mmol) in dry THF (25 mL) under N$_2$ at −78° C. was added n-BuLi (1.6 M in hexanes, 3.8 mL, 6.12 mmol) and the reaction mixture was stirred at that temperature for 1 hour. Then freshly dried zinc bromide (1.7 g, 7.65 mmol) in dry THF (15 mL) was added slowly and the reaction mixture was slowly warmed up to room temperature and 4,6-dichloro-pyrimidine (760 mg, 5.1 mmol) and Pd(PPh$_3$)$_4$ (294 mg, 0.26 mmol) was added. After 16 hours at 75° C., the reaction mixture was then concentrated and directly purified by flash chromatography (SiO$_2$, 95:5:0.5/EtOAc:MeOH:TEA) to give 3-(6-chloro-pyrimidin-4-yl)-imidazo[1,2-a]pyridine (Int-1). MS found for $C_{11}H_7ClN_4$ as $(M+H)^+$ 231.45. To a solution of Int-1 (100 mg, 0.44 mmol), 4-amino-benzoic acid (72 mg, 0.52 mmol) in dioxane (3 mL) and 2-PrOH (0.5 mL), p-TSA (83 mg, 0.44 mmol) was added and heated in a microwave (Emry's Optimizer) at 130° C. After 20 minutes, the resulting solid was filtered and washed with ether and dried to give 4-(6-imidazo[1,2-a]pyridin-3-yl-pyrimidin-4-ylamino)-benzoic acid (Int-2). MS found for $C_{18}H_{13}N_5O_2$ (m/z): 332.39 [M++1]. To Int-2 (75 mg, 0.23 mmol) in DMF (4 mL), was added HATU (129 mg, 0.34 mmol), 1,2-phenylenediamine (49 mg, 0.45 mmol) and DIPEA (0.12 mL, 0.68 mmol) and stirred at room temperature for 45 minutes. The reaction mixture was diluted with water and acetonitrile and directly purified by preparative HPLC affording the title compound as tan solid, after lyophilization. MS found for $C_{24}H_{19}N_7O$ as $(M+H)^+$ 422.09. $^1$H NMR (400 MHz, dmso-d$_6$): δ 9.89 (d, J=6.8 Hz, 1H); 8.71 (s, 1H); 8.19 (s, 1H); 7.92 (d, J=8.8 Hz, 2H); 7.80 (d, J=8.8 Hz, 2H); 7.61 (d, J=9.2 Hz, 1H); 7.42 (t, J=7.6 Hz, 1H); 7.13-6.97 (m, 4H); 6.83 (d, J=7.2 Hz, 1H); 6.69 (t, J=7.6 Hz, 1H).

Example 56

N-(2-Amino-phenyl)-4-(4-imidazo[1,2-a]pyridin-3-yl-[1,3,5]triazin-2-ylamino)-benzamide (Compound I$^b$-a3-05)

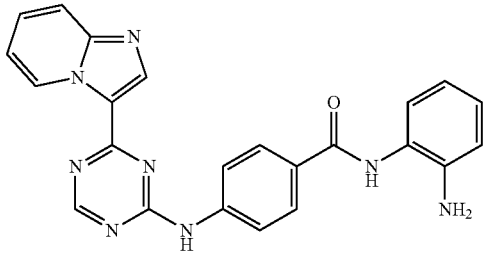

Example 56

To a solution of 2,4-dichloro-1,3,5-triazine (300 mg, 2.0 mmol), 4-aminobenzoic acid methyl ester (302 mg, 2.05 mmol) in acetonitrile (3 mL), DIPEA (0.35 mL, 2.0 mmol) was added. After 30 minutes at room temperature, resulting solid was filtered and washed with acetonitrile and dried to give methyl 4-(4-chloro-1,3,5-triazin-2-ylamino)benzoate (Int-1). MS found for $C_{11}H_9ClN_4O_2$ as $(M+H)^+$ 265.07. A mixture of 3-(4,4,5,5-tetramethyl-1,3,2-dioxaborolan-2-yl)H-imidazo[1,2-a]pyridine (139 mg, 0.57 mmol), Int-1 (150 mg, 0.57 mmol), 2.0M Sodium carbonate solution (0.6 mL, 1.25 mmol), PdCl$_2$(dppf) (14 mg, 0.02 mmol), dioxane (2 mL) was heated in a microwave (Emry's Optimizer) at 125° C. for 15 minutes. The reaction mixture was then poured into water and the resulting solid was filtered and washed with ether and dried to give 5 methyl 4-(4-(H-imidazo[1,2-a]pyridin-3-yl)-1,3,5-triazin-2-ylamino)benzoate (Int-2) which was used without further purification. MS found for $C_{18}H_{14}N_6O_2$ as $(M+H)^+$ 347.25. To solid Int-2 in MeOH (5 mL) was added 1N NaOH (5 mL) and stirred at 60° C. for 2 hours. The reaction mixture was concentrated, diluted with water and neutralized with 6N HCl (1.5 mL). The aqueous phase was then extracted with ethyl acetate and the combined organic layers were concentrated to give 4-(4-(H-imidazo[1,2-a]pyridin-3-yl)-1,3,5-triazin-2-ylamino)benzoic acid (Int-3). MS found for $C_{17}H_{12}N_6O_2$ as $(M+H)^+$ 333.34. To Int-3 in DMF (6 mL), was added HATU (260 mg, 0.7 mmol), 1,2-phenylenediamine (123 mg, 1.1 mmol) and DIPEA (0.4 mL, 2.3 mmol) and stirred at room temperature for 3 hours. The reaction mixture was diluted with water and acetonitrile and directly purified by preparative HPLC affording the title compound, after lyophilization. MS found for $C_{23}H_{18}N_8O$ as $(M+H)^+$ 423.09. $^1$H NMR (400 MHz, dmso-d$_6$): δ 10.49 (s, 1H); 9.89 (brs, 1H); 9.56 (s, 1H); 8.78 (s, 1H); 8.57 (s, 1H); 7.99-7.77 (m, 6H); 7.54 (t, J=7.6 Hz, 1H); 7.23 (t, J=6.4 Hz, 1H); 7.14 (d, J=7.6 Hz, 1H); 6.94 (m, 1H); 6.75 (d, J=8.0 Hz, 1H); 6.57 (t, J=7.6 Hz, 1H).

Examples 57 and 58

Example 57

N-Hydroxy-4-[(4-imidazo[1,2-a]pyridin-3-yl-pyrimidin-2-yl)-(2,2,2-trifluoro-ethyl)-amino]-benzamide Example 58

N-(2-Amino-phenyl)-4-[(4-imidazo[1,2-a]pyridin-3-yl-pyrimidin-2-yl)-(2,2,2-trifluoro-ethyl)-amino]-benzamide

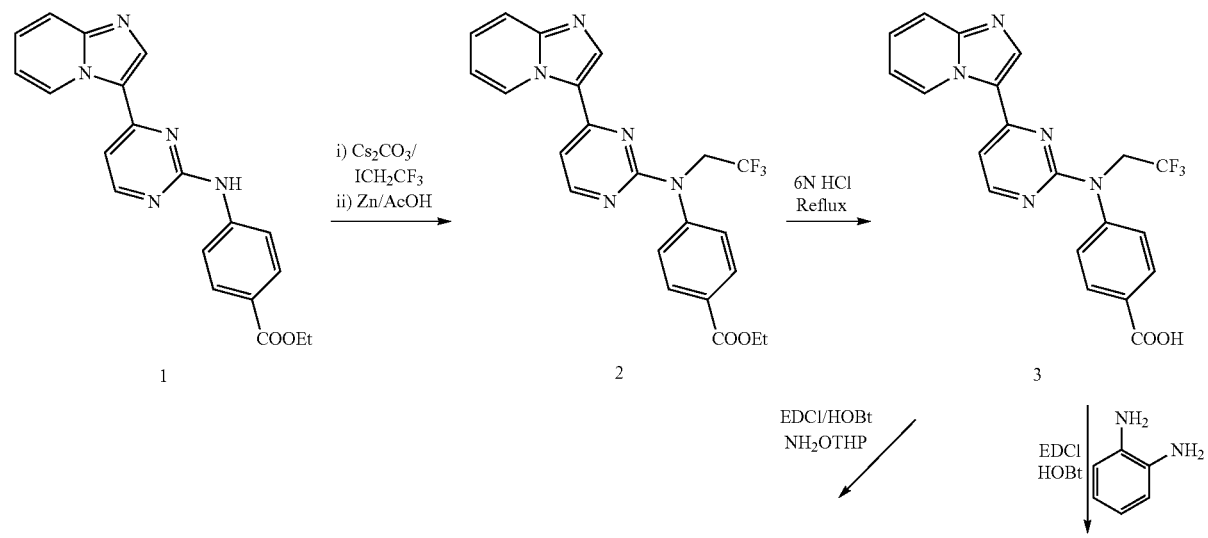

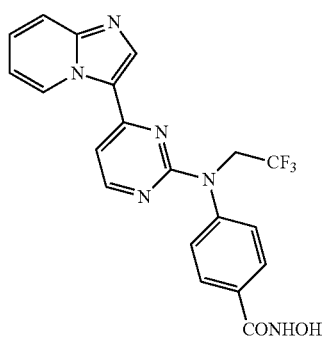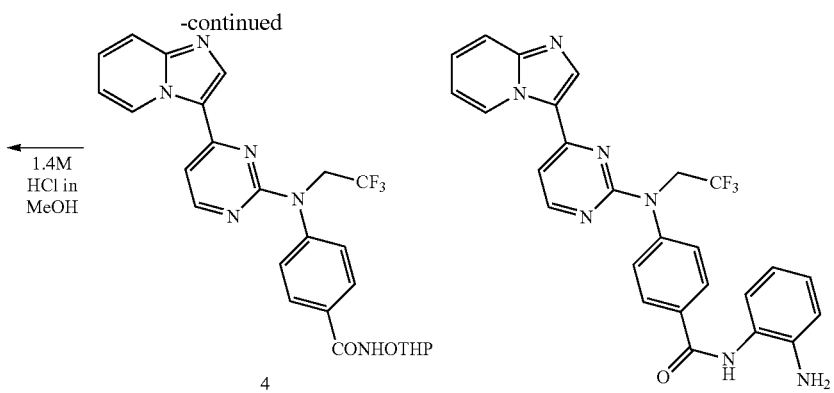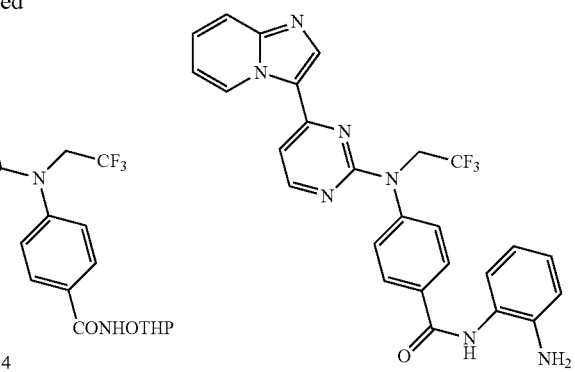

5
Example 57
(Compound I$^c$-a-01)

4

6
Example 58
(Compound I$^c$-a-05)

To a solution of earlier prepared Int-1 (1.4 g, 4.0 mmol) in DMF (4 mL) was added cesium carbonate (3.95 g, 12 mmol). The mixture was stirred for 15 minutes and then 2-iodo-1,1,1-trifluoro ethane (2 mL, 20 mmol) was added. The reaction mixture was stirred overnight at 100° C. The reaction mixture was poured in to ethyl acetate (50 mL), stirred for 5 minutes, and filtered off the solid. The residue was washed with water (40 mL) followed by ethyl acetate (30 mL). The organic layer was separated from the filtrate and washed with 1N HCl (20 mL), dried over $Na_2SO_4$, and concentrated under vacuum to afford crude product (0.560 g) along with some starting material and bi-product. The bi-product was removed. The crude mixture (560 mg) was dissolved in acetic acid (12 mL), to which Zn dust (0.17 g) was added. The mixture was stirred for 2 hours at room temperature, and filtered. The filtrate was poured into water (20 mL), neutralized with solid $NaHCO_3$ (about pH 7) and extracted with ethyl acetate. The organic layer was dried over $Na_2SO_4$, concentrated under vacuum and purified by column chromatography using EtOAc:Hexane (1:1) to provide Int-2 (0.080 g, 4%). $^1$H NMR (200 MHz, dmso-d$_6$): δ 3.93 (s, 3H), 5.00 (q, J=9.2 Hz, 2H), 6.50 (t, J=6.5, 1H), 7.38 (t, J=7.6 Hz, 1H), 7.49 (d, J=5.4 Hz, 1H) 7.63 (d, J=8.4 Hz, 2H), 7.71 (s, 1H), 8.12 (d, J=8.8 Hz, 2H), 8.49 (d, J=5.4 Hz, 1H) 8.61 (s, 1H), 8.84 (d, J=7.0 Hz, 1H). Int-2 (0.143 g, 0.33 mmol) in 6 N HCl (10 mL) was refluxed for 4 hours. The reaction mixture was cooled to room temperature and neutralized (about pH 7) with saturated $NaHCO_3$ solution. The resulting precipitated solid was filtered, washed with water, and dried under vacuum to afford Int-3 (0.1 g, 72%).

Preparation of Compound 6: To a stirred solution of Int-3 (0.05 g, 0.12 mmol) in DMF at 0° C. (3 mL) were added HOBt (0.017 g, 0.12 mmol), EDCI (0.051 g, 0.26 mmol), o-phenylenediamine (0.13 g, 0.12 mmol) and DIPEA (0.05 mL, 0.30 mmol) sequentially. The reaction mixture was stirred overnight at room temperature, and diluted with water (15 mL). The resulting precipitates were filtered, washed with water, and dried under vacuum to afford Compound 6 (0.030 g, 49%). $^1$H NMR (500 MHz, dmso-d$_6$): δ 4.977 (m, 2H), 6.84 (d, J=7.0 Hz, 1H), 7.52 (d, J=5.0 Hz, 1H), 7.56 (d, J=9.0 Hz, 2H), 7.71 (t, J=6.5 Hz, 1H), 7.87 (d, J=9.0 Hz, 1H), 7.94 (d, J=8.5 Hz, 2H), 8.60 (d, J=5.0 Hz, 1H), 8.88 (d, J=6.5 Hz, 1H), 8.93 (s, 1H), 11.39 (bs, 1H). $^{13}$C NMR (125 MHz, dmso-d$_6$): δ 108.1, 113.9, 115.9, 121.5, 123.9, 126.1, 128.4, 128.6, 129.3, 131.8, 132.4, 142.5, 145.4, 155.2, 158.7, 161.0, 163.5. Mass (m/z): 428 [M$^+$+1]. MP: 183° C.

Preparation of Compound 5: To a stirred solution of Int-3 (0.1 g, 0.24 mmol) in DMF (1 mL) at 0° C. were added EDCI (0.14 g, 0.73 mmol), HOBt (0.05 g, 0.37 mmol), and DIPEA (0.125 g, 0.968 mmol). After stirring for 10 minutes at 0° C., $NH_2$—OTHP (0.07 g, 0.6 mmol, dissolved in DMF) was added and the mixture was stirred overnight at room temperature. The product was purified directly by column chromatography ($SiO_2$) using EtOAc:Hexane to provide the THP-protected compound (Int-4) (0.08 g, 65%). $^1$H NMR (500 MHz, CDCl$_3$): δ 1.66 (m, 3H), 1.91 (m, 3H), 3.7 (d, J=11.0 Hz, 1H), 4.03 (t, J=10.0 Hz, 1H), 4.80 (q, J=9.0 Hz, 2H), 5.16 (bs, 1H), 6.60 (t, J=7.0 Hz, 1H), 7.10 (m, 1H), 7.24 (m, 1H), 7.50 (m, 2H), 7.64 (d, J=5.0 Hz, 1H), 7.95 (m, 2H), 8.26 (s, 1H), 8.39 (d, J=5.0 Hz, 1H), 8.80 (m, 1H), 8.94 (bs, 1H). Mass (m/z): 512.7 [M$^+$+1]. To the Int-4 (0.08 g, 0.15 mmol) in MeOH (1.5 mL) was added 1.4 N HCl in methanol (0.6 mL) at 0° C. and the mixture was stirred for 2 hours at room temperature. The volatiles were removed by rotavapor. The residue was dissolved in methanol (0.2 mL), and cooled to 0° C. Ether (2 mL) was added to the residue. The precipitated solid was filtered and dried under vacuum to afford pure Compound 5 (0.045 g, 68%) as an off white solid. $^1$H NMR (500 MHz, dmso-d$_6$): δ 4.98 (m, 2H), 6.91 (m, 1H), 7.55 (m, 3H), 7.80 (m, 1H), 7.94 (m, 3H), 8.62 (d, J=5.5 Hz, 1H), 8.91 (d, J=6.5 Hz, 1H), 9.04 (s, 1H). $^{13}$C NMR (125 MHz, dmso-d$_6$): δ 108.1, 113.9, 115.9, 121.5, 123.9, 126.1, 128.4, 128.6, 129.3, 131.8, 132.4, 142.5, 145.4, 155.2, 158.7, 161.0, 163.5. Mass (m/z): 428.8 [M$^+$+1]. Melting point: 198° C.

Examples 59 and 60
Example 59
N-(2-aminophenyl)-5-(4-(2-methylimidazo[1,2-a]pyridin-3-yl)pyrimidin-2-ylamino)thiophene-3-carboxamide
Example 60
N-hydroxy-5-(4-(2-methylimidazo[1,2-a]pyridin-3-yl)pyrimidin-2-ylamino)thiophene-3-carboxamide
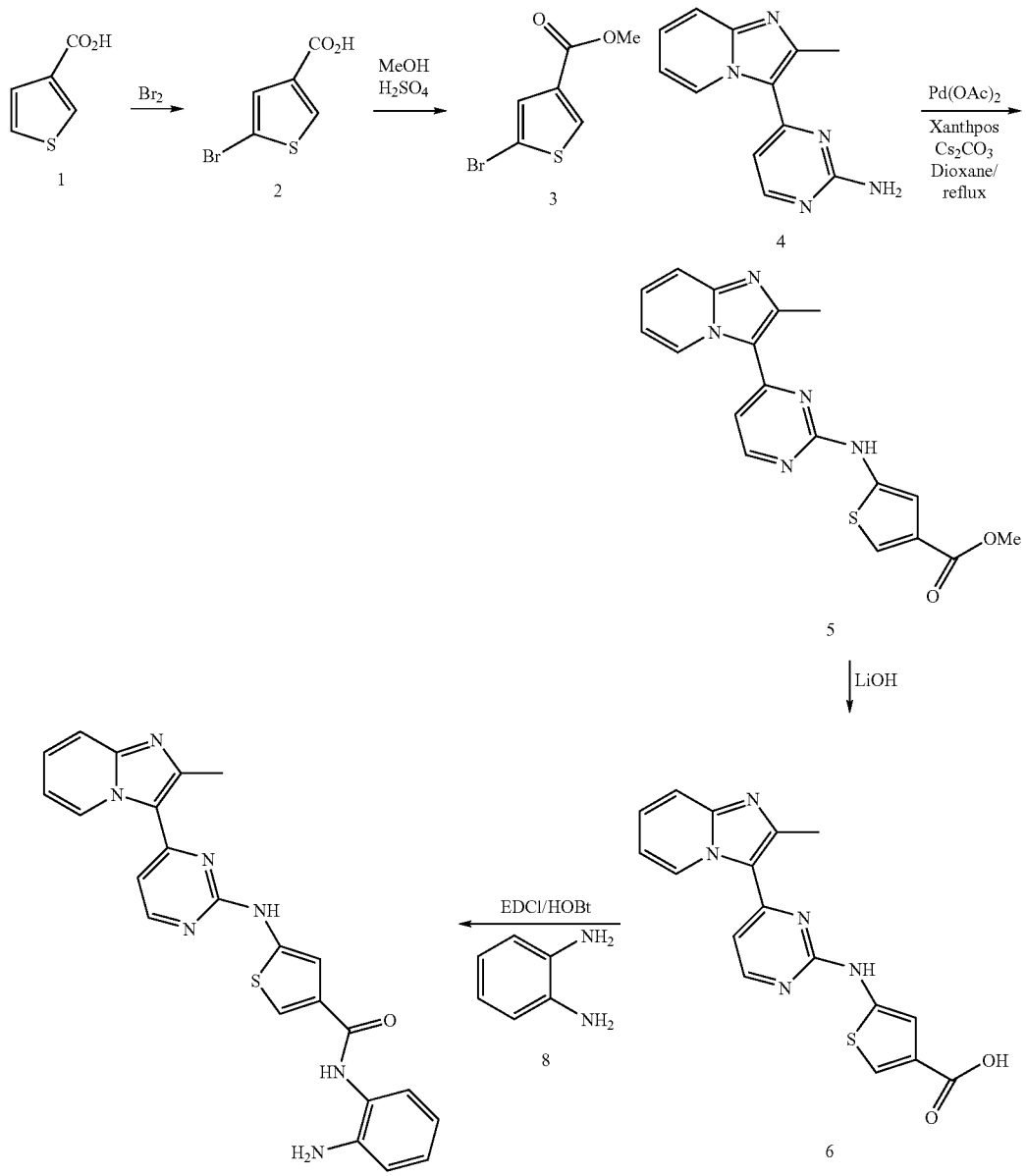
Example 60
(Compound I$^\alpha$-b1-05)

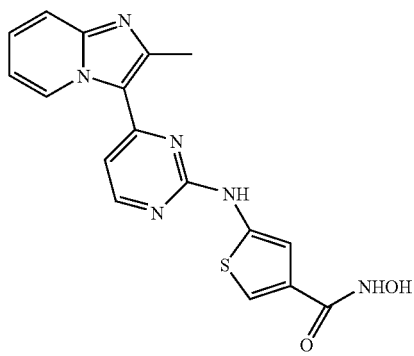

Example 59
(Compound I$^a$-b1-07)

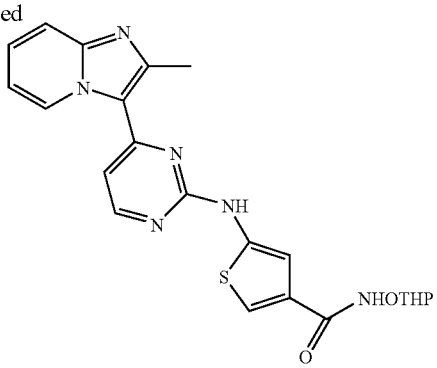

7

A solution of bromine (2 mL, 39.06 mmol) in glacial acetic acid (64 mL) was added slowly to a stirred solution of Int-1 (5 g, 39.06 mmol) in glacial acetic acid (37 mL) at 0° C. and stirred at room temperature for 20 minutes. The reaction mixture was then poured into ice water while stirring vigorously. The white precipitated solid was filtered, washed with water and recrystallised from hot water to afford pure Int-2 as white solid (3.68 g, 46%). $^1$H NMR (200 MHz, dmso-d$_6$): δ 7.55 (s, 1H), 8.17 (s, 1H). To a stirred solution of Int-2 (3.4 g, 16.42 mmol) in methanol (40 mL) was added H$_2$SO$_4$ (321 mg, 3.28 mmol) and stirred under reflux for 12 hours. Volatiles from the reaction mixture were distilled off under reduced pressure and the resulting residue was extracted with DCM (75 mL). The organic extract was washed with water (40 mL), saturated aqueous NaHCO$_3$ solution (40 mL), brine (40 mL) and dried over Na$_2$SO$_4$, filtered and concentrated under vacuum to afford pure Int-3 as colorless viscous oil (3.3 g, 91%). $^1$H NMR (200 MHz, dmso-d$_6$): δ 7.98 (s, 1H), 7.44 (s, 1H), 3.87 (s, 3H). To a stirred solution of Int-3 (0.5 g, 2.26 mmol) in dioxane (25 mL) was added Int-4 (0.51 g, 2.26 mmol) followed by Pd (OAc) 2 (105 mg, 0.45 mmol), xanthpos (265 mg, 0.497 mmol) and CS$_2$CO$_3$ (1.18 g, 3.62 mmol). The reaction mixture was degassed under vacuum, bubbled with N$_2$ for 10 minutes and stirred under reflux for 20 hours. The reaction mixture was concentrated under reduced pressure and was purified by column chromatography to isolate product and a very close spot together eluting with EtOAc. This mixture (140 mg) was further purified with preparative HPLC to obtain pure Int-5 as a yellow solid (80 mg, 10%). Mass (m/z): 366.0 [M$^+$+1]. $^1$H NMR (200 MHz, dmso-d$_6$): 9.50 (d, J=7 Hz, 1H), 8.51 (d, J=7 Hz, 1H), 8.56 (d, J=5.2 Hz, 1H), 7.74 (brs, 1H), 7.66 (d, J=11.8 Hz, 1H), 7.35 (d, J=7.4 Hz, 1H), 7.11 (s, 1H), 7.02 (d, J=5.6 Hz, 1H), 6.87 (t, J=6.8 Hz, 1H), 3.86 (s, 3H), 2.73 (s, 3H). To a stirred solution of Int-5 (0.7 g, 1.91 mmol) in THF: MeOH: H$_2$O (2:1:2) (50 ml) was added LiOH (0.24 g, 5.74 mmol) at room temperature and stirred while heating at 50° C. for 16 hours. Volatiles from the reaction mixture were distilled off under reduced pressure, the reaction mixture was acidified to about pH 5-6 with 2N HCl. The precipitated solid was filtered and dried under vacuum to afford pure Int-6 (0.51 g, 76%). Mass (m/z): 352.0 [M$^+$+1]. $^1$H NMR (200 MHz, dmso-d$_6$): δ 12.45 (brs, 1H), 10.87 (s, 1H), 9.70 ((brs, 1H), 8.60 (d, J=4.68 Hz, 1H), 7.67-7.59 (m, 2H), 7.45 (t, J=8.4 Hz, 1H), 7.13 (d, J=5.2 Hz, 1H), 7.04 (s, 2H), 2.65 (s, 3H).

Preparation of Example 59: To a stirred solution of Int-6 (0.51 mg, 1.45 mmol) in DMF (20 mL) at 10° C. was added EDCI.HCl (0.61 g, 3.19 mmol), HOBt (0.195 g, 1.45 mmol), Int-8 (0.19 g, 1.74 mmol) and finally DIPEA (0.63 mL, 3.63 mmol) was added and stirred at room temperature for 16 hours. The reaction was quenched with water (65 mL) and stirred for 15 minutes, the precipitated solid was filtered, washed with water (35 mL), dried under vacuum to obtain crude compound. This on preparative HPLC purification afforded the title compound (0.27 g, 42%) as a pale yellow solid. Mass (m/z): 442.2 [M$^+$+1]. $^1$H NMR (200 MHz, dmso-d$_6$): δ 10.90 (s, 1H), 9.76 (brs, 1H), 9.46 (s, 1H), 8.60 (d, J=5.4 Hz, 1H), δ 7.72 (s, 1H), 7.65 (d, J=9.2 Hz, 1H), 7.49-7.42 (m, 1H), 7.19-7.13 (m, 3H), 7.08-6.93 (m, 2H), 6.82 (d, J=6.6 Hz, 1H), 6.64-6.56 ((m, 1H), 4.88 (s, 2H), 2.66 (s, 3H). $^{13}$CNMR (125 MHz, dmso-d$_6$): 195.5, 181.3, 161.2, 157.6, 157.0, 147.6, 145.5, 142.9, 141.9, 134.6, 131.2, 128.2, 126.8, 126.5, 126.3, 123.3, 118.8, 117.9, 116.2, 112.8, 109.3, 16.6.

Preparation of Example 60: To a stirred solution of Int-6 (0.51 mg, 1.45 mmol) in DMF (25 mL) at 10° C. was added EDCI.HCl (0.61 g, 3.19 mmol), HOBt (0.195 g, 1.45 mmol), NH$_2$OTHP (0.34 g, 2.9 mmol) and finally DIPEA (0.63 mL, 3.63 mmol) was added and stirred at room temperature for 16 hours. The reaction was quenched with water (65 mL) and extracted with EtOAC (50 mL). The organic layer was washed with water (2×25 mL), brine (40 mL), dried over Na$_2$SO$_4$ and concentrated under vacuum to obtain crude compound which was purified by column chromatography eluting pure compound with 2% MeOH-DCM to afford pure Int-7 (0.35 g, 54%) as a yellow solid. Mass (m/z): 451.0 [M$^+$+1]. $^1$H NMR (500 MHz, dmso-d$_6$): δ 11.4 (s, 1H), 10.87 (s, 1H), 9.78 (brs, 1H), 8.58 (s, 1H), 7.63 (s, 1H), 7.44 (s, 2H), 7.18 (s, 1H), 7.02 (s, 2H), 4.88 (s, 1H), 4.18 (s, 1H), 3.58 (s, 1H), 2.67 (s, 3H), 1.75 (s, 3H), 1.58 (s, 3H). To a stirred solution of Int-7 (0.35 g, 0.78 mmol) in MeOH (15 mL) at 0-5° C. was added concentrated HCl (1.2 mL) drop wise and stirred at room temperature for 16 hours. The precipitated solid was filtered and dried under vacuum; this was then suspended in saturated aqueous NaHCO3 solution (15 mL) and stirred for 0.5 hours, this was filtered, washed with water (2×5 mL) and dried under vacuum to afford pure hydroxamic acid (0.235 g, 83%) as a yellow solid. Mass (m/z): 367.0 [M$^+$+1]. $^1$H NMR (500 MHz, dmso-d$_6$): δ 10.78 (brs, 1H), 9.78 (brs, 1H), 8.56 (d, J=5.5 Hz, 1H), 7.64 (d, J=9.5 Hz, 1H), 7.46-7.43 (m, 1H), 7.27 (s, 1H), 7.11 (s, 1H), 7.1-7.03 (m, 2H), 2.65 (s, 3H). $^{13}$CNMR (125 MHz, dmso-d$_6$): 160.9, 157.7, 156.8, 147.0, 145.5, 141.8, 133.2, 128.3, 126.7, 117.5, 116.7, 116.1, 112.8, 109.9, 109.2, and 16.6.

Examples 61 and 62

Example 61

N-hydroxy-2-(4-(2-methylimidazo[1,2-a]pyridin-3-yl)pyrimidin-2-ylamino)thiazole-4-carboxamide Example 62

N-(2-aminophenyl)-2-(4-(2-methylimidazo[1,2-a]pyridin-3-yl)pyrimidin-2-ylamino)thiazole-4-carboxamide

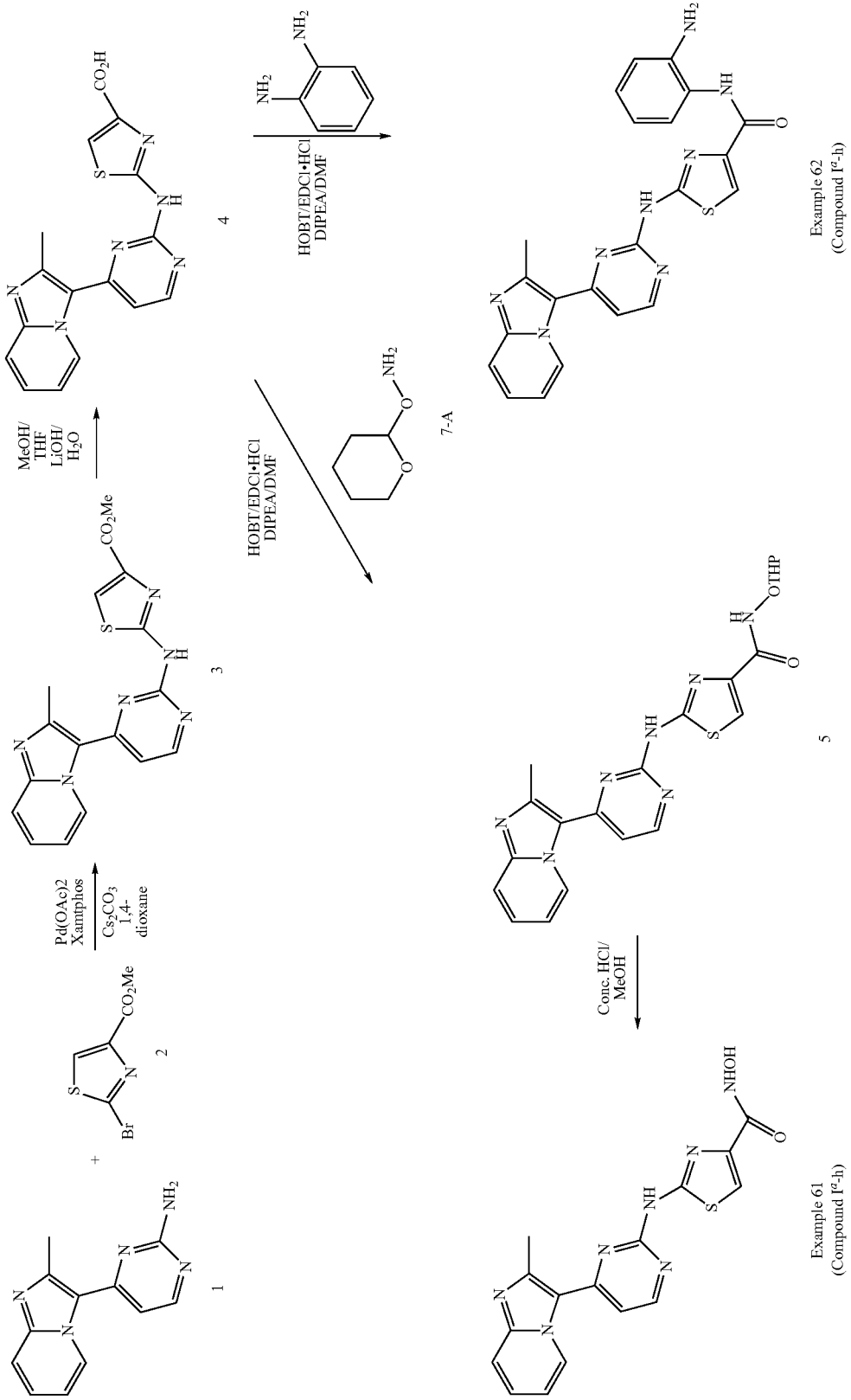

To a stirred solution of Int-1 (2.02 g, 9.0 mmol) in 1,4-dioxane (40 mL) was added Int-2 (2.0 g, 9.0 mmol) at room temperature. After being stirred for 5 minutes, Pd(OAc)$_2$ (0.082 g, 0.36 mmol), xanthpos (0.312 g, 0.54 mmol) followed by Cs$_2$CO$_3$ (4.4 g, 13.51 mmol) were added to the reaction mixture and purged with N$_2$ for 10 minutes. The resulting reaction mixture was heated at 100° C. for 16 hours. The reaction mass was allowed to cool to room temperature and the precipitated solid was filtered off to get crude product. The obtained crude material was washed with water to afford Int-3 (1.2 g, 36%) as a solid. Mass (m/z): 366 [M$^+$+1]. $^1$H NMR (200 MHz, dmso-d$_6$): δ 12.24 (brs, 1H), 10.1 (brs, 1H), 8.65 (d, J=5.4 Hz, 1H), 8.0 (s, 1H), 7.51 (t, J=4.2 Hz, 1H), 7.3 (d, J=5.6 Hz, 1H), 7.05 (t, J=7.0 Hz, 1H), 3.8 (s, 3H), 2.7 (s, 3H). To a stirred solution of Int-3 (1.2 g, 3.28 mmol) in MeOH-THF (24 mL, 1:1) was added a solution of LiOH (0.414 g, 9.836 mmol) in water (12 mL) at room temperature and then stirred for 18 hours. The volatiles were concentrated under reduced pressure and the residue was acidified to about pH 5 using 2 N HCl. The precipitated solid was filtered off and dried under reduced pressure to afford Int-4 (0.59 g). Mass (m/z): 353 [M$^+$+1]. $^1$H NMR (200 MHz, dmso-d$_6$): δ 12.15 (brs, 1H), 10.1 (brs, 1H), 8.67 (d, J=5.8 Hz, 1H), 7.9 (s, 1H), 7.67 (d, J=8.4 Hz, 1H), 7.5 (t, J=8.0 Hz, 1H), 7.3 (d, J=5.6 Hz, 1H), 7.1 (t, J=6.6 Hz, 1H), 2.7 (s, 3H). To a stirred solution of Int-4 (1.2 g, 3.41 mmol) in DMF (20 mL) were added HOBt (0.456 g, 3.41 mmol), EDCI (1.422 g, 7.5 mmol) and DIPEA (1.6 mL, 8.5 mmol) at 0° C. After being stirred for 5 minutes, NH$_2$OTHP (0.4 g, 3.41 mmol) was added to the reaction mixture. The reaction mixture was allowed to warm to room temperature and stirred further for 18 hours. The reaction mixture was diluted with water (20 mL) and stirred for 30 minutes. The precipitated solid was filtered off, washed with water and dried under vacuum. The crude material was purified over silica gel column chromatography eluting with 2% MeOH/DCM to afford Int-5 (0.7 g, 45%) as a solid. Mass (m/z): 452 [M$^+$+1]. $^1$H NMR (200 MHz, dmso-d$_6$): δ 12.0 (s, 1H), 11.0 (s, 1H), 10.1 (brs, 1H), 8.65 (d, J=5.4 Hz, 1H), 7.7 (s, 1H), 7.66 (d, J=8.4 Hz, 1H), 7.48 (t, J=8.4 Hz, 1H), 7.3 (d, J=5.6 Hz, 1H), 7.06 (t, J=6.6 Hz, 1H), 5.0 (brs, 1H), 4.1 (brs, 1H), 3.5 (d, J=11.4 Hz, 1H), 2.69 (s, 3H), 1.71 (brs, 2H), 3.5 (d, J=11.4 Hz, 1H), 2.69 (s, 3H), 1.71 (brs, 2H), 1.55 (brs, 2H), 1.2 (s, 2H).

Preparation of Example 61: To a stirred solution of Int-5 (0.7 g, 1.55 mmol) in MeOH (10 mL) was added conc. HCl (1 mL) at 0° C. The reaction mixture was warmed to room temperature and continued stirring for another 18 hours. The precipitated solid was filtered off, dried under vacuum to provide product as HCl salt. The HCl salt was treated with saturated NaHCO$_3$ solution for 30 minutes, filtered and dried under vacuum to afford the title compound (0.55 g, 95%) as a solid. Mass (m/z): 368 [M$^+$+1]. $^1$H NMR (200 MHz, dmso-d$_6$): δ 11.9 (brs, 1H), 10.65 (brs, 1H), 10.06 (d, J=7.0 Hz, 1H), 9.1 (brs, 1H), 8.65 (d, J=5.4 Hz, 1H), 7.64-7.67 (m, 2H), 7.47 (t, J=8.6 Hz, 1H), 7.29 (d, J=6.0 Hz, 1H), 7.08 (t, 1H), 2.7 (s, 3H). $^{13}$C NMR (125 MHz, dmso-d$_6$): 159.63, 157.27, 156.57, 148.2, 145.9, 143.4, 129.5, 127.34, 117.15, 116.15, 115.8, 113.2, 110.4, 17.15.

Preparation of Example 62: To a stirred solution of Int-4 (0.55 g, 1.56 mmol) in DMF (10 mL) were added HOBt (0.210 g, 1.56 mmol), EDCI (0.655 g, 3.44 mmol) and DIPEA (0.72 mL, 3.9 mmol) at 0° C. After being stirred for 5 minutes, o-phenylenediamine (0.2 g, 1.56 mmol) was added to the reaction mixture. The reaction mixture was warmed to room temperature and stirred further for 18 hours. The reaction mixture was diluted with water (20 mL) and stirred for 30 minutes. The precipitated solid was filtered off, washed with water and dried under vacuum. The crude material was purified over silica gel column chromatography eluting with 2% MeOH/DCM to afford the title compound (0.34 g, 49%) as solid. Mass (m/z): 443 [M$^+$+1]. $^1$H NMR (200 MHz, dmso-d$_6$): δ 12.2 (s, 1H), 10.1 (brs, 1H), 9.2 (brs, 1H), 8.64 (d, J=5.0 Hz, 1H), 7.70 (s, 1H), 7.60 (d, J=10 Hz, 1H), 7.47 (t, J=8.8 Hz, 1H), 7.27 (d, J=6.0 Hz, 2H), 6.98 (t, J=7.4 Hz, 1H), 6.96 (d, J=6.0 Hz, 1H), 6.80 (d, J=8.0 Hz, 1H), 6.66 (t, J=8.8 Hz, 1H), 4.8 (brs, 2H), 2.6 (s, 3H). $^{13}$C NMR (125 MHz, dmso-d$_6$): 159.5, 159.23, 157.3, 156.9, 156.5, 145.9, 144.74, 144.1, 129.56, 127.3, 125.5, 124.2, 123.7, 117.16, 117.1, 116.8, 116.1, 113.2, 110.3, 17.15.

Example 63

N-(2-aminophenyl)-2-(4-(2-methylimidazo[1,2-a]pyridin-3-yl)pyrimidin-2-ylamino)thiazole-5-carboxamide

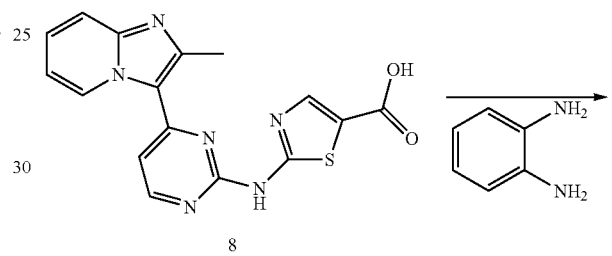

8

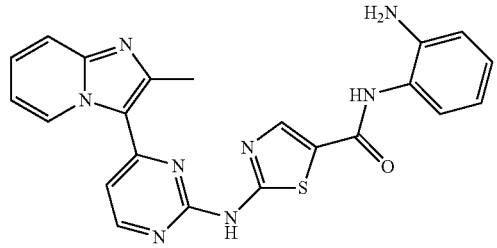

Example 63 (Compound I$^a$-h0-07)

A solution of Int-8 (900 mg, 2.556 mmol) in DMF (10 mL) was added EDCI.HCl (1.07 g, 5.623 mmol), Int-10 (276 mg, 2.556 mmol), HOBt (345 mg, 2.556 mmol) and DIPEA (1.1 mL, 824 mg, 6.39 mmol) at 0° C. The reaction mixture was warmed to room temperature and the stirring was continued overnight. The reaction mixture was diluted with water (50 mL), the precipitated solid was filtered off, dried under vacuum to afford the title compound (270 mg, 24%) as a solid. Mass (m/z): 443 [M$^+$+1]. $^1$HNMR (200 MHz, dmso-d$_6$): δ 12.2 (s, 1H), 10.09 (d, J=6 Hz, 1H), 9.57 (s, 1H), 8.71 (d, J=5.8 Hz, 1H), 8.28 (s, 1H), 7.67 (d, J=8.8 Hz, 1H), 7.49 (t, J=7.6 Hz, 1H), 7.15-6.93 (m, 3H), 6.76 (d, J=8 Hz, 1H), 6.58 (t, J=7.2 Hz, 1H) 4.94 (brs, 2H), 2.7 (s, 2H); $^{13}$C (125 MHz, dmso-d$_6$: 162.6, 159.8, 157.2, 156.9, 156.1, 148.2, 145.9, 143.1, 140.8, 129.5, 127.2, 126.7, 126.5, 126.4, 122.7, 117, 116.1, 116, 115.9, 113.1, 110.5, 17.1.

Example 64

N-hydroxy-6-(4-(2-methylimidazo[1,2-a]pyridin-3-yl)pyrimidin-2-ylamino)nicotinamide

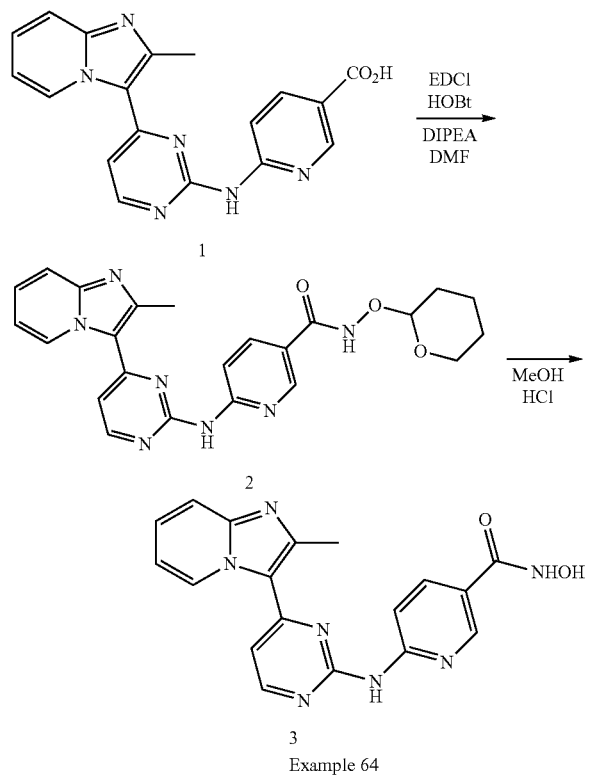

Example 64
(Compound I^a-g2-25)

To a stirred solution Int-1 (1.0 g, 2.8 mmol) in DMF (15 mL) were added HOBt (0.39 g, 2.8 mmol), EDCI (1.3 g, 7.2 mmol) and N-Ethyldiisopropylamine (1.27 mL, 7.2 mmol) at 0° C. After stirring for 15 minutes at 0° C., NH$_2$OTHP (0.5 g, 4.3 mmol) was added and the reaction mixture was stirred at room temperature for 16 hours. The reaction mixture was diluted with water (50 mL) and stirred for 10 minutes. The precipitated solid was filtered, washed with water (2×10 mL) and dried under vacuum to afford Int-2 (0.7 g, 54.6%). $^1$H NMR (200 MHz, dmso-d$_6$): δ 11.65 (brs, 1H), 10.61 (brs, 1H), 10.24 (d, J=6.2 Hz, 1H), 8.72 (s, 1H), 8.61 (d, J=5.6 Hz, 1H), 8.29 (d, J=8.8 Hz, 1H), 8.10 (d, J=8.8 Hz, 1H), 7.64 (d, J=8.6 Hz, 1H), 7.46 (t, J=7.4 Hz 1H), 7.26 (d, J=5.4 Hz, 1H), 7.05 (t, J=7.0 Hz, 1H), 5.0 (s, 1H), 4.05 (brs, 1H), 3.55 (d, J=10.6 Hz, 1H), 2.69 (s, 3H), 1.72 (brs, 3H), 1.5 (brs, 3H). To a suspension of Int-2 (0.7 g, 1.5 mmol) in methanol (10 mL) was added 12 N HCl (1.0 mL) drop wise at 0° C. and the reaction mixture was stirred at room temperature for 16 hours. The precipitated solid was filtered, dried under vacuum. This solid was suspended in saturated NaHCO$_3$ solution and stirred for 30 minutes, filtered and dried under vacuum to afford 3 (0.35 g, 61.5%) as a solid. Mass (m/z): 362 [M$^+$+1]. $^1$H NMR (200 MHz, dmso-d$_6$): δ 10.5 (brs, 1H), 10.24 (d, J=6.6 Hz, 1H), 8.70 (brs, 1H), 8.59 (d, J=5.6 Hz, 1H), 8.23 (d, J=8.8 Hz, 1H), 8.072 (d, J=7.8 Hz, 1H), 7.63 (d, J=8.8 Hz, 1H), 7.48 (t, J=6.8 Hz 1H), 7.24 (d, J=5.4 Hz, 1H), 7.05 (t, J=6.2 Hz, 1H), 2.7 (s, 3H).

Example 65

N-hydroxy-2-(4-(2-methylimidazo[1,2-a]pyridin-3-yl)pyrimidin-2-ylamino)thiazole-5-carboxamide

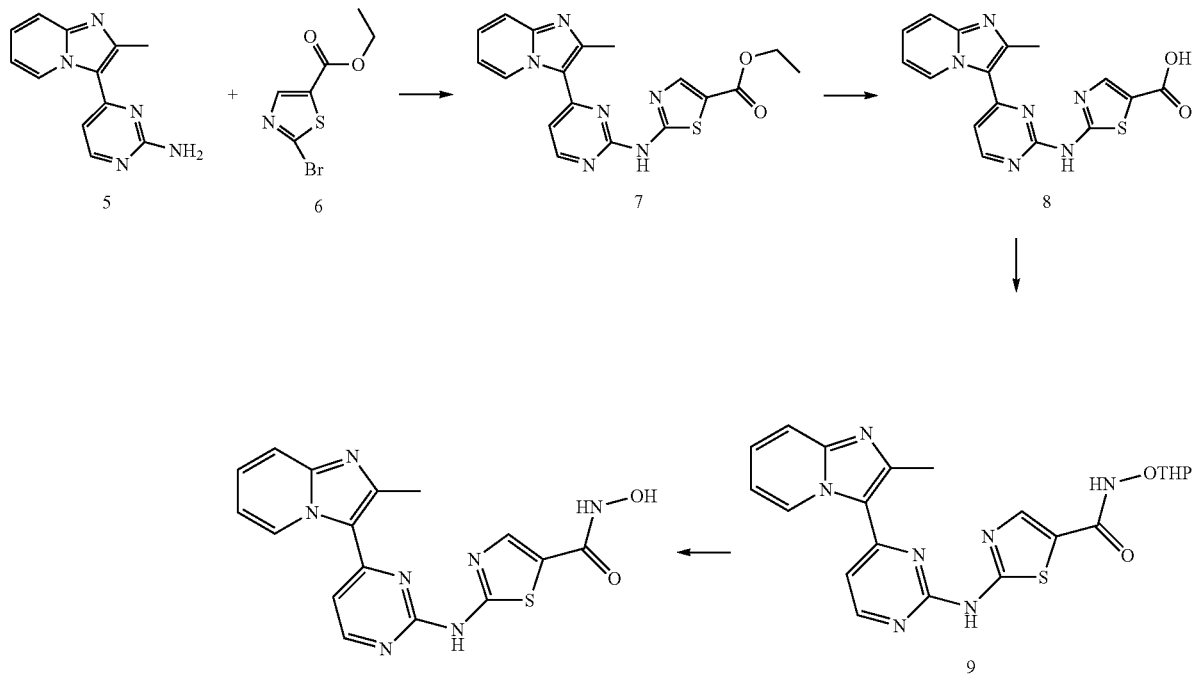

Example 65 (Compound I^a-h0-05)

To a solution of Int-5 (3 g, 13.3 mmol), Int-6 (3.13 g, 13.3 mmol) in 1,4-dioxane (30 mL) was added palladium acetate (300 mg, 1.33 mmol), Xantphos (768 mg, 1.33 mmol), cesium carbonate (2.16 g, 6.65 mmol) at room temperature. The reaction mixture was heated to 100° C. and the stirring was continued for 24 hours. The reaction mixture was allowed to room temperature and then diluted with water (100 mL). The precipitated solids were filtered off, dried under vacuum to afford Int-7 (3.1 g, 61%) as off-white solid. Mass (m/z): 381 [M$^+$+1]. $^1$H NMR (200 MHz, dmso-d$_6$): δ 12.38 (brs, 1H), 10.03 (d, J=7 Hz, 1H), 8.7 (d, J=5.4 Hz, 1H), 8.12 (s, 1H), 7.64 (d, J=8.8 Hz, 1H), 7.48 (t, J=6.8 Hz, 1H), 7.33 (d, J=5.4 Hz, 1H), 7.06 (t, J=7 Hz, 1H), 4.3-4.2 (q, 2H), 2.68 (s, 3H), 1.28 (t, J=7 Hz, 3H). A solution of Int-7 (3 g, 7.874 mmol) in THF (30 mL), water (60 mL) and methanol (10 mL) was added LiOH.H$_2$O (992 mg, 23.622 mmol) at room temperature. The reaction mixture was heated to 50° C. and the stirring was continued for 24 hours. The volatiles were concentrated under reduced pressure. The residue was diluted with water, adjusted pH to neutral by using 2N HCl. The precipitated solids were filtered off, dried under vacuum to afford Int-8 (2.2 g, 79.4%) as a solid. Mass (m/z): 353 [M$^+$+1]. $^1$H NMR (200 MHz, dmso-d$_6$): δ 11.58 (brs, 1H), 10.06 (d, J=6.2 Hz, 1H), 8.63 (d, J=5.4 Hz, 1H), 7.63 (d, J=8.4 Hz, 1H), 7.49-7.41 (m, 2H), 7.24 (d, J=5.6 Hz, 1H), 7.03 (t, J=7 Hz, 1H), 2.68 (s, 3H). A solution of Int-8 (600 mg, 1.7 mmol) in DMF (10 mL) was added EDCI.HCl (714 mg, 3.74 mmol), NH$_2$OTHP (239 mg, 2.046 mmol), HOBt (229 mg, 1.7 mmol) and DIPEA (548 mg, 4.25 mmol) at 0° C. The reaction mixture was warmed to room temperature and the stirring was continued overnight. The reaction mixture was diluted with water (50 mL), filtered the precipitated solids. The solid was dried under vacuum to afford Int-9 (450 mg, 58.6%) as a solid. Mass (m/z): 452 [M$^+$+1]. $^1$H NMR (200 MHz, dmso-d$_6$): δ 12.21 (brs, 1H), 11.47 (brs, 1H), 10.05 (d, J=5.4 Hz, 1H), 8.69 (d, J=5.6 Hz, 1H), 8.01 (s, 1H), 7.66 (d, J=8 Hz, 1H), 7.48 (t, J=7.63 (d, J=7 Hz, 1H), 7.06 (t, J=6.6 Hz, 1H), 4.93 (brs, 1H), 4.03-3.99 (m, 1H), 3.55-3.49 (m, 1H), 2.69 (s, 1H), 1.69-1.53 (m, 4H). To a solution of Int-9 (700 mg, 1.55 mmol) in methanol (15 mL) was added Con. HCl (1 mL) at 0° C. The reaction mixture was warmed to room temperature and the stirring was continued for 18 hours. The precipitated solids were filtered off, washed with methanol (10 mL) and dried under vacuum to afford the title compound (280 mg, 56%) as a solid. Mass (m/z): 368 [M$^+$+1]. $^1$HNMR 200 MHz (dmso-d$_6$): δ 12.15 (brs, 1H), 11.06 (brs, 1H), 10.07 (d, J=4.8 Hz, 1H), 9.09 (brs, 1H), 8.68 (d, J=4.8 Hz, 1H), 7.95 (brs, 1H), 7.65 (d, J=8.4 Hz, 1H), 7.48 (t, J=6.6 Hz, 1H), 7.3 (d, J=4.8 Hz, 1H), 7.06 (t, J=6.2 Hz, 1H), 2.69 (s, 3H): $^{13}$C (125 MHz, dmso-d$_6$): 162.2, 159.7, 157.3, 157, 156.1, 148.2, 145.9, 139.2, 129.7, 127.5, 124, 117, 116.1, 113.3, 110.5, 17.2.

Example 66

N-(2-aminophenyl)-6-(4-(2-methylimidazo[1,2-a]pyridin-3-yl)pyrimidin-2-ylamino)nicotinamide

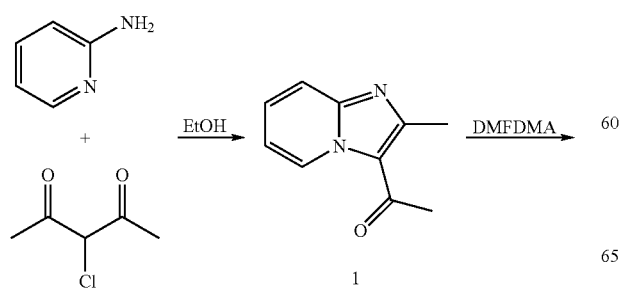

Example 66 (Compound I$^a$-g2-29)

To a stirred solution of 2-amino pyridine (20 g, 0.22 mmol) in ethanol (100 mL) was added 3-chloro-2,4-pentanedione (28.8 mL, 0.22 mmol) at room temperature and the reaction mixture was stirred under reflux for 16 hours. The volatiles from the reaction mixture were removed under reduced pressure. The resulting crude material was purified by column chromatography eluting pure compound with 60% EtOAc/hexane to afford Int-1 (14 g, 37%) as a solid. Mass (m/z): 174 [M$^+$+1]. $^1$H NMR (200 MHz, CDCl$_3$-d$_6$): δ 8.4 (d, J=6.6 Hz, 1H), 7.31-7.29 (m, 1H), 6.9-6.82 (m, 1H), 2.7 (s, 3H), 2.6 (s, 3H). A solution of Int-1 (15 g, 86 mmol) in DMFDMA (45 mL) was stirred under reflux for 48 hours. The reaction mixture was diluted with diethyl ether (70 mL) and stirred for 30 minutes. The precipitated solid was filtered, washed with diethyl ether (20 mL) and dried under vacuum to afford Int-2 (12 g, 60%) as brown color solid. Mass (m/z): 230 [M$^+$+1]. $^1$H NMR (200 MHz, CDCl$_3$-d$_6$): δ 8.4 (d, J=6.6 Hz, 14H), 7.78 (d, J=12.6 Hz, 1H), 7.31-7.29 (m, 1H), 6.78 (t, J=7.0 Hz, 1H), 6.90-6.81 (m, 1H), 5.57 (d, J=12.6 Hz, 1H), 3.04 (brs, 6H), 2.7 (s, 3H). To a stirred solution of Int-2 (3.0 g, 13.1 mmol) in DMF (15 mL) was added Int-3 (3.1 g, 32.7 mmol) followed by K$_2$CO$_3$ (5.4 g, 39.3 mmol) at room temperature and the reaction mixture was stirred at 100° C. for 16 hours. The reaction mixture was cooled to room temperature, diluted with ice cold water (45 mL) and extracted with dichloromethane (2×70 mL). Combined organic extract was washed with water (50 mL) and brine (50 mL), dried over anhydrous Na$_2$SO$_4$ filtered and concentrated under vacuum to afford Int-4 (2.2 g, 74.8%). Mass (m/z): 226 [M$^+$+1]. $^1$H NMR (200 MHz, CDCl$_3$-d$_6$): δ 9.6 (d, J=2.2 Hz, 1H), 8.35 (d, J=5.6 Hz, 1H), 7.61 (d, J=7.6 Hz, 1H), 7.3-7.21 (m, 1H), 6.89-6.81 (m, 1H), 5.14 (brs, 2H), 2.7 (s, 3H). To a stirred solution of Int-4 (4.0 g, 17.7 mmol) in dioxane (60 mL) were added Int-5 (3.83 g, 17.7 mmol), palladium (II) acetate (0.4 g, 1.7 mmol) and cesium carbonate (8.6 g, 26.6 mmol) followed by Xanthpos (1.0 g, 1.7 mmol) at room temperature. The mixture was degassed and stirred at 100° C. for 24 hours. The volatiles were evaporated under reduced pressure. The residue was diluted with water (40 mL) and stirred for 10 minutes. The precipitated solid was filtered and dried under vacuum to obtain crude compound which was purified by column chromatography eluting pure compound with 1% MeOH/DCM to afford Int-6 (4.0 g, 62.5%). $^1$H NMR (200 MHz, dmso-d$_6$): δ 10.79 (brs, 1H), 10.23 (d, J=7.0 Hz, 1H), 8.85 (d, J=2.2 Hz, 1H), 8.61 (d, J=5.4 Hz, 1H), 8.36 (d, J=8.8 Hz, 1H), 8.23 (d, J=6.6 Hz, 1H), 7.63 (d, J=8.6 Hz, 1H), 7.46 (t, J=7.0 Hz 1H), 7.28 (d, J=5.6 Hz, 1H), 7.06 (t, J=7.0 Hz, 1H), 3.84 (s, 3H), 2.68 (s, 3H). To a stirred suspension of Int-6 (4.0 g, 11.1 mmol) in methanol (4 mL) and THF (30 mL) were added lithium hydroxide (1.3 g, 4.0 mmol) and water (15 mL) and the reaction mixture was stirred at room temperature for 16 hours. The volatiles were concentrated under vacuum. The residue was diluted with water (10 mL) and neutralized to about pH 7 using 2 N HCl at 0° C. and stirred for 30 minutes. The precipitated solid was filtered, washed with water (2×30 mL) and dried under vacuum to provide Int-7 (3.4 g, 88.5%). $^1$H NMR (200 MHz, dmso-d$_6$): δ 11.12 (brs, 1H), 10.35 (d, J=7.0 Hz, 1H), 8.86 (s, 1H), 8.77 (d, J=5.2 Hz, 1H), 8.20-8.24 (m, 2H), 7.97 (d, J=3.6 Hz, 2H), 7.41-7.50 (m, 2H), 2.81 (s, 3H). To a stirred suspension of Int-7 (1.5 g, 4.3 mmol) in DMF (15 mL) were added HOBt (0.58 g, 4.3 mmol), EDCI (1.8 g, 9.5 mmol) and N-Ethyldiisopropylamine (1.39 g, 10.8 mmol) at 0° C. under inert atmosphere. After stirring for 15 minutes at 0° C., o-Phenylenediamine (0.46 g, 4.3 mmol) was added to the reaction mixture and stirred at room temperature for 16 hours. The reaction mixture was diluted with water (20 mL) and stirred for 30 minutes. The precipitated solid was filtered, washed with water (2×20 mL) and dried under vacuum to obtain crude compound which was purified by column chromatography eluting pure compound with 2% MeOH/DCM to afford the title compound (0.35 g, 20%) solid. Mass (m/z): 437 [M$^+$+1]. $^1$H NMR (200 MHz, dmso-d$_6$): δ 10.65 (brs, 1H), 10.3 (d, J=7.0 Hz, 1H), 9.7 (s, 1H), 9.0 (brs, 1H), 8.6 (d, J=5.4 Hz, 1H), 8.26-8.15 (m, 2H), 7.61-7.42 (m, 2H), 7.30-6.95 (m, 4H), 6.8 (d, J=8.0 Hz, 1H), 6.63 (t, J=7.2 Hz, 1H), 5.0 (brs, 2H), 2.63 (s, 3H). $^{13}$C NMR (125 MHz, dmso-d$_6$): 163.6, 158.3, 157.6, 155.2, 148.1, 147.9, 145.8, 143.4, 137.44, 129.9, 127.1, 126.9, 126.6, 123, 117.2, 116.1, 115.9, 113.2, 111.3, 110.2, 17.3.

Examples 67 and 68

Example 67

N-hydroxy-5-(4-(2-methylimidazo[1,2-a]pyridin-3-yl)pyrimidin-2-ylamino)pyrazine-2-carboxamide Example 68

N-(2-aminophenyl)-5-(4-(2-methylimidazo[1,2-a]pyridin-3-yl)pyrimidin-2-ylamino)pyrazine-2-carboxamide

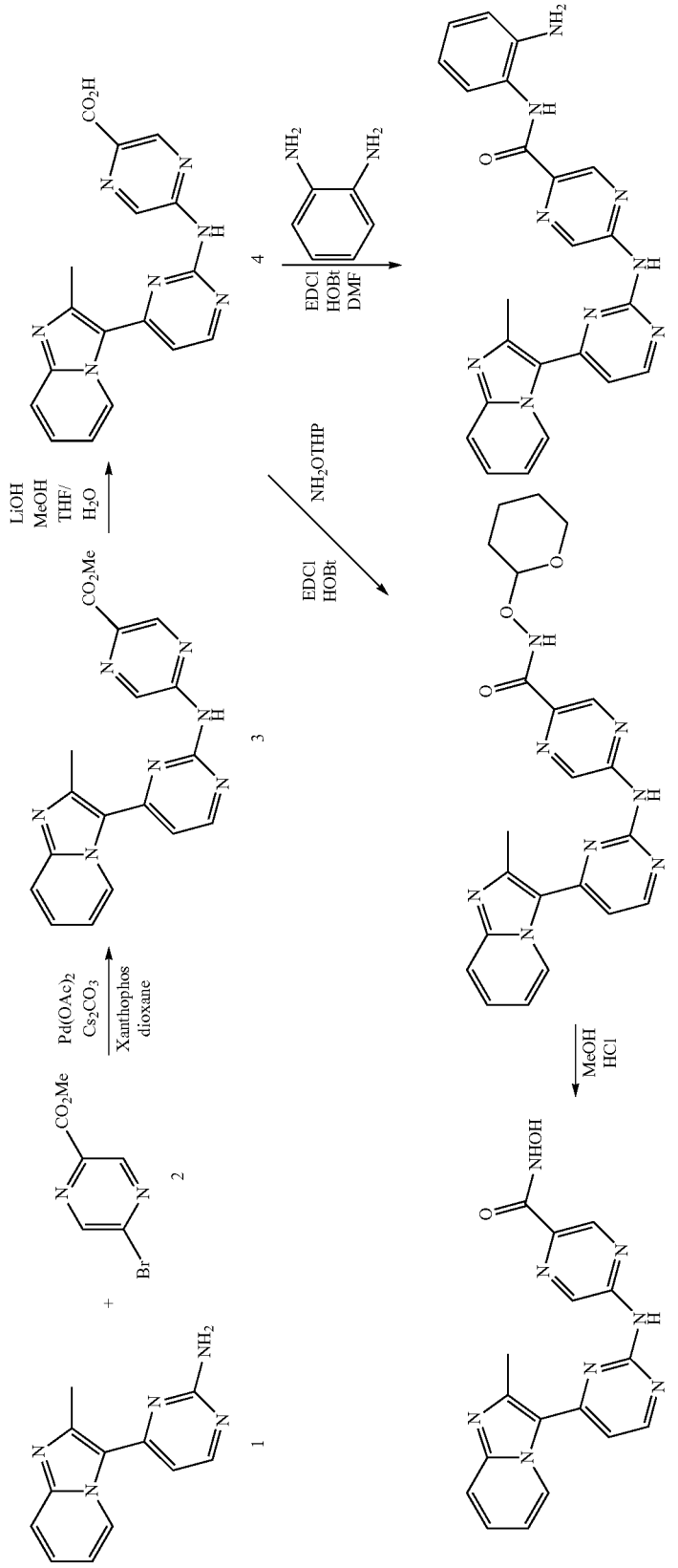

To a stirred solution of Int-1 (4.1 g, 18.4 mmol) and Int-2 (4.0 g, 18.4 mmol) in dioxane (100 mL) were added palladium (II) acetate (0.66 g, 2.94 mmol) and Xanthpos (1.55 g, 2.94 mmol) followed by cesium carbonate (9.0 g, 27.6 mmol) at room temperature. The mixture was degassed and stirred at 110° C. for 24 hours. The volatiles were concentrated under reduced pressure and the residue was diluted with water (100 mL) and stirred for 30 minutes. The precipitated solid was filtered and dried to obtain crude compound which was purified by column chromatography eluting pure compound with 2% MeOH/DCM to afford Int-3 (3.6 g, 54%) as off white solid. $^1$H NMR (200 MHz, dmso-$d_6$): δ 11.13 (s, 1H), 10.19 (d, J=6.8 Hz, 1H), 9.52 (s, 1H), 8.94 (s, 1H), 8.66 (d, J=5.6 Hz, 1H), 7.64 (d, J=8.6 Hz, 1H), 7.47 (t, J=7.2 Hz, 1H), 7.34 (d, J=5.6 Hz, 1H), 7.08 (t, J=6.6 Hz, 1H), 3.88 (s, 3H), 2.69 (s, 3H). To a stirred solution of Int-3 (3.6 g, 9.9 mmol) in methanol (22 mL), THF (22 mL) and water (13 mL) was added lithium hydroxide monohydrate (1.25 g, 29.8 mmol) and stirred at room temperature for 16 hours. The volatiles were concentrated under reduced pressure, the residue was diluted with water (30 mL) and acidified to about pH 5 using 2 N HCl at 0° C. and stirred for 30 minutes. The precipitated solid was filtered, washed with water (2×30 mL) and dried under vacuum to afford Int-4 (2.8 g, 80%) as yellowish solid. $^1$H NMR (200 MHz, dmso-$d_6$): δ 11.16 (s, 1H), 10.24 (d, J=6.8 Hz, 1H), 9.45 (s, 1H), 8.93 (s, 1H), 8.74 (d, J=5.4 Hz, 1H), 7.7-7.85 (m, 2H), 7.39 (d, J=5.4 Hz, 1H), 7.28-7.34 (m, 1H), 2.75 (s, 3H). To a stirred solution Int-4 (1.4 g, 4.0 mmol) in DMF (10 mL) were added EDCI (1.7 g, 8.8 mmol), HOBt (0.54 g, 4.0 mmol) and N-ethyldiisopropylamine (1.8 mL, 10.0 mmol) at 0° C. After being stirred for 15 minutes at 0° C., $NH_2OTHP$ (0.94 g, 8.0 mmol) was added and stirred at room temperature for 16 hours. The reaction mixture was diluted with water (30 mL) and stirred for 30 minutes, the precipitated solid was filtered, washed with water (2×10 mL) and dried under vacuum to obtain crude material which was purified by column chromatography and eluting pure compound with 2% MeOH/DCM to afford Int-5 (1.4 g, 78%) as pale yellow solid. $^1$H NMR (200 MHz, dmso-$d_6$): δ 11.79 (brs, 1H), 11.10 (s, 1H), 10.2 (d, J=7.0 Hz, 1H), 9.31 (s, 1H), 8.81 (s, 1H), 8.6 (d, J=5.4 Hz, 1H), 7.6 (d, J=9.2 Hz, 1H), 7.47-7.59 (m, 1H), 7.29 (t, J=5.6 Hz, 1H), 7.07-7.09 (m, 1H), 5.01 (s, 1H), 4.08 (brs, 1H), 3.47 (d, J=10.6 Hz, 1H), 2.63 (s, 3H), 1.7 (brs, 2H), 1.51 (brs, 2H).

Preparation of Example 67: To a solution of Int-5 (0.65 g, 1.45 mmol) in methanol (12 mL) was added 12 N HCl (1.0 mL) drop wise at 0° C. and stirred at room temperature for 16 hours. The precipitated solid was filtered, dried under vacuum; this solid was suspended in saturated $NaHCO_3$ solution and stirred for 30 minutes, filtered and dried under vacuum to the title compound (0.29 g, 55%) as pale yellow solid. Mass (m/z): 363 [M$^+$+1]. $^1$H NMR (200 MHz, dmso-$d_6$): δ 10.18 (d, J=6.8 Hz, 1H), 9.40 (s, 1H), 8.84 (s, 1H), 8.62 (d, J=5.4 Hz, 2H), 7.64 (d, J=8.8 Hz, 1H), 7.44-7.48 (m, 1H), 7.30 (d, J=6.0 Hz, 1H), 7.05-7.03 (m, 2H), 2.68 (s, 3H). $^{13}$C NMR (125 MHz, dmso-$d_6$): δ 159.45, 158.01, 156.81, 152.35, 147.16, 145.49, 139.56, 134.59, 129.14, 128.69, 126.68, 117.41, 116.05, 112.71, 108.58, 17.18.

Preparation of Example 68: To a stirred suspension of Int-4 (1.0 g, 2.87 mmol) in DMF (8 mL) were added EDCI (1.21 g, 6.32 mmol), HOBt (0.387 g, 2.87 mmol) and N-Ethyldiisopropylamine (1.28 mL, 7.18 mmol) at 0° C. After being stirred for 15 minutes, added o-Phenylenediamine (0.31 g, 2.87 mmol) and stirred at room temperature for 16 hours. The reaction mixture was diluted with water (30 mL) and stirred for 30 minutes, the precipitated solid was filtered, washed with water (2×20 mL) and dried under vacuum to obtain crude compound this was purified by column chromatography eluting pure compound with 2% MeOH/DCM to afford the title compound (0.43 g, 34%) as yellow solid. Mass (m/z): 438 [M$^+$+1]. $^1$H NMR (200 MHz, dmso-$d_6$): δ 11.0 (s, 1H), 10.23 (d, J=7.0 Hz, 1H), 9.84 (s, 1H), 9.54 (s, 1H), 9.00 (s, 1H), 8.66 (d, J=5.4 Hz, 1H), 7.65 (d, J=9.2 Hz, 1H), 7.46-7.48 (m, 2H), 7.35 (d, J=5.4 Hz, 1H), 7.08-7.06 (m, 1H), 6.96-6.94 (m, 1H), 6.81 (d, J=8.0 Hz, 1H), 6.64-6.62 (m, 1H), 4.93 (s, 2H), 2.70 (s, 3H). $^{13}$C NMR (125 MHz, dmso-$d_6$): δ 161.45, 157.74, 157.69, 157.17, 151.68, 148.12, 145.85, 141.94, 137.51, 133.37, 129.69, 127.22, 125.95, 124.85, 123.70, 117.06, 116.83, 116.59, 116.03, 113.19, 120.81, 17.23.

Examples 69 and 70

Example 69

N-hydroxy-6-(4-(2-methylimidazo[1,2-a]pyridin-3-yl)pyridin-2-ylamino)nicotinamide Example 70

N-(2-aminophenyl)-6-(4-(2-methylimidazo[1,2-a]pyridin-3-yl)pyridin-2-ylamino)nicotinamide

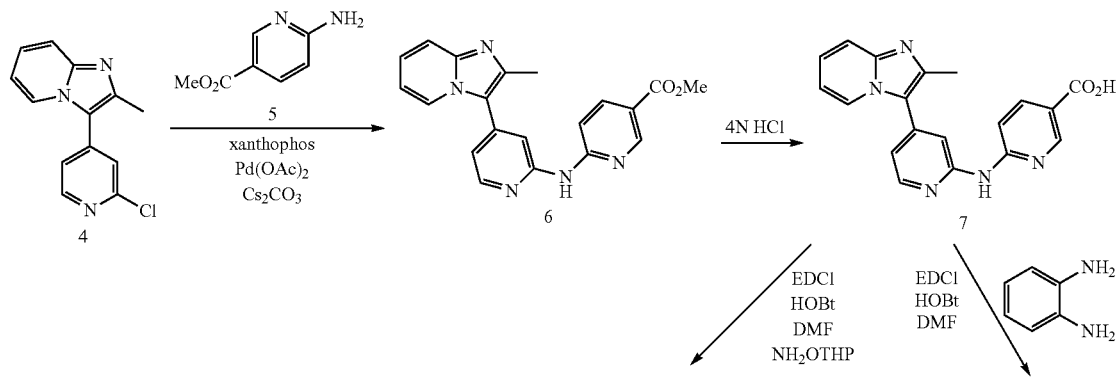

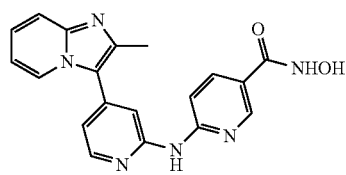

Example 69 (Compound I^a-g3-25)

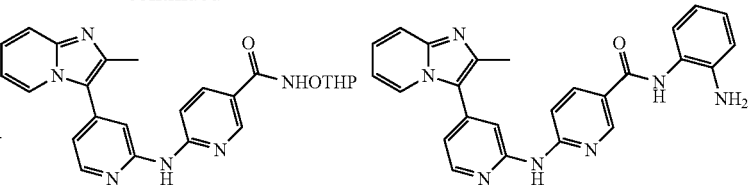

Example 70 (Compound I^a-g3-29)

To a stirred solution of Int-4 (2.0 g, 8.2 mmol) and methyl 6-aminonicotinate-5 (1.5 g, 9.8 mmol) in dioxane (25 mL) were added palladium (II) acetate (0.074 g, 0.32 mmol) and Xanthpos (0.285 g, 0.49 mmol) followed by cesium carbonate (4.0 g, 12.3 mmol) at room temperature. The reaction mixture was degassed for 30 minutes and stirred at 100° C. for 20 hours. The volatiles were concentrated under reduced pressure. The residue was diluted with water (100 mL) and stirred for 30 minutes. The precipitated solid was filtered and dried to obtain crude compound which was purified by column chromatography eluting pure compound with 2% MeOH/DCM to afford Int-6 (2.2 g, 76%) as solid. $^1$H NMR (200 MHz, CDCl$_3$): δ 8.62 (s, 1H), 8.53 (d, J=6.8 Hz, 1H), 8.41 (d, J=5.6 Hz, 1H), 8.0 (brs, 1H), 7.82 (d, J=8.4 Hz, 1H), 7.58 (d, J=8.8 Hz, 1H), 7.32 (t, J=6 Hz, 1H), 7.14 (d, J=4 Hz, 1H), 6.96 (t, J=5.4 Hz, 1H), 3.9 (brs, 2H), 2.6 (s, 3H). A mixture of Int-6 (2.2 g, 6.12 mmol) and 4 N HCl (25 mL) was stirred under reflux for 2 hours. The reaction mixture was cooled to room temperature and stirred for 20 minutes, the precipitated solid was filtered, washed with water (2×10 mL) and dried under vacuum to afford Int-7 (1.6 g, 76%) as solid. To a stirred solution Int-7 (1.0 g, 2.9 mmol) in DMF (10 mL) were added EDCI (1.39 g, 7.2 mmol), HOBt (391 mg, 2.9 mmol) and N-Ethyldiisopropylamine (1.267 mL, 7.2 mmol) at 0° C. After stirring for 15 minutes at 0° C., NH$_2$OTHP (0.5 g, 4.36 mmol) was added and stirred at room temperature for 16 hours. The reaction mixture was diluted with water (30 mL) and extracted with dichloromethane (5×50 mL), the combined organic layer was dried over anhydrous Na$_2$SO$_4$, filtered and concentrated under vacuum to obtain crude compound which was purified by column chromatography eluting pure compound with 2% MeOH/DCM to afford Int-8 (0.6 g, 50%) as pale solid Preparation of Example 69: To a stirred solution Int-8 (0.5 g, 1.12 mmol) in MeOH (20 mL) was added 12 N HCl (1 mL) at room temperature and stirred for 16 hours. The precipitated solid was filtered, washed with methanol and dried under vacuum; this solid was suspended in saturated NaHCO$_3$ solution and stirred for 20 minutes, filtered and dried under vacuum to afford the title compound (0.3 g, 73%) as pale solid. Mass (m/z): 360 [M$^+$+1]. $^1$H NMR (200 MHz, CDCl$_3$): δ 9.96 (brs, 1H), 8.53 (d, J=7.4 Hz, 2H), 8.37 (d, J=5.2 Hz, 1H), 7.92 (brs, 2H), 7.70 (d, J=8.8 Hz, 1H), 7.57 (d, J=9.2 Hz, 1H), 7.34 (t, J=7.0 Hz, 1H), 7.08 (d, J=5.2 Hz, 1H), 6.96 (t, J=6.6 Hz, 1H), 2.48 (s, 3H). $^{13}$C NMR (125 MHz, dmso-d$_6$): δ 162.7, 155.6, 154.5, 148.4, 146.6, 144.5, 142.1, 137.9, 136.1, 125.2, 124.0, 121.1, 118.8, 116.5, 115.4, 112.7, 110.9, 110.7, 14.3.

Preparation of Example 70: To a stirred solution of Int-7 (1.0 g, 2.89 mmol) in DMF (8 mL) were added EDCI (1.2 g, 6.3 mmol), HOBt (0.39 g, 2.89 mmol) and N-Ethyldiisopropylamine (1.28 mL, 7.2 mmol) at 0° C. After stirring for 15 minutes at 0° C., o-Phenylenediamine (0.31 g, 2.89 mmol) was added and stirred at room temperature for 16 hours. The reaction mixture was diluted with water (30 mL) and stirred for 20 minutes, the precipitated solid was filtered, washed with water (2×20 mL) and dried under vacuum to obtain crude compound which was purified by column chromatography eluting pure compound with 3% MeOH/DCM to afford the title compound (0.35 g, 29%) as solid. Mass (m/z): 435 [M$^+$+1]. $^1$H NMR (200 MHz, CDCl$_3$): δ 10.25 (s, 1H), 9.60 (s, 1H), 8.87 (s, 1H), 8.55 (d, J=7 Hz, 1H), 8.43 (d, J=5.6 Hz, 1H), 8.25 (d, J=2.2 Hz, 1H), 8.0 (s, 1H), 7.85 (d, J=8.8 Hz, 1H), 7.59 (d, J=8.8 Hz, 1H), 7.36 (t, J=7.6 Hz, 1H), 7.17-7.13 (m, 2H), 7.01-6.92 (m, 2H), 6.77 (d, J=7 Hz, 1H), 6.62 (t, J=7 Hz, 1H), 4.93 (brs, 2H), 2.49 (s, 3H). $^{13}$C NMR (125 MHz, dmso-d$_6$): δ 163.7, 156.0, 154.4, 148.4, 147.9, 144.5, 143.2, 142.1, 137.9, 137.1, 126.7, 126.4, 125.2, 124.0, 123.1, 122.1, 118.7, 116.5, 116.1, 116.0, 115.5, 112.6, 111.5, 110.0, 14.3.

Example 71

N-hydroxy-4-(4-(2-methylimidazo[1,2-a]pyridin-3-yl)pyrimidin-2-ylamino)thiophene-2-carboxamide

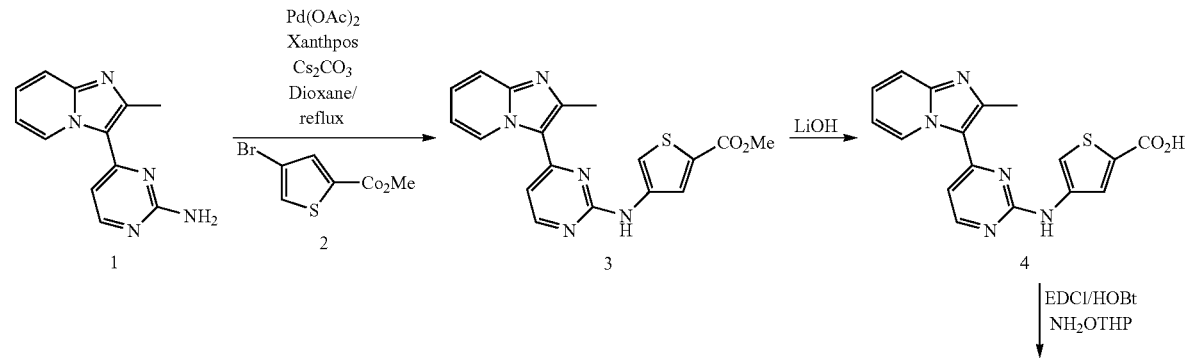

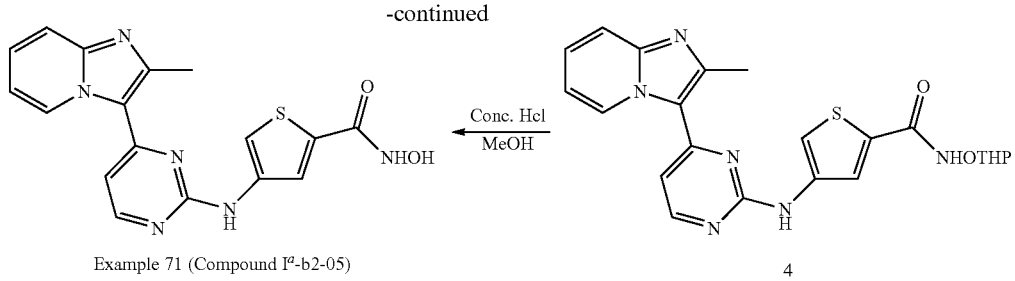

Example 71 (Compound I<sup>a</sup>-b2-05)

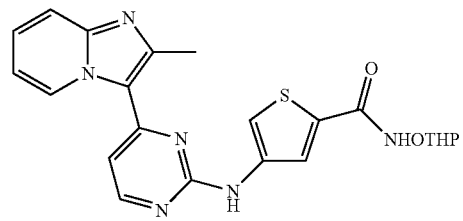

To a stirred solution of Int-2 (0.5 g, 2.26 mmol) in THF (35 mL) was added Int-1 (0.51 g, 2.26 mmol) followed by Pd(OAc)$_2$ (105 mg, 0.45 mmol), xanthpos (265 mg, 0.497 mmol) and CS$_2$CO$_3$ (1.35 g, 4.07 mmol). The reaction mixture was degassed under vacuum, bubbled with N$_2$ for 10 minutes and stirred at 130° C. in a sealed tube for 20 hours. The reaction mixture was concentrated under reduced pressure and was purified by column chromatography to isolate product and a very close spot together. This mixture of two compounds (int-3+close impurity) was used directly in the next step. (Crude yield: 0.25 g). Mass (m/z): 366.0 [M$^+$+1]. $^1$H NMR (200 MHz, dmso-d$_6$): δ 10.18 (s, 1H), 9.72 (brs, 1H), 8.59 (d, J=5.2 Hz, 1H), 7.98 (s, 1H), 7.62 (d, J=8 Hz, 1H), 7.42 (t, J=5.2 Hz, 1H), 7.18 (d, J=5.2 Hz, 1H), 7.02 (t, J=5.2 Hz, 1H), 7.11 (s, 1H), 3.82 (s, 3H), 2.62 (s, 3H). To a stirred solution of Int-3 (crude 0.25 g) in THF: MeOH: H$_2$O (2:1:2) (25 ml) was added LiOH (0.25 g, wt/wt) at 0° C. and stirred while heating at 50° C. for 6 hours. Volatiles from the reaction mixture were distilled off under reduced pressure. Water (15 mL), DCM (50 ml) were added and stirred vigorously for 15 minutes, the aqueous layer was separated and treated again with DCM (35 ml). The aqueous layer was concentrated to half of its volume under reduced pressure and was acidified to about pH 5-6 with concentrated HCl. The precipitated solid was filtered and dried under vacuum to afford pure Int-4 (0.12 g). Mass (m/z): 352.0 [M$^+$+1]. $^1$H NMR (200 MHz, dmso-d$_6$): δ 9.98 (s, 1H), 9.67 (brs, 1H), 8.60 (d, J=5.2 Hz, 1H), 7.65-7.59 (m, 3H) 7.42 (t, J=8.4 Hz, 2H), 7.15-6.98 (m, 2H), 2.67 (s, 3H). To a stirred solution of Int-4 (120 mg, 0.32 mmol) in DMF (10 mL) at 10° C. was added EDCI.HCl (136 mg, 0.71 mmol), HOBt (45 mg, 3.21 mmol), NH$_2$OTHP (76 mg, 0.64 mmol) and finally DIPEA (0.143 mL, 0.80 mmol) was added and stirred at room temperature for 16 hours. The reaction was quenched with water (45 mL) and extracted with EtOAC (40 mL). The organic layer was washed with water (2×15 mL), brine (30 mL), dried over Na$_2$SO$_4$ and concentrated under vacuum to obtain crude compound which was purified by column chromatography eluting pure compound with 2% MeOH-DCM to afford pure Int-5 (50 mg, 33%). Mass (m/z): 451.2 [M$^+$+1]. $^1$H NMR (200 MHz, dmso-d$_6$): δ 11.67 (brs, 1H), 10.06 (s, 1H), 9.74 (brs, 1H), 8.54 (d, J=5.2 Hz, 1H), 7.84 (s, 1H), 7.72 (s, 1H), 7.64 (d, J=9 Hz, 1H), 7.43 (t, J=7.8 Hz, 1H), 7.10 (d, J=5.6 Hz, 1H), 7.02 (t, J=5.8 Hz, 1H), 4.95 (s, 1H), 4.03 (s, 1H), 3.54 (s, 1H), 2.65 (s, 3H), 1.71 (s, 3H), 1.54 (s, 3H). To a stirred solution of Int-5 (50 mg, 0.105 mmol) in MeOH (4 mL) at 0-5° C. was added concentrated HCl (0.5 mL) dropwise and stirred at room temperature for 16 hours. The precipitated solid was filtered and dried under vacuum; this was then suspended in saturated aqueous HCO$_3$ solution (5 mL) and stirred for 0.5 hours, this was filtered, washed with water (2 ml) and dried under vacuum to afford the title compound as a light brown solid (30 mg, 77%). Mass (m/z): 367.1[M$^+$+1].

$^1$H NMR (500 MHz, dmso-d$_6$): δ 11.28 (brs, 1H), 10.00 (s, 1H), 9.78 (brs, 1H), 8.98 (brs, 1H), 8.54 (d, J=5.5 Hz, 1H), 7.64 (d, J=9 Hz, 1H), 7.59 (brs, 1H), 7.45-7.42 (m, 1H), 7.09 (d, J=5.5 Hz, 1H), 7.05-7.03 (m, 2H), 2.66 (s, 3H).

Example 72

N-hydroxy-2-(4-(2-methylimidazo[1,2-a]pyridin-3-yl)pyrimidin-2-ylamino)oxazole-5-carboxamide

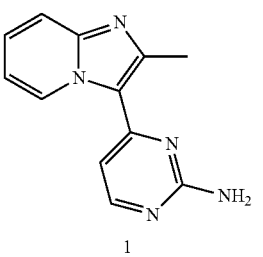
1

+

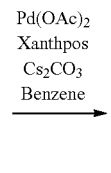
2

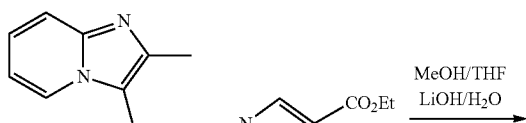
3

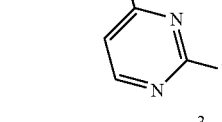

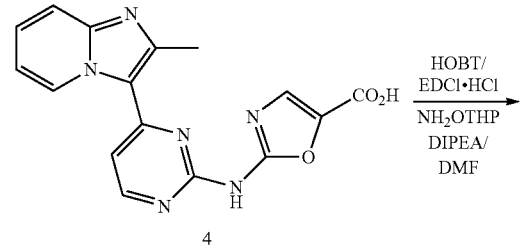
4

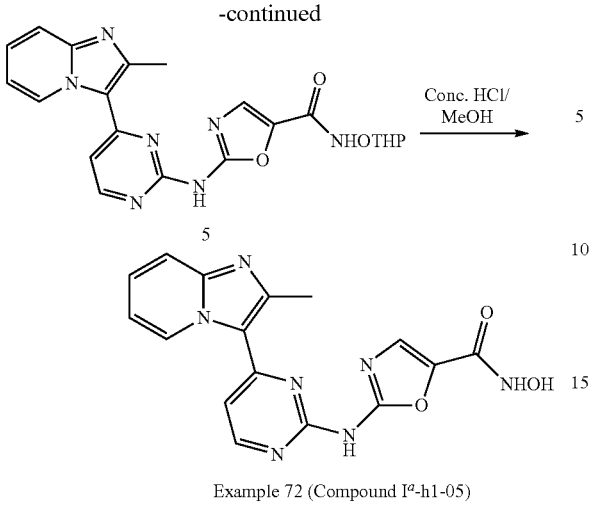

Example 72 (Compound I<sup>a</sup>-h1-05)

To a stirred solution of Int-1 (0.5 g, 2.2 mmol) in benzene (25 mL) were added Int-2 (0.38 g, 2.2 mmol), Pd(OAc)$_2$ (0.05 g, 0.2 mmol), xanthpos (0.128 g, 0.2 mmol) and Cs$_2$CO$_3$ (1.08 g, 3.3 mmol). The reaction mixture was purged with N$_2$ for 10 minutes and stirred at 95° C. for 24 hours. The volatiles were concentrated under reduced pressure and the residue was diluted with water (35 mL), the precipitated solid was filtered and dried under reduced pressure to obtain crude compound which was purified by column chromatography and eluting with pure compound with 5% MeOH/DCM to afford Int-3 (0.15 g, 18.5% yield) as a solid. $^1$H NMR (200 MHz, dmso-d$_6$): δ 10.6 (brs, 1H), 8.61 (d, J=5.6 Hz, 1H), 8.03 (s, 1H), 7.17-7.65 (m, 5H), 4.3 (q, J=7.0 Hz, 2H), 2.7 (s, 3H), 1.29 (t, J=7.0 Hz, 3H). To a stirred solution of Int-3 (0.6 g, 1.6 mmol) in MeOH:THF (21 mL, 1:20) was added a solution of LiOH (0.207 g, 4.94 mmol) in water (10 mL) and stirred at room temperature for 16 hours. The reaction mixture was concentrated under reduced pressure and the residue was acidified to about pH 5 using 2 N HCl. The precipitated solid was filtered and dried under reduced pressure to afford Int-4 (0.25 g, 45% yield) as a solid. $^1$H NMR (200 MHz, dmso-d$_6$): δ 11.65 (s, 1H), 10.6 (brs, 1H), 8.66 (d, J=5.4 Hz, 1H), 7.94 (t, J=4.0 Hz, 1H), 7.66 (d, J=9.0 Hz, 1H), 7.48-7.56 (m, 1H), 7.35 (d, J=5.4 Hz, 1H) 7.23 (t, J=7.0 Hz, 1H), 2.7 (s, 3H). To a stirred solution of Int-4 (0.25 g, 0.74 mmol) in DMF (4 mL) were added HOBt (0.1 g, 0.74 mmol), EDCI (0.35 g, 1.86 mmol) and DIPEA (0.3 mL, 1.86 mmol) at 0° C. under inert atmosphere. After being stirred for 5 minutes, added NH$_2$OTHP (0.13 g, 1.1 mmol) to the reaction mixture at 0° C. and stirred at room temperature for 16 hours. The reaction mixture was diluted with water (20 mL) and extracted with dichloromethane (2×25 mL). The combined organic extract was dried over Na$_2$SO$_4$, filtered and concentrated under reduced pressure to obtain crude compound which was purified by column chromatography and eluting pure compound with 5% MeOH/DCM to afford Int-5 (0.1 g, 31% yield) as a solid. $^1$H NMR (200 MHz, dmso-d$_6$): δ 11.6 (brs, 1H), 11.42 (brs, 1H), 10.42 (d, J=6.2 Hz, 1H), 8.62 (d, J=4.2 Hz, 1H), 7.72 (s, 1H), 7.62 (d, J=7.2 Hz, 1H), 7.51 (t, J=4.2 Hz, 1H), 7.3 (d, J=5.0 Hz, 1H), 7.1 (d, J=6.5 Hz, 1H), 4.95 (s, 1H), 4.07 (brs, 1H), 3.57 (d, J=10 Hz, 1H), 2.7 (s, 3H), 1.75 (brs, 3H), 1.53 (brs, 3H).

Preparation of Example 72: To a stirred solution of Int-5 (0.14 g, 0.32 mmol) in MeOH (10 mL) was added conc. HCl (0.2 mL) at 0° C. The reaction mixture was stirred at room temperature for 16 hours, the precipitated solid was filtered, and dried under vacuum. This solid was suspended in saturated NaHCO$_3$ solution and stirred for 30 minutes, filtered and dried under vacuum to afford the title compound (0.06 g, 53.5% yield) as a solid. Mass (m/z): 368 [M$^+$+1]. $^1$H NMR (500 MHz, dmso-d$_6$): δ 11.0 (brs, 1H), 10.4 (brs, 1H), 9.90 (brs, 1H), 8.59 (d, J=5.5 Hz, 1H), 7.67 (brs, 1H), 7.63 (d, J=9.0 Hz, 1H), 7.44-7.47 (m, 1H), 7.31 (d, J=5.5 Hz, 1H), 7.11 (t, J=6.2 Hz, 1H), 2.5 (s, 3H).

Example 73

N-hydroxy-2-(4-(2-methylimidazo[1,2-a]pyridin-3-yl)pyridin-2-ylamino)thiazole-5-carboxamide

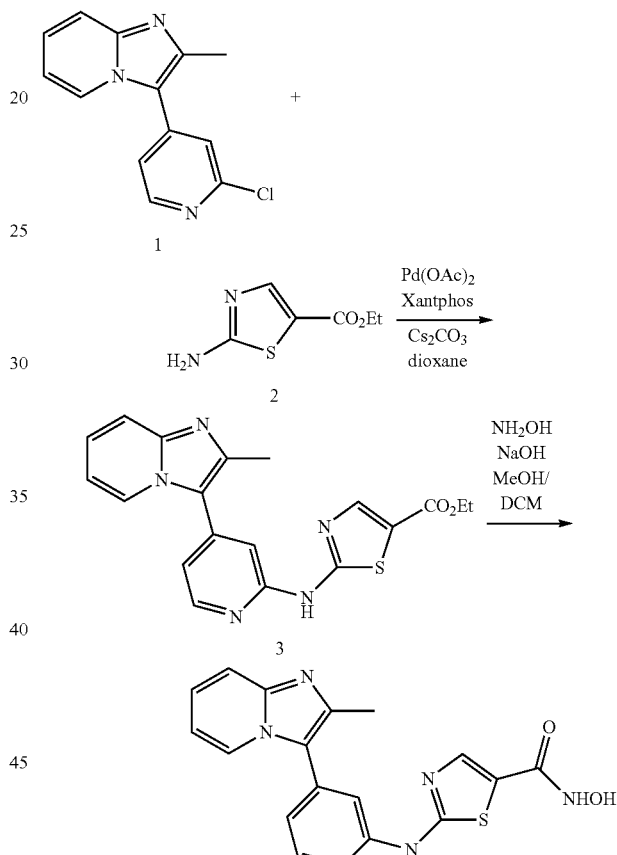

Example 73 (Compound I$^a$-h0-05)

To a stirred solution of Int-1 (1.5 g, 6.1 mmol) in 1,4-dioxane (30 mL) were added Int-2 (1.4 g, 8.6 mmol), Pd(OAc)$_2$ (139 mg, 0.6 mmol) and Xanthpos (356 mg, 0.6 mmol) followed by cesium carbonate (3.0 g, 9.2 mmol) at room temperature under inert conditions. The reaction mixture was stirred at 115-120° C. for 24 hours. The volatiles were concentrated under reduced pressure and the residue was diluted with water (50 mL) and stirred. The precipitated solid was filtered, washed with water and dried under vacuum to obtain crude compound. This was purified by column chromatography eluting with pure compound with MeOH/EtOAc (98:2) to afford Int-3 (350 mg, 15%) as white solid. $^1$H NMR (200 MHz, dmso-d$_6$): δ 11.9 (s, 1H), 8.45-8.55 (m, 2H), 8.11 (s, 1H), 7.62 (t, J=9.0 Hz, 1H), 7.2-7.39 (m, 3H), 6.96 (t, J=7.2 Hz, 1H), 4.22-4.27 (m, 2H), 1.25-1.30 (m, 3H). To a stirred solution of Int-3 (450 mg, 1.1 mmol) in MeOH:DCM (2:1, 30 mL) was added NH$_2$OH solution (12 mL) at 0° C., followed by addition of NaOH solution (388 mg, 9.8 mmol) in water (5 mL). The reaction mixture was stirred at room temperature for 16 hours. The volatiles were concentrated under vacuum, and the resulting residue was neutralized to about pH 7 with 2 N HCl. The precipitated solid was filtered, washed with water and dried under vacuum to afford the title compound (300 mg, 69.1%) as a brown color solid. Mass (m/z): 367 [M$^+$+1]. $^1$H NMR (200 MHz, dmso-d$_6$): δ 11.9 (s, 1H), 11.1 (s, 1H), 8.77 (d, J=6.6 Hz, 1H), 8.62 (d, J=5.4 Hz, 1H), 7.98 (t, J=5.8 Hz, 2H), 7.45-7.54 (m, 1H), 7.29 (s, 1H), 7.28 (d, J=4.0 Hz, 1H), 2.55 (s, 3H).

Example 74

N-hydroxy-2-(4-(2-methylimidazo[1,2-a]pyridin-3-yl)pyridin-2-ylamino)pyrimidine-5-carboxamide

[M$^+$+1]. $^1$H NMR (200 MHz, dmso-d$_6$): δ 8.22 (d, J=8 Hz, 1H), 7.47 (d, J=7.2 Hz, 1H), 7.29 (t, J=7.0 Hz, 1H), 2.35 (s, 3H). To a solution of Int-3 (6.0 g, 29.2 mmol) in IPA-H$_2$O (75 mL, 2:1) was added PdCl$_2$(dppf).DCM (4.7 g, 5.8 mmol), followed by the addition of tert-butyl amine (3.1 g, 43.8 mmol) at room temperature and the resulting reaction mixture was degassed for 15 minutes. Then Int-4 (2.9 g, 18.6 mmol) was added to the reaction mixture at room temperature. The reaction mixture was heated to 100° C. and then stirred for 16 hours. The reaction mixture was diluted with water (100 mL), extracted with EtOAc (3×100 mL), washed with water, brine and dried over anhydrous Na$_2$SO$_4$. The organic layer was concentrated under reduced pressure. The crude material was purified by column chromatography eluting with 1% MeOH/DCM to afford Int-5 (1.6 g, 28%). Mass (m/z): 244 [M$^+$+1]. $^1$H NMR (200 MHz, dmso-d$_6$): δ 8.51 (t, J=5 Hz, 2H), 7.71 (s, 1H), 7.63-7.55 (m, 2H), 7.34 (t, J=7 Hz, 1H), 6.94 (t, J=7 Hz, 1H), 2.43 (s, 3H). To a stirred mixture of 5-bromo 2-aminopyrimidine (8 g, 45.97 mmol) in MeOH—CH$_3$CN (200 mL) in

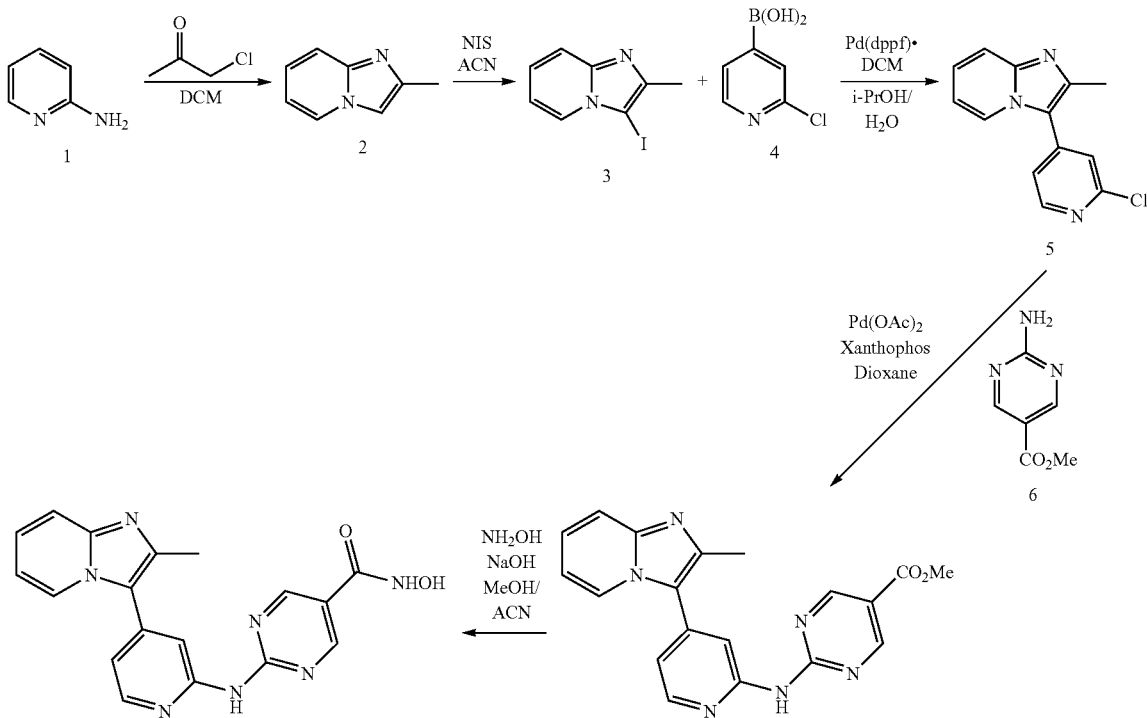

Example 74 (Compound I$^a$-g0-25)

To a solution of 2-amino pyridine (30 g, 0.31 mol) in DME (120 mL) was added chloro acetone (40.5 mL, 0.47 mol) at room temperature. The reaction mixture was heated to reflux, and then stirred for 48 hours. The volatiles were concentrated under reduced pressure. Then the residue was purified by column chromatography eluting with 1% MeOH/DCM to afford Int-2 (20 g, 48%) as a liquid. Mass (m/z): 133 [M$^+$+1]. $^1$H NMR (200 MHz, dmso-d$_6$): δ8.05 (d, J=8.2 Hz, 1H), 7.35 (s, 1H), 7.1 (t, J=6.8 Hz, 1H), 6.7 (t, J=6.8 Hz, 1H), 6.5 (d, J=8.2 Hz, 1H), 2.45 (s, 3H). To a solution of Int-2 (10 g, 76.7 mmol) in acetonitrile (50 mL) was added N-iodo succinamide (20.4 g, 80 mmol) portion wise at room temperature and then stirred for 48 hours. The precipitated solid was filtered off. The crude material was re-crystallized from ethyl acetate/water to afford Int-3 (9 g, 49%) as solid. Mass (m/z): 259 a steel bomb were added Pd(CH$_3$CN)$_2$Cl (2.38 g, 9.19 mmol), racemic-BINAP (5.7 g, 9.19 mmol), DIPEA (10.4 mL, 53.7 mmol) at room temperature and then closed the steel vessel tightly. Then CO gas (100 psi) was purged into the steel bomb and the stirring was continued at 120° C. for 45 hours. The reaction mixture was allowed to room temperature. The reaction mixture was filtered through a pad of celite. The celite pad was washed with excess of methanol and the filtrate was concentrated under vacuum. The crude material was purified by column chromatography eluting with 0.75% MeOH/DCM to afford Int-6 (5 g, 71%) as solid. Mass (m/z): 154 [M$^+$+1]. $^1$H NMR (200 MHz, dmso-d$_6$): δ 8.65 (s, 3H), 7.49 (brs, 2H), 3.58 (s, 3H) To a stirred mixture of Int-5 (3 g, 2.34 mmol) and Int-6 (1.8 g, 12.34 mmol) in 1,4-dioxane (90 mL) were added Pd(OAc)$_2$ (279 mg, 1.23 mmol) and Xanthpos (710 mg, 1.23 mmol) followed by cesium carbonate (6 g, 18.5 mmol) at room temperature. The resulting mixture was degassed and stirred at reflux temperature for 30 hours. The reaction mixture was cooled to room temperature and then stirred for 15 minutes. The precipitated solids were filtered off, washed with water (2×10 mL) and dried under vacuum. The crude material was purified by column chromatography eluting with 1.5% MeOH/DCM to afford Int-7 (0.6 g, 13.6%) as solid. Mass (m/z): 361.2 [M$^+$+1]. $^1$H NMR (500 MHz, dmso-d$_6$): δ 10.76 (brs, 1H), 8.97 (s, 2H), 8.56 (d, J=7, 1H), 8.47 (d, J=5.5 Hz, 1H), 8.38 (s, 1H), 7.58 (d, J=9.5 Hz 1H), 7.34-7.29 (m, 2H), 6.99 (t, J=76 Hz, 1H), 3.84 (s, 3H), 2.46 (s, 3H). To a stirred solution of Int-7 (0.5 g, 1.38 mmol) in MeOH—CH$_3$CN (1:2, 25 mL) was added aqueous NH$_2$OH solution (15 mL) at 0° C. After being stirred for 20 minutes at the same temperature, NaOH (0.44 g, 11.10 mmol) in water (1 mL) was added drop wise to the reaction mixture at 0° C. The reaction mixture was warmed to room temperature and stirred for 2 days. The volatiles were concentrated under vacuum and the obtained residue was diluted with water and neutralized to about pH 7 with 2 N HCl at 0° C. The precipitated solids were filtered off, washed with water (2×10 mL) and dried under vacuum to afford the title compound (0.4 g, 80%) as off-white solid. Mass (m/z): 362.1 [M$^+$+1]. $^1$H NMR (200 MHz, dmso-d$_6$): δ 11.2 (bs, 1H), 10.5 (s, 1H), 9.12 (bs, 1H), 8.84 (s, 2H), 8.57 (d, J=7.0 Hz, 1H), 8.45 (d, J=5.0 Hz, 1H), 8.38 (s, 1H), 7.58 (d, J=9.0 Hz, 1H), 7.32 (t, J=7.5 Hz, 1H), 7.25 (d, J=4.0 Hz, 1H), 6.98 (d, J=7.0 Hz, 1H), 2.49 (s, 3H). $^{13}$C NMR (125 MHz, dmso-d$_6$): δ 160.7, 157.1, 153.0, 148.7, 144.5, 142.3, 137.9, 125.2, 123.9, 118.8, 118.2, 117.0, 116.6, 112.7, 112.4, 14.3.

Example 75

N-hydroxy-5-(4-(2-methylimidazo[1,2-a]pyridin-3-yl)pyridin-2-ylamino)-1,3,4-thiadiazole-2-carboxamide

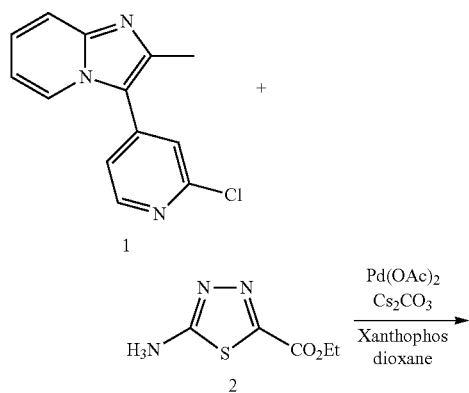

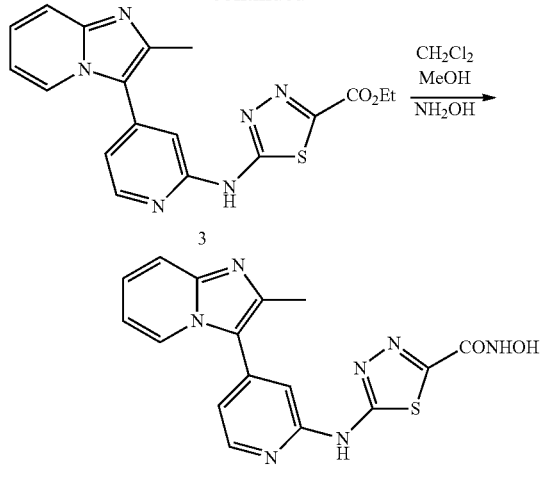

Example 75 (Compound I$^a$-h2-05)

To a stirred solution of Int-1 (2.0 g, 8.23 mmol) in 1,4-dioxane (30 mL) were added palladium (II) acetate (0.298 g, 1.31 mmol), Xanthophos (0.696 g, 1.31 mmol) and Int-2 (1.42 g, 8.23 mmol) followed by cesium carbonate (4.0 g, 12.34 mmol) at room temperature. The reaction mixture was thoroughly degassed and subjected to microwave irradiation (800 W) for 7 minutes. The volatiles were concentrated under reduced pressure; the residue was diluted with water (50 mL) and stirred for 30 minutes. The precipitated solid was filtered and dried to get crude material. The crude material was purified by column chromatography eluting with 3% MeOH/DCM to afford Int-3 (0.3 g, 9%) as yellowish solid. Mass (m/z): 381 [M$^+$+1]. $^1$H NMR (500 MHz, CDCl$_3$): δ 12.3 (brs, 1H), 8.51-8.21 (m, 2H), 7.6 (d, J=12 Hz, 1H), 7.22-7.40 (m, 3H), 6.95 (t, J=10 Hz, 1H), 4.35-4.45 (q, 2H), 1.38 (t, J=12 Hz, 3H). To a stirred solution of Int-3 (0.4 g, 1.05 mmol) in methanol (16 mL), CH$_2$Cl$_2$ (16 mL) was added 50% aqueous solution of NH$_2$OH (50%) at 0° C., and then stirred for 30 minutes. Then NaOH (0.32 g) in water (4 mL) was added to the reaction mixture at 0° C. The reaction mixture was allowed to room temperature, and then stirred for 16 hours. The volatiles were concentrated under vacuum. The residue was diluted with water (50 mL) and neutralized to about pH 7 using 2 N HCl. The precipitated solid was filtered, washed with water (30 mL) and dried under vacuum to afford the title compound (0.27 g, 69%) as light brown solid. Mass (m/z): 367.9 [M$^+$+1]. $^1$H NMR (200 MHz, dmso-d$_6$): δ 11.0 (bs, 1H), 8.52 (d, J=6.0 Hz, 2H), 7.59 (d, J=8.8 Hz, 1H), 7.37-7.25 (m, 3H), 6.96 (t, 1H), 2.46 (s, 3H). $^{13}$C NMR (125 MHz, dmso-d$_6$): 162.18, 156.59, 155.81, 150.91, 147.48, 144.69, 142.51, 138.92, 125.53, 124.11, 118.24, 116.59, 116.31, 112.82, 109.89, 14.28.

Example 76

N-hydroxy-5-(4-(2-methylimidazo[1,2-a]pyridin-3-yl)pyridin-2-ylamino)pyrazine-2-carboxamide

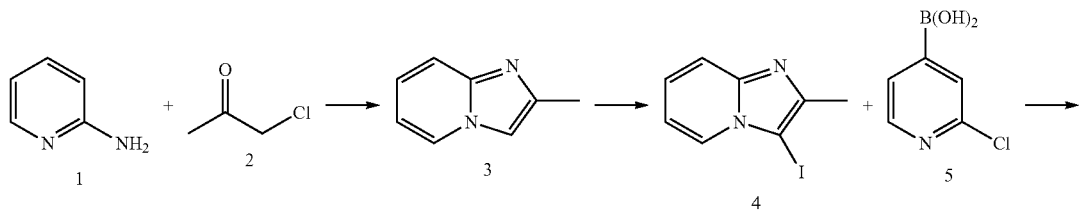

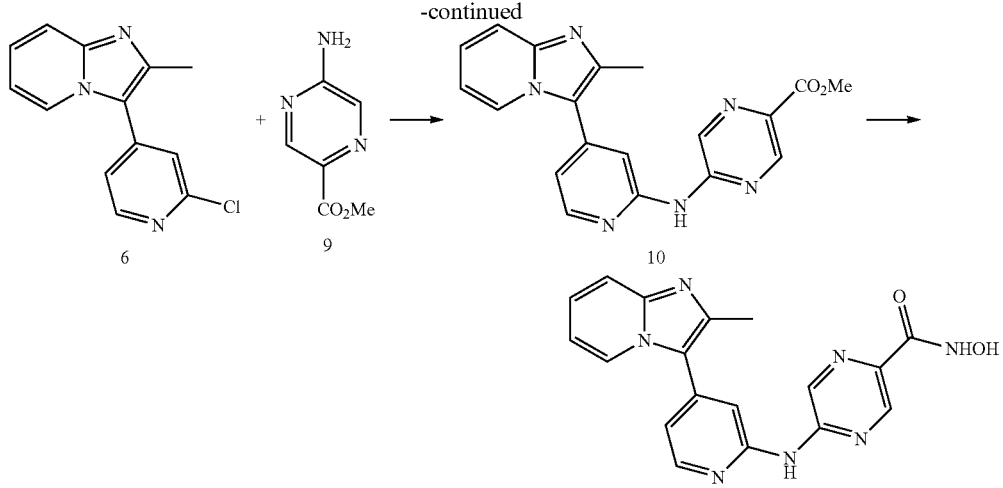

Example 76 (Compound I$^a$-g1-25)

To a solution of Int-1 (100 g, 1.063 mmol)) in DME (400 mL) was added Int-2 (155 g, 1.595 mmol) at room temperature. The reaction mixture was heated to 85° C. and stirring was continued overnight. The volatiles were concentrated under reduced pressure, then residue was diluted with water (500 mL) and dichloromethane (500 mL). The pH was adjusted to neutral by using sat. NaHCO$_3$. The organic layer was separated, dried over anhydrous Na$_2$SO$_4$ and concentrated under reduced pressure. The residue was purified through silica gel column chromatography, eluted with ethyl acetate to afford Int-3 (40 g, 28.5%) as syrup. To a solution of Int-3 (40 g, 0.303 mol) in acetonitrile (200 mL) was added N-Iodo succinamide (81 g, 0.3636 mol) at room temperature, and then stirred for 1 hour. The reaction mixture was poured into water and stirred for 30 minutes. The precipitated solids were filtered and solids were triturated in ethyl acetate (1 L), filtered solid, and washed with ethyl acetate. Then filtrate was washed with 10% Na$_2$CO$_3$ solution (250 mL), water, dried over anhydrous Na$_2$SO$_4$ and concentrated under reduced pressure to afford Int-4 (18.1 g, 23%) as a solid. Mass (m/z): 259 [M$^+$+1]. $^1$H NMR (200 MHz, dmso-d$_6$): δ 8.43 (d, J=8 Hz, 1H), 7.69-7.53 (m, 2H), 7.23 (t, J=6.6 Hz, 1H), 2.42 (s, 3H). To a suspended solution of Int-5 (12 g, 46.51 mmol) in IPA: water (80 mL: 30 mL) was added Pd Cl$_2$(dppf).DCM (7.5 g, 9.3 mmol), tertiary butyl amine (4.9 g, 69.76 mmol) and Na$_2$CO$_3$ (7.3 g, 69.76 mmol) at room temperature. The reaction mixture was heated to 100° C. and stirring was continued overnight. The reaction mixture was allowed to room temperature, and then diluted with dichloromethane (250 mL) and water. The organic layer was separated, washed with 10% Na$_2$CO$_3$ solution (75 mL), dried over anhydrous Na$_2$SO$_4$ and concentrated under reduced pressure. The residue was purified through silica gel column chromatography, eluted product with ethyl acetate to afford Int-6 (4.8 g, 42.4%) as a solid. Mass (m/z): 244 [M$^+$+1]. $^1$H NMR (200 MHz, dmso-d$_6$): δ 8.51 (t, J=5 Hz, 2H), 7.71 (s, 1H0, 7.63-7.55 (m, 2H), 7.34 (t, J=7 Hz, 1H), 6.94 (t, J=7 Hz, 1H), 2.43 (s, 3H). To a solution of Int-7 (1 g, 5.797 mmol) in THF (10 mL) was added 4-methoxy benzyl amine (1.98 g, 14.49 mmol) at room temperature and, then stirred overnight. The reaction mixture was filtered, concentrated under reduced pressure. The residue was purified through silica gel column chromatography, eluted product with 50% ethyl acetate/dichloromethane to afford Int-8 (800 mg, 50.6%) as a solid. Mass (m/z): 274 [M$^+$+1]. $^1$H NMR (200 MHz, dmso-d$_6$): δ 8.6 (s, 1H), 8.61-8.42 (brs, 1H), 8.01 (s, 1H), 7.23 (d, J=8.5 Hz, 2H), 6.83 (d, J=8.4 Hz, 2H). To a solution of Int-8 (800 mg, 2.925 mmol) in trifluoro acetic acid (5 mL) was stirred for 1 hour at 60° C. The reaction mixture was allowed to room temperature, and then quenched with solid sodium bicarbonate. The reaction mixture was diluted with ethyl acetate and water. The organic layer was separated, dried over anhydrous Na$_2$SO$_4$ and concentrated under reduced pressure rotavapour to afford Int-9 (350 mg, 78%) as a solid. Mass (m/z): 154 [M$^+$+1]. $^1$H NMR (200 MHz, dmso-d$_6$): δ 8.51 (s, 1H), 8.7.83 (s, 1H), 7.39 (brs, 2H), 3.79 (s, 3H). To a solution of Int-6 (1.58 g, 6.535 mmol) in 1,4-dioxane (25 mL) was added palladium acetate (238 mg, 1.045 mmol), Xantpos (498 mg, 1.045 mmol), Int-9 (1 g, 6.535 mmol) and cesium carbonate (3.21 g, 9.802 mmol) at room temperature. The reaction mixture was heated to 100° C. and stirring was continued for 18 hours. The reaction mixture was concentrated under reduced pressure, then residue was diluted with ethyl acetate. The precipitated solids were filtered, then washed with water (25 mL) and dried under vacuum. The solids were purified through silica gel column chromatography, eluted product with 3% methanol/ dichloromethane to afford Int-10 (200 mg, 8.5%) as a solid. Mass (m/z): 361 [M++1]. ¹H NMR (200 MHz, dmso-d₆): δ 10.8 (brs, 1H), 9.06 (s, 1H), 8.09 (s, 1H), 8.59-8.4 (m, 2H), 8.01 (s, 1H), 7.6 (d, J=7.4 Hz, 1H), 7.7.29-7.2 (m, 2H), 6.98 (t, J=7 Hz, 1H), 3.81 (s, 3H). To a solution of Int-10 (200 mg, 0.555 mmol) in methanol (4 mL) and dichloromethane (10 mL) was added hydroxyl amine solution (aqueous 50%) (4 mL) and reaction mixture was stirred for 20 minutes at 0° C. Then sodium hydroxide solution (3 mL) was added and the reaction mixture was allowed to room temperature, then stirred for 5 hours. The volatiles were concentrated under reduced pressure, then adjusted pH to neutral by using 1N HCl at 0° C. The precipitated solids were filtered, washed with water, dichloromethane and hexanes to afford the title compound (150 mg, 75%) as a solid. Mass (m/z): 362 [M++1]. (¹H NMR 200 MHz (dmso-d₆): δ 10.96 (brs, 1H), 9.01 (s, 1H), 8.72 (s, 1H), 8.54 (d, J=6.6 Hz, 1H), 8.47 (d, J=5.4 Hz, 1H), 7.99 (s, 1H), 7.6 (d, J=8.8 Hz, 1H), 7.33 (t, J=7.6 Hz, 1H), 7.24 (d, J=3.8 Hz, 1H), 6.99 (t, J=7 Hz, 1H), 6.42 (s, 1H), 2.5 (s, 3H).

Example 77

N-hydroxy-6-(4-(7-methoxy-2-methylimidazo[1,2-a]pyridin-3-yl)pyridin-2-ylamino)nicotinamide

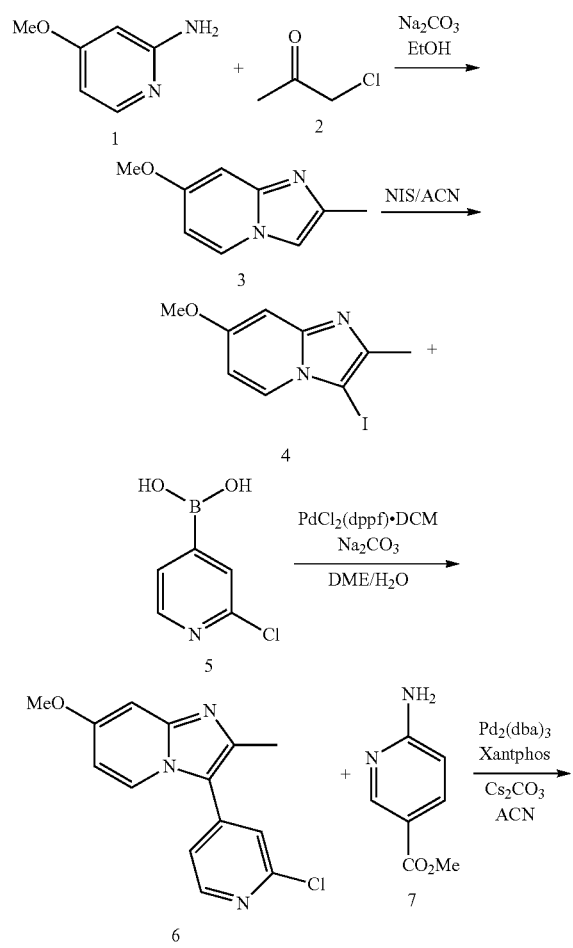

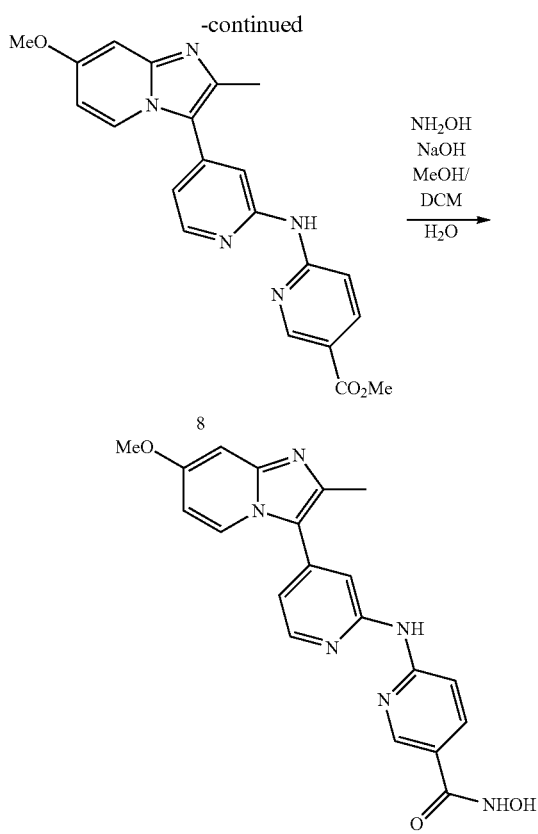

Example 77 (Compound I<sup>a</sup>-g3-78)

To a stirred solution of Int-1 (3.0 g, 24 mmol) in EtOH (150 mL) was added Na₂CO₃ (3.8 g, 35 mmol) at room temperature and stirred for 15 minutes, then Int-2 (3.4 g, 36 mmol) was added and the reaction mixture was stirred at 80° C. for 16 hours. The volatiles were concentrated under reduced pressure and the residue was diluted with water (200 mL). The aqueous layer was extracted with EtOAc (3×200 mL) and the combined organic extracts were washed with water (50 mL), brine (2×75 mL), dried over anhydrous Na₂SO₄ and concentrated under vacuum to afford Int-3 (2.5 g) as crude oil. This crude compound was taken to the next stage without any further purification. ¹H NMR (200 MHz, dmso-d₆): δ 7.83 (d, J=12 Hz, 1H), 7.18 (brs, 1H), 6.8 (s, 1H), 6.45 (d, J=12 Hz, 1H), 3.85 (s, 3H), 2.4 (s, 3H). To a stirred solution of Int-3 (2.5 g, 15 mmol) in acetonitrile (60 mL) was added NIS (4.1 g, 18 mmol) portion wise at room temperature and stirred for 2 hours. After the reaction completion, the reaction mass was diluted with excess water and the stirring was continued for another 30 minutes. The precipitated solid was filtered off and dried under vacuum to afford Int-4 (3.5 g, 79%) as solid. Mass (m/z): 389 [M++1]. ¹H NMR (200 MHz, CDCl₃): δ 7.85 (d, J=12 Hz, 1H), 6.85 (brs, 1H), 6.6 (d, J=12 Hz, 1H), 3.9 (s, 3H), 2.45 (s, 3H). Int-4 (3.5 g, 12 mmol) was dissolved in DME-H₂O (200 mL, 3:1) and purged with N₂ for 15 minutes. Then PdCl₂(dppf)-DCM (1.9 g, 2.4 mmol) and Int-5 (1.5 g, 9.6 mmol) were added and stirred for 10 minutes, finally Na₂CO₃ (1.9 g, 18 mmol) was added and the reaction mixture was stirred at 100° C. for 6 hours. After the completion of reaction, the volatiles were concentrated under vacuum. The residue was diluted with ice water (20 mL) and extracted with EtOAc (3×100 mL). The combined organic layer was dried over anhydrous Na₂SO₄ and concentrated under reduced pressure to obtain crude material, which was purified by column chromatography using 2% MeOH/DCM to afford Int-6 (0.7 g, 21%). Mass (m/z): 274.1 [M++1]. ¹H NMR (200 MHz, CDCl₃): δ 8.5 (d, J=6.8 Hz, 1H), 8.1 (d, J=6.8 Hz, 1H), 7.4 (s, 1H), 7.3 (m, 1H), 6.85 (m, 1H), 6.6 (d, J=12 Hz, 1H), 3.9 (s, 3H), 2.5 (s, 3H). To a stirred solution of Int-6 (0.7 g, 2.5 mmol) in acetonitrile (10 mL) were added tris(dibenzylideneacetone)dipalladium(0) (Pd$_2$(dba)$_3$) (0.07 g, 0.076 mmol), Xanthpos (0.106 g, 0.2 mmol), Cs$_2$CO$_3$ (1.49 g, 4.6 mmol) and Int-7 (0.38 g, 2.5 mmol) at room temperature under argon purging, then stirred for 1 hour. The reaction mixture was heated to 100° C. for 16 hours. After the reaction completion, the volatiles were concentrated under reduced pressure. The residue was washed with ether, diluted with water and stirred for 15 minutes. The precipitated solid was filtered and dried under vacuum to afford Int-8 (0.240 g, 24%). Mass (m/z): 390 [M$^+$+1]. $^1$H NMR (200 MHz, dmso-d$_6$): δ 10.2 (brs, 1H), 8.8 (brs, 1H), 8.35-8.45 (m, 2H), 8.25-8.18 (m, 1H), 7.82-7.95 (m, 1H), 7.15 (d, J=6.6 Hz, 1H), 7.0 (s, 1H), 7.0 (s, 1H), 6.65-6.76 (m, 1H), 3.85 (s, 3H), 2.45 (s, 3H). To a stirred solution of Int-8 (0.24 g, 0.61 mmol) in MeOH-DCM (25 mL, 3:1) was added 50% NH$_2$OH (6 mL) at 0° C. After being stirred for 10 minutes at 0° C., a solution of NaOH (0.2 g) in water (2 mL) was added and stirred for additional 30 minutes at 0° C. The reaction mixture was then warmed to room temperature and stirred for 2 hours. The volatiles were concentrated under reduced pressure after the reaction completion. The residue was diluted with water (15 mL) at 0° C., acidified to about pH 7 using 2 N HCl and stirred for 10 minutes. The precipitated solid was filtered and dried under vacuum to afford the title compound (0.15 g, 62%) as a solid. Mass (m/z): 391 [M$^+$+1]. $^1$H NMR (200 MHz, dmso-d$_6$): δ 10.2 (brs, 1H), 9.0 (brs, 1H), 8.6 (s, 1H), 8.35-8.45 (m, 2H), 7.85-8.05 (m, 2H), 7.78 (d, J=12.5 Hz, 1H), 7.08 (d, J=6.6 Hz, 1H), 7.0 (s, 1H), 6.65-6.75 (m, 1H), 6.41 (brs, 1H), 3.85 (s, 3H), 2.45 (s, 3H).

Example 78

4-(5-(H-imidazo[1,2-a]pyridin-3-yl)pyridazin-3-ylamino)-N-(2-aminophenyl)benzamide (Compound I$^b$-a2-05)

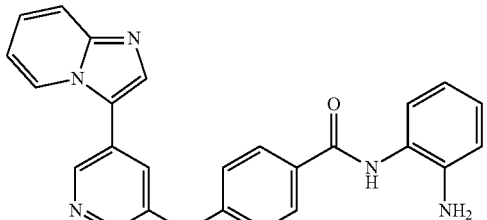

Example 78

A mixture of 3-(4,4,5,5-tetramethyl-1,3,2-dioxaborolan-2-yl)H-imidazo[1,2-a]pyridine (527 mg, 2.16 mmol), 5-iodopyridazin-3(2H)-one (Coelho et al, Tetrahedron 60 (2004), 12177) (436 mg, 1.96 mmol), 2.0M Sodium carbonate solution (2.2 mL, 4.32 mmol), PdCl$_2$(dppf) (60 mg, 0.074 mmol), dioxane (6 mL) was heated in a microwave (Emry's Optimizer) at 125° C. for 45 minutes. Additional PdCl$_2$(dppf) (120 mg, 0.148 mmol), was added and heated in oil bath in a pressure vessel at 125° C. for 16 hours. The reaction mixture was then poured into water and the resulting solid was filtered and washed with water and dried to give 5-(H-imidazo[1,2-a]pyridin-3-yl)pyridazin-3(2H)-one (Int-1). MS found for C$_{11}$H$_8$N$_4$O as (M+H)$^+$ 213.26. A mixture of Int-1 in POCl$_3$ was heated at 110° C. for 45 minutes. The reaction mixture was then cooled, concentrated and poured in to ice-water. The resulting solid was filtered and the filtrate was extracted with DCM and EtOAc and the combined organic layers were dried (MgSO$_4$). Filtration and concentration gave 3-(6-chloropyridazin-4-yl)H-imidazo[1,2-a]pyridine (Int-2). MS found for C$_{11}$H$_7$ClN$_4$ as (M+H)$^+$ 231.24. To a solution of Int-2 (45 mg, 0.2 mmol), 4-Amino-benzoic acid (40 mg, 0.29 mmol) in dioxane (3 mL), p-TSA (37 mg, 0.2 mmol) was added and heated in a pressure vessel at 125° C. After 1 hour, the resulting solid was filtered and washed with ether and dried to give 4-(5-(H-imidazo[1,2-a]pyridin-3-yl)pyridazin-3-ylamino) benzoic acid (Int-3). MS found for C$_{18}$H$_{13}$N$_5$O$_2$ (m/z): 332.25 [M$^+$+1]. To Int-3 (63 mg, 0.19 mmol) in DMF (6 mL), was added HATU (114 mg, 0.30 mmol), 1,2-phenylenediamine (43 mg, 0.40 mmol) and DIPEA (0.2 mL, 1.0 mmol) and stirred at room temperature for 1 hour. The reaction mixture was diluted with water and acetonitrile and directly purified by preparative HPLC affording the title compound as tan solid, after lyophilization. MS found for C$_{24}$H$_{19}$N$_7$O as (M+H)$^+$ 421.97. $^1$H NMR (400 MHz, dmso-d$_6$): δ 9.63 (s, 1H); 9.50 (s, 1H); 9.09 (s, 1H); 8.79 (d, J=7.2 Hz, 1H); 8.19 (s, 1H); 7.97 (d, J=8.8 Hz, 2H); 7.90 (d, J=8.8 Hz, 2H); 7.73 (d, J=8.8 Hz, 1H); 7.46 (s, 1H); 7.40 (t, J=8.0 Hz, 1H); 7.13-7.04 (m, 2H); 6.93 (t, J=6.8 Hz, 1H); 6.75 (d, J=7.2 Hz, 1H); 6.58 (t, J=7.6 Hz, 1H); 4.83 (brs, 2H).

Example 79

3-{2-[4-(2-Amino-phenylcarbamoyl)-phenylamino]-pyrimidin-4-yl}-2-methyl-imidazo[1,2-a]pyridine-7-carboxylic acid (2-methoxy-ethyl)-amide

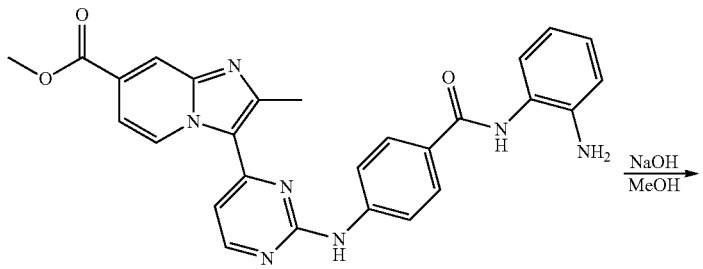

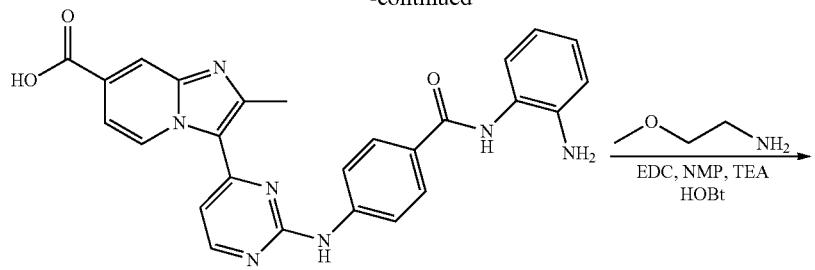

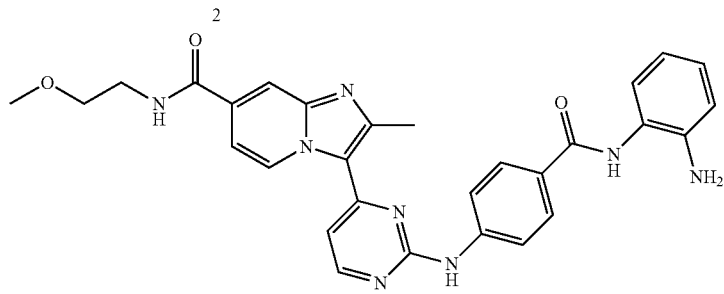

Example 79 (Compound I*ᵃ*-a-174)

Int-1 (200 mg, 0.4 mmol) was dissolved in MeOH (5 mL) and then treated with 1N NaOH (1 mL). After 2 hours the reaction mixture was evaporated and the solids were re-suspended in water and 1N HCl was slowly added to precipitate Int-2 which was then filtered and dried and used for next step without additional purification. Int-2 (60 mg, 0.125 mmol), EDC (28 mg, 1.2 eq), HOBt (20 mg, 1.2 eq), TEA (0.04 mL, 2.0 eq) and 2-methoxy-ethylamine (2.0 eq) were mixed in NMP and stirred at room temperature. After 2 hours the reaction mixture was diluted with water and extracted with EtOAc. The organic phase was dried, evaporated and purified by reverse phase chromatography to yield the title compound.

MS found for $C_{29}H_{28}N_8O_3$ as (M+H)⁺ 537.23. ¹H NMR (400 MHz, dmso-$d_6$): δ 9.98 (s, 1H), 9.71 (d, J=7.6 Hz, 1H), 9.47 (s, 1H), 8.79 (d, J=5.2 Hz, 1H), 8.58 (d, J=5.2 Hz, 1H), 8.11 (s, 1H), 7.92-7.84 (m, 4H), 7.42 (dd, J=7.2, 6.0 Hz, 1H), 7.16 (d, J=5.6 Hz, 1H), 7.10 (d, J=7.2 Hz, 1H), 6.90 (t, J=8.0 Hz, 1H), 6.72 (d, J=8.0 Hz, 1H), 6.54 (d, J=7.6 Hz, 1H), 4.82 (s, 2H), 3.43-3.40 (m, 4H), 3.22 (s, 3H), 2.64 (s, 3H).

Example 80

3-{2-[4-(2-Amino-phenylcarbamoyl)-phenylamino]-pyrimidin-4-yl}-2-methyl-imidazo[1,2-a]pyridine-7-carboxylic acid (2-dimethylamino-ethyl)-amide

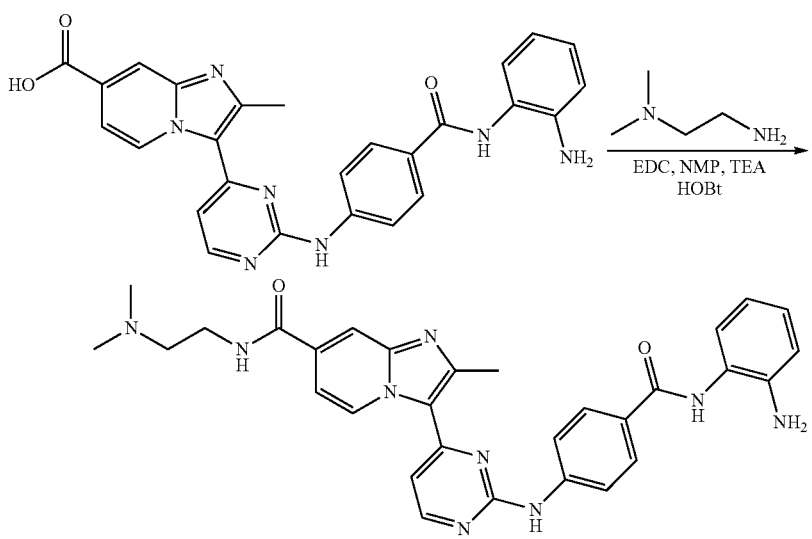

Example 80 (Compound I*ᵃ*-a-216)

The acid was coupled with 2-aminoethyldimethyl amine in the presence of EDC, HOBt and TEA in NMP and purified by reverse phase chromatography to yield the title compound.

MS found for $C_{30}H_{31}N_9O_2$ as $(M+H)^+$ 550.26. $^1$H NMR (400 MHz, dmso-$d_6$): δ 9.98 (s, 1H), 9.71 (d, J=7.6 Hz, 1H), 9.47 (s, 1H), 8.66 (d, J=5.6 Hz, 1H), 8.58 (d, J=5.2 Hz, 1H), 7.92-7.84 (m, 4H), 7.40 (dd, J=7.6, 5.6 Hz, 1H), 7.16 (d, J=5.6 Hz, 2H), 7.10 (d, J=6.8 Hz, 1H), 6.92-6.88 (m, 1H), 6.72 (d, J=7.2 Hz, 1H), 6.54 (t, J=7.6 Hz, 1H), 4.81 (s, 2H), 2.64 (s, 4H), 2.14 (s, 6H).

Example 81

N-(2-aminophenyl)-5-(4-(2-methylimidazo[1,2-a]pyridin-3-yl)pyrimidin-2-ylamino)thiophene-2-carboxamide

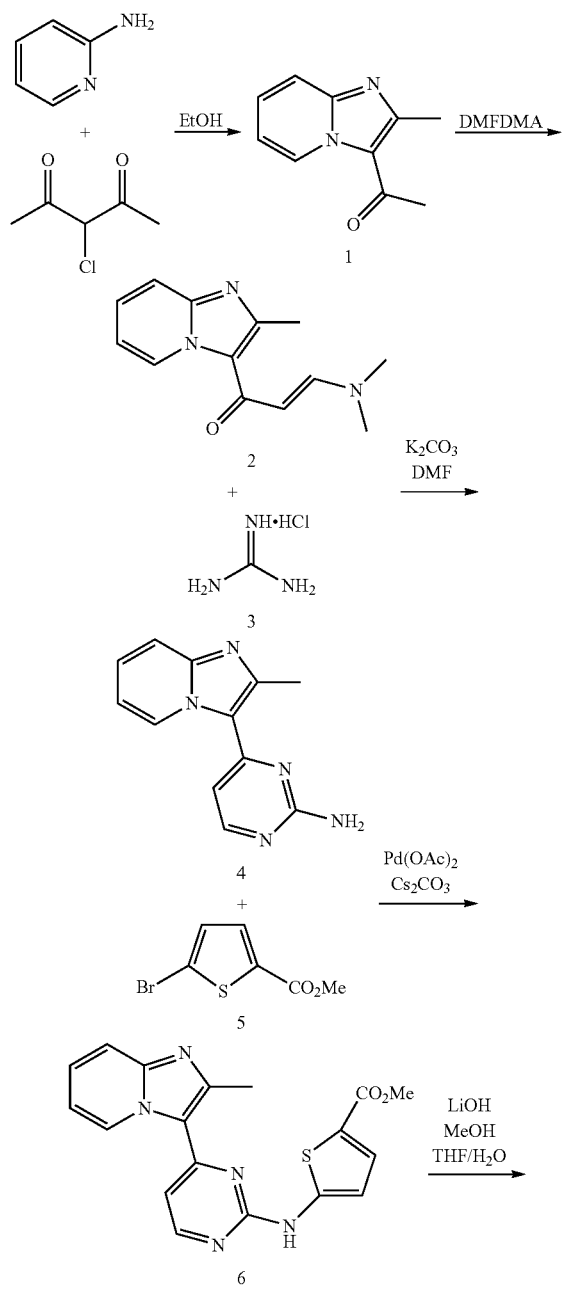

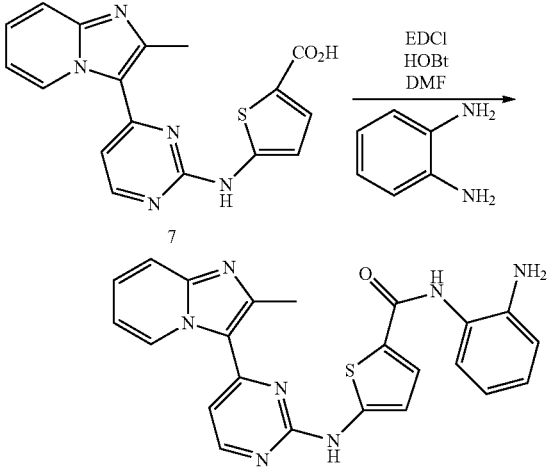

Example 81 (Compound I$^a$-b0-07)

To a solution of 2-amino pyridine (20 g, 0.22 mmol) in ethanol (100 mL) was added 3-chloro-2,4-pentanedione (30 mL, 0.26 mmol) at room temperature and the reaction mixture was stirred at reflux temperature for 16 hours. The reaction mixture was allowed to room temperature and then volatiles were concentrated under reduced pressure. The crude material was purified by column chromatography eluting with 60% EtOAc/hexane to afford Int-1 (15 g, 40%). Mass (m/z): 174 [M$^+$+1]. $^1$H NMR (200 MHz, CDCl$_3$-$d_6$): δ 8.4 (d, J=6.6 Hz, 1H), 7.31-7.29 (m, 1H), 6.9-6.82 (m, 1H), 2.7 (s, 3H), 2.6 (s, 3H). A solution of Int-1 (12 g, 68.9 mmol) in DMF-DMA (18 mL) was stirred at reflux temperature for 72 hours. The reaction mixture was diluted with diethyl ether (150 mL) and stirred for 30 minutes. The precipitated solid was filtered off, washed with diethyl ether (50 mL) and dried under vacuum to afford Int-2 (8.0 g, 54%) as brown color solid. Mass (m/z): 230 [M$^+$+1]. $^1$H NMR (200 MHz, CDCl$_3$-$d_6$): δ 8.4 (d, J=6.6 Hz, 14H), 7.78 (d, J=12.6 Hz, 1H), 7.31-7.29 (m, 1H), 6.78 (t, J=7.0 Hz, 1H), 6.90-6.81 (m, 1H), 5.57 (d, J=12.6 Hz, 1H), 3.04 (brs, 6H), 2.7 (s, 3H). To a solution of Int-2 (6.0 g, 27.5 mmol) in DMF (60 mL) was added Int-3 (6.5 g, 68.7 mmol) followed by K$_2$CO$_3$ (9.4 g, 68.7 mmol) at room temperature. The reaction mixture was heated to 100° C. and then stirred for 16 hours. The reaction mixture was warmed to room temperature, then diluted with ice cold water (80 mL) and extracted with EtOAc (2×100 mL). The combined organic extracts were washed with water (50 mL), brine (50 mL), dried over anhydrous Na$_2$SO$_4$ and concentrated under vacuum. The crude material was purified by column chromatography eluting with 2% MeOH/DCM to afford Int-4 (4.3 g, 70%). Mass (m/z): 226 [M$^+$+1]. $^1$H NMR (200 MHz, CDCl$_3$-$d_6$): δ 9.6 (d, J=2.2 Hz, 1H), 8.35 (d, J=5.6 Hz, 1H), 7.61 (d, J=7.6 Hz, 1H), 7.3-7.21 (m, 1H), 6.89-6.81 (m, 1H), 5.14 (brs, 2H), 2.7 (s, 3H). To a stirred solution of Int-4 (1.0 g, 4.4 mmol) and Int-5 (1.17 g, 5.31 mmol) in dioxane (20 mL) were added Xanthophos (0.2 g, 0.34 mmol) and cesium carbonate (1.4 g, 4.4 mmol), followed by palladium (II) acetate (60 mg, 0.26 mmol) at room temperature and then degassed with N$_2$ bubbling for 30 minutes with vacuum. The reaction mixture was then heated to 100° C. and then stirred for 16 hours. The volatiles were concentrated under reduced pressure, then the residue was diluted with EtOAc (100 mL). The organic layer was washed with water (30 mL), brine (30 mL), dried over anhydrous Na$_2$SO$_4$ and concentrated under vacuum. The crude material was purified by column chromatography eluting with 1% MeOH/DCM to afford Int-6 (0.2 g, 12%). Mass (m/z): 366 [M$^+$+1]. $^1$H NMR (200 MHz, dmso-d$_6$): δ 9.56 (d, J=9 Hz, 1H), 8.57 (d, J=5.6 Hz, 1H), 8.4 (brs, 1H), 7.68-7.62 (m, 2H), 7.36 (t, J=5.4 Hz, 1H), 7.07 (d, J=5.6 Hz, 1H), 6.9 (t, J=7.0 Hz, 1H), 6.64 (d, J=4 Hz, 1H), 3.85 (s, 3H) 2.75 (s, 3H). To a solution of Int-6 (0.5 g, 1.36 mmol) in methanol (10 mL) and THF (10 mL) was added lithium hydroxide (0.17 g, 4.0 mmol) at room temperature, followed by water (5 mL) and the reaction mixture was stirred at 60° C. for 16 hours. The volatiles were evaporated under vacuum, diluted with water (10 mL) and acidified to about pH 5 using 2 N HCl at 0° C. and stirred further for 30 minutes. The precipitated solid was filtered off, washed with water (2×5 mL) and dried under vacuum to afford Int-7 (0.25 g, 52%). Mass (m/z): 354 [M$^+$+1]. $^1$H NMR (200 MHz, dmso-d$_6$): δ 12.5 (brs, 1H), 11.31 (brs, 1H), 8.8 (brs, 1H), 8.66 (d, J=5.4 Hz, 1H), 7.69 (d, J=8.8 Hz, 1H), 7.54 (d, J=4.4 Hz, 2H), 7.2-7.16 (m, 2H), 6.76 (d, J=4.0 Hz, 1H). To a stirred solution of Int-7 (0.40 g, 1.13 mmol) in DMF (10 mL) were added HOBt (0.15 g, 1.13 mmol), EDCI (0.47 g, 2.48 mmol) and N-ethyldiisopropylamine (0.5 mL, 2.48 mmol) at 0° C. After 15 minutes stirring at 0° C., o-phenylenediamine (0.14 g, 1.36 mmol) was added to the reaction mixture. The reaction mixture was warmed to room temperature and stirred for 16 hours. The reaction mixture was diluted with water (20 mL) and stirred for 30 minutes. The precipitated solid was filtered and dried under vacuum. The crude material was purified over silica gel column chromatography eluting with 2% MeOH/DCM to afford the title compound (0.115 g, 23%). Mass (m/z): 442 [M$^+$+1]. $^1$H NMR (200 MHz, dmso-d$_6$): δ 11.2 (brs, 1H), 9.80 (brs, 1H), 9.44 (brs, 1H), 8.65 (d, J=5.4 Hz, 1H), 7.78 (d, J=4.2 Hz, 1H), 7.65 (d, J=9.2 Hz, 1H), 7.45 (t, J=7 Hz, 1H), 6.90-7.20 (m, 4H), 6.77 (d, J=4.4 Hz, 2H), 6.58 (t, J=6.7 Hz, 1H), 4.86 (bs, 2H), 2.66 (s, 3H). $^{13}$C NMR (125 MHz, dmso-d$_6$): 160.8, 157.0, 147.3, 145.6, 143.0, 128.4, 127.6, 127.3, 126.9, 126.5, 126.1, 123.4, 117.4, 116.3, 116.2, 116.1, 112.9, 110.1, 109.8, 16.6.

Example 82

N-(2-aminophenyl)-4-(4-(8-methoxy-2-methylimidazo[1,2-a]pyridin-3-yl)pyrimidin-2-ylamino)benzamide

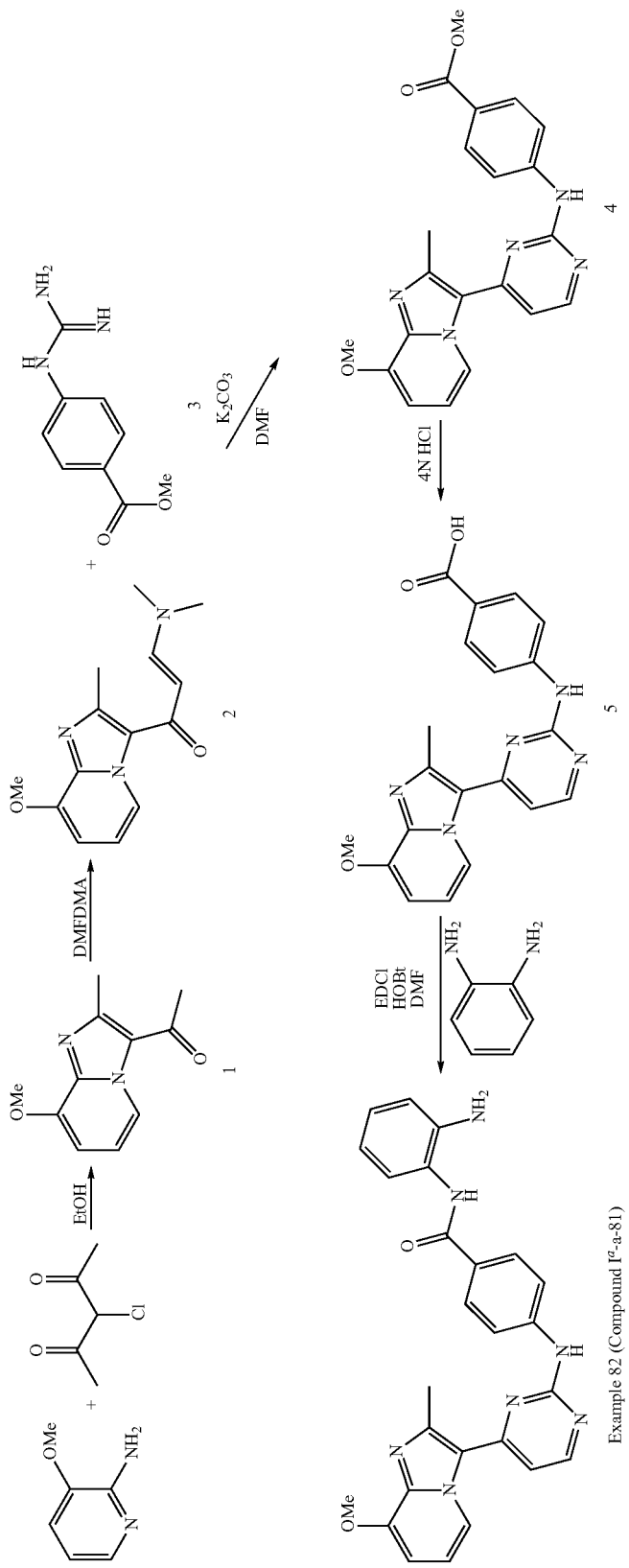

To a stirred solution of 3-methoxypyridin-2-amine (4.0 g, 32.2 mmol) in ethanol (40 mL) was added 3-chloro-2,4-pentanedione (5.5 mL, 48.0 mmol) at room temperature. The reaction mixture was heated to reflux and then stirred for 18 hours. The volatiles were concentrated under reduced pressure. The crude material was purified by column chromatography eluting with 15% EtOAc/hexane to afford Int-1 (2.5 g, 38%). Mass (m/z): 205 [M$^+$+1]. $^1$HNMR 200 MHz (CDCl$_3$): δ 9.23 (d, J=6.2 Hz, 1H), 6.78 (t, J=7.4 Hz, 1H), 6.61 (d, J=7.8 Hz, 1H), 4.01 (s, 3H), 2.77 (s, 3H), 2.67 (s, 3H). A solution of Int-1 (02.5 g, 12.2 mmol) in DMF-DMA (15 mL) was stirred at reflux temperature for 48 hours. The volatile was concentrated under reduced pressure. The residue was diluted with diethyl ether and stirred for 20 minutes. The precipitated solid was filtered off, washed with hexane-ether and dried under vacuum to afford Int-2 (2.5 g, 81%) as brown color solid. Mass (m/z): 260 [M$^+$+1]. $^1$H NMR 200 MHz (CDCl$_3$): δ 9.23 (d, J=6.2 Hz, 1H), 7.78 (t, J=12.6 Hz, 1H), 6.78 (t, J=7.4 Hz, 1H), 6.61 (d, J=7.8 Hz, 1H), 5.57 (d, J=12.4 Hz, 1H), 4.01 (s, 3H), 3.04 (brs, 6H), 2.77 (s, 3H). To a solution of Int-2 (2.5 g, 9.6 mmol) in DMF (12 mL) was added Int-3 (4.6 g, 24.0 mmol), followed by K$_2$CO$_3$ (3.9 g, 28.8 mmol) at room temperature. The reaction mixture was heated to 110° C. and then stirred for 16 hours. The reaction mixture was allowed to room temperature, diluted with ice cold water and stirred further for 20 minutes. The precipitated solid was filtered off, washed with water (2×10 mL) and dried under vacuum to afford Int-4 (2.8 g, 75%) as brown solid. Mass (m/z): 390 [M$^+$+1]. $^1$HNMR 200 MHz (dmso-d$_6$): δ 10.12 (s, 1H), 9.31 (d, J=6.2 Hz, 1H), 8.60 (d, J=5.6 Hz, 1H), 7.92-7.86 (m, 4H), 7.19 (d, J=5.4 Hz, 1H), 6.95-6.85 (m, 2H), 3.95 (s, 3H), 3.81 (s, 3H), 2.63 (s, 3H). A mixture of Int-4 (2.8 g, 7.17 mmol) and 4 N HCl (50 mL) was stirred at reflux temperature for 3 hours. The reaction mixture was cooled to 0° C. and stirred for 20 minutes. The precipitated solid was filtered off, washed with water (2×10 mL) and dried under vacuum to afford Int-5 (2.3 g, 88%) as solid. Mass (m/z): 376 [M$^+$+1]. $^1$HNMR 200 MHz (dmso-d$_6$): δ 10.12 (s, 1H), 9.31 (d, J=6.2 Hz, 1H), 8.60 (d, J=5.6 Hz, 1H), 7.92-7.86 (m, 4H), 7.19 (d, J=5.4 Hz, 1H), 6.95-6.85 (m, 2H), 3.81 (s, 3H), 2.63 (s, 3H). To a stirred suspension of Int-5 (1.0 g, 2.6 mmol) in DMF (8 mL) were added HOBt (0.35 g, 2.6 mmol), EDCI (1.1 g, 5.8 mmol), N-ethyldiisopropylamine (1.1 mL, 6.64 mmol) and o-phenylenediamine (0.28 g, 2.6 mmol) at 0° C. After the completion of addition, the reaction mixture was allowed to room temperature and the stirring was continued for 16 hours. The reaction mixture was diluted with ice cold water (80 mL) and stirred for 20 minutes. The precipitated solid was filtered off, washed with water (2×10 mL) and dried under vacuum. The crude material was purified over silica gel column chromatography eluting with 2% MeOH/DCM to afford the title compound (0.24 g, 20%) as solid. Mass (m/z): 466 [M$^+$+1]. $^1$H NMR (200 MHz, dmso-d$_6$): δ 10.0 (s, 1H), 9.53 (s, 1H), 9.33 (d, J=5.8 Hz, 1H), 8.59 (d, J=5.6 Hz, 1H), 7.93 (brs, 4H), 7.16-7.21 (m, 2H), 7.0-6.85 (m, 3H), 6.77 (d, J=7.2 Hz, 1H), 6.61 (d, J=7.0 Hz, 1H), 4.87 (bs, 2H), 3.95 (s, 3H), 2.63 (s, 3H). $^{13}$C NMR (125 MHz, dmso-d$_6$): δ 164.7, 159.2, 158.0, 156.8, 147.7, 145.6, 143.3, 143.0, 139.6, 128.4, 127.0, 126.5, 126.2, 123.6, 120.6, 118.5, 117.8, 116.2, 116.1, 112.7, 110.0, 103.9, 55.8, 16.5.

Example 83

N-hydroxy-4-(4-(8-methoxy-2-methylimidazo[1,2-a]pyridin-3-yl)pyrimidin-2-ylamino)benzamide

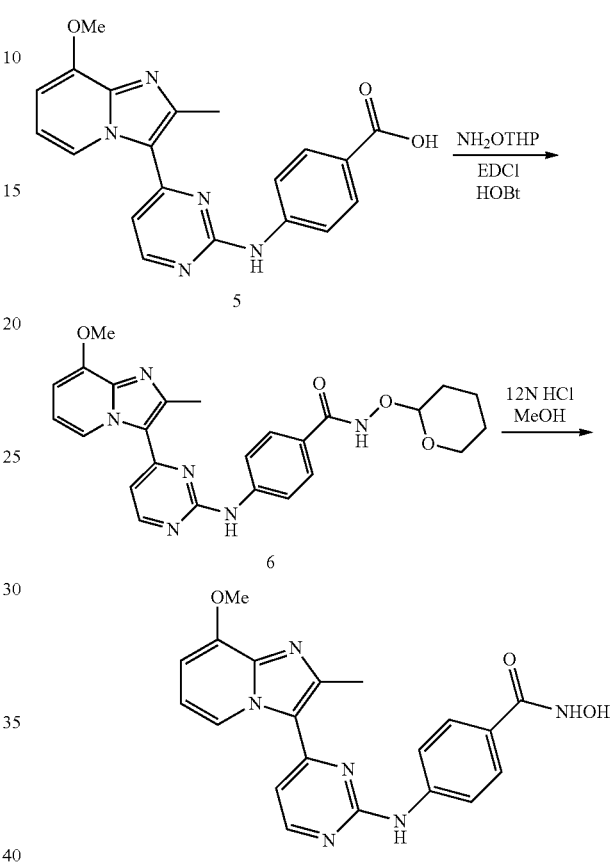

Example 83 (Compound I$^a$-a-77)

To a stirred suspension of Int-5 (1.0 g, 2.6 mmol) in DMF (8 mL) was added HOBt (0.35 g, 2.6 mmol), EDCI (1.26 g, 6.6 mmol), N-ethyldiisopropylamine (1.1 mL, 6.64 mmol) and NH$_2$OTHP (0.46 g, 3.9 mmol) at 0° C. After the completion of addition, the reaction mixture was allowed to room temperature and the stirring was continued for 16 hours. The reaction mixture was diluted with ice cold water (80 mL) and stirred for 20 minutes. The precipitated solid was filtered off, washed with water (2×10 mL) and dried under vacuum. The crude material was purified over silica gel column chromatography eluting with 2% MeOH/DCM to afford Int-6 (0.5 g, 40%) as solid. Mass (m/z): 475 [M$^+$+1]. To a solution of Int-6 (0.5 g, 1.05 mmol) in methanol (6 mL) was added concentrated HCl (1.0 mL) at 0° C. and the stirring was continued for 16 hours at room temperature. The precipitated solid was filtered and dried under vacuum to provide product as HCl salt. The HCl salt was treated with saturated NaHCO$_3$ solution for 30 minutes, filtered and dried under vacuum to afford the title compound (0.34 g, 83%). Mass (m/z): 391 [M$^+$+1]. $^1$H NMR (200 MHz, dmso-d$_6$): δ 9.90 (s, 1H), 8.52 (d, J=5.6 Hz, 1H), 8.59 (d, J=5.7 Hz, 1H), 7.75 (q, 4H), 7.12 (d, J=5.6 Hz, 1H), 6.92-6.83 (m, 2H), 3.90 (s, 3H), 2.58 (s, 3H). $^{13}$C NMR (125 MHz, dmso-d$_6$): δ 159.3, 158.0, 156.8, 147.7, 145.6, 142.8, 139.5, 127.3, 125.7, 120.7, 118.5, 118.1, 112.6, 109.8, 109.8, 103.9, 55.8, 16.5.

Example 84

Biological Assays

HDAC inhibitory activity of the compound of Example 1 was measured by two types of assays in which HDAC 1 was used as a target molecule. The first assay was carried out without preincubation after addition of the enzyme. The test compound was suspended in and titrated in dmso. It was then spotted into a 384-well test plate. The enzyme, HDAC 1, was diluted in assay buffer containing 25 mM Tris-HCl (pH 8.0), 137 mM NaCl, 2.7 mM KCl, and 0.01% Tween-20 and added to the pre-spotted compound. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The second assay is similar to the first assay described above, except that preincubation is carried out for about 3 hours after the enzyme is introduced. The test compound was suspended in, and titrated in DMSO. It was then spotted into a 384-well test plate. The enzyme, HDAC 1, was diluted in the same assay buffer as used in the previous assay and added to the pre-spotted compound. The enzyme/compound mix was incubated at room temperature for about 3 hours. The peptide substrate containing a fluorophore/quencher pair was diluted in the assay buffer and added to the compound/enzyme mix initiating the reaction. The reaction incubated at room temperature for 45 minutes. A concentrated developer solution was diluted in the assay buffer, and added to the reaction. The reaction was incubated at room temperature for about 15 minutes and relative fluorescence was read on an instrument reader.

The following table shows IC$_{50}$ data for the compound tested with the protocols described above.

TABLE 1

IC$_{50}$ of HDAC inhibitor compound

| Compound | HDAC 1 inhibitory activity (IC$_{50}$ [μM]) (3-hour preincubation) | CDK2 (IC$_{50}$ [μM]) |
|---|---|---|
| Example 1 | 0.067 | 0.044 |
| Example 2 | 0.146 | 0.134 |
| Example 3 | 0.011 | 0.18 |
| Example 4 | >50 | — |
| Example 5 | 0.02 | 0.0393 |
| Example 6 | 0.197 | 0.084 |
| Example 7 | 0.017 | 0.069 |
| Example 8 | >50 | 0.144 |
| Example 9 | 0.0392 | 0.037 |
| Example 10 | >10 | 0.084 |
| Example 11 | 0.089 | 0.07 |
| Example 12 | >10 | 0.32 |
| Example 13 | 0.04 | 0.04 |
| Example 14 | ~0.09 | 0.06 |
| Example 15 | 0.0818 | 0.18 |
| Example 16 | 0.295 | 0.16 |
| Example 17 | 0.273 | 0.034 |
| Example 18 | 0.0239 | 0.59 |
| Example 19 | 0.0937 | 0.07 |
| Example 20 | 0.165 | 0.9 |
| Example 21 | 0.289 | 1.18 |
| Example 22 | 0.071 | 2.87 |
| Example 23 | 5.29 | 0.67 |
| Example 24 | 0.18 | 0.5 |
| Example 25 | 0.128 | 1.03 |
| Example 26 | >10 | 0.53 |
| Example 27 | 0.374 | 4.64 |
| Example 28 | 0.621 | 2.53 |
| Example 29 | 0.315 | 2.13 |
| Example 30 | 0.118 | 1.07 |
| Example 31 | 0.243 | 0.4 |
| Example 32 | 0.141 | 2.58 |
| Example 33 | 0.126 | 0.22 |
| Example 34 | 1.56 | 0.86 |
| Example 35 | 0.128 | 0.06 |
| Example 36 | >10 | 0.11 |
| Example 37 | 0.132 | 1.88 |
| Example 38 | 0.312 | 2.74 |
| Example 39 | 0.563 | 7.94 |
| Example 40 | 0.347 | 7.1 |
| Example 41 | 0.877 | 4.34 |
| Example 42 | 0.388 | 0.29 |
| Example 43 | 0.14 | 0.08 |
| Example 44 | 0.251 | 0.09 |
| Example 45 | 0.178 | 0.35 |
| Example 46 | 0.13 | 1.61 |
| Example 47 | >10 | 0.14 |
| Example 48 | 0.06 | 0.14 |
| Example 49 | 0.199 | 0.06 |
| Example 50 | >20 | 0.06 |
| Example 51 | 0.211 | 0.014 |
| Example 52 | 0.31 | 0.07 |
| Example 53 | 0.021 | 3.6 |
| Example 54 | 0.053 | 13.08 |
| Example 55 | 0.2 | >40 |
| Example 57 | 0.147 | 2.87 |
| Example 58 | 5.58 | >40 |
| Example 59 | 0.993 | 0.04 |
| Example 60 | 0.164 | 0.03 |
| Example 61 | 1.8 | 0.56 |
| Example 62 | >10 | 1.36 |
| Example 63 | 0.224 | 3.53 |
| Example 64 | 0.094 | 0.52 |
| Example 65 | 0.109 | 1.86 |
| Example 66 | 0.289 | 3.48 |
| Example 67 | 0.169 | 0.68 |
| Example 68 | 0.0206 | >40 |
| Example 69 | 0.141 | 0.15 |
| Example 70 | 0.073 | 0.87 |
| Example 71 | 0.185 | 0.026 |
| Example 72 | 0.4 | >40 |
| Example 73 | 0.185 | 1.68 |
| Example 74 | 0.104 | 6.47 |
| Example 75 | 0.669 | — |
| Example 76 | 0.526 | — |
| Example 77 | 0.18 | — |

The results indicate that the compounds have inhibitory activity against HDAC and/or CDK and thus can be useful to treat or inhibit diseases caused by abnormal activities of HDAC and/or CDK.

All patents and publications cited herein are incorporated by reference into this application in their entirety.

What is claimed is:

1. A compound selected from those of Formula (I) and pharmaceutically acceptable salts thereof:

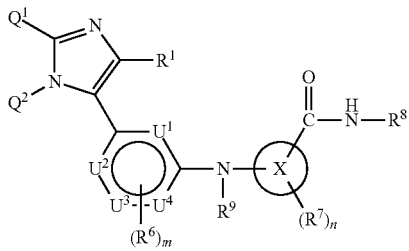

Formula (I)

wherein

R$^1$ is selected from the group consisting of H, halo, nitro, cyano, hydroxy, hydroxy(C$_{1-10}$ alkyl), amino(C$_{1-10}$ alkyl), haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, hydroxy(C$_{1-10}$ alkoxy)(C$_{1-10}$ alkoxy), (C$_{1-10}$ alkoxy)(C$_{1-10}$ alkoxy), (C$_{1-10}$ alkoxy)(C$_{1-10}$ alkyl), C$_{1-10}$ alkanoyl, C$_{1-10}$ alkanoyloxy, N—(C$_{1-10}$ alkyl)amino, N,N—(C$_{1-10}$ alkyl)$_2$-amino, C$_{1-10}$ alkanoylamino, N—(C$_{1-10}$ alkyl)carbamoyl, N,N—(C$_{1-10}$ alkyl)$_2$-carbamoyl, C$_{1-10}$ alkyl-S(O)$_a$ wherein a is 0, 1 or 2, C$_{1-10}$ alkoxycarbonyl, NH$_2$—S(O)$_2$NH—, NH$_2$—CO—NH—, N—(C$_{1-10}$ alkyl)sulphamoyl, N,N—(C$_{1-10}$ alkyl)$_2$sulphamoyl, aryl, arylalkyl, aryloxy, arylthio, cycloalkyl, cycloalkylalkyl, cycloalkyloxy, heterocyclyl, heterocyclylalkyl, heterocyclyl(C=O)—, heterocyclyloxy and heterocyclylthio, wherein R$^1$ is optionally substituted by one or more A;

Q$^1$ and Q$^2$ together form a cyclic moiety to make a fused ring together with the imidazole moiety, wherein the cyclic moiety is substituted by one or more substituents selected from R$^1$ groups, each of which is optionally substituted by one or more A;

U$^1$, U$^2$, U$^3$ and U$^4$ are independently selected from —N—, —CH—, and —CR$^6$—, with the proviso that at least one of U$^1$, U$^2$, U$^3$ and U$^4$ is —N—;

m is 0, 1, 2, or 3;

R$^6$ is halo, hydroxy, nitro, cyano, trifluoromethyl, trifluoromethoxy, amino, carboxyl, carbamoyl, sulphamoyl, C$_{1-10}$ alkyl, C$_{2-10}$ alkenyl, C$_{2-10}$ alkynyl, C$_{1-10}$ alkoxy, C$_{1-10}$ alkanoyl, N—(C$_{1-10}$ alkyl)amino, N,N—(C$_{1-10}$ alkyl)$_2$ amino, C$_{1-10}$ alkanoylamino, N—(C$_{1-10}$ alkyl) carbamoyl, N,N—(C$_{1-10}$ alkyl)$_2$ carbamoyl, C$_{1-10}$ alkyl-S(O)$_a$ wherein a is 0, 1 or 2, NH$_2$—S(O)$_2$NH—, N—(C$_{1-10}$ alkyl)sulphamoyl or N,N—(C$_{1-10}$ alkyl)$_2$sulphamoyl; wherein R$^6$ is optionally substituted by one or more B;

X is phenyl, 5-membered heteroaryl, or 6-membered heteroaryl, wherein the heteroaryl contains one or more heteroatoms selected from N, S and O;

R$^7$ represents one or more optional non-hydrogen substituents on ring X, wherein when present, each R$^7$ is independently selected from hydroxy, halo, nitro, cyano, trifluoromethyl, trifluoromethoxy, amino, carboxyl, carbamoyl, sulphamoyl, C$_{1-10}$ alkyl, C$_{2-10}$ alkenyl, C$_{2-10}$ alkynyl, C$_{1-10}$ alkoxy, C$_{1-10}$ alkanoyl, N—(C$_{1-10}$ alkyl) amino, N,N—(C$_{1-10}$ alkyl)$_2$ amino, C$_{1-10}$ alkanoylamino, N—(C$_{1-10}$ alkyl)carbamoyl, N,N—(C$_{1-10}$ alkyl)$_2$ carbamoyl, C$_{1-10}$ alkyl-S(O)$_a$ wherein a is 0, 1 or 2, NH$_2$—S(O)$_2$NH—, N—(C$_{1-10}$ alkyl)sulphamoyl, N,N—(C$_{1-10}$ alkyl)$_2$sulphamoyl, cycloalkyl, heterocyclyl and aryl;

n is 0, 1, 2, 3 or 4;

R$^8$ is hydroxy, aryl or heteroaryl, wherein aryl or heteroaryl is substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

R$^9$ is H, alkyl, haloalkyl, aminoalkyl, cycloalkyl, heterocyclyl, or aryl, wherein R$^9$ is optionally substituted by one or more D; and A, B and D are independently selected from halo, nitro, cyano, hydroxy, oxo, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$-amino, C$_{1-10}$ alkanoylamino, N—(C$_{1-10}$ alkyl)carbamoyl, N,N—(C$_{1-10}$ alkyl)$_2$-carbamoyl, C$_{1-10}$ alkyl-S(O)$_a$ wherein a is 0, 1 or 2, C$_{1-10}$ alkoxycarbonyl, N—(C$_{1-10}$ alkyl)sulphamoyl, N,N—(C$_{1-10}$ alkyl)$_2$sulphamoyl, H$_2$NS(O)$_2$NH—, N—(C$_{1-10}$ alkyl)NHS(O)$_2$NH—, N,N—(C$_{1-10}$ alkyl)$_2$NS(O)$_2$NH—, aryl, aryloxy, arylthio, cycloalkyl, cycloalkyloxy, heterocyclyl, heterocyclyl(C=O)—, heterocyclyloxy and heterocyclylthio.

2. The compound of claim 1, wherein R$^8$ is hydroxy, phenyl or 5-membered or 6-membered heteroaryl, wherein phenyl or heteroaryl is substituted with —NH$_2$ or —OH at a ring position adjacent to attachment of the —CONH-moiety, and phenyl or heteroaryl is optionally further substituted with one or more substituent selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

3. The compound according to claim 1, wherein Q$^1$ and Q$^2$ together with the imidazole ring to which they are attached form a cyclic moiety to make a fused aromatic ring system selected from the group consisting of:

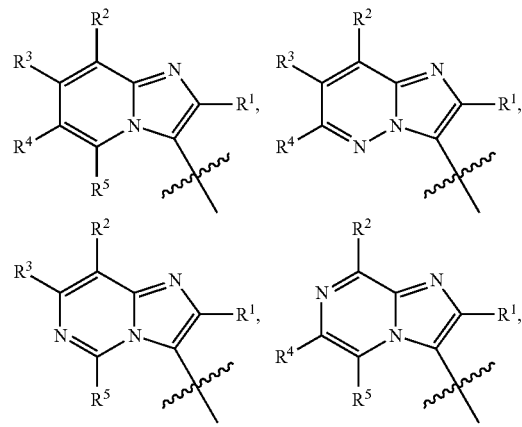

-continued

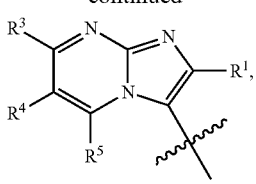

wherein the wavy lines show the point of attachment to the 6-membered nitrogen containing heteroaryl and wherein $R^2$, $R^3$, $R^4$, and $R^5$ are independently selected from groups $R^1$ optionally substituted with one or more A.

4. The compound according to claim 1, wherein $U^1$, $U^2$, $U^3$ and $U^4$ are selected to form any of the following heteroaryl moieties

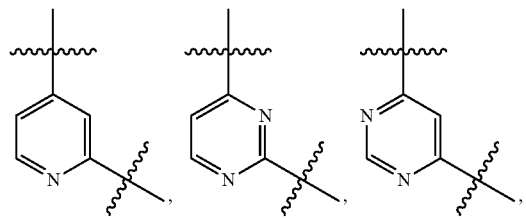

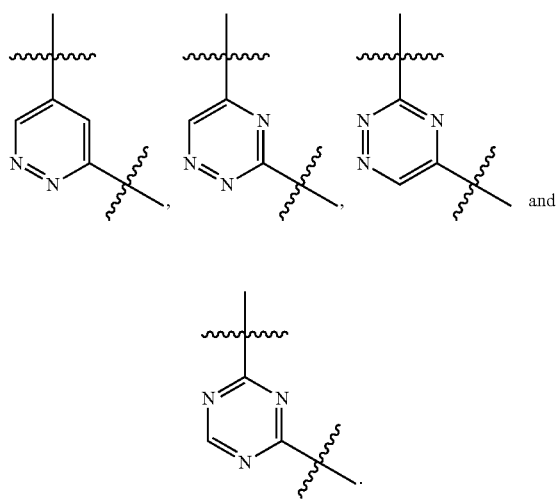

and

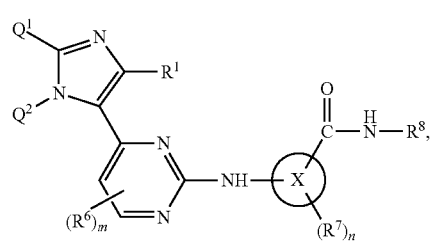

.

5. The compound of claim 1 selected from those of Formulae ($I^a$), ($I^b$) and ($I^c$) and pharmaceutically acceptable salts thereof:

Formula ($I^a$)

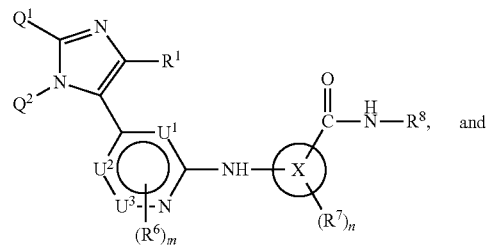

-continued

Formula ($I^b$)

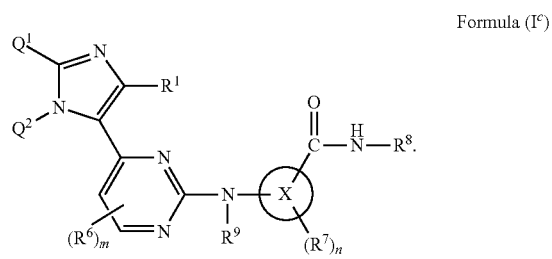

and

Formula ($I^c$)

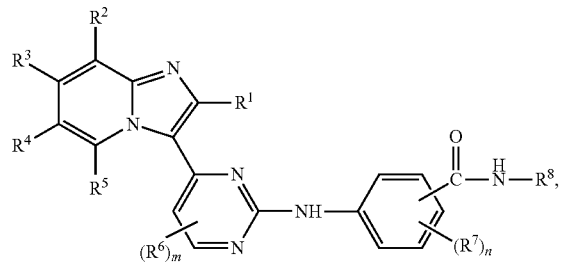

.

6. The compound of claim 5 selected from those of Formulae ($I^a$-a), ($I^a$-b), ($I^a$-c), ($I^a$-d), ($I^a$-e), ($I^a$-f), ($I^a$-g), and ($I^a$-h), and pharmaceutically acceptable salts thereof:

Formula ($I^a$-a)

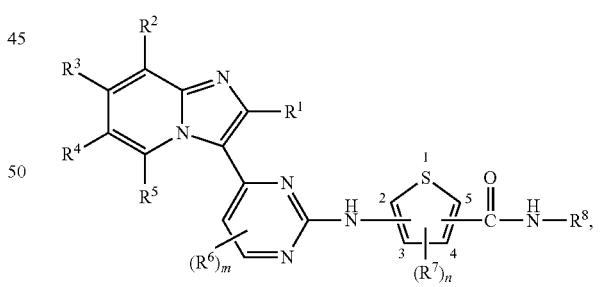

Formula ($I^a$-b)

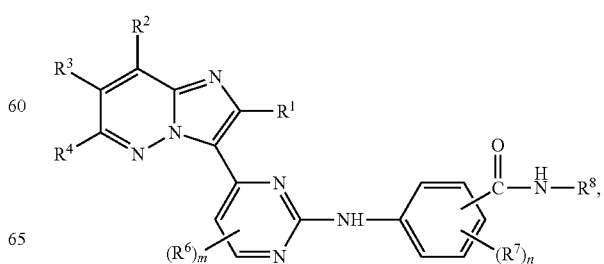

Formula ($I^a$-c)

-continued

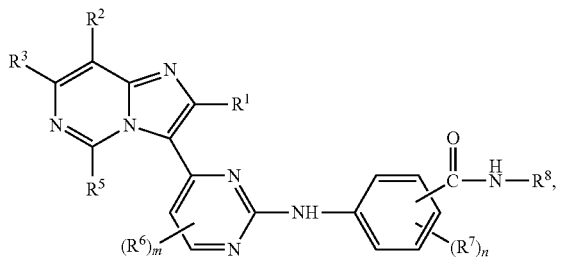

Formula (I$^a$-d)

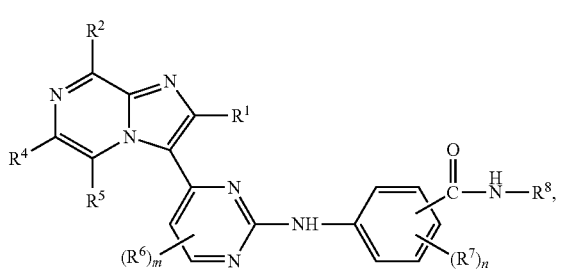

Formula (I$^a$-e)

Formula (I$^a$-f)

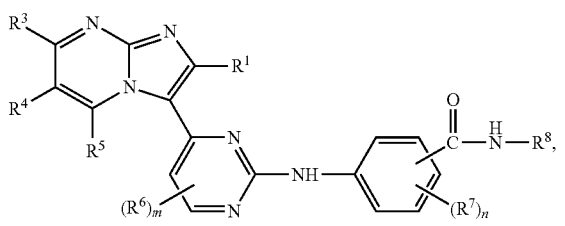

Formula (I$^a$-g)

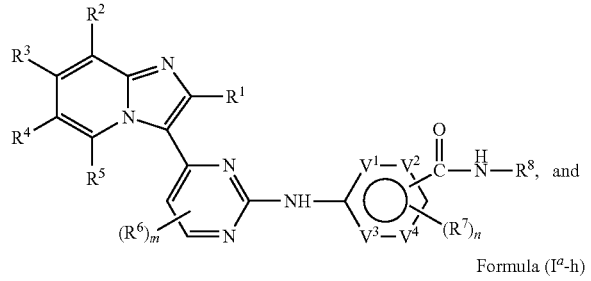

Formula (I$^a$-h)

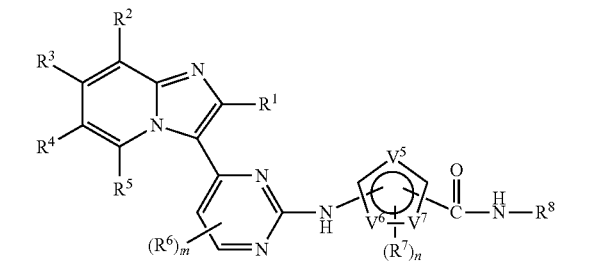

wherein
R$^1$, R$^2$, R$^3$, R$^4$ and R$^5$ are independently selected from the group consisting of H, halo, nitro, cyano, hydroxy, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$-amino, C$_{1-10}$ alkanoylamino, N—(C$_{1-10}$ alkyl)carbamoyl, N,N—(C$_{1-10}$ alkyl)$_2$-carbamoyl, C$_{1-10}$ alkyl-S(O)$_a$ wherein a is 0, 1 or 2, C$_{1-10}$ alkoxycarbonyl, NH$_2$—S(O)$_2$NH—, N—(C$_{1-10}$ alkyl) sulphamoyl, N,N—(C$_{1-10}$ alkyl)$_2$sulphamoyl, aryl, aryloxy, arylthio, cycloalkyl, cycloalkyloxy, heterocyclyl, heterocyclyl(C=O)—, heterocyclyloxy and heterocyclylthio; wherein each of R$^1$, R$^2$, R$^3$, R$^4$ and R$^5$ is optionally substituted by one or more A; and V$^1$, V$^2$, V$^3$, V$^4$, V$^5$, V$^6$, and V$^7$ are ring atoms independently selected from N, O, S, and C.

7. The compound of claim 6 selected from those of Formula (I$^a$-a), wherein at least two of R$^1$, R$^2$, R$^3$, R$^4$ and R$^5$ are H, and each non-hydrogen R$^1$, R$^2$, R$^3$, R$^4$ and R$^5$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminomethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

n is 0, 1, or 2 and m is 0 or 1;

R$^6$, if present, is halo, hydroxy, alkyl or haloalkyl;

R$^7$, if present, is fluoro, chloro, bromo, or methyl; and

R$^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl)phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropyl-prop-1-ynyl)phenyl or 2-amino-5-(3-(1-hydroxycyclopropyl)prop-1-ynyl)phenyl.

8. The compound of claim 7 which is selected from the group consisting of:

N-hydroxy-4-(4-(imidazo[1,2-a]pyridin-3-yl)pyrimidin-2-ylamino)benzamide;
N-hydroxy-3-(4-(imidazo[1,2-a]pyridin-3-yl)pyrimidin-2-ylamino)benzamide;
N-hydroxy-4-(4-(imidazo[1,2-a]pyridin-3-yl)-5-methylpyrimidin-2-ylamino)benzamide;
N-hydroxy-3-(4-(imidazo[1,2-a]pyridin-3-yl)-5-methylpyrimidin-2-ylamino)benzamide;
N-(2-aminophenyl)-4-(4-(imidazo[1,2-a]pyridin-3-yl)pyrimidin-2-ylamino)benzamide;
N-(2-aminophenyl)-3-(4-(imidazo[1,2-a]pyridin-3-yl)pyrimidin-2-ylamino)benzamide;
N-(2-aminophenyl)-4-(4-(imidazo[1,2-a]pyridin-3-yl)-5-methylpyrimidin-2-ylamino)benzamide;
N-(2-aminophenyl)-3-(4-(imidazo[1,2-a]pyridin-3-yl)-5-methylpyrimidin-2-ylamino)benzamide;
N-hydroxy-4-(4-(2-methylimidazo[1,2-a]pyridin-3-yl)pyrimidin-2-ylamino)benzamide;
N-hydroxy-3-(4-(2-methylimidazo[1,2-a]pyridin-3-yl)pyrimidin-2-ylamino)benzamide;
N-hydroxy-4-(5-methyl-4-(2-methylimidazo[1,2-a]pyridin-3-yl)pyrimidin-2-ylamino)benzamide;
N-hydroxy-3-(5-methyl-4-(2-methylimidazo[1,2-a]pyridin-3-yl)pyrimidin-2-ylamino)benzamide;
N-(2-aminophenyl)-4-(4-(2-methylimidazo[1,2-a]pyridin-3-yl)pyrimidin-2-ylamino)benzamide;
N-(2-aminophenyl)-3-(4-(2-methylimidazo[1,2-a]pyridin-3-yl)pyrimidin-2-ylamino)benzamide;
N-(2-aminophenyl)-4-(5-methyl-4-(2-methylimidazo[1,2-a]pyridin-3-yl)pyrimidin-2-ylamino)benzamide;
N-(2-aminophenyl)-3-(5-methyl-4-(2-methylimidazo[1,2-a]pyridin-3-yl)pyrimidin-2-ylamino)benzamide;
4-(4-(6-chloro-2-methylimidazo[1,2-a]pyridin-3-yl)pyrimidin-2-ylamino)-N-hydroxybenzamide;
N-(2-aminophenyl)-4-(4-(6-chloro-2-methylimidazo[1,2-a]pyridin-3-yl)pyrimidin-2-ylamino)benzamide;
N-hydroxy-4-(4-(7-methoxy-2-methylimidazo[1,2-a]pyridin-3-yl)pyrimidin-2-ylamino)benzamide;
N-(2-aminophenyl)-4-(4-(7-methoxy-2-methylimidazo[1,2-a]pyridin-3-yl)pyrimidin-2-ylamino)benzamide;
4-(4-(7-((dimethylamino)methyl)imidazo[1,2-a]pyridin-3-yl)pyrimidin-2-ylamino)-N-hydroxybenzamide;
N-(2-aminophenyl)-4-(4-(7-((dimethylamino)methyl)imidazo[1,2-a]pyridin-3-yl)pyrimidin-2-ylamino)benzamide;
N-hydroxy-4-(4-(7-(pyrrolidin-1-ylmethyl)imidazo[1,2-a]pyridin-3-yl)pyrimidin-2-ylamino)benzamide;
N-(2-aminophenyl)-4-(4-(7-(pyrrolidin-1-ylmethyl)imidazo[1,2-a]pyridin-3-yl)pyrimidin-2-ylamino)benzamide;
N-hydroxy-4-(4-(7-(morpholinomethyl)imidazo[1,2-a]pyridin-3-yl)pyrimidin-2-ylamino)benzamide;
N-(2-aminophenyl)-4-(4-(7-(morpholinomethyl)imidazo[1,2-a]pyridin-3-yl)pyrimidin-2-ylamino)benzamide;
N-hydroxy-4-(4-(2-methyl-6-(trifluoromethyl)imidazo[1,2-a]pyridin-3-yl)pyrimidin-2-ylamino)benzamide;
N-(2-aminophenyl)-4-(4-(2-methyl-6-(trifluoromethyl)imidazo[1,2-a]pyridin-3-yl)pyrimidin-2-ylamino)benzamide;
N-hydroxy-4-(4-(2-methyl-7-(trifluoromethyl)imidazo[1,2-a]pyridin-3-yl)pyrimidin-2-ylamino)benzamide;
N-(2-aminophenyl)-4-(4-(2-methyl-7-(trifluoromethyl)imidazo[1,2-a]pyridin-3-yl)pyrimidin-2-ylamino)benzamide;
3-(2-(4-(hydroxycarbamoyl)phenylamino)pyrimidin-4-yl)-N-(2-methoxyethyl)-2-methylimidazo[1,2-a]pyridine-7-carboxamide;
3-(2-(4-(2-aminophenylcarbamoyl)phenylamino)pyrimidin-4-yl)-N-(2-methoxyethyl)-2-methylimidazo[1,2-a]pyridine-7-carboxamide;
4-(4-(7-cyano-2-methylimidazo[1,2-a]pyridin-3-yl)pyrimidin-2-ylamino)-N-hydroxybenzamide;
N-(2-aminophenyl)-4-(4-(7-cyano-2-methylimidazo[1,2-a]pyridin-3-yl)pyrimidin-2-ylamino)benzamide;
3-(2-(4-(hydroxycarbamoyl)phenylamino)pyrimidin-4-yl)-2-methyl-N-(2-morpholinoethyl)imidazo[1,2-a]pyridine-7-carboxamide;
3-(2-(4-(2-aminophenylcarbamoyl)phenylamino)pyrimidin-4-yl)-2-methyl-N-(2-morpholinoethyl)imidazo[1,2-a]pyridine-7-carboxamide;
methyl 3-(2-(4-(hydroxycarbamoyl)phenylamino)pyrimidin-4-yl)-2-methylimidazo[1,2-a]pyridine-7-carboxylate;
methyl 3-(2-(4-(2-aminophenylcarbamoyl)phenylamino)pyrimidin-4-yl)-2-methylimidazo[1,2-a]pyridine-7-carboxylate;
N-hydroxy-4-(4-(2-methyl-7-(4-methylpiperazine-1-carbonyl)imidazo[1,2-a]pyridin-3-yl)pyrimidin-2-ylamino)benzamide;
N-(2-aminophenyl)-4-(4-(2-methyl-7-(4-methylpiperazine-1-carbonyl)imidazo[1,2-a]pyridin-3-yl)pyrimidin-2-ylamino)benzamide;
3-(2-(4-(hydroxycarbamoyl)phenylamino)pyrimidin-4-yl)-2-methylimidazo[1,2-a]pyridine-7-carboxylic acid;
3-(2-(4-(2-aminophenylcarbamoyl)phenylamino)pyrimidin-4-yl)-2-methylimidazo[1,2-a]pyridine-7-carboxylic acid;
N-hydroxy-4-(4-(2-methyl-7-(2-morpholinoethoxy)imidazo[1,2-a]pyridin-3-yl)pyrimidin-2-ylamino)benzamide;
N-(2-aminophenyl)-4-(4-(2-methyl-7-(2-morpholinoethoxy)imidazo[1,2-a]pyridin-3-yl)pyrimidin-2-ylamino)benzamide;
4-(4-(7-(2-(dimethylamino)ethoxy)-2-methylimidazo[1,2-a]pyridin-3-yl)pyrimidin-2-ylamino)-N-hydroxybenzamide;
N-(2-aminophenyl)-4-(4-(7-(2-(dimethylamino)ethoxy)-2-methylimidazo[1,2-a]pyridin-3-yl)pyrimidin-2-ylamino)benzamide;
N-hydroxy-4-(4-(7-(2-methoxyethoxy)-2-methylimidazo[1,2-a]pyridin-3-yl)pyrimidin-2-ylamino)benzamide;
N-(2-aminophenyl)-4-(4-(7-(2-methoxyethoxy)-2-methylimidazo[1,2-a]pyridin-3-yl)pyrimidin-2-ylamino)benzamide;
4-(4-(7-(2-(dimethylamino)ethylamino)-2-methylimidazo[1,2-a]pyridin-3-yl)pyrimidin-2-ylamino)-N-hydroxybenzamide;
N-(2-aminophenyl)-4-(4-(7-(2-(dimethylamino)ethylamino)-2-methylimidazo[1,2-a]pyridin-3-yl)pyrimidin-2-ylamino)benzamide;
3-(2-(4-(hydroxycarbamoyl)phenylamino)pyrimidin-4-yl)-N-(2-methoxyethyl)-2-methylimidazo[1,2-a]pyridine-6-carboxamide;
3-(2-(4-(2-aminophenylcarbamoyl)phenylamino)pyrimidin-4-yl)-N-(2-methoxyethyl)-2-methylimidazo[1,2-a]pyridine-6-carboxamide;
N-hydroxy-4-(4-(2-methyl-6-(4-methylpiperazine-1-carbonyl)imidazo[1,2-a]pyridin-3-yl)pyrimidin-2-ylamino)benzamide;

N-(2-aminophenyl)-4-(4-(2-methyl-6-(4-methylpiperazine-1-carbonyl)imidazo[1,2-a]pyridin-3-yl)pyridin-2-ylamino)benzamide;
3-(2-(4-(hydroxycarbamoyl)phenylamino)pyrimidin-4-yl)-2-methyl-N-(2-morpholinoethyl)imidazo[1,2-a]pyridine-6-carboxamide;
3-(2-(4-(2-aminophenylcarbamoyl)phenylamino)pyrimidin-4-yl)-2-methyl-N-(2-morpholinoethyl)imidazo[1,2-a]pyridine-6-carboxamide;
N-hydroxy-4-(4-(6-(2-methoxyethoxy)-2-methylimidazo[1,2-a]pyridin-3-yl)pyrimidin-2-ylamino)benzamide;
N-(2-aminophenyl)-4-(4-(6-(2-methoxyethoxy)-2-methylimidazo[1,2-a]pyridin-3-yl)pyrimidin-2-ylamino)benzamide;
N-hydroxy-4-(4-(6-methoxy-2-methylimidazo[1,2-a]pyridin-3-yl)pyrimidin-2-ylamino)benzamide;
N-(2-aminophenyl)-4-(4-(6-methoxy-2-methylimidazo[1,2-a]pyridin-3-yl)pyrimidin-2-ylamino)benzamide;
4-(4-(8-fluoro-2-methylimidazo[1,2-a]pyridin-3-yl)pyrimidin-2-ylamino)-N-hydroxybenzamide;
N-(2-aminophenyl)-4-(4-(8-fluoro-2-methylimidazo[1,2-a]pyridin-3-yl)pyrimidin-2-ylamino)benzamide;
4-(4-(7-((dimethylamino)methyl)-2-methylimidazo[1,2-a]pyridin-3-yl)pyrimidin-2-ylamino)-N-hydroxybenzamide;
N-(2-aminophenyl)-4-(4-(7-((dimethylamino)methyl)-2-methylimidazo[1,2-a]pyridin-3-yl)pyrimidin-2-ylamino)benzamide;
4-(4-(6-bromo-2-methylimidazo[1,2-a]pyridin-3-yl)pyrimidin-2-ylamino)-N-hydroxybenzamide;
N-(2-aminophenyl)-4-(4-(6-bromo-2-methylimidazo[1,2-a]pyridin-3-yl)pyrimidin-2-ylamino)benzamide;
N-hydroxy-4-(4-(7-methoxy-2-(trifluoromethyl)imidazo[1,2-a]pyridin-3-yl)pyrimidin-2-ylamino)benzamide;
N-(2-aminophenyl)-4-(4-(7-methoxy-2-(trifluoromethyl)imidazo[1,2-a]pyridin-3-yl)pyrimidin-2-ylamino)benzamide;
N-hydroxy-4-(4-(2-(trifluoromethyl)imidazo[1,2-a]pyridin-3-yl)pyrimidin-2-ylamino)benzamide;
N-(2-aminophenyl)-4-(4-(2-(trifluoromethyl)imidazo[1,2-a]pyridin-3-yl)pyrimidin-2-ylamino)benzamide;
4-(4-(7-cyano-2-methylimidazo[1,2-a]pyridin-3-yl)pyrimidin-2-ylamino)-N-hydroxybenzamide;
N-(2-aminophenyl)-4-(4-(7-cyano-2-methylimidazo[1,2-a]pyridin-3-yl)pyrimidin-2-ylamino)benzamide;
methyl 3-(2-(4-(hydroxycarbamoyl)phenylamino)pyrimidin-4-yl)-2-methylimidazo[1,2-a]pyridine-7-carboxylate;
methyl 3-(2-(4-(2-aminophenylcarbamoyl)phenylamino)pyrimidin-4-yl)-2-methylimidazo[1,2-a]pyridine-7-carboxylate;
3-(2-(4-(hydroxycarbamoyl)phenylamino)pyrimidin-4-yl)-2-methylimidazo[1,2-a]pyridine-7-carboxylic acid;
3-(2-(4-(2-aminophenylcarbamoyl)phenylamino)pyrimidin-4-yl)-2-methylimidazo[1,2-a]pyridine-7-carboxylic acid;
3-fluoro-N-hydroxy-4-(4-(2-methylimidazo[1,2-a]pyridin-3-yl)pyrimidin-2-ylamino)benzamide;
N-(2-aminophenyl)-3-fluoro-4-(4-(2-methylimidazo[1,2-a]pyridin-3-yl)pyrimidin-2-ylamino)benzamide;
2-fluoro-N-hydroxy-4-(4-(2-methylimidazo[1,2-a]pyridin-3-yl)pyrimidin-2-ylamino)benzamide;
N-(2-aminophenyl)-2-fluoro-4-(4-(2-methylimidazo[1,2-a]pyridin-3-yl)pyrimidin-2-ylamino)benzamide;
N-(2-(dimethylamino)ethyl)-3-(2-(4-(hydroxycarbamoyl)phenylamino)pyrimidin-4-yl)-2-methylimidazo[1,2-a]pyridine-6-carboxamide;
3-(2-(4-(2-aminophenylcarbamoyl)phenylamino)pyrimidin-4-yl)-N-(2-(dimethylamino)ethyl)-2-methylimidazo[1,2-a]pyridine-6-carboxamide;
4-(5-fluoro-4-(imidazo[1,2-a]pyridin-3-yl)pyrimidin-2-ylamino)-N-hydroxybenzamide;
N-(2-Amino-phenyl)-4-[4-(2-methyl-7-morpholin-4-yl-imidazo[1,2-a]pyridin-3-yl)-pyrimidin-2-ylamino]-benzamide;
N-(2-aminophenyl)-4-(5-fluoro-4-(imidazo[1,2-a]pyridin-3-yl)pyrimidin-2-ylamino)benzamide; and
pharmaceutically acceptable salts thereof.

9. The compound of claim 6 selected from those of Formulae (I$^a$-b0), (I$^a$-b1), and (I$^a$-b2) and pharmaceutically acceptable salts thereof:

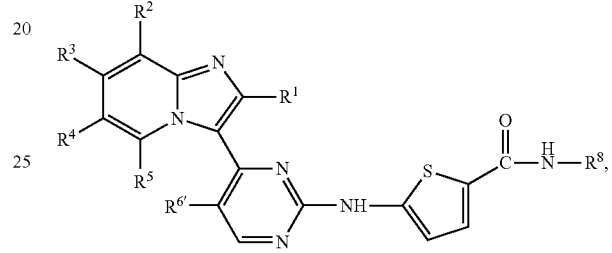

Formula (I$^a$-b0)

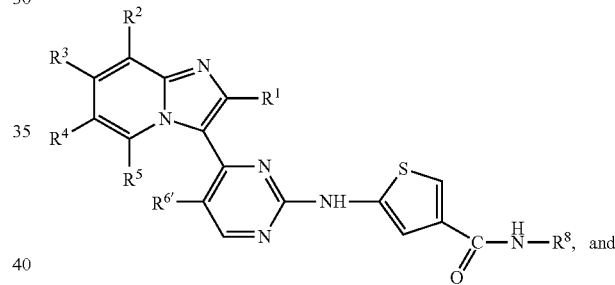

Formula (I$^a$-b1)

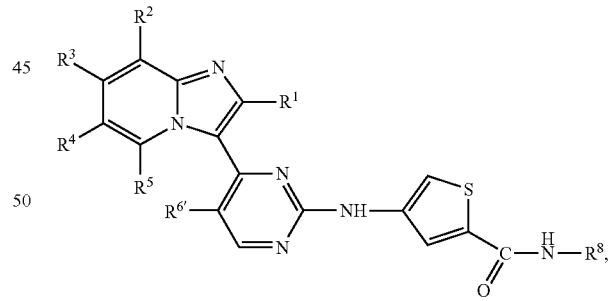

Formula (I$^a$-b2)

wherein R$^{6'}$ is H or R$^6$.

10. The compound of claim 9 which is selected from the group consisting of:
N-hydroxy-5-(4-(imidazo[1,2-a]pyridin-3-yl)pyrimidin-2-ylamino)thiophene-2-carboxamide;
N-(2-aminophenyl)-5-(4-(imidazo[1,2-a]pyridin-3-yl)pyrimidin-2-ylamino)thiophene-2-carboxamide;
N-hydroxy-5-(4-(2-methylimidazo[1,2-a]pyridin-3-yl)pyrimidin-2-ylamino)thiophene-2-carboxamide;
N-(2-aminophenyl)-5-(4-(2-methylimidazo[1,2-a]pyridin-3-yl)pyrimidin-2-ylamino)thiophene-2-carboxamide;

N-hydroxy-5-(4-(7-methoxy-2-methylimidazo[1,2-a]pyridin-3-yl)pyrimidin-2-ylamino)thiophene-2-carboxamide;

N-(2-aminophenyl)-5-(4-(7-methoxy-2-methylimidazo[1,2-a]pyridin-3-yl)pyrimidin-2-ylamino)thiophene-2-carboxamide;

N-hydroxy-5-(4-(2-methyl-6-(trifluoromethyl)imidazo[1,2-a]pyridin-3-yl)pyrimidin-2-ylamino)thiophene-2-carboxamide;

N-(2-aminophenyl)-5-(4-(2-methyl-6-(trifluoromethyl)imidazo[1,2-a]pyridin-3-yl)pyrimidin-2-ylamino)thiophene-2-carboxamide;

N-hydroxy-5-(4-(2-methyl-7-(trifluoromethyl)imidazo[1,2-a]pyridin-3-yl)pyrimidin-2-ylamino)thiophene-2-carboxamide;

N-(2-aminophenyl)-5-(4-(2-methyl-7-(trifluoromethyl)imidazo[1,2-a]pyridin-3-yl)pyrimidin-2-ylamino)thiophene-2-carboxamide;

N-hydroxy-5-(4-(7-methoxy-2-(trifluoromethyl)imidazo[1,2-a]pyridin-3-yl)pyrimidin-2-ylamino)thiophene-2-carboxamide;

N-(2-aminophenyl)-5-(4-(7-methoxy-2-(trifluoromethyl)imidazo[1,2-a]pyridin-3-yl)pyrimidin-2-ylamino)thiophene-2-carboxamide;

N-hydroxy-5-(4-(2-(trifluoromethyl)imidazo[1,2-a]pyridin-3-yl)pyrimidin-2-ylamino)thiophene-2-carboxamide;

N-(2-aminophenyl)-5-(4-(2-(trifluoromethyl)imidazo[1,2-a]pyridin-3-yl)pyrimidin-2-ylamino)thiophene-2-carboxamide;

N-hydroxy-5-(4-(2-methylimidazo[1,2-a]pyridin-3-yl)pyrimidin-2-ylamino)thiophene-2-carboxamide;

N-(2-aminophenyl)-5-(4-(2-methylimidazo[1,2-a]pyridin-3-yl)pyrimidin-2-ylamino)thiophene-2-carboxamide;

N-hydroxy-5-(4-(2-methylimidazo[1,2-a]pyridin-3-yl)pyrimidin-2-ylamino)thiophene-3-carboxamide;

N-(2-aminophenyl)-5-(4-(2-methylimidazo[1,2-a]pyridin-3-yl)pyrimidin-2-ylamino)thiophene-3-carboxamide;

N-hydroxy-4-(4-(2-methylimidazo[1,2-a]pyridin-3-yl)pyrimidin-2-ylamino)thiophene-2-carboxamide; and pharmaceutically acceptable salts thereof.

11. The compound of claim 6 selected from those of Formula (I$^a$-c), wherein at least two of $R^1$, $R^2$, $R^3$ and $R^4$ are H, and each of non-hydrogen $R^1$, $R^2$, $R^3$ and $R^4$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyraziny-loxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

n is 0, 1, or 2 and m is 0 or 1;

$R^6$, if present, is halo, hydroxy, alkyl or haloalkyl;

$R^7$, if present, is fluoro, chloro, bromo, or methyl; and $R^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl)phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropyl-prop-1-ynyl)phenyl or 2-amino-5-(3-(1-hydroxycyclopropyl)prop-1-ynyl)phenyl.

12. The compound of claim 11 which is selected from the group consisting of:

N-hydroxy-4-(4-(imidazo[1,2-b]pyridazin-3-yl)pyrimidin-2-ylamino)benzamide;

N-(2-aminophenyl)-4-(4-(imidazo[1,2-b]pyridazin-3-yl)pyrimidin-2-ylamino)benzamide;

N-hydroxy-4-(4-(2-methylimidazo[1,2-b]pyridazin-3-yl)pyrimidin-2-ylamino)benzamide;

N-(2-aminophenyl)-4-(4-(2-methylimidazo[1,2-b]pyridazin-3-yl)pyrimidin-2-ylamino)benzamide;

N-hydroxy-4-(4-(7-methoxy-2-methylimidazo[1,2-b]pyridazin-3-yl)pyrimidin-2-ylamino)benzamide;

N-(2-aminophenyl)-4-(4-(7-methoxy-2-methylimidazo[1,2-b]pyridazin-3-yl)pyrimidin-2-ylamino)benzamide;

N-hydroxy-4-(4-(2-methyl-6-(trifluoromethyl)imidazo[1,2-b]pyridazin-3-yl)pyrimidin-2-ylamino)benzamide;

N-(2-aminophenyl)-4-(4-(2-methyl-6-(trifluoromethyl)imidazo[1,2-b]pyridazin-3-yl)pyrimidin-2-ylamino)benzamide;

N-hydroxy-4-(4-(2-methyl-7-(trifluoromethyl)imidazo[1,2-b]pyridazin-3-yl)pyrimidin-2-ylamino)benzamide;

N-(2-aminophenyl)-4-(4-(2-methyl-7-(trifluoromethyl)imidazo[1,2-b]pyridazin-3-yl)pyrimidin-2-ylamino)benzamide;

N-hydroxy-4-(4-(7-methoxy-2-(trifluoromethyl)imidazo[1,2-b]pyridazin-3-yl)pyrimidin-2-ylamino)benzamide;

N-(2-aminophenyl)-4-(4-(7-methoxy-2-(trifluoromethyl)imidazo[1,2-b]pyridazin-3-yl)pyrimidin-2-ylamino)benzamide; and pharmaceutically acceptable salts thereof.

13. The compound of claim 6 selected from those of Formula (I$^a$-d), wherein at least two of $R^1$, $R^2$, $R^3$ and $R^5$ are H, and each of non-hydrogen $R^1$, $R^2$, $R^3$ and $R^5$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

n is 0, 1, or 2 and m is 0 or 1;

$R^6$, if present, is halo, hydroxy, alkyl or haloalkyl;

$R^7$, if present, is fluoro, chloro, bromo, or methyl; and $R^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl)phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropylprop-1-ynyl)phenyl or 2-amino-5-(3-(1-hydroxycyclopropyl)prop-1-ynyl)phenyl.

14. The compound of claim 13 which is selected from the group consisting of:

N-hydroxy-4-(4-(imidazo[1,2-c]pyrimidin-3-yl)pyrimidin-2-ylamino)benzamide;

N-(2-aminophenyl)-4-(4-(imidazo[1,2-c]pyrimidin-3-yl)pyrimidin-2-ylamino)benzamide;

N-hydroxy-4-(4-(2-methylimidazo[1,2-c]pyrimidin-3-yl)pyrimidin-2-ylamino)benzamide;

N-(2-aminophenyl)-4-(4-(2-methylimidazo[1,2-c]pyrimidin-3-yl)pyrimidin-2-ylamino)benzamide;

N-hydroxy-4-(4-(7-methoxy-2-methylimidazo[1,2-c]pyrimidin-3-yl)pyrimidin-2-ylamino)benzamide;

N-(2-aminophenyl)-4-(4-(7-methoxy-2-methylimidazo[1,2-c]pyrimidin-3-yl)pyrimidin-2-ylamino)benzamide;

N-hydroxy-4-(4-(2-methyl-7-(trifluoromethyl)imidazo[1,2-c]pyrimidin-3-yl)pyrimidin-2-ylamino)benzamide;

N-(2-aminophenyl)-4-(4-(2-methyl-7-(trifluoromethyl)imidazo[1,2-c]pyrimidin-3-yl)pyrimidin-2-ylamino)benzamide;

N-hydroxy-4-(4-(7-methoxy-2-(trifluoromethyl)imidazo[1,2-c]pyrimidin-3-yl)pyrimidin-2-ylamino)benzamide;

N-(2-aminophenyl)-4-(4-(7-methoxy-2-(trifluoromethyl)imidazo[1,2-c]pyrimidin-3-yl)pyrimidin-2-ylamino)benzamide; and pharmaceutically acceptable salts thereof.

15. The compound of claim 6 selected from those of Formula (I$^a$-e), wherein at least two of $R^1$, $R^2$, $R^4$ and $R^5$ are H, and each of non-hydrogen $R^1$, $R^2$, $R^4$ and $R^5$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

n is 0, 1, or 2 and m is 0 or 1;

$R^6$, if present, is halo, hydroxy, alkyl or haloalkyl;

$R^7$, if present, is fluoro, chloro, bromo, or methyl; and $R^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl)phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropyl-prop-1-ynyl)phenyl or 2-amino-5-(3-(1-hydroxycyclopropyl)prop-1-ynyl)phenyl.

16. The compound of claim 15 which is selected from the group consisting of:
N-hydroxy-4-(4-(imidazo[1,2-a]pyrazin-3-yl)pyrimidin-2-ylamino)benzamide;
N-(2-aminophenyl)-4-(4-(imidazo[1,2-a]pyrazin-3-yl)pyrimidin-2-ylamino)benzamide;
N-hydroxy-4-(4-(2-methylimidazo[1,2-a]pyrazin-3-yl)pyrimidin-2-ylamino)benzamide;
N-(2-aminophenyl)-4-(4-(2-methylimidazo[1,2-a]pyrazin-3-yl)pyrimidin-2-ylamino)benzamide;
N-hydroxy-4-(4-(2-methyl-6-(trifluoromethyl)imidazo[1,2-a]pyrazin-3-yl)pyrimidin-2-ylamino)benzamide;
N-(2-aminophenyl)-4-(4-(2-methyl-6-(trifluoromethyl)imidazo[1,2-a]pyrazin-3-yl)pyrimidin-2-ylamino)benzamide; and
pharmaceutically acceptable salts thereof.

17. The compound of claim 6 selected from those of Formula (I$^a$-f), wherein
at least two of R$^1$, R$^3$, R$^4$ and R$^5$ are H, and each of non-hydrogen R$^1$, R$^3$, R$^4$ and R$^5$ is independently selected from the group consisting of chloro, fluoro, bromo, methyl, ethyl, propyl, isopropyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminoethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;
n is 0, 1, or 2 and m is 0 or 1;
R$^6$, if present, is halo, hydroxy, alkyl or haloalkyl;
R$^7$, if present, is fluoro, chloro, bromo, or methyl; and
R$^8$ is hydroxy, 2-hydroxyphenyl, 2-aminophenyl, 2-amino-6-fluorophenyl, 2-amino-5-fluorophenyl, 2-amino-5-trifluoromethylphenyl, 4-aminobiphenyl-3-yl, 4'-fluoro-4-aminobiphenyl-3-yl, 2-amino-5-(thiophen-2-yl)phenyl, 5'-chloro-2-amino-5-(thiophen-2-yl)phenyl, 5'-methyl-2-amino-5-(thiophen-2-yl)phenyl, 2-amino-5-(thiophen-3-yl)phenyl, 2-aminopyridin-3-yl, 4-amino-1-phenyl-1H-pyrazol-3-yl, 2-amino-5-(3-hydroxy-3-methylbut-1-ynyl)phenyl, 2-amino-5-(4,4,4-trifluoro-3-hydroxy-3-(trifluoromethyl)but-1-ynyl)phenyl, 2-amino-5-(3-cyclopropyl-prop-1-ynyl)phenyl or 2-amino-5-(3-(1-hydroxycyclopropyl)prop-1-ynyl)phenyl.

18. The compound of claim 17 which is selected from the group consisting of:
N-hydroxy-4-(4-(imidazo[1,2-a]pyrimidin-3-yl)pyrimidin-2-ylamino)benzamide;
N-(2-aminophenyl)-4-(4-(imidazo[1,2-a]pyrimidin-3-yl)pyrimidin-2-ylamino)benzamide;
N-hydroxy-4-(4-(2-methylimidazo[1,2-a]pyrimidin-3-yl)pyrimidin-2-ylamino)benzamide;
N-(2-Amino-phenyl)-4-[4-(2-methyl-imidazo[1,2-a]pyrimidin-3-yl)-pyrimidin-2-ylamino]-benzamide;
N-hydroxy-4-(4-(7-methoxy-2-methylimidazo[1,2-a]pyrimidin-3-yl)pyrimidin-2-ylamino)benzamide;
N-(2-aminophenyl)-4-(4-(7-methoxy-2-methylimidazo[1,2-a]pyrimidin-3-yl)pyrimidin-2-ylamino)benzamide;
N-hydroxy-4-(4-(2-methyl-6-(trifluoromethyl)imidazo[1,2-a]pyrimidin-3-yl)pyrimidin-2-ylamino)benzamide;
N-(2-aminophenyl)-4-(4-(2-methyl-6-(trifluoromethyl)imidazo[1,2-a]pyrimidin-3-yl)pyrimidin-2-ylamino)benzamide;
N-hydroxy-4-(4-(2-methyl-7-(trifluoromethyl)imidazo[1,2-a]pyrimidin-3-yl)pyrimidin-2-ylamino)benzamide;
N-(2-aminophenyl)-4-(4-(2-methyl-7-(trifluoromethyl)imidazo[1,2-a]pyrimidin-3-yl)pyrimidin-2-ylamino)benzamide;
N-hydroxy-4-(4-(7-methoxy-2-(trifluoromethyl)imidazo[1,2-a]pyrimidin-3-yl)pyrimidin-2-ylamino)benzamide;
N-(2-aminophenyl)-4-(4-(7-methoxy-2-(trifluoromethyl)imidazo[1,2-a]pyrimidin-3-yl)pyrimidin-2-ylamino)benzamide; and
pharmaceutically acceptable salts thereof.

19. The compound of claim 6 selected from those of Formulae (I$^a$-g0), (I$^a$-g1), (I$^a$-g2), and (I$^a$-g3), and pharmaceutically acceptable salts thereof:

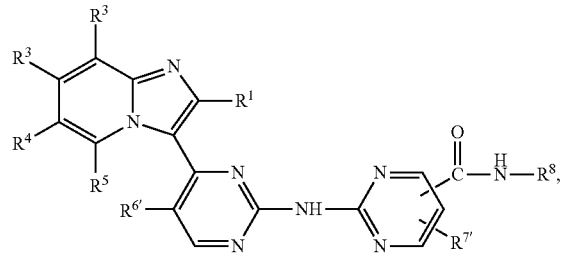

Formula (I$^a$-g0)

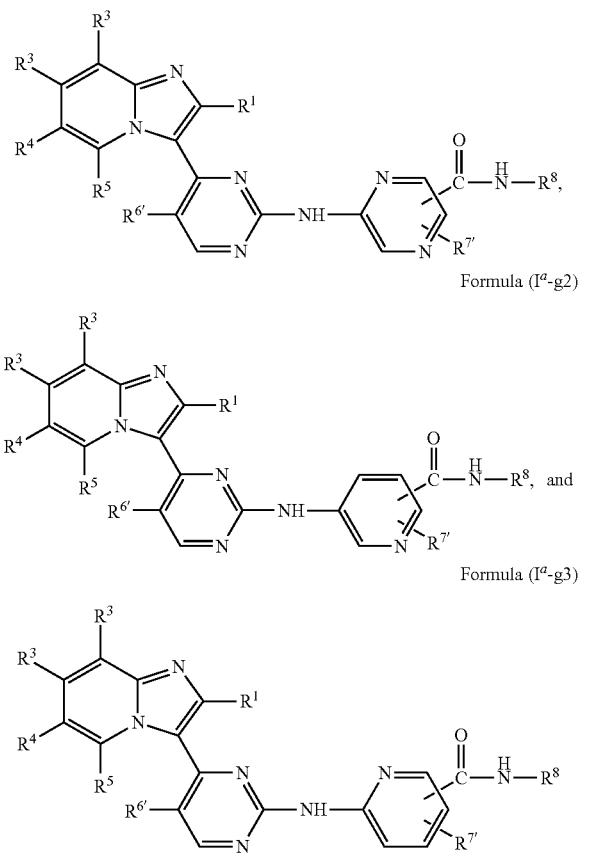

Formula (I$^a$-g1)

Formula (I$^a$-g2)

Formula (I$^a$-g3)

wherein R$^{6'}$ is H or R$^6$, and R$^{7'}$ is H or R$^7$.

20. The compound of claim 19 which is selected from the group consisting of:

N-hydroxy-6-(4-(2-methylimidazo[1,2-a]pyridin-3-yl)pyrimidin-2-ylamino)nicotinamide;

N-(2-aminophenyl)-6-(4-(2-methylimidazo[1,2-a]pyridin-3-yl)pyrimidin-2-ylamino)nicotinamide;

N-hydroxy-5-(4-(2-methylimidazo[1,2-a]pyridin-3-yl)pyrimidin-2-ylamino)pyrazine-2-carboxamide;

N-(2-aminophenyl)-5-(4-(2-methylimidazo[1,2-a]pyridin-3-yl)pyrimidin-2-ylamino)pyrazine-2-carboxamide;

N-hydroxy-6-(4-(2-methylimidazo[1,2-a]pyridin-3-yl)pyridin-2-ylamino)nicotinamide;

N-(2-aminophenyl)-6-(4-(2-methylimidazo[1,2-a]pyridin-3-yl)pyridin-2-ylamino)nicotinamide;

N-hydroxy-2-(4-(2-methylimidazo[1,2-a]pyridin-3-yl)pyridin-2-ylamino)pyrimidine-5-carboxamide;

N-hydroxy-5-(4-(2-methylimidazo[1,2-a]pyridin-3-yl)pyridin-2-ylamino)pyrazine-2-carboxamide;

N-hydroxy-6-(4-(7-methoxy-2-methylimidazo[1,2-a]pyridin-3-yl)pyridin-2-ylamino)nicotinamide; and pharmaceutically acceptable salts thereof.

21. The compound of claim 6 selected from those of Formulae (I$^a$-h0), (I$^a$-h1), and (I$^a$-h2), and pharmaceutically acceptable salts thereof:

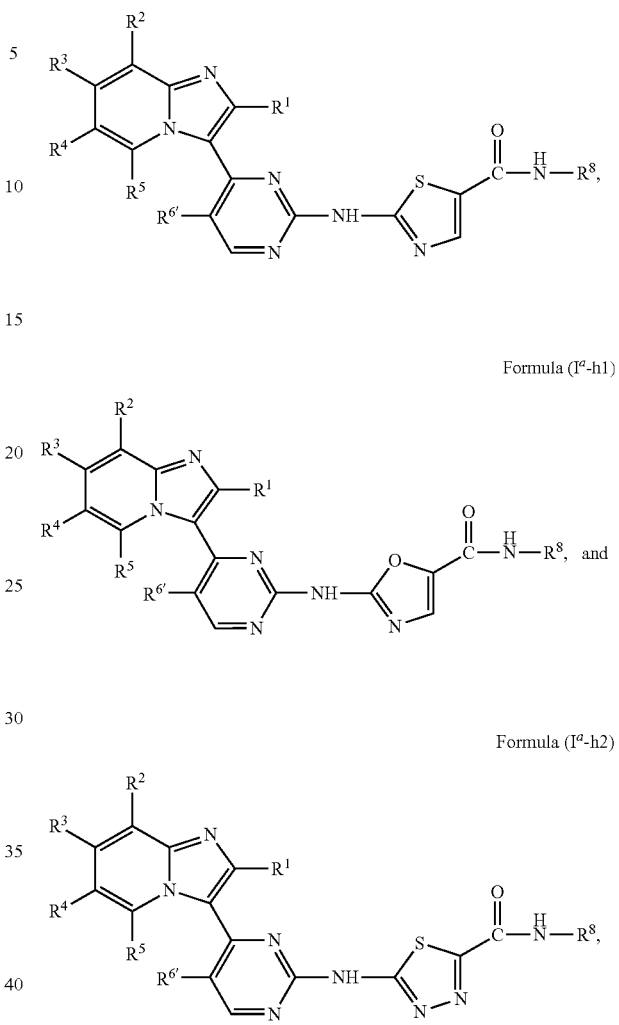

Formula (I$^a$-h0)

Formula (I$^a$-h1)

Formula (I$^a$-h2)

wherein R$^{6'}$ is H or R$^6$.

22. The compound of claim 21 which is selected from the group consisting of:

N-(2-aminophenyl)-2-(4-(2-methylimidazo[1,2-a]pyridin-3-yl)pyrimidin-2-ylamino)thiazole-4-carboxamide;

N-(2-aminophenyl)-2-(4-(2-methylimidazo[1,2-a]pyridin-3-yl)pyrimidin-2-ylamino)thiazole-5-carboxamide;

N-hydroxy-2-(4-(2-methylimidazo[1,2-a]pyridin-3-yl)pyrimidin-2-ylamino)thiazole-4-carboxamide;

N-hydroxy-2-(4-(2-methylimidazo[1,2-a]pyridin-3-yl)pyrimidin-2-ylamino)thiazole-5-carboxamide;

N-hydroxy-2-(4-(2-methylimidazo[1,2-a]pyridin-3-yl)pyrimidin-2-ylamino)oxazole-5-carboxamide;

N-hydroxy-2-(4-(2-methylimidazo[1,2-a]pyridin-3-yl)pyridin-2-ylamino)thiazole-5-carboxamide;

N-hydroxy-5-(4-(2-methylimidazo[1,2-a]pyridin-3-yl)pyridin-2-ylamino)-1,3,4-thiadiazole-2-carboxamide; and pharmaceutically acceptable salts thereof.

23. The compound of claim 5 selected from those of Formula (I$^b$-a) and pharmaceutically acceptable salts thereof:

Formula (I$^b$-a)

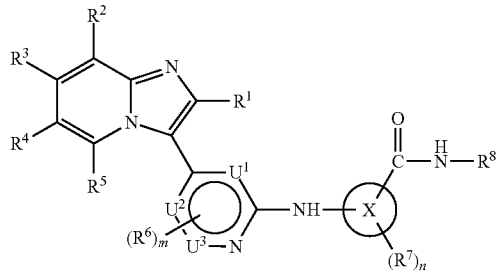

wherein

R$^1$, R$^2$, R$^3$, R$^4$ and R$^5$ are independently selected from the group consisting of H, halo, nitro, cyano, hydroxy, hydroxyalkyl, haloalkyl, haloalkoxy, amino, azido, carboxyl, carbamoyl, mercapto, sulphamoyl, C$_{1-10}$ alkyl, C$_{2-10}$ alkenyl, C$_{2-10}$ alkynyl, C$_{1-10}$ alkoxy, C$_{1-10}$ alkanoyl, C$_{1-10}$ alkanoyloxy, N—(C$_{1-10}$ alkyl)amino, N,N—(C$_{1-10}$ alkyl)$_2$-amino, C$_{1-10}$ alkanoylamino, N—(C$_{1-10}$ alkyl)carbamoyl, N,N—(C$_{1-10}$ alkyl)$_2$-carbamoyl, C$_{1-10}$ alkyl-S(O)$_a$ wherein a is 0, 1 or 2, C$_{1-10}$ alkoxycarbonyl, NH$_2$—S(O)$_2$NH—, N—(C$_{1-10}$ alkyl) sulphamoyl, N,N—(C$_{1-10}$ alkyl)$_2$sulphamoyl, aryl, aryloxy, arylthio, cycloalkyl, cycloalkyloxy, heterocyclyl, heterocyclyl(C=O)—, heterocyclyloxy and heterocyclylthio; wherein each of R$^1$, R$^2$, R$^3$, R$^4$ and R$^5$ is optionally substituted by one or more A.

24. The compound of claim 23 selected from those of Formulae (I$^b$-a1), (I$^b$-a2) (I$^b$-a3) and (I$^b$-a4) and pharmaceutically acceptable salts thereof:

Formula (I$^b$-a1)

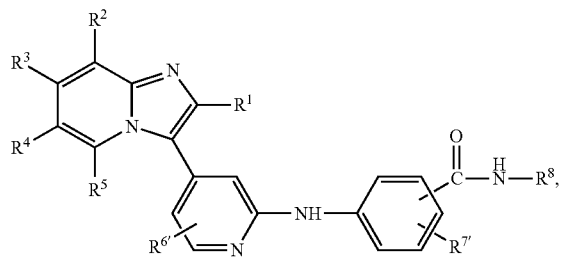

Formula (I$^b$-a2)

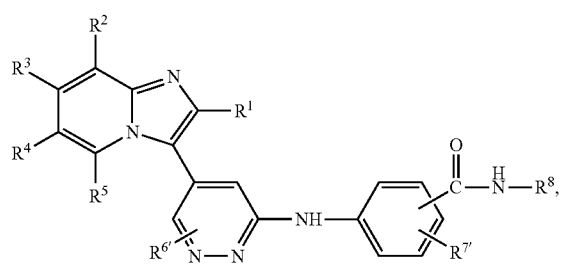

Formula (I$^b$-a3)

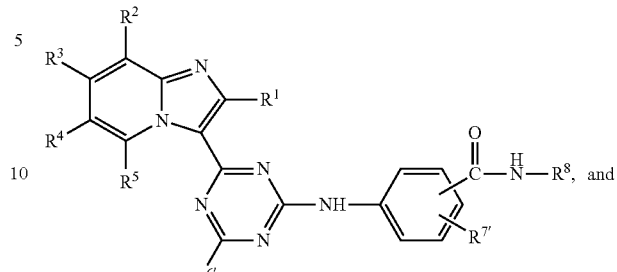

Formula (I$^b$-a4)

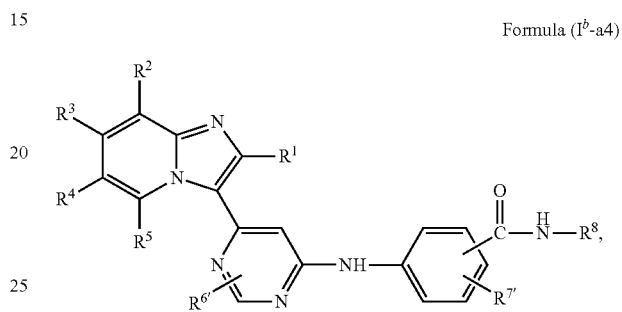

wherein R$^{6'}$ is H or R$^6$; and R$^{7'}$ is H or R$^7$.

25. The compound of claim 24 which is selected from the group consisting of:

N-hydroxy-4-(4-(2-methylimidazo[1,2-a]pyridin-3-yl)pyridin-2-ylamino)benzamide;

N-(2-aminophenyl)-4-(4-(2-methylimidazo[1,2-a]pyridin-3-yl)pyridin-2-ylamino)benzamide;

N-hydroxy-4-(5-(imidazo[1,2-a]pyridin-3-yl)pyridazin-3-ylamino)benzamide;

N-(2-aminophenyl)-4-(5-(imidazo[1,2-a]pyridin-3-yl)pyridazin-3-ylamino)benzamide;

N-hydroxy-4-(4-(imidazo[1,2-a]pyridin-3-yl)-1,3,5-triazin-2-ylamino)benzamide;

N-(2-aminophenyl)-4-(4-(imidazo[1,2-a]pyridin-3-yl)-1,3,5-triazin-2-ylamino)benzamide;

N-(2-aminophenyl)-4-(6-(imidazo[1,2-a]pyridin-3-yl)pyrimidin-4-ylamino)benzamide;

and pharmaceutically acceptable salts thereof.

26. The compound of claim 5 selected from those of Formulae (I$^c$-a) and (I$^c$-b) and pharmaceutically acceptable salts thereof:

Formula (I$^c$-a)

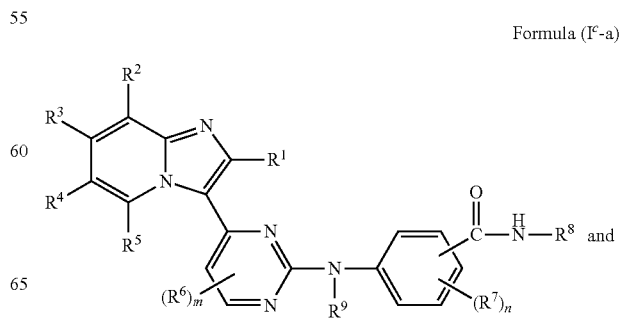

-continued

Formula (I<sup>c</sup>-b)

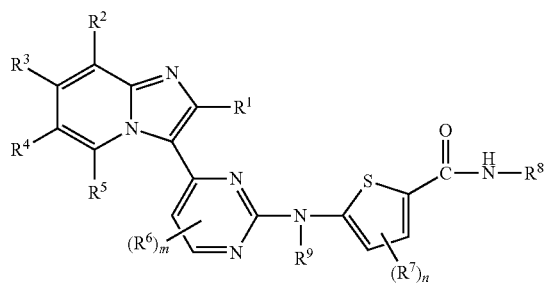

wherein R⁹ is alkyl, haloalkyl or aminoalkyl; and m is 0 or 1.

27. The compound of claim 26 which is selected from the group consisting of:
 N-hydroxy-4-((4-(imidazo[1,2-a]pyridin-3-yl)pyrimidin-2-yl)(methyl)amino)benzamide;
 N-(2-aminophenyl)-4-((4-(imidazo[1,2-a]pyridin-3-yl)pyrimidin-2-yl)(methyl)amino)benzamide;
 4-(ethyl(4-(imidazo[1,2-a]pyridin-3-yl)pyrimidin-2-yl)amino)-N-hydroxybenzamide;
 N-(2-aminophenyl)-4-(ethyl(4-(imidazo[1,2-a]pyridin-3-yl)pyrimidin-2-yl)amino)benzamide;
 N-hydroxy-4-((4-(imidazo[1,2-a]pyridin-3-yl)pyrimidin-2-yl)(2,2,2-trifluoroethyl)amino)benzamide;
 N-(2-aminophenyl)-4-((4-(imidazo[1,2-a]pyridin-3-yl)pyrimidin-2-yl)(2,2,2-trifluoroethyl)amino)benzamide; and
 pharmaceutically acceptable salts thereof.

28. A pharmaceutical composition comprising an effective amount of one or more compounds according to claim 1 and a pharmaceutically-acceptable carrier.

29. The pharmaceutical composition according to claim 28, further comprising one or more anti-cancer agents selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

* * * * *